(12) United States Patent
Liu et al.

(10) Patent No.: US 12,059,526 B2
(45) Date of Patent: Aug. 13, 2024

(54) SYSTEMS AND METHODS FOR DELIVERING A RESPIRATORY GAS

(71) Applicant: BMC MEDICAL CO., LTD., Beijing (CN)

(72) Inventors: Lijun Liu, Beijing (CN); Jianxin Zhi, Beijing (CN); Zhi Zhuang, Beijing (CN); Min Chang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 0 days.

(21) Appl. No.: 18/331,201

(22) Filed: Jun. 8, 2023

(65) Prior Publication Data

US 2023/0310772 A1     Oct. 5, 2023

Related U.S. Application Data

(63) Continuation of application No. 16/988,595, filed on Aug. 7, 2020, which is a continuation of application No. PCT/CN2018/111996, filed on Oct. 26, 2018.

(51) Int. Cl.
*A61M 16/00*     (2006.01)
*A61L 9/20*      (2006.01)
(Continued)

(52) U.S. Cl.
CPC .......... *A61M 16/0066* (2013.01); *A61L 9/20* (2013.01); *A61M 16/1075* (2013.01);
(Continued)

(58) Field of Classification Search
CPC ............ A61M 2209/086; A61M 16/08; A61M 16/0816; A61M 16/16; A61M 16/109; A61M 16/0066
See application file for complete search history.

(56) References Cited

U.S. PATENT DOCUMENTS 6,256,454 B1   7/2001  Dykes
7,111,624 B2   9/2006  Thudor et al.
(Continued)

FOREIGN PATENT DOCUMENTS

CN    201622851 U    11/2010
CN    204193230 U     3/2015
(Continued)

OTHER PUBLICATIONS

Machine Translation of Description_CN106310475A; Aug. 23, 2023 (Year: 2017).*
(Continued)

*Primary Examiner* — Kendra D Carter
*Assistant Examiner* — Mautin I Ashimiu
(74) *Attorney, Agent, or Firm* — METIS IP LLC

(57) ABSTRACT

A respiratory ventilation apparatus configured to deliver a respiratory gas to a patient interface is provided. The apparatus may include a gas pressurization unit configured to generate a pressurized respiratory gas, a gas inlet port configured to introduce the respiratory gas into the respiratory ventilation apparatus, a gas outlet port configured to discharge the pressurized respiratory gas to a respiration tube, a detection module configured to detect the pressure of the pressurized respiratory gas, at least one non-volatile memory configured to store a plurality of parameters and a plurality of programs, and one or more controllers. The one or more controllers may be configured to initiate the respiratory ventilation apparatus upon a boot operation, and/or initiate a program that constantly reads information from the detection module, and controls the pressure of the pressurized respiratory gas using the information read from the detection module and at least one parameter.

19 Claims, 77 Drawing Sheets

(51) Int. Cl.
- *A61M 11/00* (2006.01)
- *A61M 16/04* (2006.01)
- *A61M 16/06* (2006.01)
- *A61M 16/08* (2006.01)
- *A61M 16/10* (2006.01)
- *A61M 16/16* (2006.01)
- *G16H 20/40* (2018.01)
- *G16H 40/63* (2018.01)

(52) U.S. Cl.
CPC .......... *A61M 16/109* (2014.02); *A61M 16/16* (2013.01); *A61M 16/161* (2014.02); *G16H 20/40* (2018.01); *A61L 2209/12* (2013.01); *A61M 2016/0027* (2013.01); *A61M 2016/003* (2013.01); *A61M 16/0465* (2013.01); *A61M 16/06* (2013.01); *A61M 16/0616* (2014.02); *A61M 16/0666* (2013.01); *A61M 16/1055* (2013.01); *A61M 16/107* (2014.02); *A61M 2205/3306* (2013.01); *A61M 2205/3368* (2013.01); *A61M 2205/3584* (2013.01); *A61M 2205/3592* (2013.01); *A61M 2205/42* (2013.01); *A61M 2205/505* (2013.01); *A61M 2205/52* (2013.01); *A61M 2205/587* (2013.01); *A61M 2209/10* (2013.01); *A61M 2230/42* (2013.01)

(56) References Cited

U.S. PATENT DOCUMENTS

| | | |
|---|---|---|
| 7,637,288 B2 | 12/2009 | Kressierer/Huber et al. |
| 9,884,163 B2 | 2/2018 | Mayer et al. |
| 2002/0024155 A1 | 2/2002 | Kusano et al. |
| 2004/0055597 A1 | 3/2004 | Virr et al. |
| 2004/0076412 A1 | 4/2004 | Kanzaki et al. |
| 2004/0175288 A1 | 9/2004 | Horton, III |
| 2006/0118112 A1 | 6/2006 | Cattano et al. |
| 2007/0079826 A1 | 4/2007 | Kramer et al. |
| 2007/0157928 A1 | 7/2007 | Pujol et al. |
| 2007/0169776 A1* | 7/2007 | Kepler ............... A61M 16/107 128/200.14 |
| 2007/0193580 A1 | 8/2007 | Feldhahn et al. |
| 2009/0120434 A1* | 5/2009 | Smith ............... A61M 16/0075 128/202.13 |
| 2009/0194106 A1* | 8/2009 | Smith ............... A61M 16/0057 128/203.16 |
| 2010/0043791 A1 | 2/2010 | McAuley et al. |
| 2010/0175560 A1 | 7/2010 | Blanc et al. |
| 2010/0192094 A1 | 7/2010 | Jeha et al. |
| 2012/0073573 A1 | 3/2012 | Thudor et al. |
| 2012/0160243 A1 | 6/2012 | Berthon-Jones et al. |
| 2012/0171058 A1 | 7/2012 | Grasmuck |
| 2012/0301267 A1 | 11/2012 | Baecke et al. |
| 2013/0008440 A1 | 1/2013 | Maurer et al. |
| 2013/0174843 A1 | 7/2013 | Smith et al. |
| 2013/0206140 A1 | 8/2013 | Kepler et al. |
| 2014/0014109 A1 | 1/2014 | Grasmuck |
| 2014/0109909 A1 | 4/2014 | Shelly et al. |
| 2014/0332003 A1 | 11/2014 | Crumblin et al. |
| 2015/0023782 A1* | 1/2015 | Velzy ............... F04D 29/701 415/119 |
| 2015/0040903 A1 | 2/2015 | Matthews et al. |
| 2015/0059748 A1 | 3/2015 | Hsiao et al. |
| 2015/0359982 A1 | 12/2015 | Garde et al. |
| 2016/0022954 A1* | 1/2016 | Bath ............... A61M 16/024 128/203.12 |
| 2016/0082220 A1 | 3/2016 | Barker et al. |
| 2016/0310689 A1 | 10/2016 | Osborne et al. |
| 2016/0310691 A1 | 10/2016 | Bath et al. |
| 2016/0312801 A1 | 10/2016 | Jing et al. |
| 2016/0339193 A1 | 11/2016 | Daly et al. |
| 2017/0340847 A1 | 11/2017 | Taylor et al. |
| 2017/0361053 A1 | 12/2017 | Dimatteo et al. |
| 2018/0056020 A1 | 3/2018 | Dimatteo et al. |
| 2018/0185606 A1 | 7/2018 | Van Schalkwyk et al. |
| 2018/0193577 A1 | 7/2018 | Cariola et al. |
| 2018/0228996 A1 | 8/2018 | Kat |
| 2018/0236191 A1 | 8/2018 | Martin et al. |
| 2020/0101258 A1* | 4/2020 | Dimatteo ............ A61M 16/162 |
| 2020/0179629 A1 | 6/2020 | Burgess et al. |
| 2020/0306489 A1* | 10/2020 | Wright ............... A61M 16/109 |
| 2021/0001070 A1 | 1/2021 | Cariola et al. |
| 2021/0077760 A1 | 3/2021 | Wada et al. |
| 2021/0260316 A1 | 8/2021 | Crumblin et al. |
| 2021/0379322 A1* | 12/2021 | Maurer ................ A61M 16/16 |
| 2022/0016382 A1 | 1/2022 | Smith et al. |
| 2022/0288345 A1 | 9/2022 | Walls et al. |
| 2023/0099377 A1 | 3/2023 | Velzy et al. |

FOREIGN PATENT DOCUMENTS

| | | | | |
|---|---|---|---|---|
| CN | 204352325 U | | 5/2015 | |
| CN | 105963842 A | | 9/2016 | |
| CN | 106310475 A | * | 1/2017 | ............ A61M 16/00 |
| CN | 106345033 A | | 1/2017 | |
| CN | 106362256 A | * | 2/2017 | ............ A61M 16/00 |
| CN | 106362256 A | | 2/2017 | |
| CN | 206081270 U | | 4/2017 | |
| CN | 206566314 U | | 10/2017 | |
| CN | 107626022 A | | 1/2018 | |
| CN | 207092800 U | | 3/2018 | |
| CN | 108042837 A | | 5/2018 | |
| CN | 207711705 U | | 8/2018 | |
| CN | 109758654 A | | 5/2019 | |
| EP | 1733751 A1 | | 12/2006 | |
| EP | 2703034 A2 | | 3/2014 | |
| EP | 3091238 B1 | * | 4/2018 | ............ A61M 16/00 |
| EP | 3482788 A1 | * | 5/2019 | ........ A61M 16/0066 |
| EP | 2809383 B1 | | 4/2021 | |
| JP | 2004068546 A | | 3/2004 | |
| WO | 2014138804 A1 | | 9/2014 | |

OTHER PUBLICATIONS

Machine Translation of Description_CN106362256A; Aug. 23, 2023 (Year: 2017).*
Machine Translation of Description_EP3482788A1; Sep. 7, 2023 (Year: 2019).*
First Office Action in Chinese Application No. 202011539459.0 mailed on Apr. 22, 2022, 23 pages.
The Extended European Search Report in European Application No. 18938141.1 mailed on Feb. 17, 2021, 8 pages.
The Extended European Search Report in European Application No. 20214993.6 mailed on Apr. 26, 2021, 6 pages.
The Extended European Search Report in European Application No. 20215012.4 mailed on Mar. 30, 2021, 8 pages.
The Extended European Search Report in European Application No. 20215064.5 mailed on Apr. 23, 2021, 10 pages.
First Office Action in Chinese Application No. 202310897712.7 mailed on Feb. 1, 2024, 16 pages.
Office Action in Chinese Application No. 202310899276.7 mailed on Jan. 19, 2024.

* cited by examiner

601

600

801

1401

1401

1401

1401

2900

2920

2920

3000

3000

3300

3310

SYSTEMS AND METHODS FOR DELIVERING A RESPIRATORY GAS

CROSS-REFERENCE TO RELATED APPLICATIONS

This application is a continuation of U.S. patent application Ser. No. 16/988,595, filed on Aug. 7, 2020, which is a continuation of International Patent Application No. PCT/CN2018/111996, filed on Oct. 26, 2018, the contents of which are hereby incorporated by reference.

TECHNICAL FIELD

This disclosure generally relates to the detection, diagnosis, treatment, prevention and amelioration of respiratory-related disorders, and more particularly, relates to systems and methods for delivering a respiratory gas.

BACKGROUND

Respiration is significant for the maintenance of the vitality of a subject (e.g., a human body). The respiratory system of the subject can facilitate gas exchange. The nose and/or mouth of the subject form the entrance to the airways of the subject. A range of respiratory disorders (e.g., apnea, hypopnea, hyperpnea, snore, or the like) exist. The respiratory disorders can threaten the health (and/or life) of the subject. Therefore, it is desirable to develop system(s) and method(s) for delivering a respiratory gas for the subject.

SUMMARY

In one embodiment, a humidification assembly is configured to humidify the pressurized respiratory gas from a respiratory ventilation apparatus, wherein the humidification assembly including a liquid chamber configured to accommodate one or more liquids, wherein the liquid chamber including a tank, a tank cover, and a humidification assembly gas inlet port configured to introduce the pressurized respiratory gas, via a first gas passage, into the tank, wherein the first gas passage includes an output port.

In one embodiment, the liquid chamber of the humidification assembly further includes: a humidification assembly gas outlet port configured to introduce the humidified and pressurized respiratory gas, via a second gas passage back into a main body of the respiratory ventilation apparatus, wherein the second gas passage includes an input port.

In one embodiment, the liquid chamber of the humidification assembly comprises a shell, wherein the humidification assembly gas inlet port of the liquid chamber and/or the humidification assembly gas outlet port of the liquid chamber are set on a first side surface of the shell of the liquid chamber, and wherein the output port of the first gas passage for connecting the first gas passage with the tank and/or the input port of the second gas passage for connecting the second gas passage with the tank are set inside the shell of the liquid chamber. In one embodiment the shell comprises an inner shell and a cover shell in a layered structure. Such layered structure may allow the shell to be dissembled and cleaned easily.

By forming the first and second gas passages in the shell of the liquid chamber, the tank may comprise a simple design with a much wider opening and volume allowing it to be more easily maintained and filled, e.g., comparing filling the water through one of the gas passages.

In one embodiment, the output port of the first gas passage faces a second side surface of the shell of the liquid chamber, the input port of the second gas passage faces a third side surface of the shell of the liquid chamber, and the second side surface of the shell of the liquid chamber is opposite to the third surface of the shell of the liquid chamber.

By spacing the input and output ports apart, gas flow may travel a longer distance while being exposed to the liquid(s) in the tank, thus, increasing the efficiency of the humidification.

In one embodiment, the liquid chamber includes a guide plate set on an upper edge of the output port of the first gas passage, the guide plate being configured to guide the pressurized respiratory gas to flow downward to the tank.

In one embodiment, the first gas passage includes a first portion and a second portion, wherein the first portion of the first gas passage extends from the humidification assembly gas inlet port of the liquid chamber to a first common plane, wherein the second portion of the first gas passage extends from the first common plane to the output port of the first gas passage. Such shape of the gas passage reduces the noise within the liquid chamber exiting through the gas passage.

In addition thereto or alternatively, the second gas passage includes a first portion and a second portion according to one embodiment, wherein the first portion of the second gas passage extends from the input port of the second gas passage to a second common plane, wherein the second portion of the second gas passage extends from the second common plane to the humidification assembly gas outlet port of the liquid chamber.

By forming the first and second gas passage with a common plane, a compact design may be achieved.

Additionally, or alternatively, the first and second gas passages has a substantially rectangular cross-section. Such rectangular cross-section may save dead space comparing to tubular cross-section and/or increasing the area of the cross-section, thus allowing a more compact design and/or a lower resistance for the pressurized gas.

In one embodiment, the first gas passage and the second gas passage cross each other; wherein the distance between the output port and the humidification assembly gas inlet port is larger than the distance between the output port and the humidification assembly gas outlet port.

Additionally, or alternatively, the distance between the input port and the humidification assembly gas outlet port is larger than the distance between the input port and the humidification assembly gas inlet port.

By crossing the first and second gas passage, mechanical noise from a main body of a respiratory ventilation apparatus for connected to the humidification assembly gas inlet port of the first gas passage and bubbling noise in the tank and propagating through the second gas passages are reduced with a compact design reducing the dead space. Liquid in the tank is also less likely reaching the inlet and outlet ports.

In one embodiment, the first portion of the first gas passage is substantially parallel to the second portion of the second gas passage along a direction having an angle with the first side surface of the shell of the liquid chamber. Additionally, or alternatively, the second portion of the first gas passage and the first portion of the second gas passage are set in different layers according to one embodiment. Additionally, or alternatively, a first projection of the second portion of the first gas passage on a horizontal plane and a second projection of the first portion of the second gas passage on the horizontal plane are intersecting or at least partially overlapping according to one embodiment.

In one embodiment, the second portion of the first gas passage is set below the first portion of the second gas passage, or the first portion of the second gas passage is set below the second portion of the first gas passage.

In one embodiment, an area of a first cross section of the first gas passage on the first common plane is equal to or less than half of an area of the humidification assembly gas inlet port of the liquid chamber, and/or an area of a second cross section of the second gas passage on the second common plane is equal to or less than half of an area of the humidification assembly gas outlet port of the liquid chamber.

In one embodiment, the liquid chamber further includes: a first inclined plate set between the first cross section and the humidification assembly gas inlet port of the liquid chamber, the first inclined plate being configured to smooth flowing of the pressurized respiratory gas in the first gas passage, and a second inclined plate set between the second cross section and the humidification assembly gas outlet port of the liquid chamber, the second inclined plate being configured to smooth flowing of the humidified and pressurized respiratory gas in the second gas passage.

In one embodiment, the liquid chamber further includes a connecting plate, the connecting plate including a first aperture and a second aperture, the first aperture and the second aperture corresponding to the humidification assembly gas inlet port and the humidification assembly gas outlet port of the liquid chamber respectively, the connecting plate being configured to allow a sealed connection between the liquid chamber and the main body of the respiratory ventilation apparatus.

In one embodiment, the liquid chamber further includes: a first groove set between the humidification assembly gas inlet port of the liquid chamber and the connecting plate, the first groove being configured to accommodate a first portion of the one or more liquids and prevent the first portion of the one or more liquids from entering the main body of the respiratory ventilation apparatus when the liquid chamber is tilted, and/or a second groove set between the humidification assembly gas outlet port of the liquid chamber and the connecting plate, the second groove being configured to accommodate a second portion of the one or more liquids and prevent the second portion of the one or more liquids from entering the main body of the respiratory ventilation apparatus when the liquid chamber is tilted.

In one embodiment, at least a portion of a bottom of the first gas passage is below a lower edge of the humidification assembly gas inlet port of the liquid chamber, and/or at least a portion of a bottom of the second gas passage is below a lower edge of the humidification assembly gas outlet port of the liquid chamber.

The arrangement may prevent fluid, e.g. condensed water, exit from the gas passages through the gas outlet port and/or enter the gas outlet port, when the tank cover is closed, or reduce such risks.

In one embodiment the shell is connected and/or connectable to the tank and/or to the tank cover and arranged pivotally relative to the tank. As the first and/or second gas passages are formed with the shell, the structure of the tank can be formed in a very simple manner allowing better access for cleaning and liquid filling.

In one embodiment, a liquid contacting side wall of the liquid chamber is at least partially formed by an outer side wall of the tank forming the outer surface of the humidification assembly. Additionally or alternatively, the tank is formed with only one opening for filling liquid and for exchange of pressurized gas. Comparing to some known designs, the liquid chamber and/or the tank may be formed in a simpler manner, e.g., with single layer side wall, and/or e.g., with an upper side substantially open thus reducing the weight and the size, increasing the liquid-gas contacting surface and making access to the tank/liquid chamber easier.

In one embodiment, the tank cover is pivotally connected to the tank through a connection mechanism; wherein at least a portion of the side of the first gas passage near the connection mechanism is covered in the flow direction by a side edge of the humidification assembly gas inlet port of the liquid chamber, and/or wherein at least a portion of the side of the second gas passage near the connection mechanism is covered in the flow direction by a side edge of the humidification assembly gas outlet port of the liquid chamber.

Once the tank cover is opened by pivoting the tank cover around a rotational axis defined by the connection mechanism, the side of the first and/or second gas passages near the connection mechanism will be turned into a lower position than other sides of the first and/or second gas passages. By covering at least a portion of such side, liquid within the first and/or second gas passages is prevented from flowing or dripping out damaging e.g. electronic components or dropping on e.g. the surface on which the humidification assembly is placed.

In one embodiment, the tank cover is pivotally connected to the tank through a connection mechanism, and wherein the distance between the connection mechanism and the humidification assembly gas outlet port is less than the distance between the connection mechanism and the humidification assembly gas inlet port.

Due to connection mechanism and the leverage effect, the port near the connection mechanism, e.g. a pivotable hinge connection, may have a tighter seal and/or less gap error than the port far away from the connection mechanism. By arranging the humidification assembly gas outlet port near the connection mechanism, the sealing of the humidified gas flowing through the humidification assembly gas outlet port in improved, which may be more critical than the sealing of the not yet humidified gas entering the humidification assembly through the humidification assembly gas inlet port in some circumstances.

In one embodiment, a respiratory ventilation apparatus is configured to deliver a respiratory gas to a patient interface, comprising an above-mentioned humidification assembly and further comprises: a gas pressurization unit configured to generate the pressurized respiratory gas by pressurizing the respiratory gas, the gas pressurization unit being located in a main body of the respiratory ventilation apparatus, the main body of the respiratory ventilation apparatus including a housing with a first side wall configured to discharge the pressurized respiratory gas; a main gas inlet port configured to introduce the respiratory gas into the respiratory ventilation apparatus, the main gas inlet port being set on a second side wall of the housing of the main body of the respiratory ventilation apparatus; and a main gas outlet port configured to discharge the humidified and pressurized respiratory gas to a respiration tube.

In one embodiment, the main gas outlet port is for setting on the main body of a respiratory ventilation apparatus.

In one embodiment, the main gas outlet port is set on the liquid chamber.

In one embodiment, the first side surface of the shell of the liquid chamber faces the first side wall of the housing of the main body of the respiratory ventilation apparatus.

In one embodiment, a respiratory ventilation apparatus is configured to deliver a respiratory gas to a patient interface, comprising: a gas pressurization unit located in a main body of the respiratory ventilation apparatus; a humidification assembly being removably coupled to the main body of the respiratory ventilation apparatus; wherein the humidification assembly includes: a liquid chamber configured to accommodate one or more liquids.

In one embodiment, the liquid chamber comprises a tank and a tank cover, which is pivotally connected to the tank through a connection mechanism with a rotational axis; wherein the tank comprises an opening for filling at least one of the one or more liquids, wherein the opening is openable by opening the tank cover and/or closable by closing the tank cover; and wherein the humidification assembly and the main body of the respiratory ventilation apparatus are fluidically connectable by closing the tank cover and/or fluidically disconnectable by opening the tank cover.

By allowing the main body and the humidification assembly be fluidically connected to form the flow channel for the pressurized gas and/or humidified and pressurized gas using the pivotable tank cover, the mechanical connection between the main body and the tank (often filled with water) may be isolated from the fluidically sealing, making the mechanical connection between the main body and the tank to be more easy to operate while the fluidically connection is secured to be gas-tight under pressure. Further, a lever effect of the tank cover can be used to ensure that the fluid connection is tight against the pressurized gas at one hand, easy to operate with less force on the other hand. In some embodiments, the liquid chamber may be directly mounted on the main body of the respiratory ventilation apparatus, the liquid chamber and the main body of the respiratory ventilation apparatus may be fluidically connectable through at least a connecting port for forming at least one flow channel between the main body of the respiratory ventilation apparatus and the liquid chamber, and the liquid chamber may include the tank cover that can be opened. In order to fill liquid(s) in the liquid chamber, the user only needs to open the tank cover and fill the liquid(s) in the tank. When filling the liquid(s), the fluid connection between the liquid chamber and the main body may be disconnected. Therefore, the respiratory ventilation apparatus has simplified structure and is easy to use. In some embodiments, the main body of the respiratory ventilation apparatus may include a blower of the gas pressurization unit, and/or a heating component configured to heat the liquid(s) in the liquid chamber. The heating component may be mounted on a side surface of the main body. The heating component and the main body may be configured as an integral piece, or the heating component may be detachable from the main body. In some embodiments, the tank and the tank cover may be locked when the tank cover is closed. In some embodiments, the liquid chamber and the heating component may be locked. In some embodiments, the tank cover may not be locked to the main body, and the tank cover is fixed to the main body via the locking between the tank and the tank cover, and the locking between the tank and the main body. When the liquid chamber is mounted with the heating component, the tank cover may be opened by unlocking the tank cover from the tank. Therefore, the opening and closing of the tank cover, and the fluid connection and disconnection between the tank cover and the main body may be facilitated. It should be noted that any other locking mode between the tank and the tank cover may realize the functions illustrated above without unlocking the liquid chamber from the main body.

In some embodiments, the tank and the main body are attachable with each other by moving the tank in an attaching direction relative to the main body with an angle between the rotational axis and the attaching direction between 20°-160°, or in some embodiments between 45°-135°, or in some further embodiments, between 60°-120°; and/or wherein the tank and the main body are unlockable from each other by moving the tank in an unlocking direction relative to the main body with an angle between the rotational axis and the unlocking direction between 20°-160°, or in some embodiments between 45°-135°, or in some further embodiments, between 60°-120°.

By arranging the rotational axis relative to the attaching direction in said manners, closing the tank cover may be in a direction perpendicular to the rotational axis and may have a component in the attaching direction. Thus, closing the tank cover towards the tank may also result in attaching the tank with the main body. The user comfort is thus improved.

In some embodiments, the angle between attaching direction and the unlocking direction is between −45° and 45°, in some further embodiments, between −30° and 30°, and in some further embodiments, between −15° and 15°. In one embodiment, the attaching direction and the unlocking direction may be substantially in the same direction. This can be further combined with a rotational axis allowing the tank cover only to be opened in a substantially opposite direction than the unlocking direction to avoid the user unlock the tank accidentally by opening the tank cover. The user comfort is increased.

In some embodiments, the humidification assembly and the main body of the respiratory ventilation apparatus are fluidically connectable through at least a connecting port for forming at least one flow channel between the main body of the respiratory ventilation apparatus and the liquid chamber; wherein the at least one connecting port comprises a gas inlet port and a gas outlet port; wherein the connecting port comprises an axial sealing member for fluidically sealingly connecting the gas inlet port and the gas outlet port; wherein an inner surface of the axial sealing member forms at least partially the flow channel and wherein the axial sealing member defines a sealing plane.

By using an axial sealing member, the sealing member creates, e.g., comparing to a cone-shaped connector forming a radial sealing, less frictional forces during connection and disconnection, thus improving the user comfort and operational safety.

In some embodiments, the angle between the sealing plane and the liquid level in the liquid chamber is between −75°-75°, in some further embodiments, between −30° and 30°, and in some further embodiments, between 15° and 65°; and/or wherein the angle between the sealing plane and the attaching direction is between 15°-165°, in some further embodiments, between 30° and 150°, and in some further embodiments, between 45° and 135°, and in some further embodiments, between 70° and 110°; and/or wherein the angle between the liquid level and the unlocking direction is between 15°-165°, in some further embodiments, between 30° and 150°, and in some further embodiments, between 45° and 135°, and in some further embodiments, between 70° and 110°.

By arranging the sealing plane in the said manners relative to the liquid level (e.g., the horizontal plane), and/or, by arranging the attaching direction in the said manners relative to the liquid level, the risks of the liquid being spilled out during the sealing, unlocking and/or attaching is reduced. The liquid level is the designed level of the liquid during normal use of the respiratory ventilation apparatus and the humidification assembly.

In some embodiments, the inner surface of the axial sealing member forms at least partially the flow channel and/or the overlapping section of the gas inlet and outlet port in a sealed state is less than 5 mm, such that the gas inlet port is disconnectable from the gas outlet port without the gas inlet port contacting the gas outlet port; wherein the axial sealing member comprises one or more elastical materials with a shore hardness of less than 70 (e.g., 20-70, 60, or the like), according to ASTM D2240 Typ A and wherein the axial sealing member is compressed along the axial direction by 10%-50% and/or by 0.5-6 mm (e.g., 1-3 mm) in a sealed state comparing to a state, wherein the main body and the humidification assembly are unlocked.

In some embodiments, the gas inlet port comprises an inlet aperture and the gas outlet port comprises an outlet aperture, wherein the inlet and outlet apertures are formed by one or more materials having a higher hardness than an elastical material forming the axial sealing member.

In some embodiments, the axial sealing member is formed around the inlet aperture and/or around the outlet aperture.

In some embodiments, the inlet aperture and the outlet aperture are formed by materials having a higher hardness than the elastic material forming the axial sealing member, and the inlet aperture and the outlet aperture are spaced apart by the axial sealing member in the axial direction of axial sealing member. In some embodiments, the inlet aperture and the outlet aperture are spaced apart at least 1 mm, in some further embodiments, at least 5 mm by the axial sealing member in the axial direction thereof in a sealed and attached state of the humidification assembly. By spacing the inlet and the outlet apertures apart in the axial direction, not only friction force between the gas inlet and outlet ports is minimized, collision between the materials forming the inlet and outlet apertures having a higher hardness is also minimized, reducing the sudden noise during the assembly and/or disassembly of the respiratory ventilation apparatus. Shortly before the inlet and outlet apertures are connected, the relative movement between the humidification assembly and the main body of the respiratory ventilation apparatus is also buffered by the axial sealing member, which further increases the user comfort.

In some embodiments, the axial sealing member comprises multiple parts consisting of the one or more elastic material and are configured such that a dynamic frictional force exists only between such parts during coupling or de-coupling of the humidification assembly.

In some embodiments, the axial sealing member comprises a sealing lip protruding from at least one of the inlet and the outlet apertures, wherein the sealing lip is inclined toward the center of the flow channel and is configured to bend towards the center of the flow channel if pressed and/or compressed by connecting the gas inlet port with the gas outlet port.

In some embodiments, the liquid chamber is in detachable connection with the main body of the respiratory ventilation apparatus through a push-push mechanism.

In some embodiments, a push direction of the push-push mechanism is substantially perpendicular to the rotational axis of the connection mechanism, wherein the humidification assembly and the main body of the respiratory ventilation apparatus are fluidically connectable by closing the tank cover in the push direction of the push-push mechanism while the tank is attached to the main body, and by attaching the liquid chamber to the main body in the push direction while the tank cover is closed.

In some embodiments, the gas pressurization unit is configured to generate a pressurized respiratory gas by pressurizing the respiratory gas; the main body of the respiratory ventilation apparatus includes a housing provided with a first side wall configured to discharge the pressurized respiratory gas; the humidification assembly is configured to humidify the pressurized respiratory gas; the respiratory ventilation apparatus further comprising: a first gas inlet port configured to introduce the respiratory gas into the respiratory ventilation apparatus, the first gas inlet port being set on a second side wall of the housing of the main body of the respiratory ventilation apparatus; and a first gas outlet port configured to discharge the humidified and pressurized respiratory gas to a respiration tube; wherein the liquid chamber being openable from a front surface of the respiratory ventilation apparatus; wherein the humidification assembly further includes a heater plate configured to heat the one or more liquids and generate vapor to humidify the pressurized respiratory gas.

In some embodiments, the liquid chamber is in detachable connection with the main body of the respiratory ventilation apparatus.

In some embodiments, the liquid chamber comprises: a tank; and a tank cover pivotally connected to the tank through a connection mechanism.

In some embodiments, the tank cover includes a second gas inlet port, the second gas inlet port being configured to introduce the pressurized respiratory gas from the main body of the respiratory ventilation apparatus into the liquid chamber.

In some embodiments, the first gas outlet port is set on the liquid chamber.

In some embodiments, the respiratory ventilation apparatus further comprises: a connecting piece configured to provide a sealed connection between the tank cover and the main body of the respiratory ventilation apparatus, the connecting piece including a declining surface facing the tank cover, the tank cover includes a corresponding declining surface facing the connecting piece, and the declining surface of the tank cover includes the second gas inlet port.

In some embodiments, the connecting piece includes a gasket, the gasket includes a first aperture, the first aperture corresponds to the second gas inlet port of the tank cover, so that when the tank cover is closed, the tank cover is in sealed connection with the main body of the respiratory ventilation apparatus through the gasket, the first aperture and the gas inlet port of the tank cover are capable of introducing the pressurized respiratory gas from the main body of the respiratory ventilation apparatus into the liquid chamber.

In some embodiments, the respiratory ventilation apparatus further comprises: a connecting piece configured to provide a sealed connection between the tank cover and the main body of the respiratory ventilation apparatus, the connecting piece including a first thread hose, the first thread hose corresponding to the second gas inlet port of the tank cover.

In some embodiments, the tank cover includes a second gas inlet port and a second gas outlet port, the second gas inlet port being configured to introduce the pressurized respiratory gas from the main body of the respiratory ventilation apparatus into the liquid chamber, the second gas outlet port being configured to discharge the humidified and pressurized respiratory gas from the liquid chamber back into the main body of the respiratory ventilation apparatus.

In some embodiments, the respiratory ventilation apparatus further comprises: a connecting piece configured to provide a sealed connection between the tank cover and the main body of the respiratory ventilation apparatus.

In some embodiments, the connecting piece includes a declining surface facing the tank cover, the tank cover includes a corresponding declining surface facing the connecting piece, and the declining surface of the tank cover includes the second gas inlet port and the second gas outlet port.

In some embodiments, an angle between the declining surface of the connecting piece and a horizontal plane is substantially within 45°-60°.

In some embodiments, wherein the connecting piece includes a gasket, the gasket includes a first aperture and a second aperture, the first aperture corresponds to the second gas inlet port of the tank cover, the second aperture corresponds to the second gas outlet port of the tank cover, so that when the tank cover is closed, the tank cover is in sealed connection with the main body of the respiratory ventilation apparatus through the gasket, the first aperture and the second gas inlet port of the tank cover are capable of introducing the pressurized respiratory gas from the main body of the respiratory ventilation apparatus into the liquid chamber, and the second aperture and the second gas outlet port of the tank cover are capable of introducing the humidified and pressurized respiratory gas from the liquid chamber back into the main body of the respiratory ventilation apparatus.

In some embodiments, the connecting piece includes a first thread hose and a second thread hose, the first thread hose corresponds to the second gas inlet port of the tank cover, the second thread hose corresponds to the second gas outlet port of the tank cover.

In some embodiments, the first thread hose and the second thread hose are substantially vertical, and the second gas inlet port and the second gas outlet port of the tank cover are set in a horizontal surface facing the first thread hose and the second thread hose, so that when the tank cover is closed, the tank cover is in sealed connection with the main body of the respiratory ventilation apparatus through the first thread hose and the second thread hose, the first thread hose and the second gas inlet port of the tank cover are capable of introducing the pressurized respiratory gas from the main body of the respiratory ventilation apparatus into the liquid chamber, and the second thread hose and the second gas outlet port of the tank cover are capable of introducing the humidified and pressurized respiratory gas from the liquid chamber back into the main body of the respiratory ventilation apparatus.

In some embodiments, the tank cover includes a handle and a buckle on a back of the handle, the tank includes a notch in a position relative to the handle of the tank cover, and the tank cover is fastened with the tank through the cooperation of the buckle and the notch when the tank cover is closed.

In some embodiments, the handle is set on a front surface of the respiratory ventilation apparatus, and the connection mechanism between the tank and the tank cover is set on a back surface of the respiratory ventilation apparatus, so that when the tank cover is opened, an undersurface of the tank cover is substantially upright and facing the front surface of the respiratory ventilation apparatus.

In some embodiments, the connection mechanism between the tank and the tank cover comprises:
one or more first connecting pieces set on the tank; and
one or more second connecting pieces set on the tank cover, the one or more second connecting pieces being in pivot connection with the one or more first connecting pieces.

In some embodiments, each of the one or more first connecting pieces includes a pin hole, and each of the one or more second connecting pieces includes a pin.

In some embodiments, wherein each of the one or more second connecting pieces includes a pin hole, and each of the one or more first connecting pieces includes a pin.

In some embodiments, each of the one or more first connecting pieces includes a first inclined guide surface, each of the one or more second connecting pieces includes a second inclined guide surface, and the first inclined guide surface and the second inclined guide surface are configured to facilitate installation of the tank cover on the tank.

In some embodiments, at least one of the one or more first connecting pieces includes a protruding column, at least one of the one or more second connecting pieces includes a groove, and the groove is configured to accommodate the protruding column and limit a back rotary movement of the tank cover when the tank cover is opened to a certain angle.

In some embodiments, the at least one of the one or more second connecting pieces further includes a guide slot, the guide slot being set along a portion of a moving path of the protruding column, the guide slot being configured to smooth a movement of the protruding column.

In some embodiments, the guide slot includes a first end adjacent to the groove and a second end away from the groove, and the depth of the guide slot is gradually changed from a relatively small value at the first end to a relatively large value at the second end.

In some embodiments, the one or more second connecting pieces include a baffle configured to limit a maximum rotary movement of the tank cover when the tank cover is opened.

In some embodiments, a respiratory ventilation apparatus configured to deliver a respiratory gas to a patient interface, may include: a gas pressurization unit configured to generate a pressurized respiratory gas by pressurizing the respiratory gas, the gas pressurization unit being located in a main body of the respiratory ventilation apparatus, the main body of the respiratory ventilation apparatus including a housing with a first side wall configured to discharge the pressurized respiratory gas; a gas inlet port configured to introduce the respiratory gas into the respiratory ventilation apparatus, the gas inlet port being set on a second side wall of the housing of the main body of the respiratory ventilation apparatus; a gas filter component configured to filter the respiratory gas introduced into the respiratory ventilation apparatus and/or the pressurized respiratory gas discharged from the gas pressurization unit; and a gas outlet port configured to discharge the pressurized respiratory gas to a respiration tube.

In some embodiments, the gas filter component may include: a housing in detachable connection with the gas inlet port of the respiratory ventilation apparatus; and one or more gas filter units mounted in the housing, the one or more gas filter units being configured to filter the respiratory gas entering the respiratory ventilation apparatus.

In some embodiments, the one or more gas filter units may include a first gas filter unit, the first gas filter unit being a coarse filter.

In some embodiments, the one or more gas filter units may include a second gas filter unit, the second gas filter unit being a fine filter.

In some embodiments, the housing may include a gas inlet end and a gas outlet end, the gas inlet end including a first cover plate having at least one hole, the gas outlet end including a second cover plate having at least one hole.

In some embodiments, the one or more gas filter units may include a coarse filter and a fine filter, and the coarse filter may be positioned closer to the gas inlet end of the housing than the fine filter.

In some embodiments, the gas inlet end may have a larger intake area than the gas outlet end.

In some embodiments, the gas filter component may further include a baffle, the baffle having an area less than the gas inlet end of the housing, the baffle being mounted in the housing, the baffle being positioned closer to the gas inlet end of the housing than the one or more gas units.

In some embodiments, the gas outlet end of the housing may be in a sealed connection with the gas inlet port of the respiratory ventilation apparatus via a silicone gasket.

In some embodiments, the gas filter component may include a third gas filter unit mounted inside the gas inlet port of the respiratory ventilation apparatus, the third gas filter unit being configured to filter the respiratory gas entering the respiratory ventilation apparatus.

In some embodiments, the third gas filter unit may include a coarse filter and/or a fine filter.

In some embodiments, the gas filter component may include a fourth gas filter unit configured to filter one or more gases with pungent smell in one or more gas passages of the respiratory ventilation apparatus, the fourth gas filter unit including a membrane manufactured by one or more nanomaterials having adsorption ability.

In some embodiments, the one or more nanomaterials may include at least one of activated carbon or graphene.

In some embodiments, the fourth gas filter unit may be mounted outside the gas inlet port of the respiratory ventilation apparatus, at the gas inlet port of the respiratory ventilation apparatus, inside the gas inlet port of the respiratory ventilation apparatus, between the gas inlet port of the respiratory ventilation apparatus and a gas inlet port of the gas pressurization unit, at the gas inlet port of the gas pressurization unit, at a gas outlet port of the gas pressurization unit, between the gas outlet port of the gas pressurization unit and the gas outlet port of the respiratory ventilation apparatus, and/or at the gas outlet port of the respiratory ventilation apparatus.

In some embodiments, the gas filter component may include a fifth gas filter unit configured to filter bacteria in one or more gases in one or more gas passages of the respiratory ventilation apparatus.

In some embodiments, the fifth gas filter unit may be mounted outside the gas inlet port of the respiratory ventilation apparatus, at the gas inlet port of the respiratory ventilation apparatus, inside the gas inlet port of the respiratory ventilation apparatus, between the gas inlet port of the respiratory ventilation apparatus and a gas inlet port of the gas pressurization unit, at the gas inlet port of the gas pressurization unit, at a gas outlet port of the gas pressurization unit, between the gas outlet port of the gas pressurization unit and the gas outlet port of the respiratory ventilation apparatus, and/or at the gas outlet port of the respiratory ventilation apparatus.

In some embodiments, the respiratory ventilation apparatus may further include a humidification assembly configured to humidify the pressurized respiratory gas discharged from the gas pressurization unit, and the fifth gas filter unit may be mounted in a gas passage between the humidification assembly and the gas outlet port of the respiratory ventilation apparatus.

In some embodiments, the respiratory ventilation apparatus may further include: a respiration mask; and a respiration tube configured to introduce the pressurized respiratory gas from the gas outlet port of the respiratory ventilation apparatus to the respiration mask.

In some embodiments, the gas filter component may include one or more gas filter units, and at least one of the one or more gas filter units may be mounted in the respiration tube or the respiration mask.

In some embodiments, the respiratory ventilation apparatus may further include a humidification assembly configured to humidify the pressurized respiratory gas discharged from the gas pressurization unit.

In some embodiments, a respiratory ventilation apparatus configured to deliver a respiratory gas to a patient interface may include: a gas pressurization unit configured to generate a pressurized respiratory gas by pressurizing the respiratory gas, the gas pressurization unit being located in a main body of the respiratory ventilation apparatus; and a connecting piece configured to fix the gas pressurization unit to an internal space of the main body of the respiratory ventilation apparatus and/or damp vibration of the gas pressurization unit.

In some embodiments, the main body of the respiratory ventilation apparatus may include a housing with a first side wall configured to discharge the pressurized respiratory gas. The respiratory ventilation apparatus may further include: a gas inlet port configured to introduce the respiratory gas into the respiratory ventilation apparatus, the gas inlet port being set on a second side wall of the housing of the main body of the respiratory ventilation apparatus; and a gas outlet port configured to discharge the humidified and pressurized respiratory gas to a respiration tube.

In some embodiments, the connecting piece may include: a connecting part configured to connect an outlet port of the gas pressurization unit and form a sealed connection between the connecting piece and the gas pressurization unit; and a fixing part configured to fix the connecting piece to the internal space of the main body of the respiratory ventilation apparatus and form a fastening connection between the connecting piece and the main body of the respiratory ventilation apparatus.

In some embodiments, the fixing part may have a sheet structure and may include an aperture configured to allow the pressurized respiratory gas to pass.

In some embodiments, the connecting part may have a tubular structure; a first end of the connecting part may be fixed to the fixing part; a second end of the connecting part may be connected to the outlet port of the gas pressurization unit; and the connecting part may be capable of allowing the pressurized respiratory gas to pass through the tubular structure to the aperture of the fixing part.

In some embodiments, the second end of the connecting part may be an annular double-layer port including an inner layer and an outer layer.

In some embodiments, the inner layer may be connected to an outer surface of the outlet port of the gas pressurization unit.

In some embodiments, the outer surface of the outlet port of the gas pressurization unit may include one or more protruding bumps, and an inner surface of the inner layer may include one or more corresponding grooves to match with the one or more protruding bumps; or the outer surface of the outlet port of the gas pressurization unit may include one or more grooves, and the inner surface of the inner layer may include one or more corresponding protruding bumps to match with the one or more grooves.

In some embodiments, the outer layer may include a first annular flexible structure configured to damp vibration of the gas pressurization unit along an axial direction of the connecting part.

In some embodiments, the first annular flexible structure may have at least one of a U shape, a V shape, a Z shape, an M shape, an S shape, a C shape, an O shape, or one or more folds.

In some embodiments, the outer layer may be connected to an inner surface of the outlet port of the gas pressurization unit.

In some embodiments, the inner surface of the outlet port of the gas pressurization unit may include one or more protruding bumps, and an outer surface of the outer layer may include one or more corresponding grooves to match with the one or more protruding bumps; or the inner surface of the outlet port of the gas pressurization unit may include one or more grooves, and the outer surface of the outer layer may include one or more corresponding protruding bumps to match with the one or more grooves.

In some embodiments, the inner layer may include a first annular flexible structure configured to damp vibration of the gas pressurization unit along an axial direction of the connecting part.

In some embodiments, the first annular flexible structure may have at least one of a U shape, a V shape, a Z shape, an M shape, an S shape, a C shape, an O shape, or one or more folds.

In some embodiments, a joint of the inner layer and the outer layer may include a second annular flexible structure configured to damp vibration of the gas pressurization unit along a radial direction of the connecting part.

In some embodiments, the second annular flexible structure may have at least one of a U shape, a V shape, a Z shape, an M shape, an S shape, a C shape, an O shape, or one or more folds.

In some embodiments, the fixing part and the connecting part may be integral.

In some embodiments, two opposite sides of the fixing part may be stuck into two slots of the main body of the respiratory ventilation apparatus.

In some embodiments, the fixing part or the connecting part may include a flexible material.

In some embodiments, the flexible material may include at least one of an elastic material or a wear-resistant material.

In some embodiments, the gas outlet port may be set on the main body of the respiratory ventilation apparatus.

In some embodiments, the gas outlet port may be set on the liquid chamber.

In some embodiments, the respiratory ventilation apparatus may include one or more gas filter units mounted on the housing; wherein the one or more gas filter units may extend vertically from the lower edge of the gas pressurization unit to the upper edge of the gas pressurization unit, and/or wherein the one or more gas filter units may extend horizontally from one side of the gas pressurization unit to the opposite side of the gas pressurization unit.

In some embodiments, a respiratory ventilation apparatus configured to deliver a respiratory gas to a patient interface may include: a gas pressurization unit configured to generate a pressurized respiratory gas by pressurizing the respiratory gas, the gas pressurization unit being located in a main body of the respiratory ventilation apparatus; a main gas outlet port configured to discharge a humidified and pressurized respiratory gas to a respiration tube.

In some embodiments, the main body of the respiratory ventilation apparatus may include a housing with a first side wall configured to discharge the pressurized respiratory gas; the respiratory ventilation apparatus may further include: a main gas inlet port configured to introduce the respiratory gas into the respiratory ventilation apparatus, the main gas inlet port being set on a second side wall of the housing of the main body of the respiratory ventilation apparatus; and a gas parameter detection assembly configured to detect one or more gas parameters of the respiratory ventilation apparatus.

In some embodiments, the gas parameter detection assembly may include: an acquisition part configured to acquire a gas flow; a first sensor configured to measure a pressure of the gas flow; and a first tube configured to introduce the gas flow from the acquisition part to a surface of the first sensor.

In some embodiments, the first sensor may be a pressure sensor.

In some embodiments, the first sensor may be integrated into a printed circuit board (PCB) mounted in an inner space of the respiratory ventilation apparatus.

In some embodiments, the acquisition part may face the main gas outlet port of the respiratory ventilation apparatus.

In some embodiments, the acquisition part may include: an input port set at a first surface of the acquisition part, the first surface facing the main gas outlet port of the respiratory ventilation apparatus; an output port set at a second surface of the acquisition part, the second surface being different from the first surface; and a curved channel set inside the acquisition part, the curved channel being configured to connect the input port and the output port; wherein the second surface of the acquisition part may be in a sealed connection with an inner surface of the main body of the respiratory ventilation apparatus; and the input port may be set above the second surface of the acquisition part, or the acquisition part is protruding from the inner surface of the main body of the respiratory ventilation apparatus, to prevent water from flowing in the acquisition part.

In some embodiments, the input port may be set below a top of the curved channel, so as to prevent condensate water from flowing through the curved channel to the surface of the first sensor.

In some embodiments, the input port may be set below an upper edge of the main gas outlet port of the respiratory ventilation apparatus but above a lower edge of the main gas outlet port of the respiratory ventilation apparatus.

In some embodiments, the output port may be set below the input port.

In some embodiments, the gas parameter detection assembly may be further configured to detect a flux of one or more gases in one or more passages of the respiratory ventilation apparatus.

In some embodiments, the gas parameter detection assembly may further include: a second sensor configured to detect a flux signal associated with the one or more gases in the one or more passages of the respiratory ventilation apparatus; a second tube configured to introduce a gas flow from the acquisition part to a surface of the second sensor; an auxiliary acquisition port set at upstream of the one or more gases; and a third tube configured to introduce a gas flow from the auxiliary acquisition port to a surface of the second sensor.

In some embodiments, the first sensor and the second sensor may share a same acquisition part.

In some embodiments, the second sensor may be a flow sensor.

In some embodiments, the acquisition part may include silicone.

In some embodiments, the acquisition part may be in detachable connection with the respiratory ventilation apparatus.

In some embodiments, the respiratory ventilation apparatus may further include a pressure sensor and a flow sensor for snore detection, and a humidified gas inlet port configured to introduce pressurized and humidified gas from a humidification assembly; and the pressure sensor and the flow sensor may be connected via a curved channel to a section between the main gas outlet port of the respiratory ventilation apparatus and the humidified gas inlet port.

In some embodiments, the gas parameter detection assembly may be configured to detect one or more gas parameters of the humidified and pressurized respiratory gas.

In some embodiments, the respiratory ventilation apparatus may further include a humidification assembly configured to generate the humidified and pressurized respiratory gas, and the gas parameter detection assembly may include an acquisition part placed in a downstream of the humidified and pressurized respiratory gas relative to the humidification assembly.

In some embodiments, an input port of the acquisition part may be set below an upper edge of the main gas outlet port of the respiratory ventilation apparatus but above a lower edge of the main gas outlet port of the respiratory ventilation apparatus.

In some embodiments, a respiratory ventilation apparatus configured to deliver a respiratory gas to a patient interface may include: a gas pressurization unit being located in a main body of the respiratory ventilation apparatus; a humidification assembly being removably coupled to the main body of the respiratory ventilation apparatus, the humidification assembly including a liquid chamber configured to accommodate one or more liquids; wherein the liquid chamber may be in detachable connection with the main body of the respiratory ventilation apparatus through a push-push mechanism.

In some embodiments, the gas pressurization unit may be configured to generate a pressurized respiratory gas by pressurizing the respiratory gas, wherein the main body of the respiratory ventilation apparatus includes a housing with a first side wall configured to discharge the pressurized respiratory gas; the humidification assembly may be configured to humidify the pressurized respiratory gas; the respiratory ventilation apparatus may further include: a gas inlet port configured to introduce the respiratory gas into the respiratory ventilation apparatus, the gas inlet port being set on a second side wall of the housing of the main body of the respiratory ventilation apparatus; and a gas outlet port configured to discharge the humidified and pressurized respiratory gas to a respiration tube.

In some embodiments, the push-push mechanism may include: a guide slot set on the main body of the respiratory ventilation apparatus; a slide block set on the main body of the respiratory ventilation apparatus, the slide block being positioned in the guide slot, the slide block being movable along the guide slot in a first direction back and forth; and a pushrod set on the liquid chamber, the pushrod being movable along a second direction back and forth, the second direction being perpendicular to the first direction; wherein the slide block may include a guide block, the guide block including a first slope, a groove and a second slope, the guide block being configured to guide or limit a moving position of the pushrod.

In some embodiments, an inclined direction of the first slope may be different from an inclined direction of the second slope; and a first angle between the first slope and a vertical direction may be greater than a second angle between the second slope and the vertical direction.

In some embodiments, the guide block may have a frame similar to character A.

In some embodiments, the push-push mechanism may further include: a first spring including a first end and a second end, the first end of the first spring being connected to a first end of the guide block, the second end of the first spring being fixed to the main body of the respiratory ventilation apparatus; and a second spring including a first end and a second end, the first end of the second spring being connected to a second end of the guide block, the second end of the second spring being fixed to the main body of the respiratory ventilation apparatus; wherein the first spring may be capable of being compressed when the guide block is driven to move along the first direction; and the compressed first spring may be capable of driving the guide block to move along an opposite direction of the first direction.

In some embodiments, upon being driven by a first pushing force, the pushrod may be capable of pushing the guide block to move along the first direction while the pushrod is moving along the second direction and sliding down along the first slope of the guide block; upon releasing the first pushing force, the pushrod may be capable of moving along an opposite direction of the second direction while the guide block is moving along an opposite direction of the first direction so that the pushrod is stuck into the groove of the guide block; upon being driven by a second pushing force, the pushrod may be capable of moving along the second direction and moving out of the groove while the guide block is moving along the opposite direction of the first direction so that the pushrod is released from the groove; and upon releasing the second pushing force, the pushrod may be capable of moving along the opposite direction of the second direction and sliding up along the second slope of the guide block, while the guide block is moving along the opposite direction of the first direction, so that the liquid chamber is released from the main body.

In some embodiments, the slide block may further include a bump below the groove of the guide block, the bump being configured to guide the pushrod to be stuck into the groove upon releasing the first pushing force.

In some embodiments, the pushrod may be set below a bottom surface of the liquid chamber; the guide slot and the slide block may be set below an interface of the liquid chamber and the main body of the respiratory ventilation apparatus; a plate on the interface may include a first hole; and the pushrod may be capable of passing through the first hole to interact with the slide block.

In some embodiments, the plate on the interface may include a second hole; the humidification assembly may further include a heater plate, the heater plate being configured to heat the one or more liquids and generate vapor to humidify the pressurized respiratory gas; and the heater plate may be mounted on a base of the respiratory ventilation apparatus through one or more springs, so that the heater plate is capable of moving up and down through the second hole upon being driven by a pressure or upon releasing the pressure.

In some embodiments, the liquid chamber may include a bottom, the bottom including a metallic heat conducting material; and the bottom of the liquid chamber may be in close contact with the heater plate when the liquid chamber is mounted on the main body of the respiratory ventilation apparatus.

In some embodiments, the gas outlet port may be set on the main body of the respiratory ventilation apparatus.

In some embodiments, the gas outlet port may be set on the liquid chamber.

In some embodiments, the push-push mechanism may be configured for unlocking the liquid chamber from the main body of the respiratory ventilation apparatus by pushing the liquid chamber in a push direction substantially perpendicular to a liquid level in the liquid chamber. Since pushing is easier than pulling and can be performed single handedly, the user comfort is improved. In addition thereto, any locking and/or connecting mechanism between the liquid chamber and the main body will experience less pulling force and their life time is increased, since such mechanism usually can withstand much higher pushing force than pulling force. In addition thereto, pushing to unlock also decreases the chance that the liquid is spilled out from the tank during disassembling.

In some embodiments, the push-push mechanism may be configured to comprise an energy storage means for storing the energy of the pushing action and for releasing the stored energy after the liquid chamber is unlocked by applying a force on the liquid chamber substantially in the opposite direction of the push direction.

In some embodiments, the liquid chamber may include: a tank; and a tank cover pivotally connected to the tank through a connection mechanism; wherein the tank cover may be configured to be closable by pushing in the push direction and/or is configured to be openable by pulling substantially in a direction opposite to the push direction. As the tank cover can be closed in the same direction, one single pushing action can close the tank cover and attach the liquid chamber to the main body at the same time, thus increases the comfort. As the tank cover is opened in the opposite direction, the chance for user to mix up opening the tank cover and removing the liquid chamber from the main body is minimized, thus avoiding the situation that the user accidentally open the tank cover while intending only to disconnect the humidification assembly and spill the liquid out.

In some embodiments, a method for operating a respiratory ventilation apparatus may include comprising: coupling the humidification assembly with the main body of the respiratory ventilation apparatus by pushing the liquid chamber in a push direction, and unlocking the humidification assembly with the main body by pushing the liquid chamber substantially in the push direction.

In some embodiments, the liquid chamber may include: a tank; and a tank cover pivotally connected to the tank through a connection mechanism; and the method may further include: placing the humidification assembly on a surface of the respiratory ventilation apparatus before the step of coupling; the step of coupling the humidification assembly may further include locking the tank cover with the tank by pushing the tank cover substantially in the push direction.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
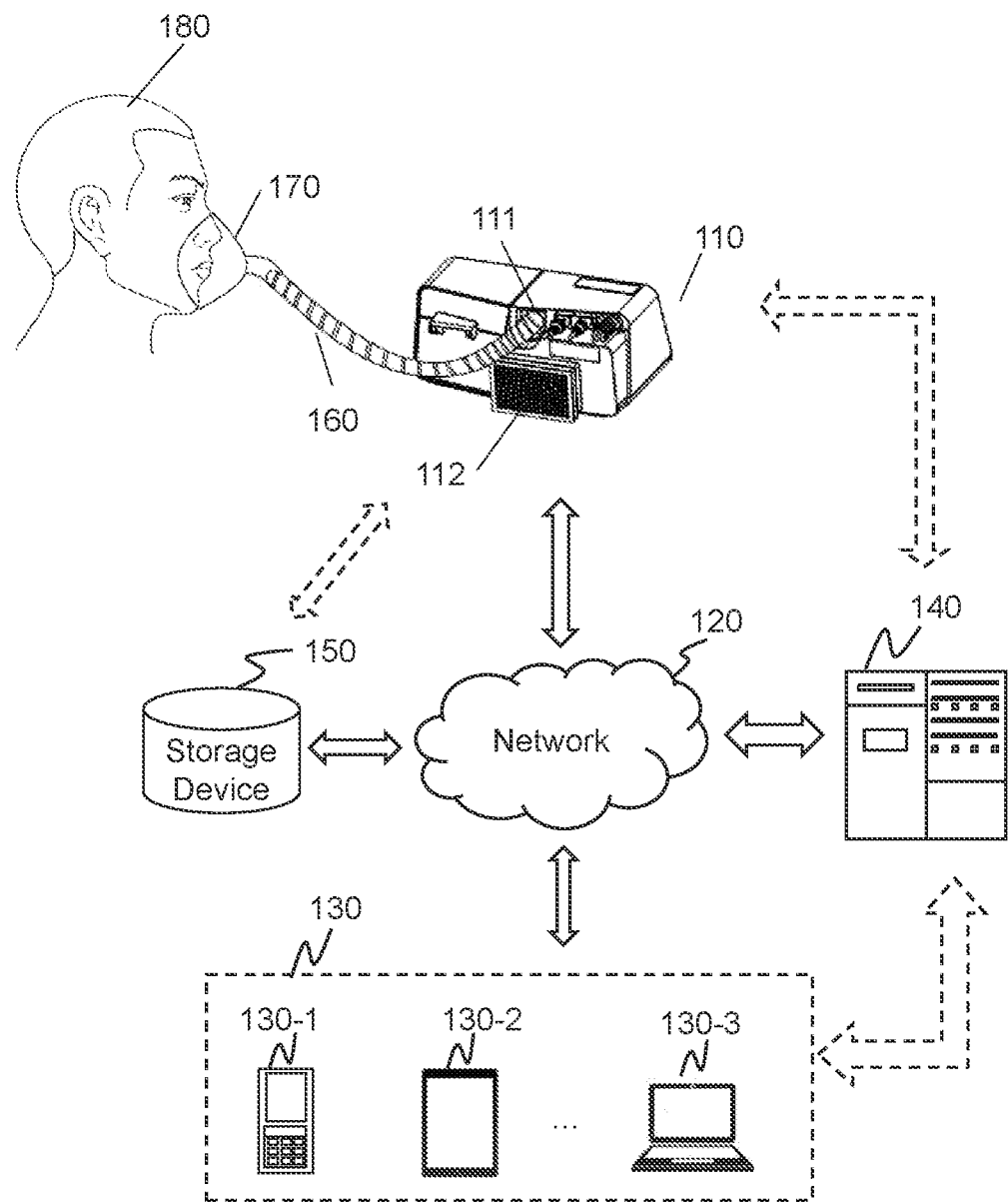
FIG. 1 is a schematic diagram illustrating an exemplary system for delivering a respiratory gas according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is to describe particular exemplary embodiments only and is not intended to be limiting. As used herein, the singular forms "a," "an," and "the" may be intended to include the plural forms as well, unless the context expressly indicates otherwise. It will be further understood that the terms "comprise," "comprises," and/or "comprising," "include," "includes," and/or "including," when used in the present disclosure, specify the presence of stated features, integers, steps, operation, elements, and/or components, but do not preclude the presence or addition of one or more other features, integers, steps, operation, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of the present disclosure. It is to be expressly understood, however, that the drawings are for illustration and description only, and are not intended to limit the scope of the present disclosure. It is understood that the drawings are not to scale.

It will be understood that the term "system," "engine," "unit," and/or "module" used herein are one method to distinguish different components, elements, parts, sections, or assemblies of different levels in ascending order. However, the terms may be displaced by other expressions if they achieve the same purpose.

It will be understood that when a unit, engine, or module is referred to as being "on," "connected to," or "coupled to," another unit, engine, or module, it may be directly on, connected or coupled to, or communicate with the other unit, engine, or module, or an intervening unit, engine, or module may be present, unless the context clearly indicates otherwise. As used herein, the term "and/or" includes any and all combinations of one or more of the associated listed items.

The term "ambient" used herein refers to the external of the system 100 and/or the subject 180, or surrounding the system 100 and/or the subject 180. The "ambient gas" used herein may refer to the gas at the external of the system 100 and/or the subject 180, or surrounding the system 100 and/or the subject 180. The term "ambient humidity" with respect to a humidifier may refer to the humidity of gas surrounding the humidifier (e.g. the humidity in the room where the respiratory ventilation apparatus 110 and/or the subject 180 are located). The term "ambient pressure" may refer to the pressure surrounding or external to the subject 180. The term "ambient (e.g. acoustic) noise" may refer to the background noise level in the room where the respiratory ventilation apparatus 110 and/or the subject 180 are located), other than for example, noise generated by the respiratory ventilation apparatus 110 or emanating from the subject interface 170.

The flowcharts used in the present disclosure illustrate operation that systems implement according to some embodiments of the present disclosure. It is to be expressly understood, the operation of the flowcharts may be implemented not in order. Conversely, the operation may be implemented in inverted order, or simultaneously. Moreover, one or more other operation may be added to the flowcharts. One or more operations may be omitted from the flowcharts.

FIG. 1 is a schematic diagram illustrating an exemplary system for delivering a respiratory gas according to some embodiments of the present disclosure. In some embodiments, the respiratory gas may include natural air (or atmospheric air), purified air, oxygen, atmospheric air enriched with oxygen, a therapeutic drug, pressurized air, humidified air, or the like, or a combination thereof. As illustrated, the system 100 may include a respiratory ventilation apparatus 110, a respiration tube 160, and a subject interface 170. In some embodiments, the respiratory ventilation apparatus 110 may be a non-invasive ventilator. In some embodiments, the system 100 may further include a network 120, a terminal 130, a processing device 140, and a storage device 150. It should be noted that one or more of the network 120, the terminal 130, the processing device 140, and the storage device 150 may be omitted. The components in the system 100 may be connected in one or more of various ways. Merely by way of example, as illustrated in FIG. 1, the respiratory ventilation apparatus 110 may be connected to the processing device 140 through the network 120. As another example, the respiratory ventilation apparatus 110 may be connected to the processing device 140 directly as indicated by the bi-directional arrow in dotted lines linking the respiratory ventilation apparatus 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120. In the present disclosure, "respiratory ventilation apparatus" and "continuous positive airway pressure (CPAP) apparatus" are used interchangeably.

The respiratory ventilation apparatus 110 may be configured to detect, diagnose, treat, prevent, and/or ameliorate respiratory-related disorders of a subject 180. In some embodiments, the respiratory ventilation apparatus 110 may deliver a pressurized respiratory gas to a subject 180 (e.g., the nose and/or the mouth of the subject 180). In some embodiments, the respiratory ventilation apparatus 110 may include a gas inlet port 112 and a gas outlet port 111. The gas inlet port 112 may be configured to introduce a respiratory gas into the respiratory ventilation apparatus 110. In some embodiments, the respiratory ventilation apparatus 110 may pressurize the respiratory gas introduced via the gas inlet port 112. In some embodiments, the gas outlet port 111 may be connected to the respiration tube 160. The gas outlet port 111 may be configured to discharge the pressurized respiratory gas to the respiration tube 160. In some embodiments, the respiration tube 160 may be connected to the subject interface 170. Therefore, the pressurized respiratory gas generated by the respiratory ventilation apparatus 110 may be discharged to the subject 180 via the respiration tube 160 and the subject interface 170. In some embodiments, the respiratory ventilation apparatus 110 may include one or more gas passages (not shown in FIG. 1) configured to guide the respiratory gas to flow in the respiratory ventilation apparatus 110. More descriptions of the respiratory ventilation apparatus 110 may be found elsewhere in the present disclosure (e.g., FIGS. 3A-3D and 5A-5E and the descriptions thereof).

In some embodiments, the respiratory ventilation apparatus 110 may further include one or more controllers. The controllers may connect to one or more components of the respiratory ventilation apparatus 110 directly or via a network (e.g., a wired network, a wireless network). The controllers may control the operation(s) of one or more components of the respiratory ventilation apparatus 110. In some embodiments, the controller(s) may be configured to initiate the respiratory ventilation apparatus 110 upon a boot operation. For example, the controller(s) may initiate a random access memory of the respiratory ventilation apparatus 110, read one or more parameters from one or more storage device 150 (e.g., a non-volatile memory) of the respiratory ventilation apparatus 110, and/or initiate the detection module 250. In some embodiments, the parameter(s) may include at least one parameter used to control the pressure of the pressurized respiratory gas. In some embodiments, the controller(s) may be configured to initiate a program that constantly reads information from the detection module 250, and control the pressure of the pressurized respiratory gas using at least the information read from the detection module 250 and one or more of the parameter(s).

In some embodiments, the respiratory ventilation apparatus 110 may further include or be equipped with one or more sensors configured to detect parameters relating to the respiratory gas, the expired gas of the subject 180, and/or the operation status of the respiratory ventilation apparatus 110. The parameters relating to the respiratory gas may include, for example, the flux of the respiratory gas, a flow rate of the respiratory gas, a temperature of the respiratory gas, a humidity of the respiratory gas, or the like, or a combination thereof. The parameters relating to the expired gas of the subject 180 may include a snore of the subject 180, a respiratory rate of the subject 180, a tidal volume of the subject 180, a pressure of the expired gas of the subject 180, an air leakage of the expired gas of the subject 180, an autonomous respiration ratio of the subject 180, or the like, or a combination thereof. The parameters relating to the operation status of the respiratory ventilation apparatus 110 may include a running time of the respiratory ventilation apparatus 110, a time of delay for pressurizing the respiratory gas, an air leakage of the pressurized respiratory gas, an input voltage of the gas pressurization unit 210, or the like, or a combination thereof.

In some embodiments, the respiratory ventilation apparatus 110 may further include or be equipped with one or more gas filter units configured to filter and/or purify the respiratory gas delivered to the subject 180. In some embodiments, the gas filter unit(s) (e.g., a coarse filter, a fine filter, or the like) may filter one or more particles in the respiratory gas. In some embodiments, the gas filter unit(s) may filter bacteria in the respiratory gas. In some embodiments, the gas filter unit(s) may filter pungent gas in the respiratory gas.

In some embodiments, the subject 180 may be a healthy person. In some embodiments, the subject 180 may be a patient. In some embodiments, the patient may have one or more respiratory-related disorders. In some embodiments, the respiratory-related disorders may be characterized by apneas, hypopneas, or hyperpneas, or the like. Exemplary respiratory-related disorders may include, for example, obstructive sleep apnea (OSA), Cheyne-stokes respiration (CSR), obesity hyperventilation syndrome (OHS), chronic obstructive pulmonary disease (COPD), neuromuscular disease (NMD), chest wall disorders, or the like. The obstructive sleep apnea (OSA) is a form of sleep disordered breathing, and may cause affected patient to stop breathing for one or more periods (e.g., 30 to 120 seconds duration, or 200 to 300 times per night). The Cheyne-stokes respiration (CSR) is another form of sleep disordered breathing, and may be harmful because of repetitive hypoxia. The obesity hyperventilation syndrome (OHS) is defined as the combination of severe obesity and awake chronic hypercapnia, and may cause dyspnea, morning headache, excessive daytime sleepiness, or the like. The chronic obstructive pulmonary disease (COPD) may include increased resistance to air movement, extended expiratory phase of respiration, or loss of the normal elasticity of the lung, or the like. The chronic obstructive pulmonary disease (COPD) may cause dyspnea on exertion, chronic cough, sputum production, or the like. The neuromuscular disease (NMD) may include diseases and ailments that impair the functioning of the muscles either directly via intrinsic muscle pathology, or indirectly via nerve pathology. The neuromuscular disease (NMD) may cause increasing generalized weakness, dysphagia, dyspnea on exertion and at rest, fatigue, sleepiness, morning headache, difficulties with concentration and mood changes, or the like. The chest wall disorders are a group of thoracic deformities that result in inefficient coupling between respiratory muscles and the thoracic cage. The chest wall disorders may cause dyspnea on exertion, peripheral edema, orthopnea, repeated chest infections, morning headaches, fatigue, poor sleep quality, loss of appetite, or the like.

In some embodiments, the subject interface 170 may be configured to interface the respiratory ventilation apparatus 110 to the subject 180, for example, by providing a flow of respiratory gas (e.g., air). In some embodiments, the subject interface 170 may include a gas passage to guide the respiratory gas. The subject interface 170 may include a mask, a tube, or the like. For example, the subject interface 170 may be a nasal mask, a full-face mask, a tube connected to the mouth of the subject 180, a tracheostomy tube connected to the trachea of the subject 180. In some embodiments, the subject interface 170 may form a sealed connection with a face region of the subject 180 to facilitate the delivery of the respiratory gas at a pressure that has a sufficient variance with ambient pressure to effect therapy (e.g., a positive pressure of about 10 $cmH_2O$). For example, the subject interface 170 may be fixed to the nose of the subject 180 by various fixing ways (e.g., through a fixing rope or a fixing ring). In some embodiments, the subject interface 170 may not form a sealed connection with a face region of the subject 180 that is sufficient to facilitate delivery of the respiratory gas to the subject 180 at a positive pressure of about 10 $cmH_2O$. In some embodiments, the subject interface 170 may further include a filter configured to filter the respiratory gas. More descriptions of the filter may be found elsewhere in the present disclosure (e.g., FIGS. 6A-6E, 7A, and 7B and the descriptions thereof). In some embodiments, the subject interface 170 may further include or be equipped with one or more sensors configured to detect parameters relating to the respiratory gas and/or the expired gas of the subject 180. In some embodiments, the subject interface 170 may further include or be equipped with one or more gas filter units configured to filter and/or purify the respiratory gas delivered to the subject 180. In some embodiments, the gas filter unit(s) (e.g., a coarse filter, a fine filter, or the like) may filter one or more particles in the respiratory gas. In some embodiments, the gas filter unit(s) may filter bacteria in the respiratory gas. In some embodiments, the gas filter unit(s) may filter pungent gas in the respiratory gas.

In some embodiments, the respiration tube 160 may be configured to guide the respiratory gas from the respiratory ventilation apparatus 110 to the subject interface 170. The respiration tube 160 may include a gas passage to guide the respiratory gas. In some embodiments, the respiration tube 160 may form a sealed connection with the gas outlet port 111 of the respiratory ventilation apparatus 110. In some embodiments, the respiration tube 160 may form a sealed connection with the subject interface 170. In some embodiments, the respiration tube 160 may further include a heater configured to heat the respiration tube 160, so that the respiratory gas flowing through the respiration tube 160 can be maintained at a certain temperature, preferably, at a temperature that human beings are comfortable with, such as, a temperature within 16-43° C., a temperature within 28-38° C. In some embodiments, the respiration tube 160 may further include or be equipped with one or more sensors configured to detect parameters relating to the respiratory gas and/or the expired gas of the subject 180. In some embodiments, the respiration tube 160 may further include or be equipped with one or more gas filter units configured to filter and/or purify the respiratory gas delivered to the subject 180. In some embodiments, the gas filter unit(s) (e.g., a coarse filter, a fine filter, or the like) may filter one or more particles in the respiratory gas. In some embodiments, the gas filter unit(s) may filter bacteria in the respiratory gas. In some embodiments, the gas filter unit(s) may filter pungent gas in the respiratory gas.

In some embodiments, the network 120 may include any suitable network that can facilitate the exchange of information and/or data for the system 100. In some embodiments, one or more components of the system 100 (e.g., the respiratory ventilation apparatus 110, the terminal 130, the processing device 140, or the storage device 150) may communicate information and/or data with one or more other components of the system 100 via the network 120. For example, the processing device 140 may obtain signals from the respiratory ventilation apparatus 110 via the network 120. As another example, the processing device 140 may obtain user instructions from the terminal 130 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the system 100 may be connected to the network 120 to exchange data and/or information.

In some embodiments, the terminal 130 may include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart video camera, an interphone, or the like, or any combination thereof. In some embodiments, the wearable device may include a smart bracelet, smart footgear, a pair of smart glasses, a smart helmet, a smartwatch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include Google Glasses, an Oculus Rift, a Hololens, a Gear VR, etc. In some embodiments, the terminal 130 may remotely operate the respiratory ventilation apparatus 110. In some embodiments, the terminal 130 may operate the respiratory ventilation apparatus 110 via a wireless connection. In some embodiments, the terminal 130 may receive information and/or instructions inputted by a user, and send the received information and/or instructions to the respiratory ventilation apparatus 110 or to the processing device 140 via the network 120. In some embodiments, the terminal 130 may receive data and/or information from the processing device 140. In some embodiments, the terminal 130 may display information relating to the system 100. In some embodiments, the terminal 130 may be part of the processing device 140. In some embodiments, the terminal 130 may be omitted. In some embodiments, via the terminal 130, a user may remotely update software of the respiratory ventilation apparatus 110, and/or adjust or set one or more parameters of the respiratory ventilation apparatus 110.

In some embodiments, the processing device 140 may process data and/or information obtained from the respiratory ventilation apparatus 110, the terminal 130, and/or the storage device 150. For example, the processing device 140 may obtain signals detected by one or more sensors in the respiratory ventilation apparatus 110, the respiration tube 160, and/or the subject interface 170, and may process and/or analyze the signals to obtain one or more parameters relating to the respiratory gas, the expired gas of the subject 180, and/or the operation status of the respiratory ventilation apparatus 110. In some embodiments, the processing device 140 may be a single server, or a server group. The server group may be centralized, or distributed. In some embodiments, the processing device 140 may be local or remote.

For example, the processing device 140 may access information and/or data stored in the respiratory pressure therapy device 110, the terminal 130, and/or the storage device 150 via the network 120. As another example, the processing device 140 may be directly connected to the respiratory ventilation apparatus 110, the terminal 130, and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device of the respiratory ventilation apparatus 110.

In some embodiments, the processing device 140 may include an acquisition unit and a processing unit. The acquisition unit may be configured to obtain information relating to the system 100 (e.g., the respiratory ventilation apparatus 110, the processing device 140, the storage device 150, the terminal 130, etc.). The information may include signals detected by the detection module 250, data read from the storage device 150, instructions or data provided by the terminal 130, etc. In some embodiments, the information may be transmitted to the processing unit for processing. In some embodiments, the acquisition unit may obtain or transmit the information via a tangible transmission media or a Carrier-wave transmission media. The tangible transmission media may include, for example, a coaxial cable, a copper wire, a fiber optics, or the like. The Carrier-wave transmission media may take the form of electric or electromagnetic signals (e.g., signals generated during radio frequency (RF) data communications). The processing unit may be configured to process the information obtained by the acquisition unit. The processing unit may include an advanced RISC machines processor (ARM), a programmable logic device (PLD), a microprogrammed control unit (MCU), a digital signal processor (DSP), a field-programmable gate array (FPGA), a system on chip (SoC) or the like, or any combination thereof.

In some embodiments, the storage device 150 may store data and/or instructions. In some embodiments, the storage device 150 may store data or information obtained from the respiratory ventilation apparatus 110. For example, the processing device 140 may determine one or more parameters relating to the respiratory gas, the expired gas of the subject 180, and/or the operation status of the respiratory ventilation apparatus 110 based on the signals obtained from one or more sensors of the respiratory ventilation apparatus 110, the respiration tube 160, and/or the subject interface 170. The determined parameter(s) may be stored in the storage device 150 for further use or processing. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components in the system 100 (e.g., the respiratory ventilation apparatus 110, the processing device 140, the terminal 130, etc.). One or more components in the system 100 may access the data or instructions stored in the storage device 150 via the network 120. In some embodiments, the storage device 150 may be directly connected to or communicate with one or more components in the system 100 (e.g., respiratory ventilation apparatus 110, the processing device 140, the terminal 130, etc.). In some embodiments, the storage device 150 may be part of the processing device 140. In some embodiments, the storage device 150 may be part of the respiratory ventilation apparatus 110.

Figure 2:
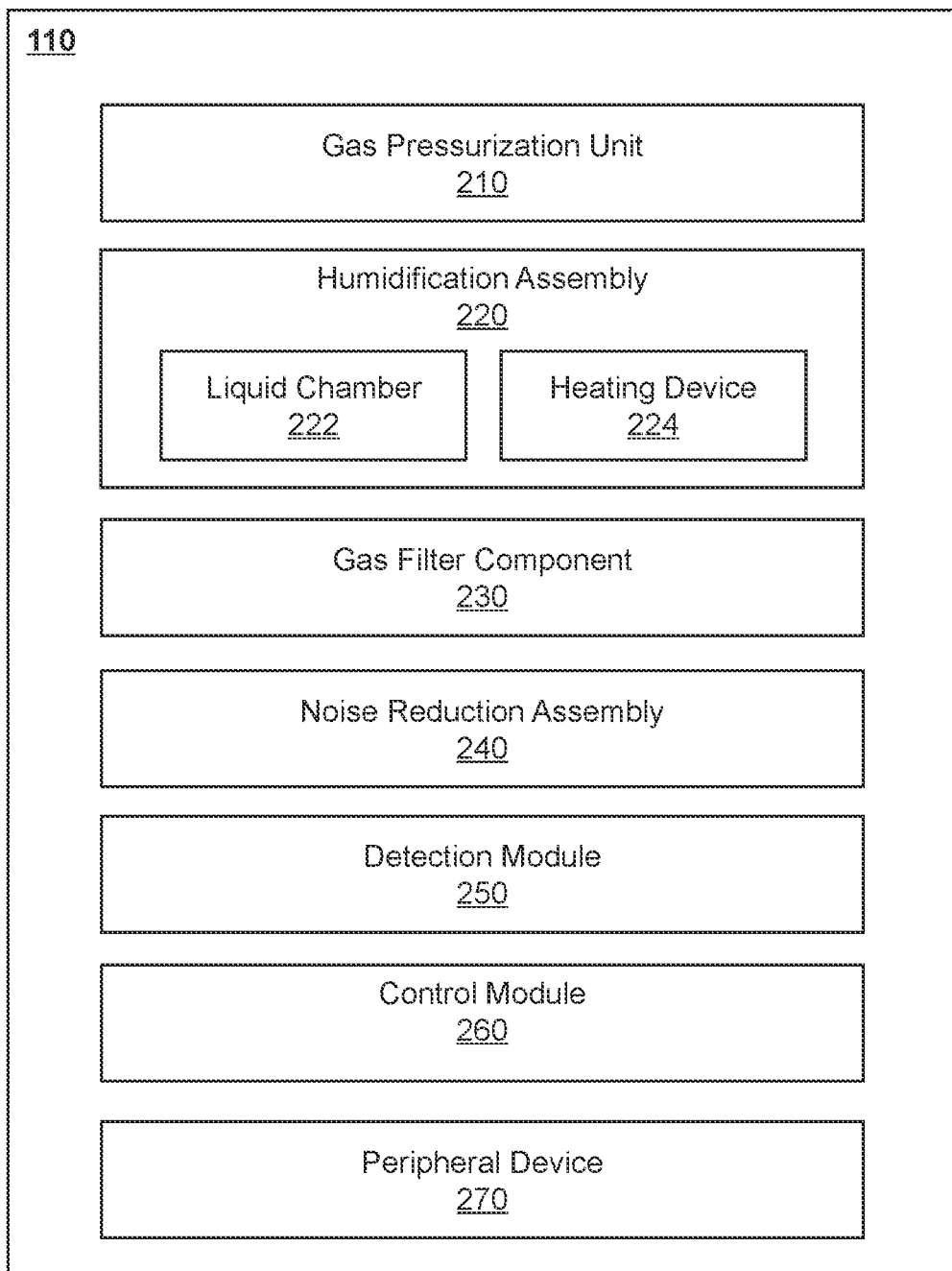
FIG. 2 is a block diagram illustrating an exemplary respiratory ventilation apparatus according to some embodiments of the present disclosure.

FIG. 2 is a block diagram illustrating an exemplary respiratory ventilation apparatus 110 according to some embodiments of the present disclosure. As illustrated in FIG. 2, the respiratory ventilation apparatus 110 may include a gas pressurization unit 210, a humidification assembly 220, a gas filter component 230, a noise reduction assembly 240, a detection module 250, a control module 260, and one or more peripheral devices 270.

The gas pressurization unit 210 may be configured to pressurize the respiratory gas introduced in the respiratory ventilation apparatus 110. In some embodiments, the gas pressurization unit 210 may generate a pressurized respiratory gas based on an ambient gas (e.g., atmospheric air) introduced in the respiratory ventilation apparatus 110. In some embodiments, the gas pressurization unit 210 may provide a pressurized respiratory gas for the subject 180. In some embodiments, the gas pressurization unit 210 may include a blower (e.g., a motor-driven blower). In some embodiments, the gas pressurization unit 210 may include a compressed gas reservoir. In some embodiments, when the blower is running, the respiratory gas (e.g., ambient gas) can be successively sucked into the respiratory ventilation apparatus 110 via the gas inlet port 112, and then the respiratory gas can be pressurized. The pressurized respiratory gas generated by the gas pressurization unit 210 may be further discharged to the respiration tube 160 via the gas outlet port 111. In some embodiments, the gas pressurization unit 210 may be controlled by the controller(s) of the respiratory ventilation apparatus 110. For example, the starting, running (e.g., the rotation speed), and/or stopping of the gas pressurization unit 210 may be controlled (and/or adjusted) by the controller(s) of the respiratory ventilation apparatus 110.

The humidification assembly 220 may be configured to humidify the (pressurized) respiratory gas. In some embodiments, the humidification assembly 220 may humidify the (pressurized) respiratory gas by introducing water vapor into the (pressurized) respiratory gas. In some embodiments, the humidification assembly 220 may include a liquid chamber 222 and/or a heating device 224. The liquid chamber 222 may be configured to accommodate one or more liquids (e.g., water). The heating device 224 may be configured to heat the one or more liquids accommodated in the liquid chamber 222 and/or generate water vapor in a temperature range of e.g., 30-50 degree centigrade. The water vapor may be introduced into the (pressurized) respiratory gas, and then the (pressurized) respiratory gas can be humidified. In some embodiments, the liquid chamber 222 may include a tank and/or a tank cover. The tank may be configured to accommodate the one or more liquids. The tank cover may be configured to introduce (pressurized) respiratory gas onto the surface of the one or more liquids, and/or introduce humidified (pressurized) respiratory gas out of the liquid chamber 222. In some embodiments, the tank cover may include a shell, a gas inlet port configured to introduce the (pressurized) respiratory gas, via a first gas passage, into the liquid chamber 222, and/or a gas outlet port configured to introduce the humidified (pressurized) respiratory gas, via a second gas passage, back into the respiratory ventilation apparatus 110. In some embodiments, the heating device 224 may include a heater plate, one or more heating rods, one or more heating electrodes, or the like, or any combination thereof, mounted beneath a baseplate of the tank or inside the tank.

In some embodiments, the humidification assembly 220 may humidify the (pressurized) respiratory gas by introducing one or more water droplets into the (pressurized) respiratory gas. In some embodiments, the humidification assembly 220 may include a liquid chamber 222 and/or an ultrasonic atomizer (e.g., a ceramic diaphragm) not shown. The ceramic diaphragm may be controlled by the controller(s) of the respiratory ventilation apparatus 110 to vibrate at an ultrasonic frequency to generate a plurality of water droplets. The water droplets may be introduced into the (pressurized) respiratory gas, and then the (pressurized) respiratory gas can be humidified. More descriptions of the humidification assembly 220 may be found elsewhere in the present disclosure (e.g., FIGS. 17-22D, 30A-36B and the descriptions thereof).

The gas filter component 230 may be configured to filter the respiratory gas introduced into the respiratory ventilation apparatus 110. In some embodiments, the gas filter component 230 may filter the pressurized respiratory gas discharged from the gas pressurization unit 210. In some embodiments, the gas filter component 230 may include a housing. In some embodiments, the housing of the gas filter component 230 may be in detachable connection with the gas inlet port 112 of the respiratory ventilation apparatus 110. In some embodiments, the gas filter component 230 may include a plurality of gas filter units. In some embodiments, one or more of the gas filter unit(s) may be mounted in the housing. In some embodiments, one or more of the gas filter unit(s) may be mounted in any other locations of the respiratory ventilation apparatus 110, the respiration tube 160, and/or the subject interface 170. In some embodiments, one or more of the gas filter unit(s) may be configured to filter the respiratory gas entering the respiratory ventilation apparatus 110. In some embodiments, one or more of the gas filter unit(s) may be configured to filter the respiratory gas entering the gas pressurization unit 210. In some embodiments, one or more of the gas filter unit(s) may be configured to filter the pressurized respiratory gas flowing from the gas pressurization unit 210. In some embodiments, one or more of the gas filter unit(s) may be configured to filter the pressurized respiratory gas entering the humidification assembly 220. In some embodiments, one or more of the gas filter unit(s) may be configured to filter the humidified and pressurized respiratory gas flowing from the humidification assembly 220.

In some embodiments, the gas filter component 230 may include one or more ultra-fine filter units mounted outside the gas inlet port 112, one or more gas filter units mounted inside the gas inlet port 112, one or more gas filter units with an antibacterial membrane or a deodorization membrane in the gas passage(s) of the respiratory ventilation apparatus 110, the respiration tube 160, and/or the subject interface 170.

Merely by way of example, in some embodiments, the gas filter component 230 may include a first gas filter unit. The first gas filter unit may be a coarse filter. In some embodiments, the gas filter component 230 may include a second gas filter unit. The second gas filter unit may be a fine filter. In some embodiments, the gas filter component 230 may include a third gas filter unit. The third gas filter unit may be mounted inside the gas inlet port 112 of the respiratory ventilation apparatus 110. The third gas filter unit may be configured to filter ambient gas entering the respiratory ventilation apparatus 110. In some embodiments, the third gas filter unit may include a coarse filter and/or a fine filter. In some embodiments, the gas filter component 230 may include a fourth gas filter unit. The fourth gas filter unit may be configured to filter one or more gases with pungent smell (also referred to as pungent gas(es)) in one or more gas passages of the respiratory ventilation apparatus 110. In some embodiments, the fourth gas filter unit may include a membrane manufactured by one or more nanomaterials having adsorption ability (e.g., activated carbon, graphene, etc.). In some embodiments, the gas filter component 230 may include a fifth gas filter unit. The fifth gas filter unit may be configured to filter bacteria in one or more gases in one or more gas passages of the respiratory ventilation apparatus 110, the respiration tube 160, and/or the subject interface 170. More descriptions of the gas filter component 230 may be found elsewhere in the present disclosure (e.g., FIGS. 6A-7B and the descriptions thereof).

The noise reduction assembly 240 may be configured to reduce the noise generated by the operation of the gas pressurization unit 210 (e.g., a blower) and/or the flowing of the respiratory gas. In some embodiments, the noise reduction assembly 240 may include a noise reduction box accommodating the gas pressurization unit 210. In some embodiments, the noise reduction box may include one or more sound absorbing materials set on the inner walls of the noise reduction box. In some embodiments, the noise reduction box may include one or more frames configured to fix the one or more sound absorbing materials. Exemplary sound absorbing materials may include organic fiber, inorganic fiber, inorganic foam, foam plastic, or the like, or any other material with the function of absorbing sound. More descriptions of the noise reduction assembly 240 may be found elsewhere in the present disclosure (e.g., FIGS. 8A-11F and the descriptions thereof).

The detection module 250 may be configured to detect one or more parameters relating to the system 100 (e.g., the respiratory ventilation apparatus 110, the subject 180). Exemplary parameters may include the flux of the respiratory gas, a flow rate of the respiratory gas, a temperature of the respiratory gas, a humidity of the respiratory gas, a snore of the subject 180, a respiratory rate of the subject 180, a tidal volume of the subject 180, or the like, or a combination thereof. In some embodiments, the parameters may include operation status of the respiratory ventilation apparatus 110 (e.g., a running time of the respiratory ventilation apparatus 110, a time of delay for pressurizing the respiratory gas, an air leakage of the pressurized respiratory gas, an input voltage of the gas pressurization unit 210, or the like).

In some embodiments, the detection module 250 may include one or more sensors configured to detect the parameter(s). Exemplary sensors may include a flow sensor, a pressure sensor, a humidity sensor, a temperature sensor, a timer, etc. For example, the detection module 250 may include a snoring detection assembly (e.g., a pressure sensor) (see FIGS. 15A and 15B) configured to detect a snore of a user of the respiratory ventilation apparatus 110 (e.g., the subject 180). As another example, the detection module 250 may include a flow detection assembly (see FIGS. 15A and 15B) configured to detect a flux of one or more gases in one or more passages of the respiratory ventilation apparatus 110. In some embodiments, the detection module 250 may further include a liquid level detection assembly (e.g., a liquid level sensor) configured to detect the liquid level in the tank of the liquid chamber 222.

The control module 260 may be configured to control the operation of the components of the system 100 (e.g., the gas pressurization unit 210, the humidification assembly 220, the gas filter component 230, the detection module 250, the processing device 140, the storage device 150, the terminal 130, or the like). In some embodiments, the control module 260 may be configured to initiate the respiratory ventilation apparatus 110 upon a boot operation. For example, the control module 260 may load a bootstrap program from the storage device 150, load a user program from the storage device 150, initiate one or more peripheral devices of the control module 260 (e.g., a communication interface, a timer, an AD acquisition interface, an indicator light, a button, a knob, a power switch, etc.), initiate one or more sensors, initiate the gas pressurization unit 210, initiate one or more configuration parameters, and/or initiate one or more treatment parameters. As another example, the control module 260 may initiate a random access memory of the respiratory ventilation apparatus 110, read one or more parameters from the storage device 150 (e.g., a non-volatile memory) of the respiratory ventilation apparatus 110, and/or initiate the detection module 250. In some embodiments, the control module 260 may be configured to initiate a program that constantly reads information from the detection module 250, and control the pressure of the pressurized respiratory gas using at least the information read from the detection module 250 and one or more of the parameters. In some embodiments, the control module 260 may cause the sensor(s) to detect one or more parameters (e.g., a pressure) of the pressurized respiratory gas, and/or adjust a rotated speed of the gas pressurization unit 210 to maintain the detected pressure of the pressurized respiratory gas within a predetermined range. In some embodiments, in response to an abnormal condition determined based on a comparison between a current state of the respiratory ventilation apparatus 110 and the plurality of parameters read from the storage device 150, the control module 260 may cause the respiratory ventilation apparatus 110 to provide an alert or reminder to a user. In some embodiments, the current state of the respiratory ventilation apparatus 110 may include the pressure of the respiratory gas. In some embodiments, the parameter(s) read from the storage device 150 may include one or more thresholds relating to an upper limit of the pressure, an upper limit of an air leakage of the pressurized respiratory gas, a lower limit of the air leakage of the pressurized respiratory gas, a lower limit of a respiratory rate, or a lower limit of an input voltage of the respiratory ventilation apparatus 110, or the like. In some embodiments, the control module 260 may adjust the rotated speed of the gas pressurization unit 210 to pressurize the respiratory gas with a delay after the initiation of the respiratory ventilation apparatus 110.

The control module 260 may be implemented as software and/or hardware modules (e.g., controllers) and may be stored in any type of non-transitory computer-readable medium or other storage device. For example, the control module 260 may be stored in the processing device 140. In some embodiments, a software module may be compiled and linked into an executable program. It will be appreciated that software modules can be callable from other modules or from themselves, and/or can be invoked in response to detected events or interrupts. Software modules configured for execution on computing devices (e.g., a processor of the processing device 140) can be provided on a computer-readable medium, such as a compact disc, a digital video disc, a flash drive, a magnetic disc, or any other tangible medium, or as a digital download (and can be originally stored in a compressed or installable format that requires installation, decompression, or decryption prior to execution). Such software code can be stored, partially or fully, on a memory device of the executing computing device, for execution by the computing device. Software instructions can be embedded in a firmware, such as an EPROM. It will be further appreciated that hardware modules can be included of connected logic units, such as gates and flip-flops, and/or can be included of programmable units, such as programmable gate arrays or processors. The modules or computing device functionality described herein can be implemented as software modules, and can be represented in hardware or firmware. In general, the modules described herein refer to logical modules that can be combined with other modules or divided into sub-modules despite their physical organization or storage. In some embodiments, the control module 260 or controllers may include signal processing circuitry, memory circuitry, one or more processors, a single chip microcomputer, or the like, or a combination thereof. In some embodiments, at least a portion of the control module 260 or controllers may be integrated in one or more printed circuit boards of the respiratory ventilation apparatus 110.

The peripheral device 270 may be configured to facilitate the operation or use of the respiratory ventilation apparatus 110. In some embodiments, the peripheral device 270 may include the respiration tube 160, the subject interface 170, or the like, or a combination thereof. More descriptions of the peripheral device 270 may be found elsewhere in the present disclosure (e.g., FIG. 1 and the descriptions thereof).

It should be noted that the above description of the respiratory ventilation apparatus 110 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, the respiratory ventilation apparatus 110 may include one or more additional modules, units, assemblies, devices, or the like.

For example, the respiratory ventilation apparatus 110 may include a storage module configured to store data generated during the operation of the respiratory ventilation apparatus 110.

As another example, the respiratory ventilation apparatus 110 may include one or more ultraviolet lamps set in one or more gas passages of the respiratory ventilation apparatus 110, the respiration tube 160, and/or the subject interface 170. The ultraviolet lamp(s) may be configured to sterilize one or more gases flowing in the respiratory ventilation apparatus 110, one or more gas passages in the respiratory ventilation apparatus 110, or one or more components of the respiratory ventilation apparatus 110 (e.g., the humidification assembly 220), or the like.

As a further example, the respiratory ventilation apparatus 110 may include one or more display panels configured to display information relating to the system 100.

As a further example, the respiratory ventilation apparatus 110 may include a communication module configured to communicate information with the processing device 140, the terminal 130, etc. The communication module may be connected to a network (e.g., the network 120) to facilitate data communications. The communication module may establish connections between the processing device 140 and the respiratory ventilation apparatus 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication module may include a standardized communication port, such as RS232, RS485, etc. In some embodiments, the communication module may include a specially designed communication port.

As a further example, the respiratory ventilation apparatus 110 may include a remote-control unit. The remote-control unit may be configured to remotely operate the respiratory ventilation apparatus 110. A user (e.g., the subject 180) may operate the respiratory ventilation apparatus 110 via the remote-control unit without adjusting one or more components of the respiratory ventilation apparatus 110 (e.g., the on-off key 311, the display panel 312, the knob 313, the home button 314, or the like, as illustrated in FIG. 3).

In some embodiments, one or more components of the respiratory ventilation apparatus 110 may be omitted. For example, the heating device 224 may be omitted and/or replaced by an ultrasonic atomizer. As another example, the humidification assembly 220 may be omitted. As a further example, the gas filter component 230 may be omitted.

Figure 3A:
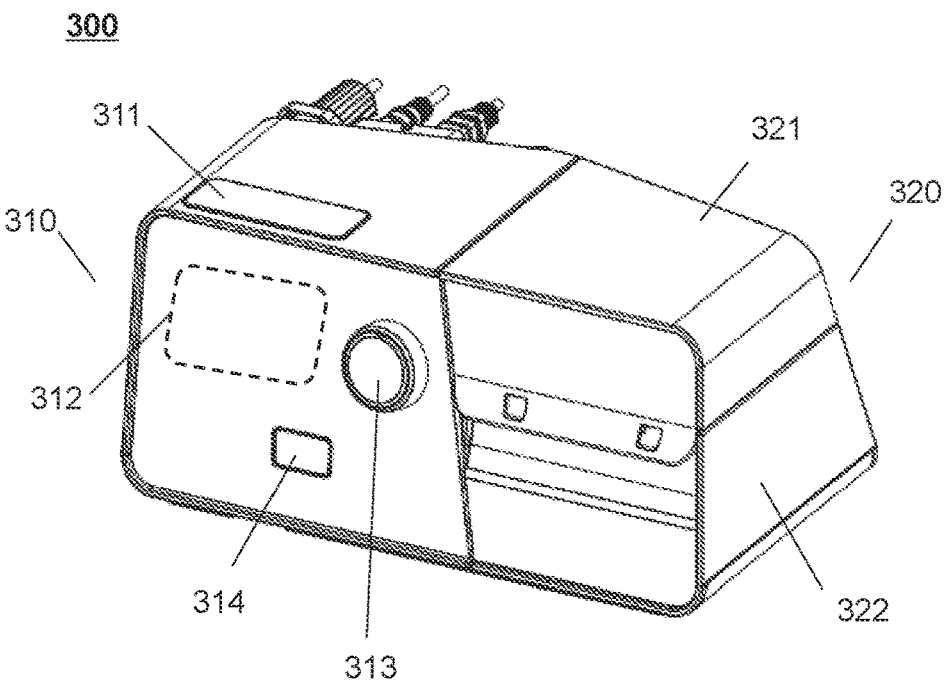
FIGS. 3A-3D illustrate an exemplary respiratory ventilation apparatus according to some embodiments of the present disclosure.
Figure 3B:
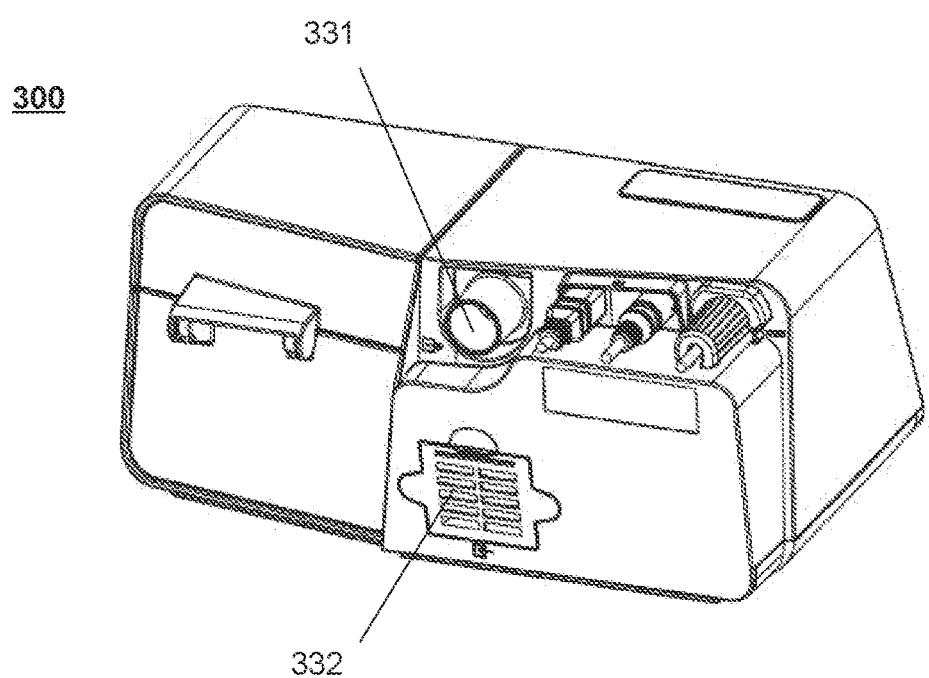
Figure 3C:
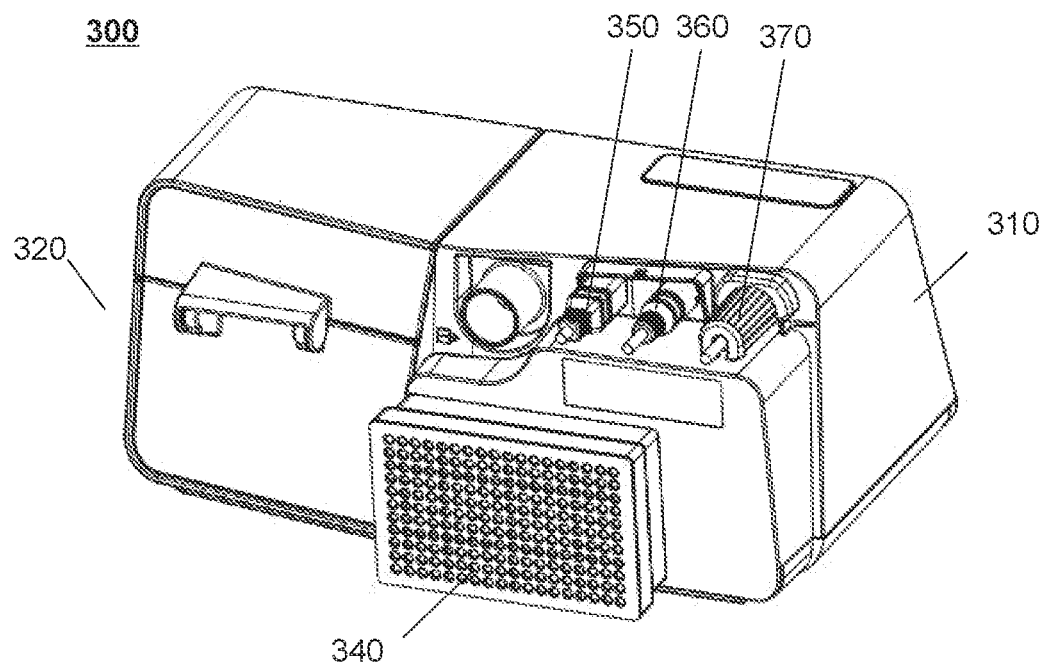
Figure 3D:
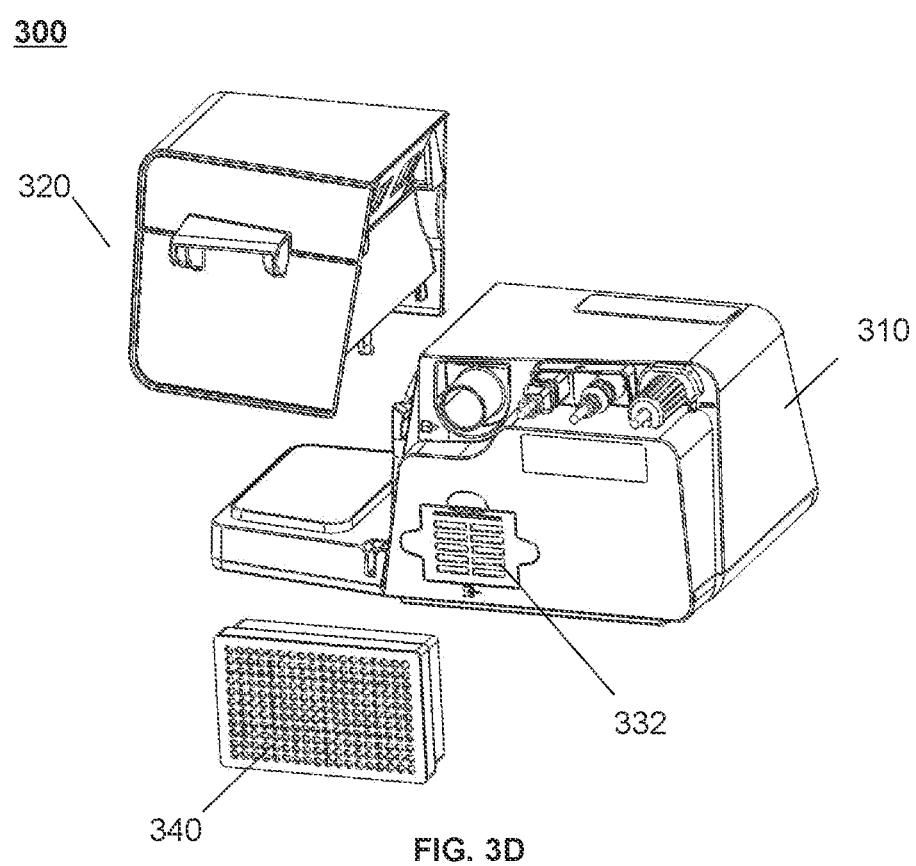

FIGS. 3A-3D illustrate an exemplary respiratory ventilation apparatus according to some embodiments of the present disclosure. FIG. 3A shows a front side of the respiratory ventilation apparatus 300. FIG. 3B shows a rear side of the respiratory ventilation apparatus 300. FIG. 3C shows another rear side of the respiratory ventilation apparatus 300. FIG. 3D shows main components of the respiratory ventilation apparatus 300. As illustrated in FIGS. 3A-3D, the respiratory ventilation apparatus 300 may include a main body 310 and a liquid chamber 320.

As illustrated in FIG. 3A, the main body 310 of the respiratory ventilation apparatus 300 may include an on-off key 311, a display panel 312, a knob 313, a home button 314, or the like. The on-off key 311 may be configured to cause the respiratory ventilation apparatus 300 to switch between a boot state and a shutdown state. For example, if the respiratory ventilation apparatus 300 is switched off, a user (e.g., the subject 180) may press the on-off key 311 to boot the respiratory ventilation apparatus 300. As another example, if the respiratory ventilation apparatus 300 is switched on, the user (e.g., the subject 180) may press the on-off key 311 to shut down the respiratory ventilation apparatus 300. The display panel 312 may be configured to display information relating to the respiratory ventilation apparatus 300. The information displayed may include, for example, the parameters relating to the respiratory gas, the expired gas of the subject 180, and/or the operation status of the respiratory ventilation apparatus 110. More descriptions of the parameters may be found elsewhere in the present disclosure (e.g., FIG. 1 and the descriptions thereof). In some embodiments, the display panel 312 may be configured as a software operation interface of the respiratory ventilation apparatus 110. In some embodiments, the display panel 312 may be a touch panel.

The knob 313 may be configured to facilitate a user (e.g., the subject 180) to adjust and/or set the value(s) of one or more parameters illustrated above and/or a menu item of software implemented in the respiratory ventilation apparatus 110. In some embodiments, the knob 313 may be turned and/or pressed. For example, the subject 180 may turn the knob 313 to adjust the value(s) of the pressure of the respiratory gas, the humidity of the respiratory gas, etc. As another example, the subject 180 may press the knob 313 to confirm an adjusted (or set) parameter, select a menu item, exit from a functional interface, etc. As a further example, the subject 180 may long press the knob 313 (or short press the knob 313 two times) to access a doctor's interface. In the doctor's interface, a doctor may be allowed to adjust and/or set one or more parameters associated with the respiratory ventilation apparatus 110. The home button 314 may be pressed to switch to a main interface of the software. In some embodiments, the home button 314 may be long pressed to mute the hardware and/or software of the respiratory ventilation apparatus 110. One or more of the on-off key 311, the display panel 312, the knob 313, and the home button 314 may be set on the front side, the rear side, the top side, the left side, or the right side of the respiratory ventilation apparatus 300, the rear side of the respiratory ventilation apparatus 300.

As illustrated in FIG. 3A, the liquid chamber 320 may include a tank 322 and a tank cover 321. The liquid chamber 320 may be removably coupled to the main body 310 of the respiratory ventilation apparatus 300 (see FIG. 3D). In some embodiments, the liquid chamber 320 may be in detachable connection with the main body 310 of the respiratory ventilation apparatus 300. A user (e.g., the subject 180) may discharge the liquid chamber 320 from the respiratory ventilation apparatus 300, so that liquid filling in the tank 322, liquid exchange of the tank 322, washing of the tank 322, and/or sterilization of the liquid chamber 320 may be facilitated. More descriptions of the liquid chamber 320 may be found elsewhere in the present disclosure (e.g., FIGS. 18A, 18B, 23A, 26B, 30A, 30B, 36A, and 36B, and the descriptions thereof). As illustrated in FIG. 3A, the liquid chamber 320 is set on the right side of the main body 310 for illustration purposes. It should be noted that in some embodiments, the liquid chamber 320 may be set on the left side of the main body 310.

As illustrated in FIG. 3B, the respiratory ventilation apparatus 300 may include a gas inlet port 332 and a gas outlet port 331. In some embodiments, the main body 310 of the respiratory ventilation apparatus 300 may include a housing. The housing may include a first side wall (e.g., the interface between the main body 310 and the liquid chamber 320) and a second side wall (e.g., the rear side). The first side wall may be configured to discharge the pressurized respiratory gas. The gas inlet port 332 may be set on the main body 310. In some embodiments, the gas inlet port 332 may be set on the second side wall of the housing of the main body 310 of the respiratory ventilation apparatus 300. In some embodiments, the gas inlet port 332 may be set on the front side, the rear side, the top side of the respiratory ventilation apparatus 300. In some embodiments, the gas inlet port 332 may be set on a side of the respiratory ventilation apparatus 300 opposite to the liquid chamber 320. As illustrated in FIGS. 3A and 3B, as the liquid chamber 320 is set on the right side of the main body 310, the gas inlet port 332 may be set on the left side of the respiratory ventilation apparatus 300. In FIG. 3B, the gas outlet port 331 is set on the main body 310. The gas outlet port 331 may be set on the same side of the respiratory ventilation apparatus 300 as the gas inlet port 332. In some embodiments, the gas outlet port 331 and the gas inlet port 332 may be set on different sides of the respiratory ventilation apparatus 300. In some embodiments, the gas outlet port 331 may be set on the liquid chamber 320. In some embodiments, the respiratory ventilation apparatus 300 may include or be equipped with one or more gas filter units (e.g., a coarse filter, a fine filter, or the like) inside the gas inlet port 332 to filter the respiratory gas entering the gas inlet port 332.

As illustrated in FIG. 3C, the respiratory ventilation apparatus 300 may include a gas filter component 340. The gas filter component 340 may be configured to filter the respiratory gas entering the respiratory ventilation apparatus 300. The gas filter component 340 may be removably coupled to the gas inlet port 332 of the respiratory ventilation apparatus 300 (see FIG. 3D). The gas filter component 340 may include a coarse filter and/or a fine filter (not shown in FIGS. 3A-3D). It should be noted that the gas filter component 340 may be optional. In some embodiments, the respiratory ventilation apparatus 300 may not include the gas filter component 340 as illustrated in FIG. 3B. As illustrated in FIG. 3D, the liquid chamber 320 and/or the gas filter component 340 may be in detachable connection with the main body 310 of the respiratory ventilation apparatus 300. More descriptions of the gas filter component 340 may be found elsewhere in the present disclosure (e.g., FIG. 6A-7B and the descriptions thereof).

As illustrated in FIG. 3C, the respiratory ventilation apparatus 300 may include a first interface 350, a second interface 360, and a third interface 370. The first interface 350 may be configured to supply electric power for the heating device 224 of the respiratory ventilation apparatus 300. The second interface 360 may be configured as an interface for software upgrading and/or data reading (or transmission). The third interface 370 may be configured to supply electric power for the respiratory ventilation apparatus 300.

Figure 4:
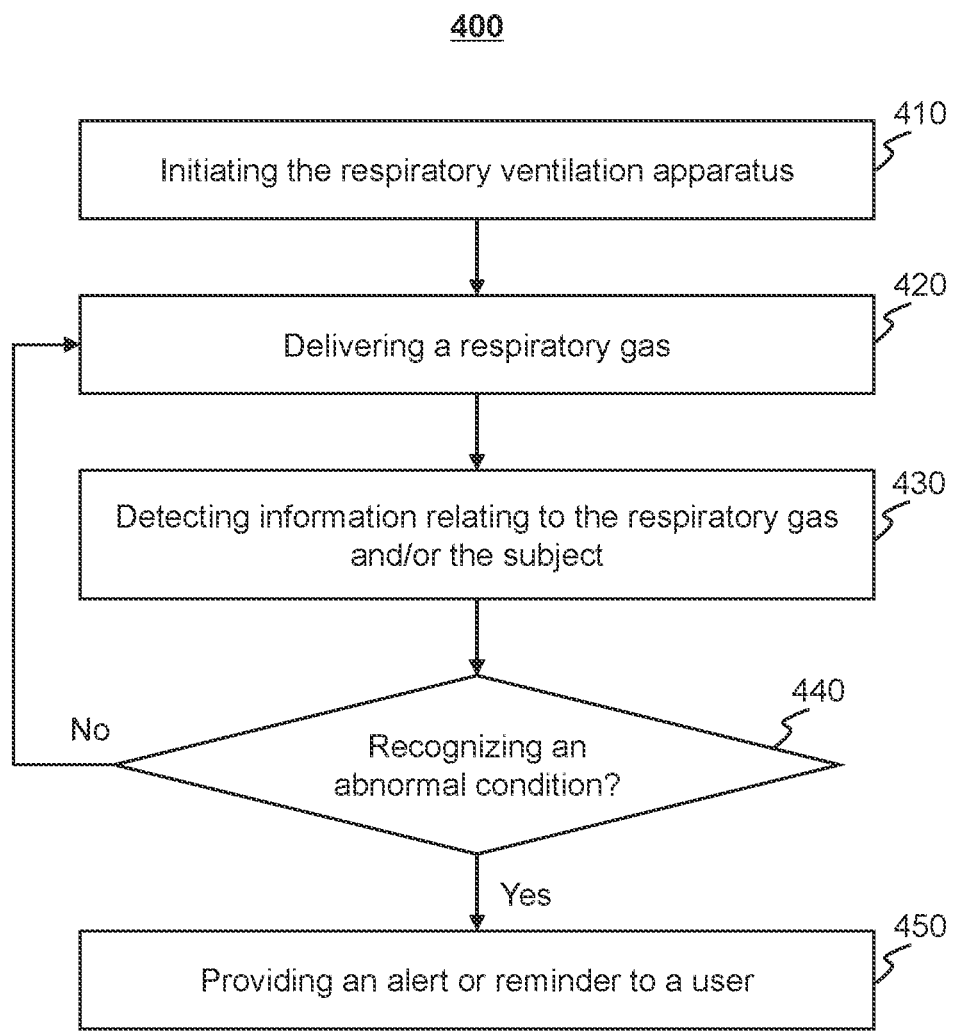
FIG. 4 illustrates an exemplary process for delivering a respiratory gas according to some embodiments of the present disclosure.

FIG. 4 illustrates an exemplary process for delivering a respiratory gas according to some embodiments of the present disclosure. In some embodiments, one or more operations of process 400 illustrated in FIG. 4 for delivering a respiratory gas may be implemented in the system 100 illustrated in FIG. 1. For example, the process 400 illustrated in FIG. 4 may be stored in the storage device 150 in the form of instructions, and invoked and/or executed by the processing device 140. As another example, a portion of the process 400 may be implemented on the respiratory ventilation apparatus 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 4 and described below is not intended to be limiting.

In 410, the respiratory ventilation apparatus 110 (e.g., the control module 260) may initiate one or more components of the respiratory ventilation apparatus 110. In some embodiments, the respiratory ventilation apparatus 110 may be initiated upon a boot operation (e.g., a user presses the on-off button the respiratory ventilation apparatus 110). In some embodiments, the control module 260 may load a bootstrap program from a storage device (e.g., a RAM, a ROM, a flash memory, a secure digital (SD) memory card, etc.) of the respiratory ventilation apparatus 110, load a user program from the storage device of the respiratory ventilation apparatus 110, initiate one or more peripheral devices of the control module 260 (e.g., a communication interface, a timer, an AD acquisition interface, an indicator light, a button, a knob, a power switch, etc.), initiate one or more sensors, initiate the gas pressurization unit 210, initiate one or more configuration parameters, and/or initiate one or more treatment parameters. In some embodiments, the control module 260 may initiate a random access memory of the respiratory ventilation apparatus 110, read one or more parameters from a storage device of the main body (e.g., a non-volatile memory, a flash memory, an SD card) of the respiratory ventilation apparatus 110 and/or from the network 120, and/or initiate the detection module 250. In some embodiments, the control module 260 may initiate a program that constantly reads information from the detection module 250, and control the pressure of the pressurized respiratory gas using at least the information read from the detection module 250 and one or more of the parameters. In some embodiments, the parameter(s) read from a storage device of the main body (e.g., a non-volatile memory, a flash memory, an SD card) of the respiratory ventilation apparatus 110 and/or from the network 120 may include one or more thresholds relating to an upper limit of the pressure, an upper limit of an air leakage of the pressurized respiratory gas, a lower limit of the air leakage of the pressurized respiratory gas, a lower limit of a respiratory rate, or a lower limit of an input voltage of the respiratory ventilation apparatus 110, or the like.

In 420, the respiratory ventilation apparatus 110 may deliver a respiratory gas to a user (e.g., the subject 180). In some embodiments, the control module 260 may control or adjust the rotated speed of the gas pressurization unit 210 to pressurize the respiratory gas, and the pressurized respiratory gas may be discharged (or delivered) to the subject 180 via one or more gas passaged in the respiratory ventilation apparatus 110, the respiration tube 160, and/or the subject interface 170. In some embodiments, the control module 260 may adjust the rotated speed of the gas pressurization unit 210 to pressurize the respiratory gas with a delay after the initiation of the respiratory ventilation apparatus 110. In some embodiments, the delay may be preset by the user.

In 430, the respiratory ventilation apparatus 110 may detect information relating to the respiratory gas and/or the subject 180. In some embodiments, the control module 260 may cause the detection module 250 (e.g., one or more sensors) to detect one or more parameters (e.g., a pressure) of the pressurized respiratory gas. The detected information may include parameters relating to the respiratory gas, the expired gas of the subject 180, and/or the operation status of the respiratory ventilation apparatus 110. More descriptions of the parameters may be found elsewhere in the present disclosure (e.g., FIG. 2 and the descriptions thereof). In some embodiments, the control module 260 may determine one or more parameters based on the operation condition(s) of one or more components of the respiratory ventilation apparatus 110. For example, the control module 260 may determine the pressure of the respiratory gas based on the rotation speed, input voltage, and/or real-time power of the gas pressurization unit 210. In some embodiments, the control module 260 may adjust the rotation speed of the gas pressurization unit 210 to maintain the detected pressure of the pressurized respiratory gas within a predetermined range.

In 440, the respiratory ventilation apparatus 110 may determine whether an abnormal condition is recognized. In some embodiments, the control module 260 may recognize an abnormal condition based on a comparison between a current state of the respiratory ventilation apparatus 110 and the plurality of parameters read from a storage device of the main body of the respiratory ventilation apparatus 110 and/or from the network 120. In some embodiments, the current state of the respiratory ventilation apparatus 110 may include for example, the pressure of the respiratory gas, an air leakage of the pressurized respiratory gas, a respiratory rate, an input voltage of the gas pressurization unit 210, etc. In response to a determination that an abnormal condition is recognized, the process 400 may proceed to 450. In response to a determination that no abnormal condition is recognized, the process 400 may return to 420, i.e., the respiratory ventilation apparatus 110 may continue delivering the respiratory gas.

In 450, the respiratory ventilation apparatus 110 may provide an alert or reminder to a user (e.g., the subject 180). The alert or reminder may include a voice, a text, etc. For example, in response to an abnormal condition, the respiratory ventilation apparatus 110 may make an alarm sound, the respiratory ventilation apparatus 110 may display a notice on a displayer, and/or the control module 260 may send an instruction to the terminal 130 to display a notice or make an alarm sound, etc. In some embodiments, after the respiratory ventilation apparatus 110 provides an alert or reminder to the user, the process may return to 420, i.e., the respiratory ventilation apparatus 110 may continue delivering the respiratory gas.

Figure 5A:
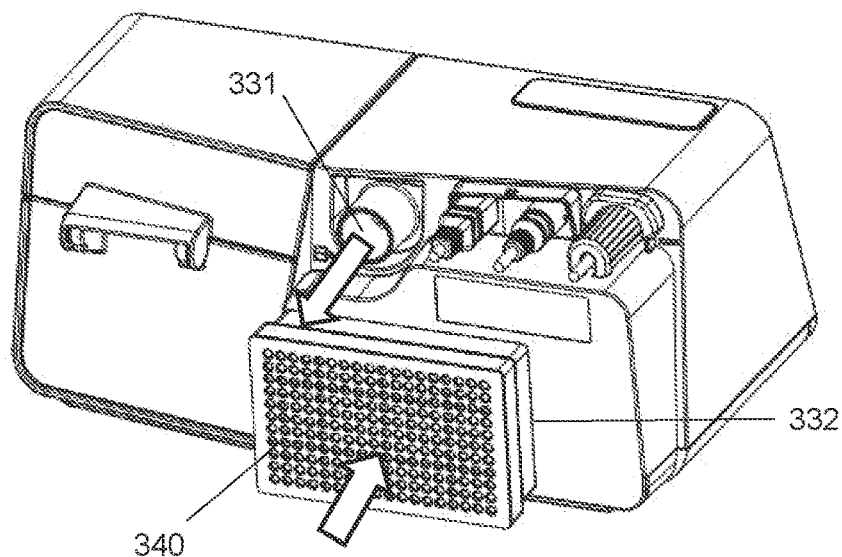
FIGS. 5A-5E illustrate exemplary gas passages of a respiratory ventilation apparatus according to some embodiments of the present disclosure.
Figure 5B:
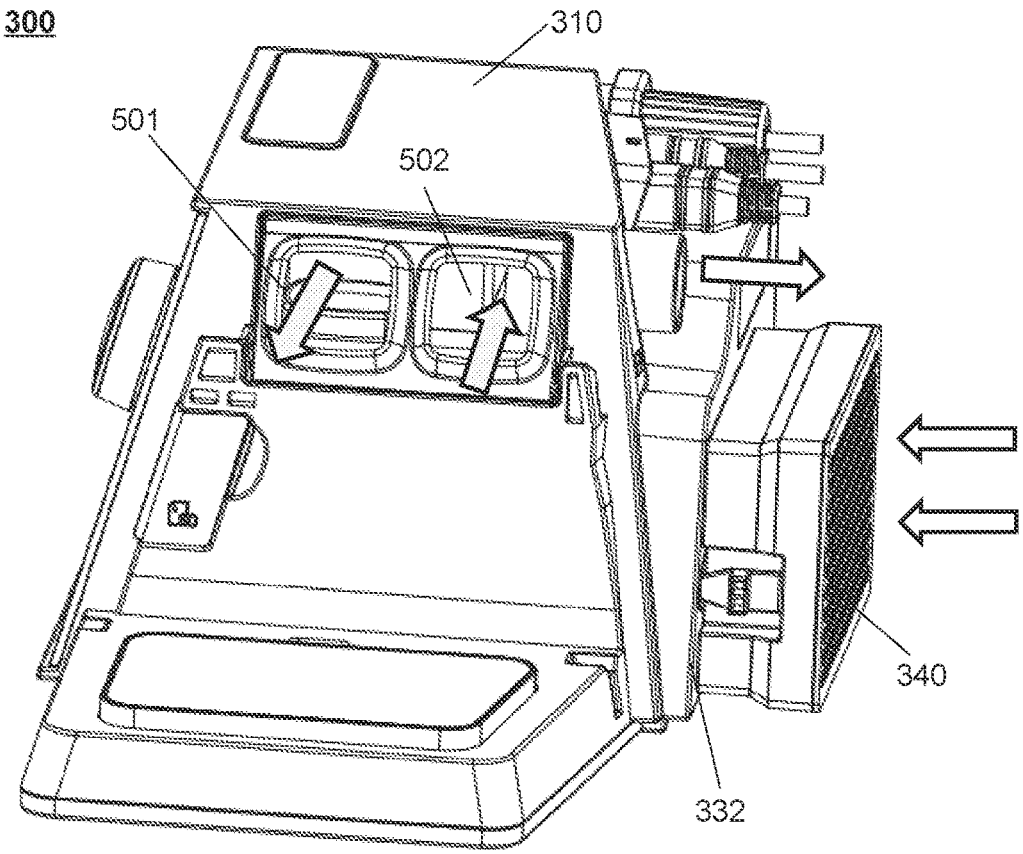
Figure 5C:
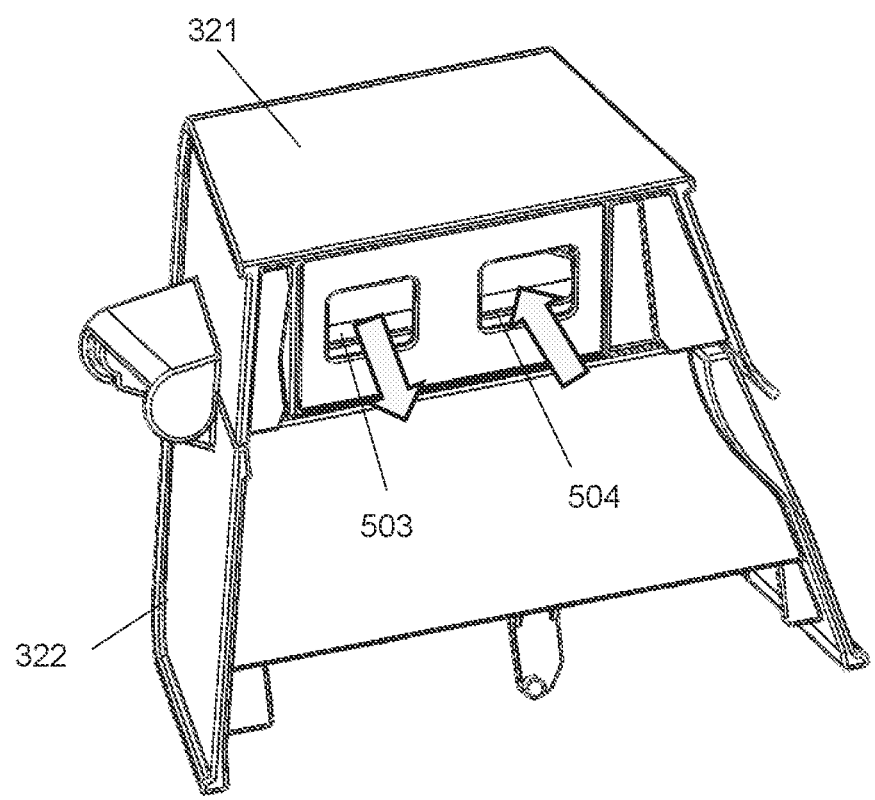
Figure 5D:
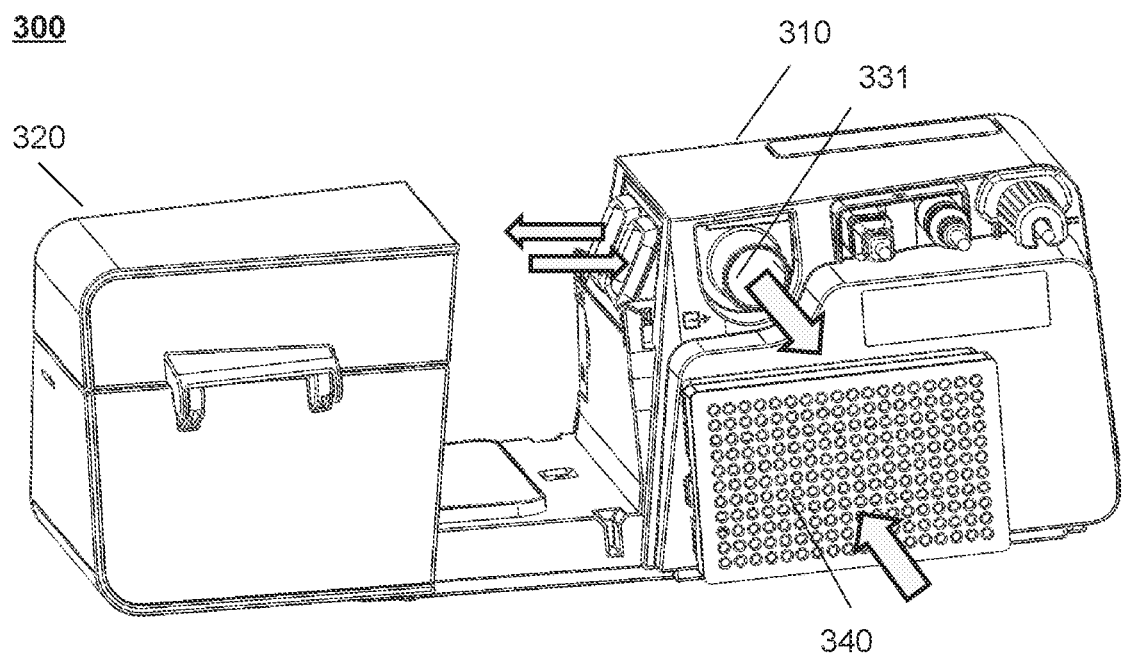
Figure 5E:
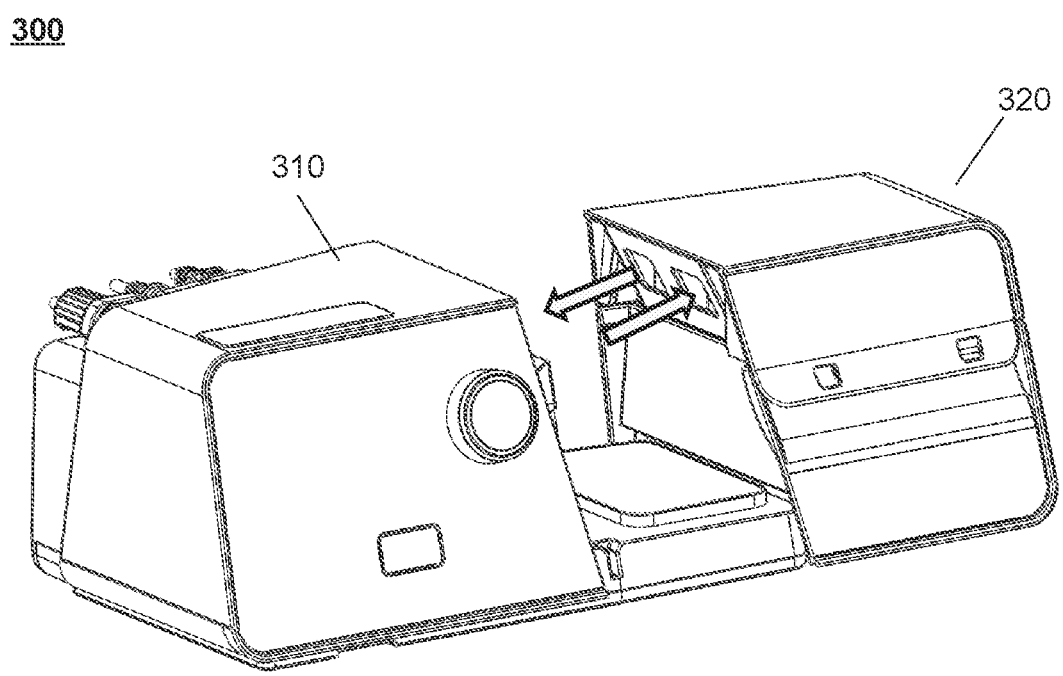

FIGS. 5A-5E illustrate exemplary gas passages of a respiratory ventilation apparatus according to some embodiments of the present disclosure. As illustrated in FIG. 5A, a flow of respiratory gas (e.g., ambient gas) may flow from a gas inlet port 332 into the respiratory ventilation apparatus 300 and out of the respiratory ventilation apparatus 300 from the gas outlet port 331. In some embodiments, the respiratory ventilation apparatus 300 may further include a gas filter component 340 mounted outside the gas inlet port 332. The respiratory gas may be filtered by the gas filter component 340 before entering the respiratory ventilation apparatus 300 via the gas inlet port 332. As illustrated in FIG. 5B, a side of the main body 310 attached with the liquid chamber 320 may include an outlet port 501 and an inlet port 502. The respiratory gas filtered by the gas filter component 340 may be pressurized by the gas pressurization unit 210 and then pass through the outlet port 501 of the main body 310. As illustrated in FIG. 5C, the liquid chamber 320 may include the tank 322 and the tank cover 321, and a side of the tank cover 321 attached with the main body 310 may include an outlet port 503 and an inlet port 504. The filtered and pressurized respiratory gas passing through the outlet port 501 of the main body 310 may enter the liquid chamber 320 from the inlet port 504 of the tank cover 321 and be humidified in the tank 322. The outlet port 503 of the tank cover 321 may output the pressurized and humidified respiratory gas. As illustrated in FIGS. 5D and 5E, the pressurized and humidified respiratory gas output by the outlet port 503 of the tank cover 321 may return to the main body 310 from the inlet port 502 of the main body 310 and flow out of the respiratory ventilation apparatus 300 from the gas outlet port 331 of the respiratory ventilation apparatus 300.

It should be noted that the above description of the respiratory ventilation apparatus 300 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the respiratory ventilation apparatus 300 may not include the humidification assembly 220 (i.e., the liquid chamber 320 may be omitted). In some embodiments, the gas outlet port 331 of the respiratory ventilation apparatus 300 may be set on the liquid chamber 320, and accordingly, the inlet port 502 of the respiratory ventilation apparatus 300 and the outlet port 503 of the liquid chamber 320 may be omitted. That is, the pressurized respiratory gas may be introduced into the liquid chamber 320 via the outlet port 501 of the main body 310 and the inlet port 504 of the liquid chamber 320, and then be discharged to a respiration tube via a gas outlet port set on the liquid chamber 320. Correspondingly, the humidified respiratory gas may not flow back to the main body 310.

Figure 6A:
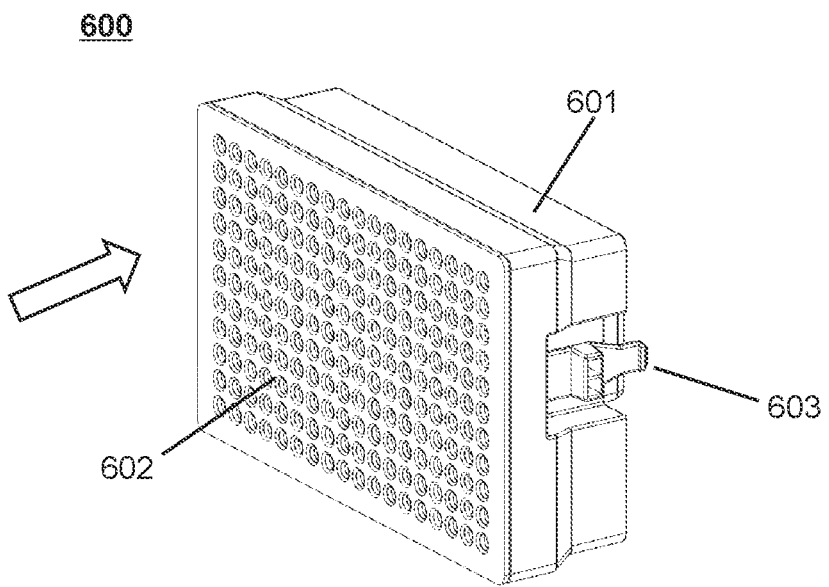
FIGS. 6A-6E illustrate an exemplary gas filter component according to some embodiments of the present disclosure.
Figure 6B:
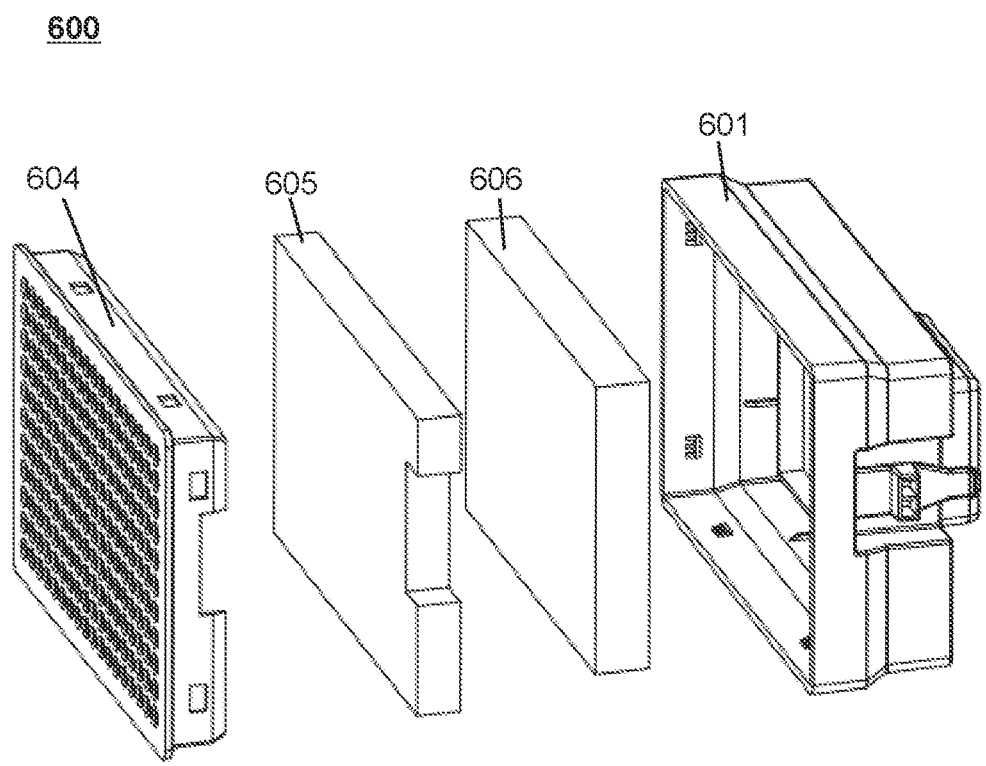
Figure 6C:
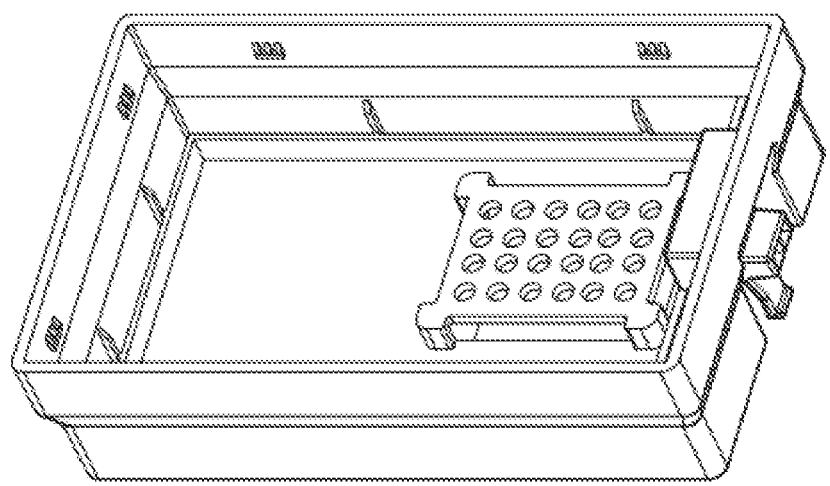
Figure 6D:
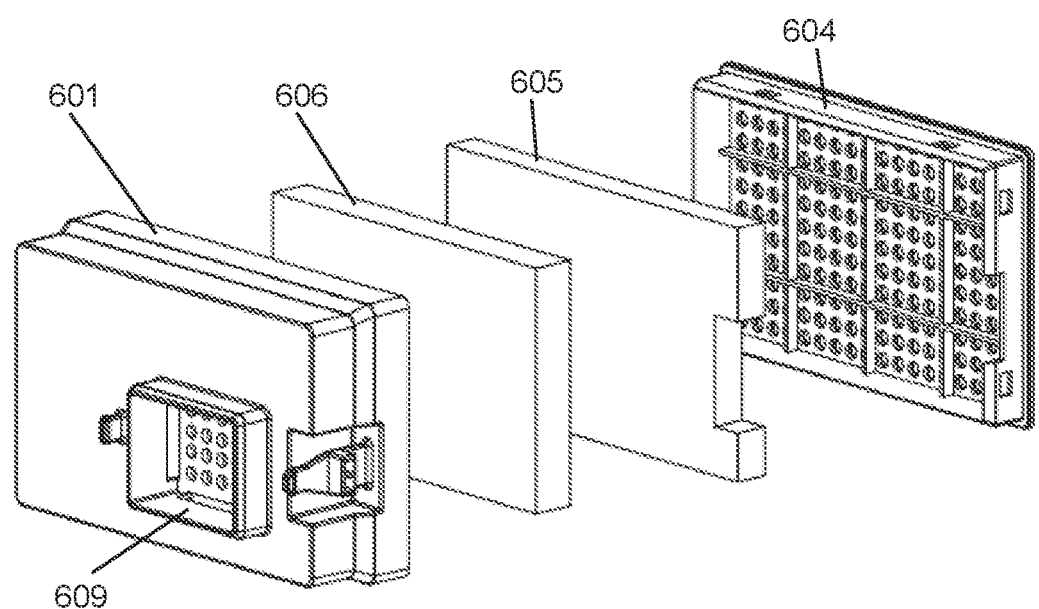
Figure 6E:
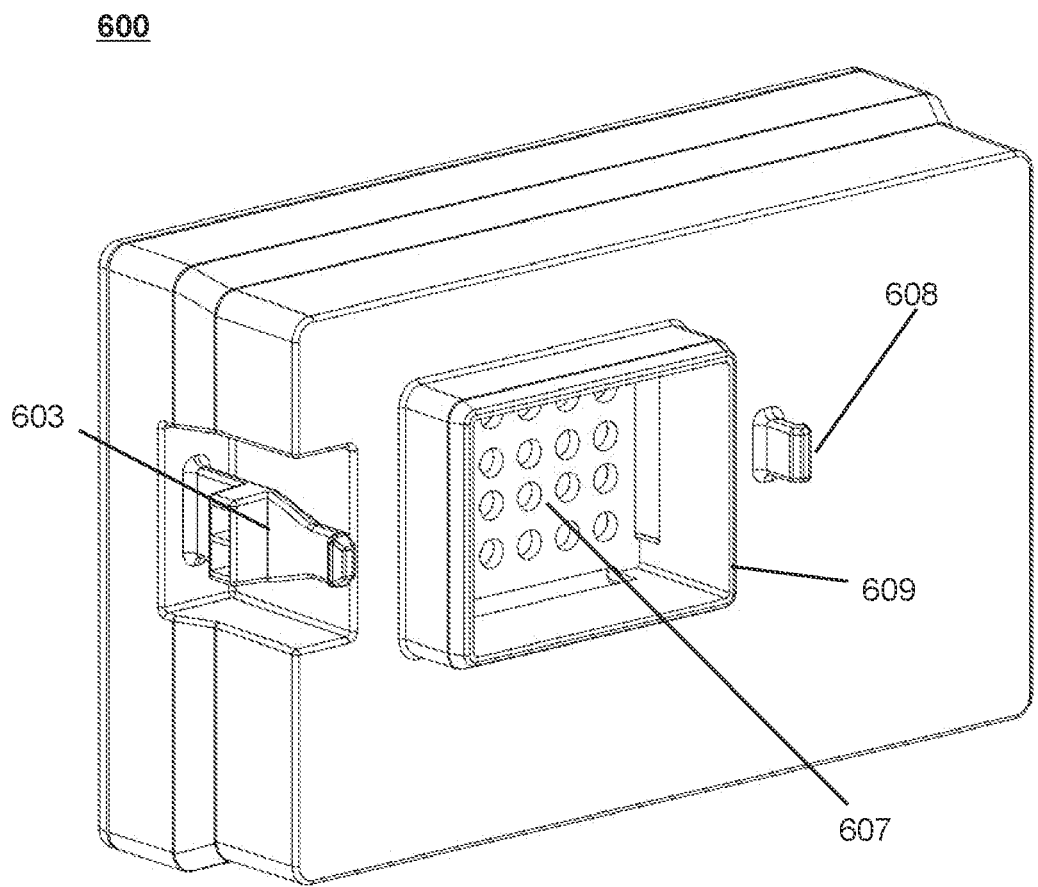

FIGS. 6A-6E illustrate an exemplary gas filter component according to some embodiments of the present disclosure. FIG. 6A shows a first axonometric drawing of the gas filter component 600 illustrating a front side, a left side, and a top side of the gas filter component 600. FIG. 6B shows a first exploded view of the gas filter component 600. FIG. 6C shows an internal structure of a housing of the gas filter component 600. FIG. 6D shows a second exploded view of the gas filter component 600. FIG. 6E shows a second axonometric drawing of the gas filter component 600 illustrating a rear side, a left side, and a top side of the gas filter component 600. In some embodiments, the gas filter component 600 may be in detachable connection with the gas inlet port 112 of the respiratory ventilation apparatus 110.

The gas filter component 600 may include a housing 601 and one or more gas filter units (e.g., a first gas filter unit 605, a second gas filter unit 606, etc.). In some embodiments, a respiratory gas (e.g., an ambient gas) may enter the respiratory ventilation apparatus 300 (e.g., when the gas pressurization unit 210 is in operation) via the gas filter component 600 along a direction indicated by the arrow shown in FIG. 6A. The gas filter component 600 (e.g., the first gas filter unit 605, the second gas filter unit 606, etc.) may filter the respiratory gas entering the respiratory ventilation apparatus 300. In some embodiments, the one or more gas filter units may filter the respiratory gas in different levels.

The housing 601 may include a gas inlet end 602 and a gas outlet end 609. The gas inlet end 602 may include a first cover plate 604. The gas outlet end 609 may include a second cover plate 607. In some embodiments, the first cover plate 604 may have a same size as the gas inlet end 602. In some embodiments, the first cover plate 604 may include at least one hole allowing the respiratory gas to enter the gas filter component 600. In some embodiments, the second cover plate 607 may have a smaller size than the gas outlet end 609. In some embodiments, the second cover plate 607 may include at least one hole allowing the respiratory gas to exit the gas filter component 600 and enter the respiratory ventilation apparatus 300. In some embodiments, the first cover plate 604 may be in detachable connection with the housing 601. In some embodiments, the first cover plate 604 may include a frame. In some embodiments, the frame of the first cover plate 604 may include one or more holes or grooves, and the housing 601 may include one or more corresponding protruding structures (or vice versa), so that the first cover plate 604 may be connected with the housing 601. In some embodiments, the second cover plate 607 may be fixed on the gas outlet end 609 of the housing 601 through a sealed connection. In some embodiments, the second cover plate 607 and the housing 601 may be configured as an integral piece. In some embodiments, the first cover plate 604 and/or the second cover plate 607 may be configured to prevent one or more gas filter units (e.g., the first gas filter unit 605 and/or the second gas filter unit 606) of the gas filter component 600 from deformation. In some embodiments, the housing 601 of the gas filter component 600 may be configured to facilitate the disassembly of the gas filter component 600, and/or facilitate the replacement of the gas filter unit(s) (e.g., the first gas filter unit 605 and/or the second gas filter unit 606) of the gas filter component 600.

In some embodiments, the gas filter component 600 may have a stepped or tapered three-dimensional structure. In some embodiments, the gas filter component 600 may have the shape of a cuboid. In some embodiments, the gas filter component 600 may have the shape of a funnel. In some embodiments, the gas outlet end 609 of the housing 601 may have the shape of a funnel. In some embodiments, the gas inlet end 602 may have a same size as the gas outlet end 609. In some embodiments, the gas inlet end 602 may have a larger size than the gas outlet end 609, so that the intake volume of the respiratory gas flowing into the gas filter component 600 can be increased. In some embodiments, the gas outlet end 609 may have the shape of a funnel, so that the gas outlet end 609 can be connected with the gas inlet port 112 of the respiratory ventilation apparatus 110. In some embodiments, a cross section (perpendicular to the inflow direction of the respiratory gas) of the gas inlet end 602 (or the first cover plate 604) of the gas filter component 600 may be larger than that of the gas outlet end 609 (or the second cover plate 607), which means the gas inlet end 602 (or the first cover plate 604) may have a larger intake area than the gas outlet end 609 (or the second cover plate 607).

In some embodiments, the first cover plate 604 (or the gas inlet end 602) and the second cover plate 607 (or the gas outlet end 609) may have the same shape. In some embodiments, the first cover plate 604 (or the gas inlet end 602) and the second cover plate 607 (or the gas outlet end 609) may have different shapes. For example, the first cover plate 604 and the second cover plate 607 may have a shape of a rounded rectangle. As another example, the first cover plate 604 and the second cover plate 607 may have a shape of a circle. As still another example, the first cover plate 604 may have a shape of a rounded rectangle, while the second cover plate 607 may have a shape of a circle. As still another example, the first cover plate 604 may have a shape of a circle, while the second cover plate 607 may have a shape of a rounded rectangle.

The first cover plate 604 may include a plurality of holes. The holes of the first cover plate 604 may be configured to facilitate the respiratory gas to flow through the first cover plate 604 and reach the gas filter unit(s) to be filtered. After flowing through the plurality of holes of the first cover plate 604, the respiratory gas may be filtered by the gas filter unit(s). Then the filtered respiratory gas may flow through the second cover plate 607 and enter the gas inlet port 112 of the respiratory ventilation apparatus 110. The second cover plate 607 may include one or more holes. The holes of the second cover plate 607 may be configured to facilitate the filtered respiratory gas to flow through the second cover plate 607 and reach the gas inlet port 112. In some embodiments, the number of the holes set on the first cover plate 604 may be larger than the number of the holes set on the second cover plate 607.

In some embodiments, the holes of the first cover plate 604 and/or the second cover plate 607 may have a shape of a strip, circle, rectangle, triangle, rhombus, hexagon, star-like, or the like, or any combine thereof. The holes may have a relatively small size so that a finger of a user cannot be put in. In some embodiments, the holes of the first cover plate 604 and/or the second cover plate 607 may be evenly distributed. As show in FIG. 6A, 198 round holes are evenly distributed on the first cover plate 604 to form an array of 11 rows and 18 columns. As show in FIG. 6E, 16 round holes are evenly distributed on the second cover plate 607 to form an array of 4 rows and 4 columns. It should be noted that in some embodiments, the holes of the first cover plate 604 and/or the second cover plate 607 may be unevenly distributed. In some embodiments, the holes of the first cover plate 604 and/or the second cover plate 607 may help to adjust the gas flow of the respiratory gas entering the gas inlet port 112 of the respiratory ventilation apparatus 110, so that the noise generated by the gas flow may be reduced.

In some embodiments, the first gas filter unit 605 may be a coarse filter. In some embodiments, the coarse filter may be positioned close to the first cover plate 604. The coarse filter may include a coarse filter sponge (also refer to coarse filter foam). In some embodiments, the first gas filter unit 605 may include one or more layers of coarse filter sponge (or a multilayer filtration membrane). The coarse filter sponge may be configured to filter or adsorb solid particulates (such as dust, stive, pollen, etc.) in the respiratory gas entering the gas filter component 600. In some embodiments, the size of the particulates filtered by the coarse filter sponge may be larger than 5 micrometers. In some embodiments, the coarse filter may further include a fixing part configured to fix the coarse filter sponge in the housing 601.

In some embodiments, the second gas filter unit 606 may be a fine filter. The fine filter may include a fine filter sponge (also refer to fine filter foam). In some embodiments, the second gas filter unit 606 may include one or more layers of fine filter sponge (or a multilayer ultrafiltration membrane). The fine filter sponge may be configured to filter or adsorb solid particulates with a size larger than 1 micrometer, such as PM2.5 particles. Exemplary components of the coarse filter sponge and/or the fine filter sponge may include synthetic fibers, polyester fibers, glass gibers, or the like, or any combination thereof. In some embodiments, the fine filter may further include a fixing part configured to fix the fine filter sponge in the housing 601. In some embodiments, the housing 601 may include one or more frames configured to fix the first gas filter unit 605 and/or the second gas filter unit 606. In some embodiments, the first gas filter unit 605 may be positioned closer to the first cover plate 604 than the second gas filter unit 606 (i.e., the distance between the first gas filter unit 605 and the first cover plate 604 may be less than the distance between the second gas filter unit 606 and the first cover plate 604).

In some embodiments, the second gas filter unit 606 may be mounted behind the first gas filter unit 605 in the gas flow direction. In some embodiments, the respiratory gas may flow through the first gas filter unit 605 first and then flow through the second gas filter unit 606. In some embodiments, one or more grilles may be set between the first gas filter unit 605 and the second gas filter unit 606, so that there may be a certain distance between the first gas filter unit 605 and the second gas filter unit 606, thereby facilitating the respiratory gas to flow through the first gas filter unit 605 and the second gas filter unit 606, and enhancing the filtering effect of the first gas filter unit 605 and the second gas filter unit 606. In some embodiments, the first gas filter unit 605 and the second gas filter unit 606 may be independently mounded in the housing 601. In some embodiments, the replacement cycle of the first gas filter unit 605 may be less than the replacement cycle of the second gas filter unit 606. In some embodiments, the first gas filter unit 605 and the second gas filter unit 606 may be detachably connected with the housing 601. The detachable connection may include snap connection, screw connection, hinge connection, or the like, or any combine thereof.

In some embodiments, the housing 601 of the gas filter component 600 may further include a connection part configured to connect the gas filter component 600 with the gas inlet port 112 of the respiratory ventilation apparatus 110. As shown in FIG. 6E, the connection part may include a position claw 608 on the rear side of the housing 601 and a snap claw 603 on the left side (or the right side) of the housing 601. By pressing and/or holding the snap claw 603, a user (e.g., the subject 180) may easily connect (or disconnect) the gas filter component 600 with (or from) the respiratory ventilation apparatus 110. Accordingly, a pair of limitation holes 704 (see FIG. 7B) may be set at two sides of the gas inlet port 112 to cooperate with the snap claw 603 and the snap claw 603 respectively, so that the gas filter component 600 can be fixed on the respiratory ventilation apparatus 110.

For ensuring a sealed connection between the gas filter component 600 and the respiratory ventilation apparatus 110, a sealing element (e.g., a silicone gasket) may be set between the gas outlet end 609 and the gas inlet port 112 of the respiratory ventilation apparatus 110. For example, a sealing element may be set at the gas outlet end 609. As another example, a sealing element may be set at the gas inlet port 112 of the respiratory ventilation apparatus 110 (see 706 in FIG. 7B).

In some embodiments, the gas filter component 600 may further include a first baffle (not shown). In some embodiments, the first baffle may have an area less than the gas inlet end 602 of the housing 601. In some embodiments, the first baffle may be mounted in the housing 601 closer to the gas inlet end 602 than the gas filter unit(s). In some embodiments, the coarse filter may be positioned closer to the gas inlet end 602 of the housing 601 than the fine filter. For example, the first baffle may be mounted between the first cover plate 604 and the first gas filter unit 605. In some embodiments, the first baffle may cause the respiratory gas to flow from one or more sides (e.g., four sides) of the first baffle into the gas filter component 600, so that the noise generated by the gas flowing may be reduced.

In some embodiments, the gas filter component 600 may be set between the gas outlet port of the respiratory ventilation apparatus 300 and the respiration tube 160. In some embodiments, the gas outlet end 609 may have the shape of a funnel, so that the gas outlet end 609 can be connected with the respiration tube 160.

It should be noted that in some embodiments, the gas filter component 600 may be configured as protruding out of the shell of the respiratory ventilation apparatus 110. In some embodiments, there may be a certain distance between the first gas filter unit 605 and the second gas filter unit 606. In some embodiments, the gas filter component 600 may be equipped with one or more grilles between the first gas filter unit 605 and the second gas filter unit 606. In some embodiments, the first gas filter unit 605 may be set on the first cover plate 604. In some embodiments, the second gas filter unit 606 may be set on the second cover plate 607. In some embodiments, both the first gas filter unit 605 and the second gas filter unit 606 may be set on the first cover plate 604. In some embodiments, both the first gas filter unit 605 and the second gas filter unit 606 may be set on the second cover plate 607. In some embodiments, the number of the holes set on the first cover plate 604 may be larger than the number of the holes set on the second cover plate 607.

Figure 7A:
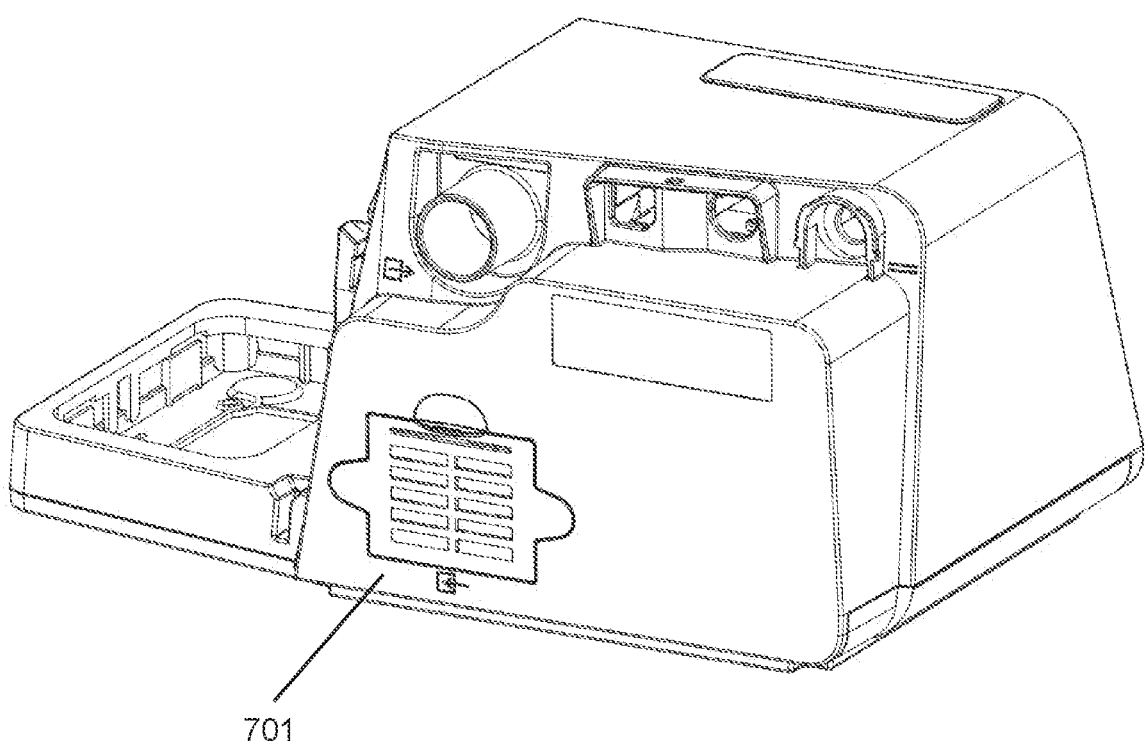
FIGS. 7A and 7B illustrate an exemplary gas filter unit according to some embodiments of the present disclosure.
Figure 7B:
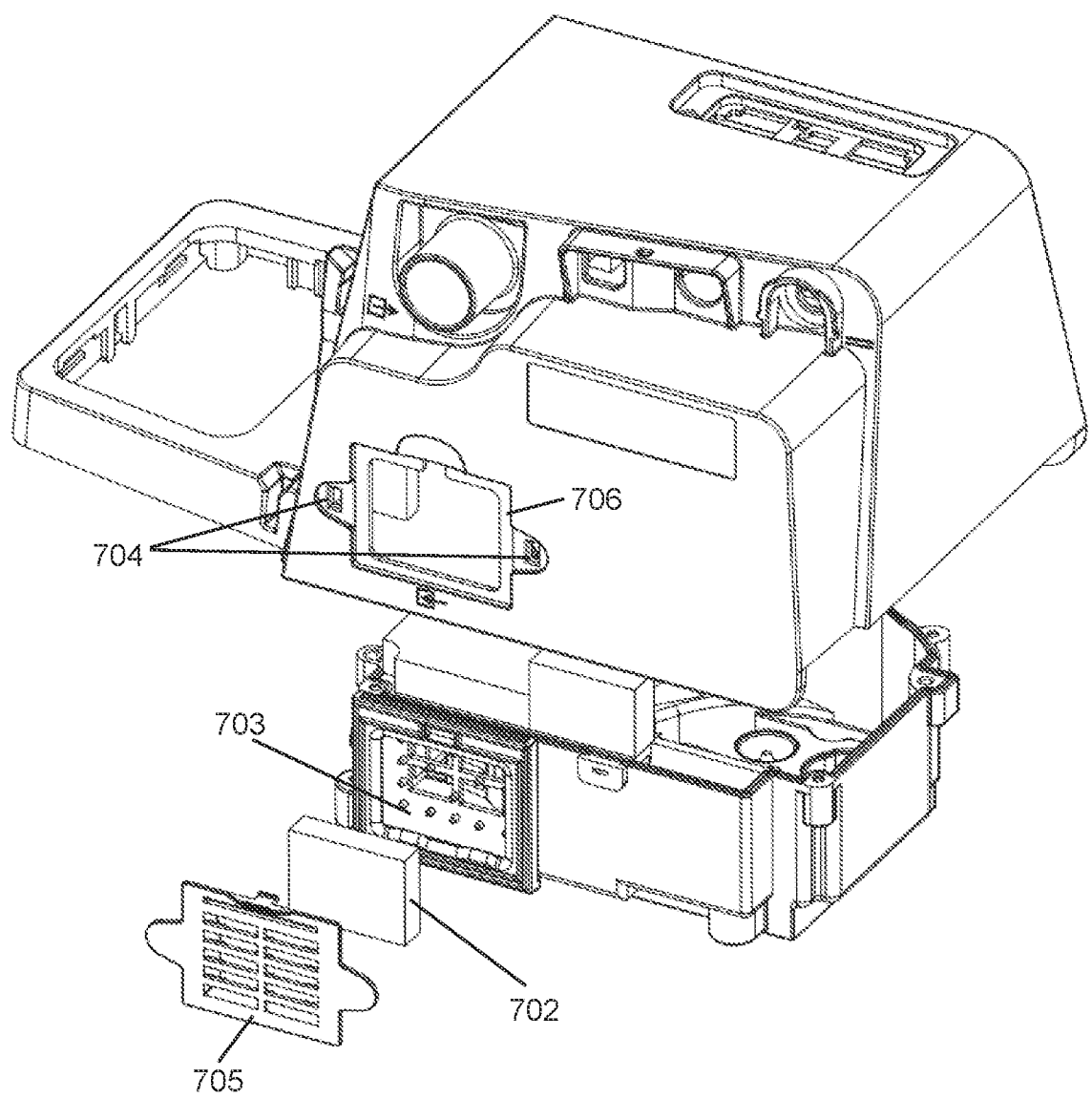

FIGS. 7A and 7B illustrate an exemplary gas filter unit according to some embodiments of the present disclosure. FIG. 7A shows an axonometric drawing of the respiratory ventilation apparatus 300 (without the humidification assembly 220) illustrating a rear side of the respiratory ventilation apparatus 300. FIG. 7B shows an exploded view of the respiratory ventilation apparatus 300.

The respiratory ventilation apparatus 300 may include a third gas filter unit 702. In some embodiments, the third gas filter unit 702 may be set at the gas inlet port 701 of the respiratory ventilation apparatus 300. In some embodiments, the third gas filter unit 702 may be configured to filter the respiratory gas (e.g., ambient gas) entering the gas inlet port 701. The third gas filter unit 702 may include a coarse filter and/or a fine filter. More descriptions of the coarse filter and/or the fine filter may be found elsewhere in the present disclosure (e.g., FIGS. 6A-6E and the descriptions thereof). In some embodiments, the third gas filter unit 702 may be mounted inside the gas inlet port of the respiratory ventilation apparatus 300, between the gas inlet port of the respiratory ventilation apparatus 300 and a gas inlet port of the gas pressurization unit 210, at the gas inlet port of the gas pressurization unit 210, at a gas outlet port of the gas pressurization unit 210, between the gas outlet port of the gas pressurization unit 210 and the gas outlet port of the respiratory ventilation apparatus 300, at the gas outlet port of the respiratory ventilation apparatus 300, in the respiration tube 160, and/or in the subject interface 170. For example, the third gas filter unit 702 may be set between the gas outlet port of the respiratory ventilation apparatus 300 and the respiration tube 160.

In some embodiments, the gas inlet port 701 may include or be equipped with a second baffle 705 and/or a third baffle 703. In some embodiments, one or more limitation holes 704 may be set at one or more sides of the gas inlet port 701. The limitation hole(s) 704 may be configured to facilitate the fixation of an additional gas filter component (e.g., the gas filter component 600 shown in FIGS. 6A-6E). The second baffle 705 and the third baffle 703 may be configured to fix the third gas filter unit 702 at the gas inlet port 701. In some embodiments, the third gas filter unit 702 may be fixed between the second baffle 705 and the third baffle 703. The second baffle 705 may include a plurality of holes, so that the respiratory gas can flow through the second baffle 705. The holes may have various shapes. For example, as shown in FIG. 7B, the holes may have a shape of a strip. It should be noted that in some embodiments, if an additional gas filter component (e.g., the gas filter component 600 shown in FIGS. 6A-6E) is in use, the second baffle 705 may be discharged from the gas inlet port 701. If the additional gas filter component is not in use, the second baffle 705 may be mounted at the gas inlet port 701, and the second baffle 705 may cover the limitation hole(s) 704. In some embodiments, the third baffle 703 may be a cross baffle. The third baffle 703 may include a plurality of protrusions configured to support the third gas filter unit 702. In some embodiments, the edge 706 of the gas inlet port 701 may include or be equipped with a sealing element, so as to form a sealing connection between the additional gas filter component and the gas inlet port 701.

In some embodiments, the respiratory ventilation apparatus 300 may include a fourth gas filter unit. The fourth gas filter unit may be configured to filter one or more gases with pungent smell and/or one or more harmful gases (e.g., methanol) in one or more gas passages of the respiratory ventilation apparatus 300. In some embodiments, the fourth gas filter unit may include a membrane manufactured by one or more nanomaterials having adsorption ability. The one or more nanomaterials may include activated carbon, graphene, graphene oxide, carbon nanotube, or the like, or any combine thereof. The one or more nanomaterials may have large specific surface area. A large specific surface area may indicate a large number of surface atoms. Surface atoms may be more reactive than inner layer atoms and may be more likely to adsorb gas molecules. Therefore, a larger specific surface area of a nanomaterial may indicate a stronger adsorption ability.

If the respiratory ventilation apparatus 300 is used by a patient in a hospital, the pungent smell may be a smell of hospital disinfectant. If the respiratory ventilation apparatus 300 is used by a user at home, the pungent smell may be a smell of smoking and/or cooking fume. In some embodiments, the fourth gas filter unit may be mounted outside the gas inlet port of the respiratory ventilation apparatus 300, at the gas inlet port of the respiratory ventilation apparatus 300, inside the gas inlet port of the respiratory ventilation apparatus 300, between the gas inlet port of the respiratory ventilation apparatus 300 and a gas inlet port of the gas pressurization unit 210, at the gas inlet port of the gas pressurization unit 210, at a gas outlet port of the gas pressurization unit 210, between the gas outlet port of the gas pressurization unit 210 and the gas outlet port of the respiratory ventilation apparatus 300, at the gas outlet port of the respiratory ventilation apparatus 300, in the respiration tube 160, and/or in the subject interface 170. For example, the fourth gas filter unit may be set between the gas outlet port of the respiratory ventilation apparatus 300 and the respiration tube 160.

In some embodiments, the respiratory ventilation apparatus 300 may include a fifth gas filter unit. The fifth gas filter unit may be configured to filter bacteria in one or more gases in one or more gas passages of the respiratory ventilation apparatus 300. In some embodiments, after long-term use, a large amount of bacteria may be propagated in the respiratory ventilation apparatus 300. The fifth gas filter unit may include a membrane to filter bacteria. The membrane may use one or more physical or chemical techniques to realize bacteria filtration. The physical or chemical techniques may include high efficiency particulate air filter (HEPA) with H13 grade or above, plasma sterilizing technology, photo catalyst sterilizing technology (e.g., titanium dioxide as the catalyst for base material, CH-CUT technology with CH-CUT nanomaterial as the core, etc.), semiconductor catalytic sterilization technology, or the like, or any combine of thereof. In some embodiments, the fifth gas filter unit may be mounted outside the gas inlet port of the respiratory ventilation apparatus 300, at the gas inlet port of the respiratory ventilation apparatus 300, inside the gas inlet port of the respiratory ventilation apparatus 300, between the gas inlet port of the respiratory ventilation apparatus 300 and a gas inlet port of the gas pressurization unit 210, at the gas inlet port of the gas pressurization unit 210, at a gas outlet port of the gas pressurization unit 210, between the gas outlet port of the gas pressurization unit 210 and the gas outlet port of the respiratory ventilation apparatus 300, at the gas outlet port of the respiratory ventilation apparatus 300, in the respiration tube 160, and/or in the subject interface 170. For example, the fifth gas filter unit may be set between the gas outlet port of the respiratory ventilation apparatus 300 and the respiration tube 160. In some embodiments, considering moist gas may be more suitable for bacteria breeding, the fifth gas filter unit may be mounted in a gas passage between the liquid chamber 222 and the gas outlet port of the respiratory ventilation apparatus 300. In some embodiments, the respiratory ventilation apparatus 300 may include one or more gas filter units (e.g. the third gas filter unit, the fourth gas filter unit, the fifth gas filter unit, etc.) mounted in the respiration tube 160 and/or the subject interface 170.

It should be noted that in some embodiments, the filter sponges of one or more of the first gas filter unit, the second filter unit, the third filter unit, the fourth gas filter unit, and the fifth gas filter unit, may have different materials, different shapes, and/or different colors. In some embodiments, to facilitate the replacement of the filter unit(s), the first gas filter unit, the second filter unit, the third filter unit, the fourth gas filter unit, and/or the fifth gas filter unit may be mounted at a connection position of two components of the respiratory ventilation apparatus 300 (e.g., a connection position between the main body of the respiratory ventilation apparatus 300 and the liquid chamber, a connection position between the gas outlet port of the respiratory ventilation apparatus 300 and the respiration tube 160, a connection position between the respiration tube 160 and the subject interface 170, etc.). In some embodiments, the filter unit(s) may be discharged from the respiratory ventilation apparatus 300 and may be stored under appropriate conditions (e.g., a drying closet, a sterilizer, a storage box, a dust-proof box, etc.).

In some embodiments, an ultrasonic atomizer may be used in the humidification assembly 220, and droplets of one or more therapeutic drugs and/or one or more liquids may be generated and introduced into the respiratory gas. In some embodiments, one or more filter units illustrated above may be used to filter harmful particulates in the droplets of therapeutic drugs and/or liquids, and/or the respiratory gas. In some embodiments, the filter sponges of the filter unit(s) may include a hydrophobic surface.

Figure 8A:
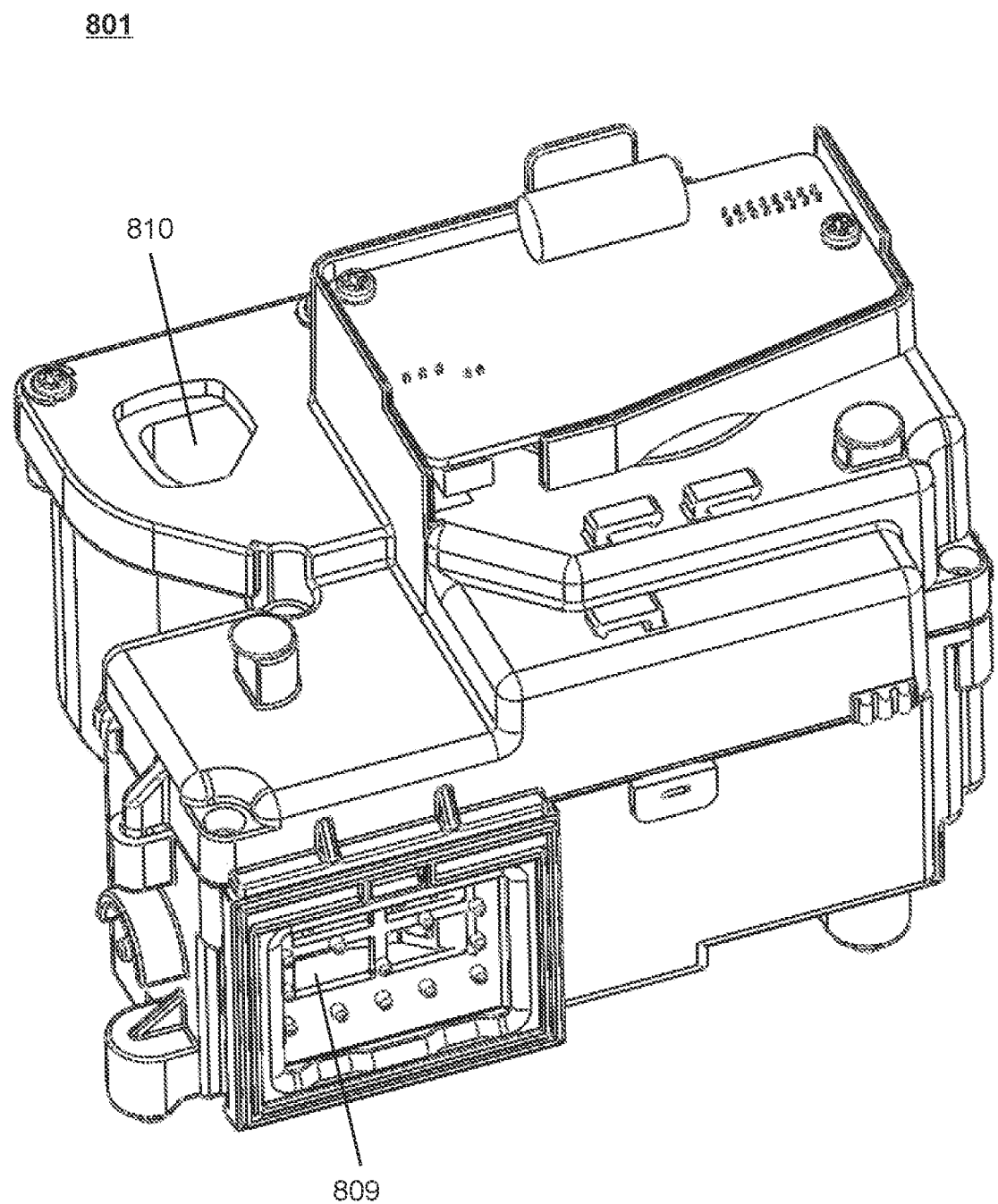
FIGS. 8A-8D illustrate different views of an exemplary noise reduction assembly according to some embodiments of the present disclosure.
Figure 8B:
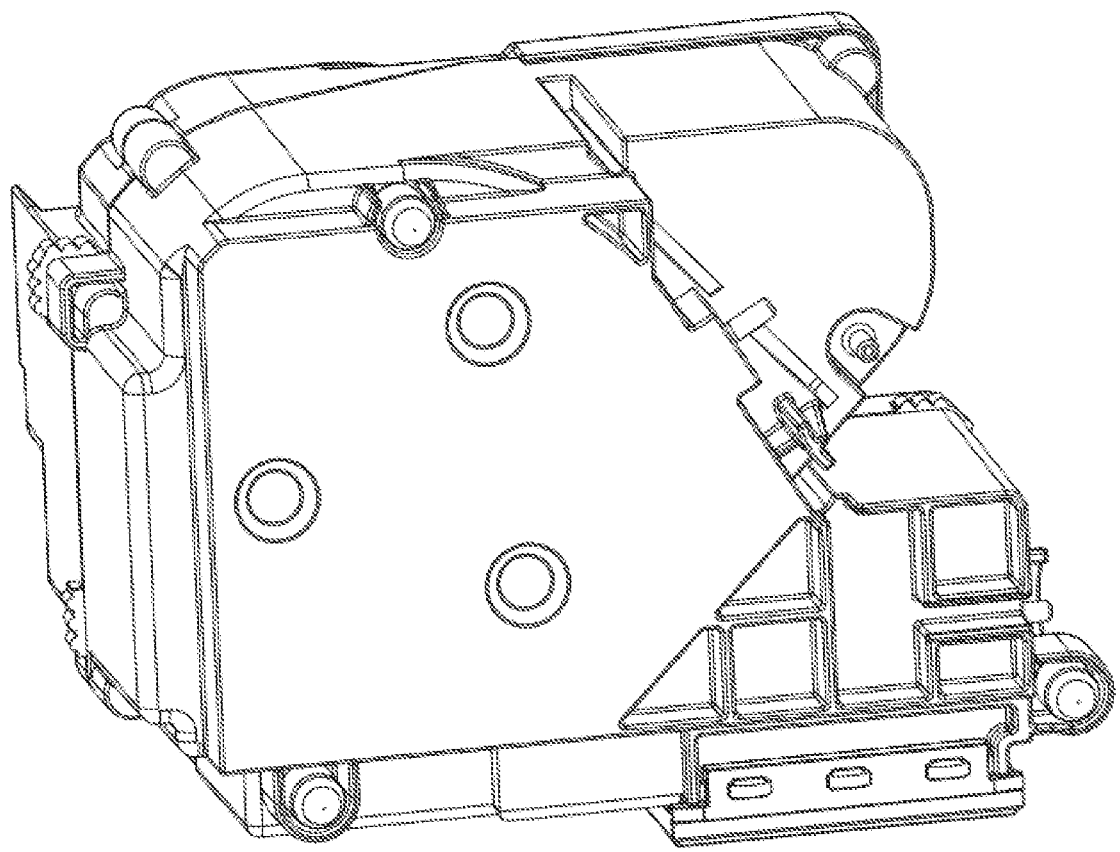
Figure 8C:
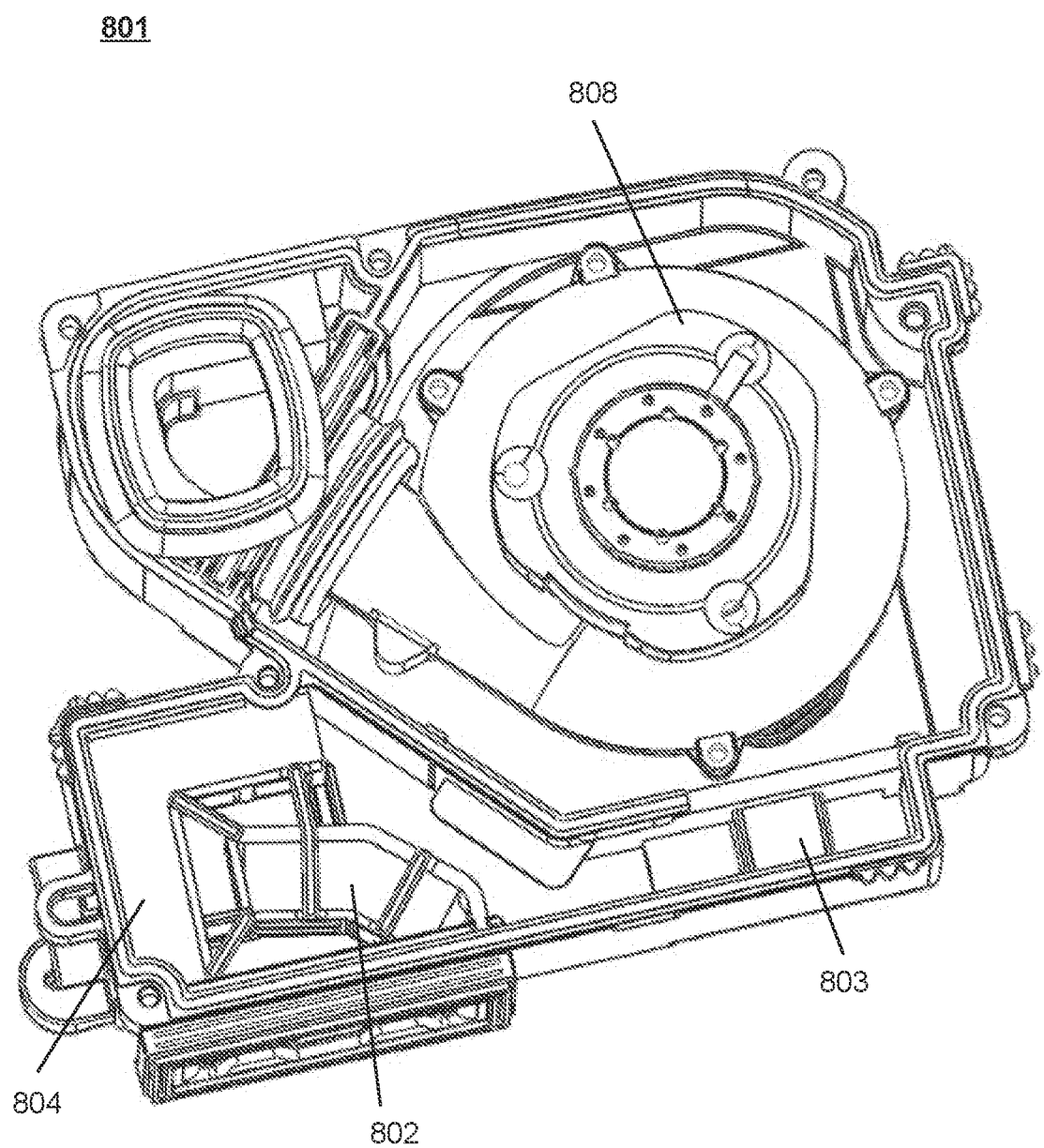
Figure 8D:
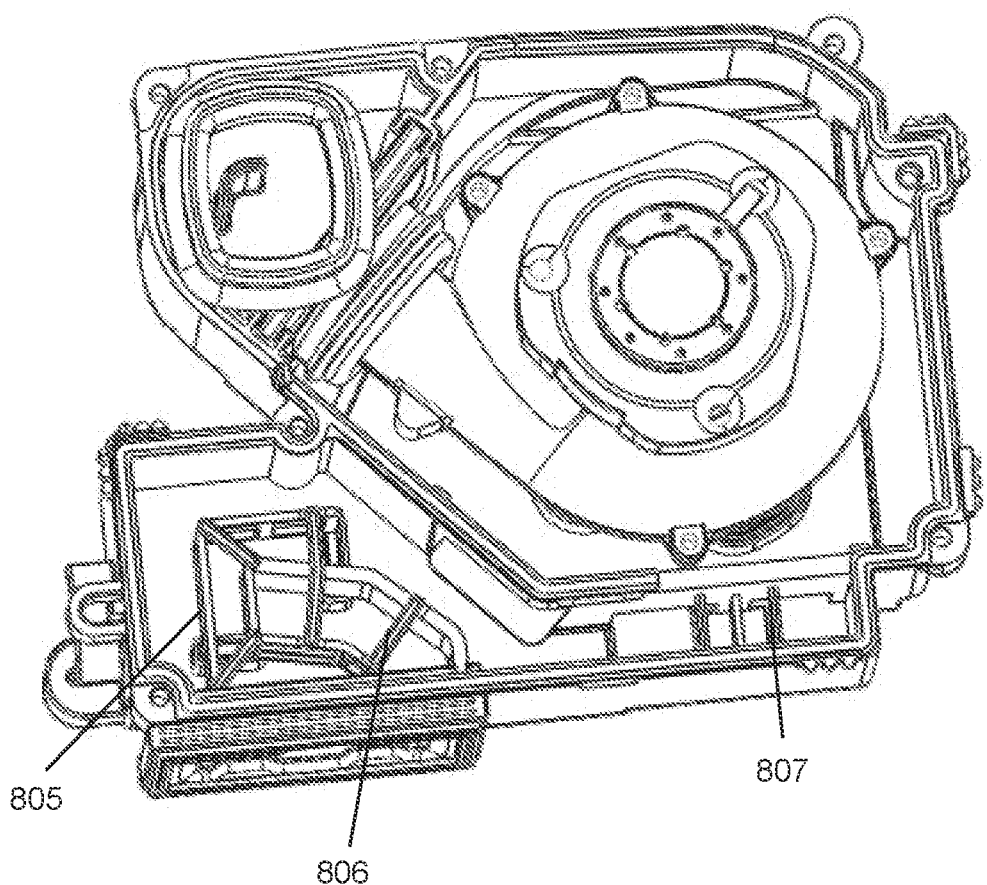
Figure 9A:
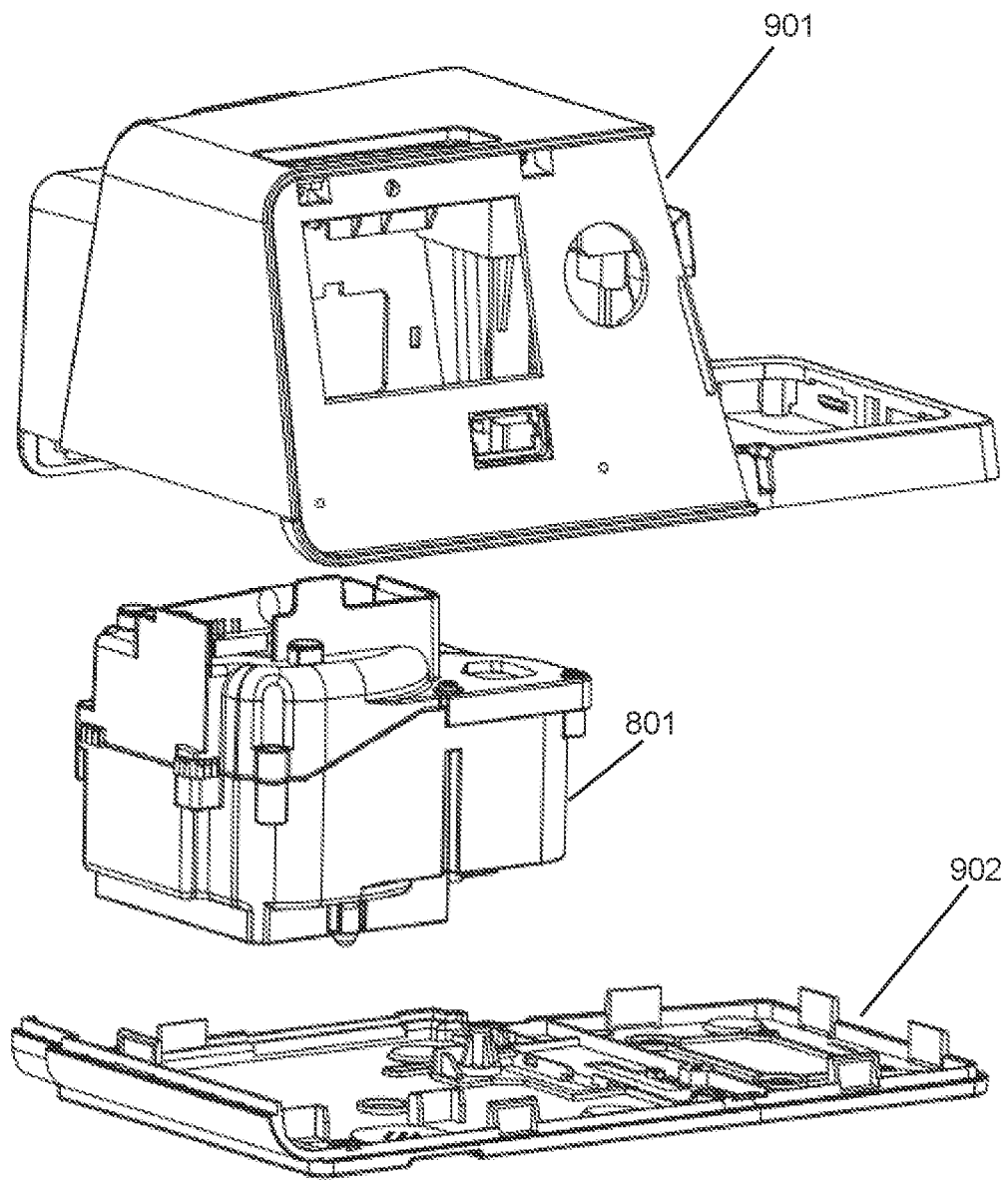
FIGS. 9A-9E illustrate an exemplary connection between a noise reduction assembly and a main body of a respiratory ventilation apparatus according to some embodiments of the present disclosure.
Figure 9B:
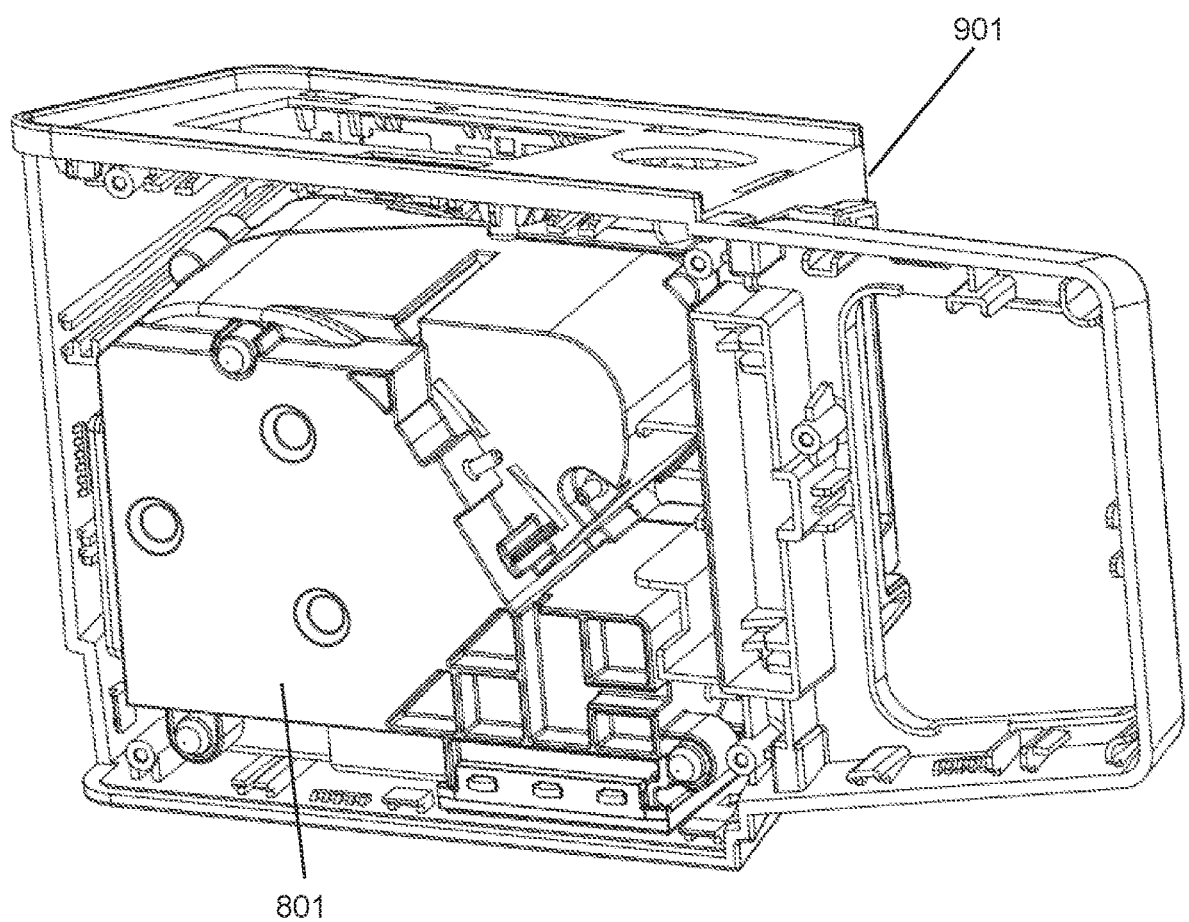
Figure 9C:
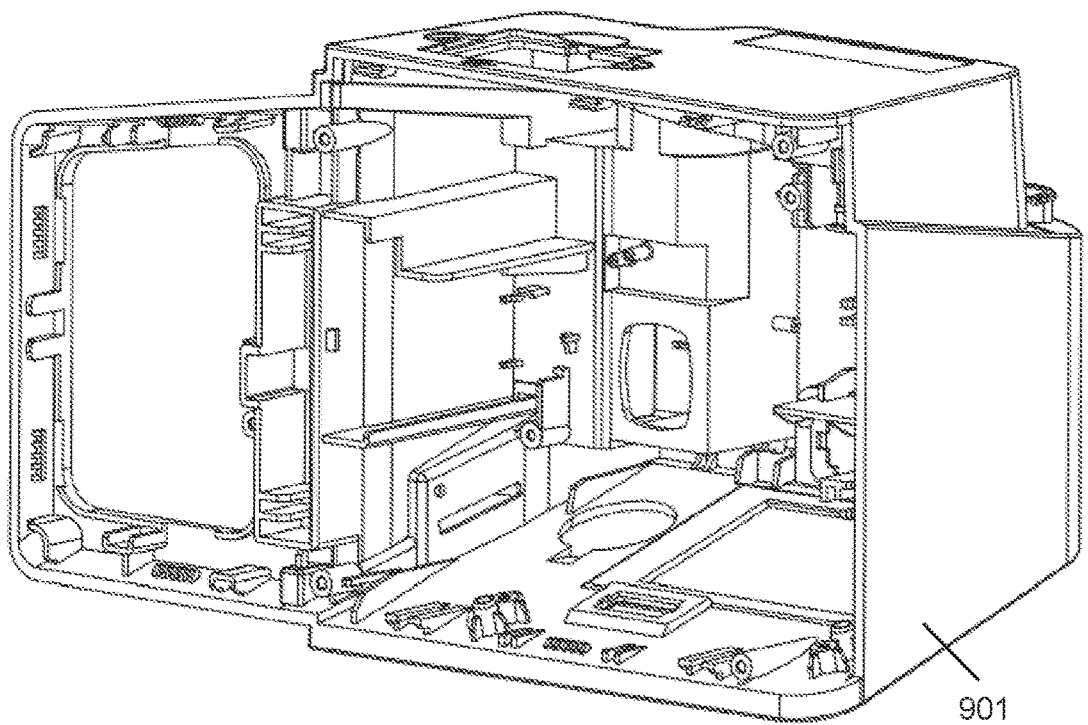
Figure 9D:
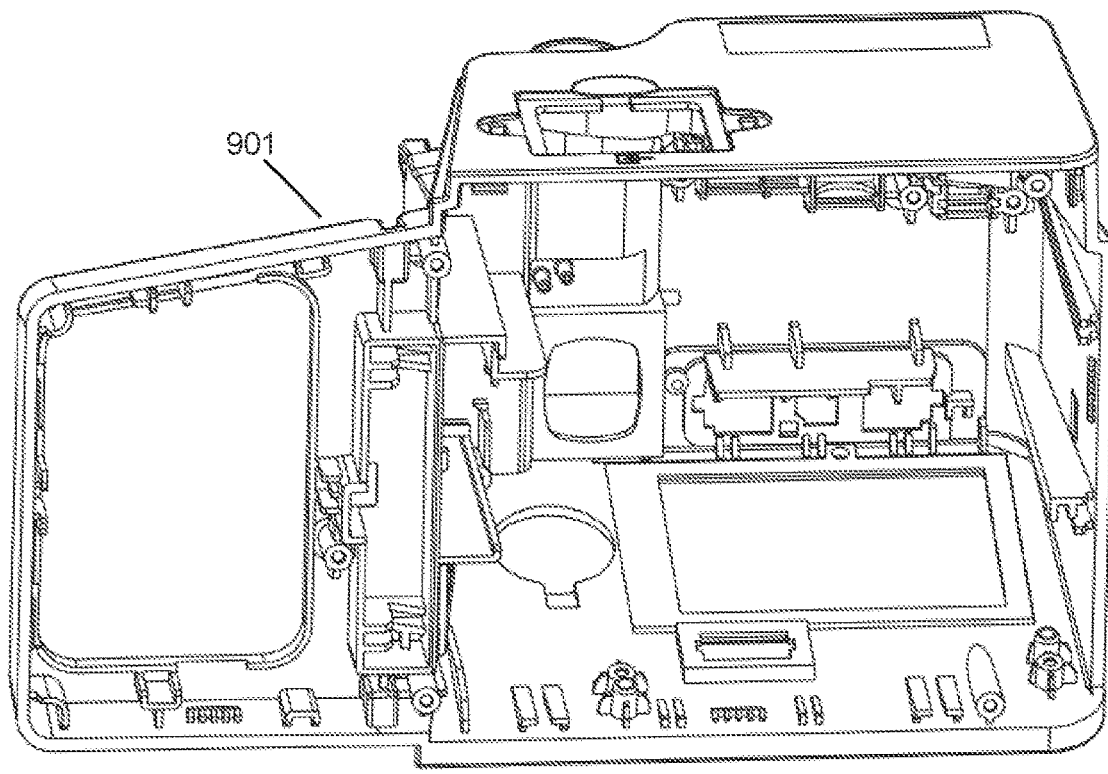
Figure 9E:
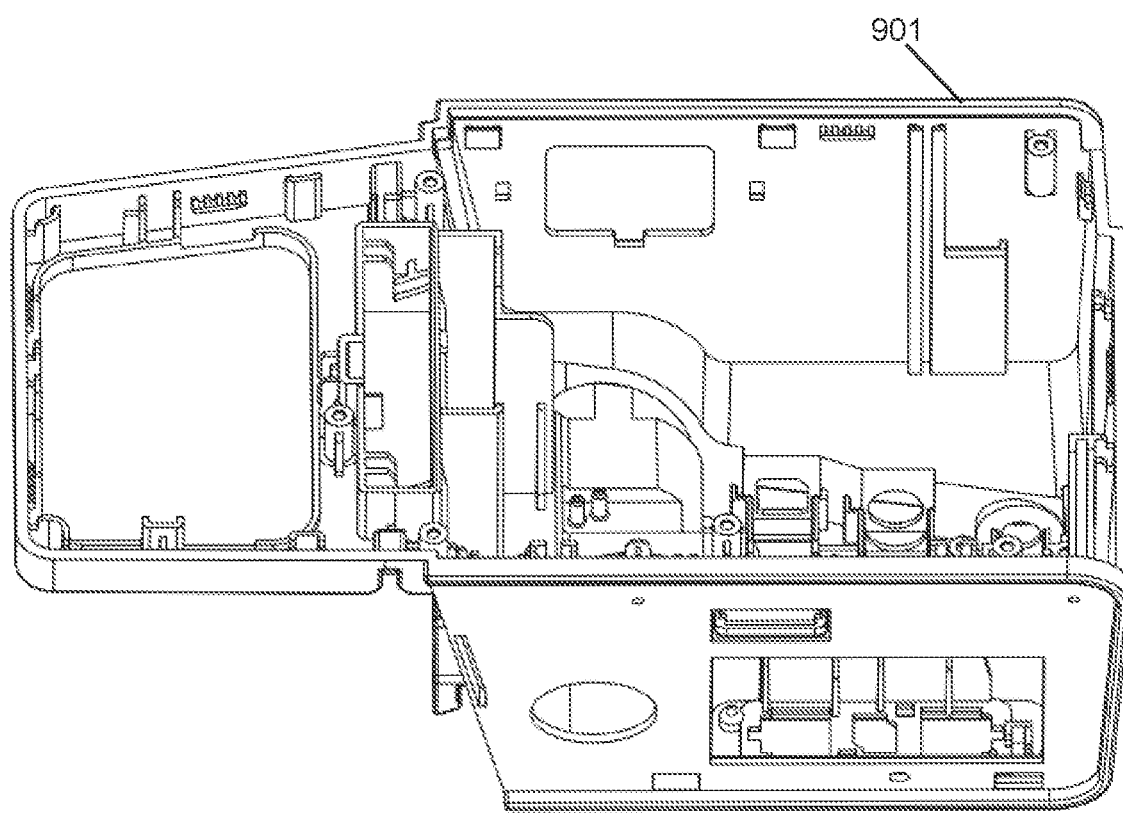

FIGS. 8A-8D illustrate different views of an exemplary noise reduction assembly according to some embodiments of the present disclosure. FIG. 8A shows an axonometric drawing of the noise reduction assembly 8. FIG. 8B shows a bottom surface of the noise reduction assembly 8. FIG. 8C shows an internal structure of the noise reduction assembly 8 with sound absorbing materials. FIG. 8D shows an internal structure of the noise reduction assembly 8 without sound absorbing materials. The noise reduction assembly 8 may be configured to reduce noise generated by a gas pressurization unit 808 and/or the noise generated by the flowing of the (pressurized) respiratory gas in the gas passage(s) of the respiratory ventilation apparatus 110. The noise reduction assembly 8 may include a noise reduction box 801, one or more sound absorbing materials, and/or one or more frames.

In some embodiments, the noise reduction box 801 may be a sealed box with a gas inlet port 809 (e.g., a gas inlet port for introducing respiratory gas into the noise reduction box 801) and a gas outlet port 810 (e.g., a gas outlet port for outputting (pressurized) respiratory gas). In some embodiments, the gas inlet port 809 of the noise reduction box 801 may be in a sealed connection with an inner side of the gas inlet port 112 of the respiratory ventilation apparatus 110, so that the respiratory gas entering the gas inlet port 112 of the respiratory ventilation apparatus 110 may directly flow into the noise reduction box 801. In some embodiments, the gas inlet port 809 of the noise reduction box 801 may be configured as the gas inlet port 112 of the respiratory ventilation apparatus 110.

The noise reduction box 801 may accommodate the gas pressurization unit 808. The gas pressurization unit 808 may include a blower (not shown) configured to generate a flow of pressurized respiratory gas based on the gas introduced in the respiratory ventilation apparatus 110. In some embodiments, after being filtered by one or more gas filter units mounted inside the gas inlet port, the respiratory gas may enter the gas pressurization unit 808 and be pressurized by the blower, and pressurized respiratory gas may be generated. The pressurized respiratory gas may be discharged from the noise reduction box 801 to an inner gas passage of the respiratory ventilation apparatus 110 via the gas outlet port 810.

In some embodiments, the noise reduction box 801 may include one or more sound absorbing materials (e.g. an L-type sound absorbing material 804, a broken line type sound absorbing material 802, a rectangular sound absorbing material 803). The sound absorbing materials may be set on the inner walls of the noise reduction box 801. As shown in FIG. 8C, the L-type sound absorbing material 804 and the broken line type sound absorbing material 802 may be set close to the gas inlet port 809. A rectangular sound absorbing material 803 may be set close to the gas pressurization unit 808.

In some embodiments, the one or more sound absorbing materials may include porous materials, panel materials, resonance materials, or the like, or any combine thereof. Exemplary porous materials may include carpet, draperies, spray-applied cellulose, aerated plaster, fibrous mineral wool and glass fiber, open-cell foam, felted or cast porous ceiling tile, or the like, or a combination thereof. In some embodiments, porous materials may be the most commonly used sound absorbing materials. In some embodiments, the thickness of the porous materials may be important in sound absorption. The sound-absorbing effect of the porous materials may stem from the fact that the sound energy may penetrate the porous materials when hitting the surface of the porous materials. In some embodiments, the sound energy may be converted into heat energy, so that only a relatively small part may be reflected in the form of sound energy. In other words, the porous material may absorb a portion of the sound. In some embodiments, panel materials may be non-rigid, non-porous materials. The panel materials may be placed over an airspace that vibrates in a flexural mode in response to sound pressure exerted by adjacent gas molecules. Exemplary panel (or membrane) materials may include thin wood. In some embodiments, panel materials may be configured to absorb low-frequency noises. Resonance materials may be configured to absorb sound in a relatively narrow frequency range. Resonance materials may include some perforated materials and materials that have openings (holes and slots). An exemplary resonance material may include the Helmholtz resonance material, which may have a shape of a bottle. The resonant frequency may be governed by the size of the opening, the length of the neck, and the volume of gas trapped in the bottle-shaped chamber.

In some embodiments, the noise reduction box 801 may further include one or more frames configured to fix the one or more sound absorbing materials. In some embodiments, the size and/or shape of the frame(s) and that of the corresponding sound absorbing materials may be matched. As shown in FIG. 8D, a frame 805 and a frame 806 may be configured to fix the L-type sound absorbing material 804 and the broken line type sound absorbing material 802 on the inner walls of noise reduction box 801, respectively. A frame 807 may be configured to fix the rectangular sound absorbing material 803. It should be noted that not all of the sound absorbing materials and the frames are shown in FIGS. 8C and 8D. For the purpose of illustration, only three sound absorbing materials and their corresponding frames are described in the preset disclosure, but not intended to limit the scope of the present disclosure.

As shown in FIGS. 8C and 8D, the one or more sound absorbing materials and/or the one or more frames may form a gas passage with one or more twists and/or one or more turns in the noise reduction box 801. The gas passage in the noise reduction box 801 may be divided into a plurality of sub gas passages with different cross sections. The noise generated by the blower may constantly collide with the sound absorbing materials, resulting in that the vibration energy may be continuously absorbed which and the noise may be effectively reduced in decibels. In some embodiments, the sub gas passages may form at least two damping spaces including a first damping space close to the gas inlet port 809 and a second damping space around the gas pressurization unit 808. The first damping space and the second damping space may be connected by a sub gas passage between them. In some embodiments, the at least two damping space may provide a greater arear for the respiratory gas than the sub gas passage connecting them, and then a relatively low resistance of the respiratory gas may be achieved at a relatively high velocity. Therefore, the noise (especially high frequency components of the noise) generated by the flowing of the respiratory gas may be effectively reduced.

FIGS. 9A-9E illustrate an exemplary connection between a noise reduction assembly and a main body of a respiratory ventilation apparatus according to some embodiments of the present disclosure. In some embodiments, the noise reduction box 801 may be fixed between a shell cover 901 of the respiratory ventilation apparatus 110 and a baseplate 902 of the respiratory ventilation apparatus 110. In some embodiments, the noise reduction box 801 may include one or more protruding structures and/or one or more grooves. In some embodiments, the shell cover 901 and/or the baseplate 902 may including one or more corresponding grooves and/or one or more corresponding protruding structures configured to cooperate with the protruding structure(s) and/or the groove(s), so that the noise reduction box 801 may be fixed between the shell cover 901 and the baseplate 902.

Figure 10A:
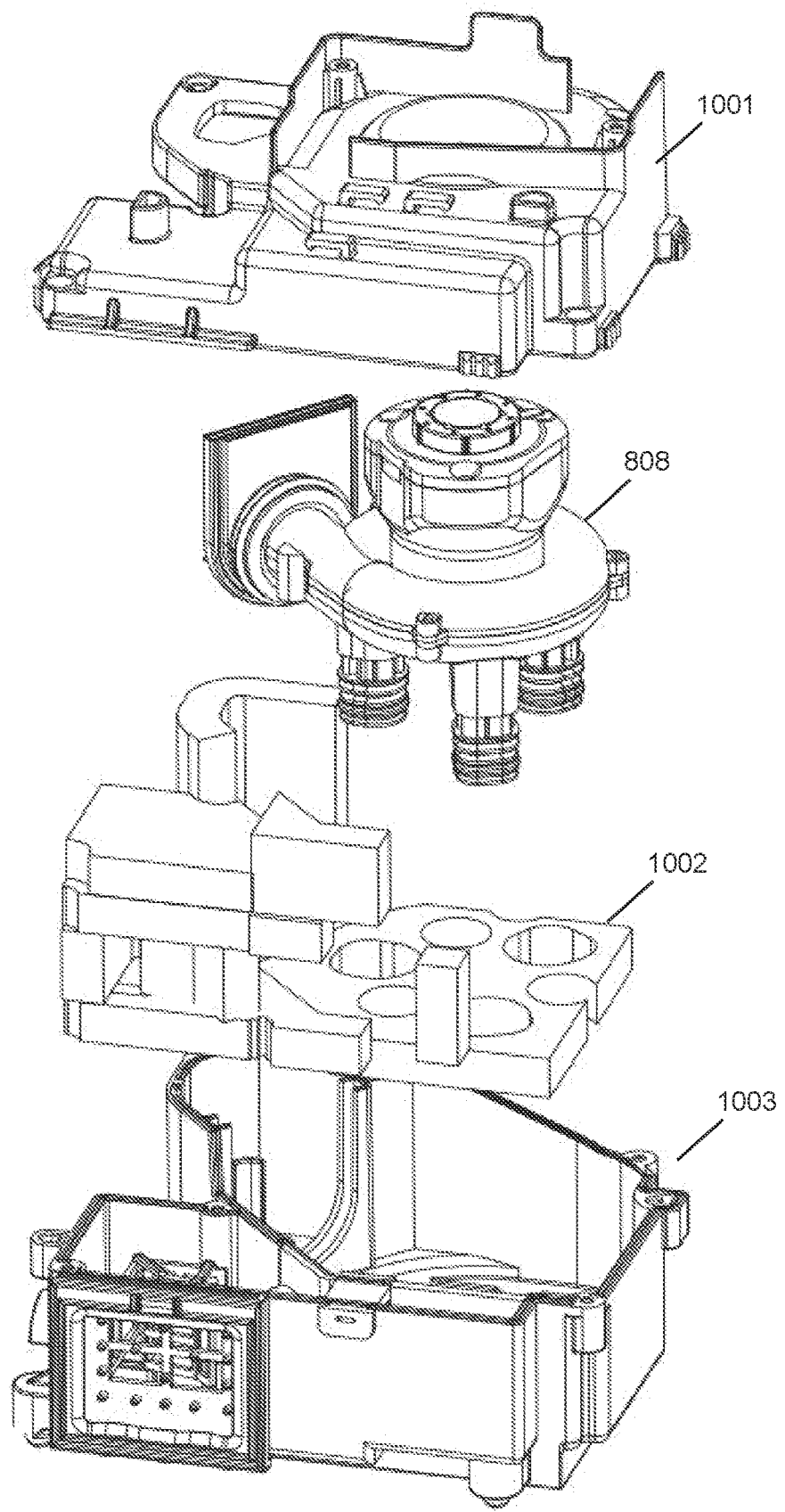
FIGS. 10A-10C illustrate exemplary exploded views of a noise reduction assembly according to some embodiments of the present disclosure.
Figure 10B:
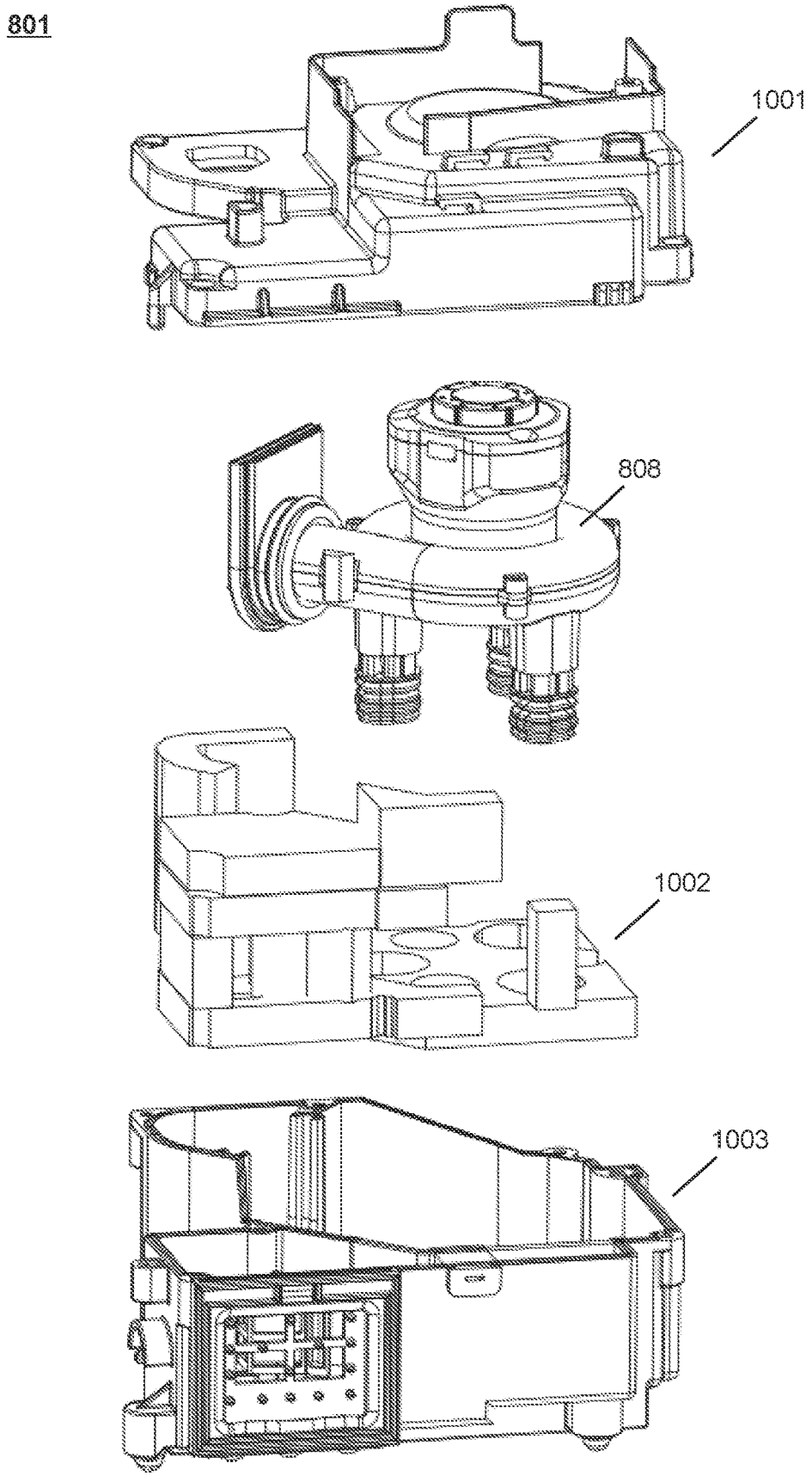
Figure 10C:
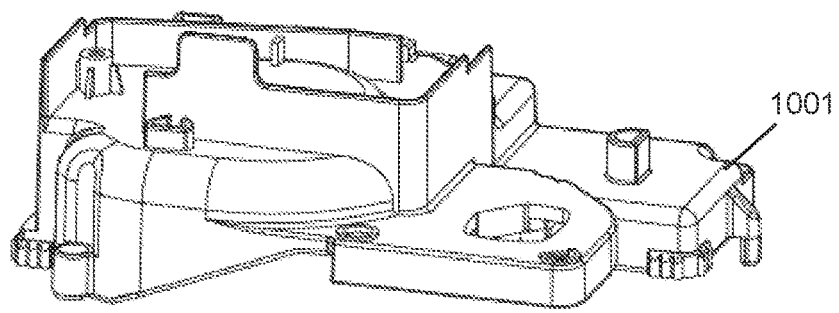
Figure 10C:
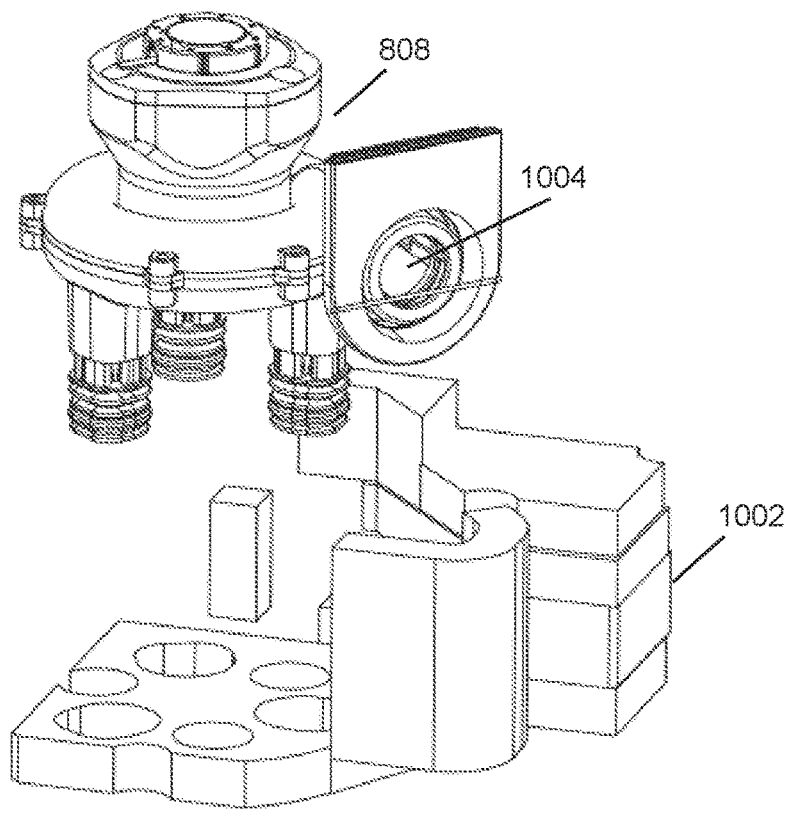
Figure 10C:
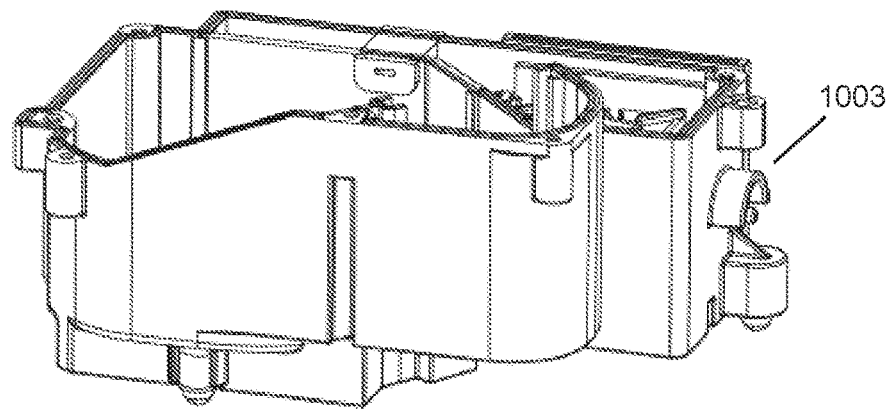

FIGS. 10A-10C illustrate exemplary exploded views of a noise reduction assembly according to some embodiments of the present disclosure. The noise reduction box 801 may include a box cover 1001, a box body 1003, and a filling part 1002. The noise reduction box 801 may accommodate the gas pressurization unit 808. In some embodiments, the filling part 1002 may be set around the gas pressurization unit 808. The filling part 1002 may include a plurality of sound absorbing materials configured to reduce noise generated in the noise reduction box 801. The gas pressurization unit 808 may include a gas inlet port (not shown in FIGS. 10A-10C) and a gas outlet port 1004. The gas inlet port of the gas pressurization unit 808 may be configured to introduce respiratory gas from the noise reduction box 801 into the gas pressurization unit 808. The gas outlet port 1004 may be configured to discharge the pressurized respiratory gas from the gas pressurization unit 808 to the gas passages of the main body of the respiratory ventilation apparatus 110.

FIGS. 11A-11F illustrate an exemplary connection between a gas pressurization unit and a noise reduction box according to some embodiments of the present disclosure. In some embodiments, the noise reduction box 801 may further include one or more supports (e.g., three supports) 1102 configured to support the gas pressurization unit 808 in an inner space of the box body 1003 of the noise reduction box 801 (see FIGS. 11E and 11F). In some embodiments, the box body 1003 of the noise reduction box 801 may include one or more corresponding limitation holes 1104 configured to limit the position of the supports 1102. In some embodiments, each of the supports 1102 may include a support portion and a buffer portion. The support portion of each of the supports 1102 may be manufactured by a hard material to fix the gas pressurization unit 808 in the noise reduction box 801. The buffer portion of each of the supports 1102 may be manufactured by flexible material (e.g. silicone) to damp the vibration of the gas pressurization unit 808 to reduce noise.

In some embodiments, the gas pressurization unit 808 may include a gas inlet port 1103 configured to introduce respiratory gas from the noise reduction box 801 into the gas pressurization unit 808. In some embodiments, the gas pressurization unit 808 may include a connecting piece 1101 configured to fix the gas pressurization unit to an internal space of the noise reduction box 801. In some embodiments, the box body 1003 of the noise reduction box 801 may include a limitation groove 1105. The connecting piece 1101 may be fixed in the limitation groove 1105 so that the gas pressurization unit 808 may be fixed in the internal space of the noise reduction box 801 (see FIGS. 11E and 11F). In some embodiments, the connecting piece 1101 may damp vibration of the gas pressurization unit 808 in one or more directions. More descriptions of the connecting piece 1101 may be found elsewhere in the present disclosure (e.g., FIGS. 13A and 13B, and the descriptions thereof).

Figure 12A:
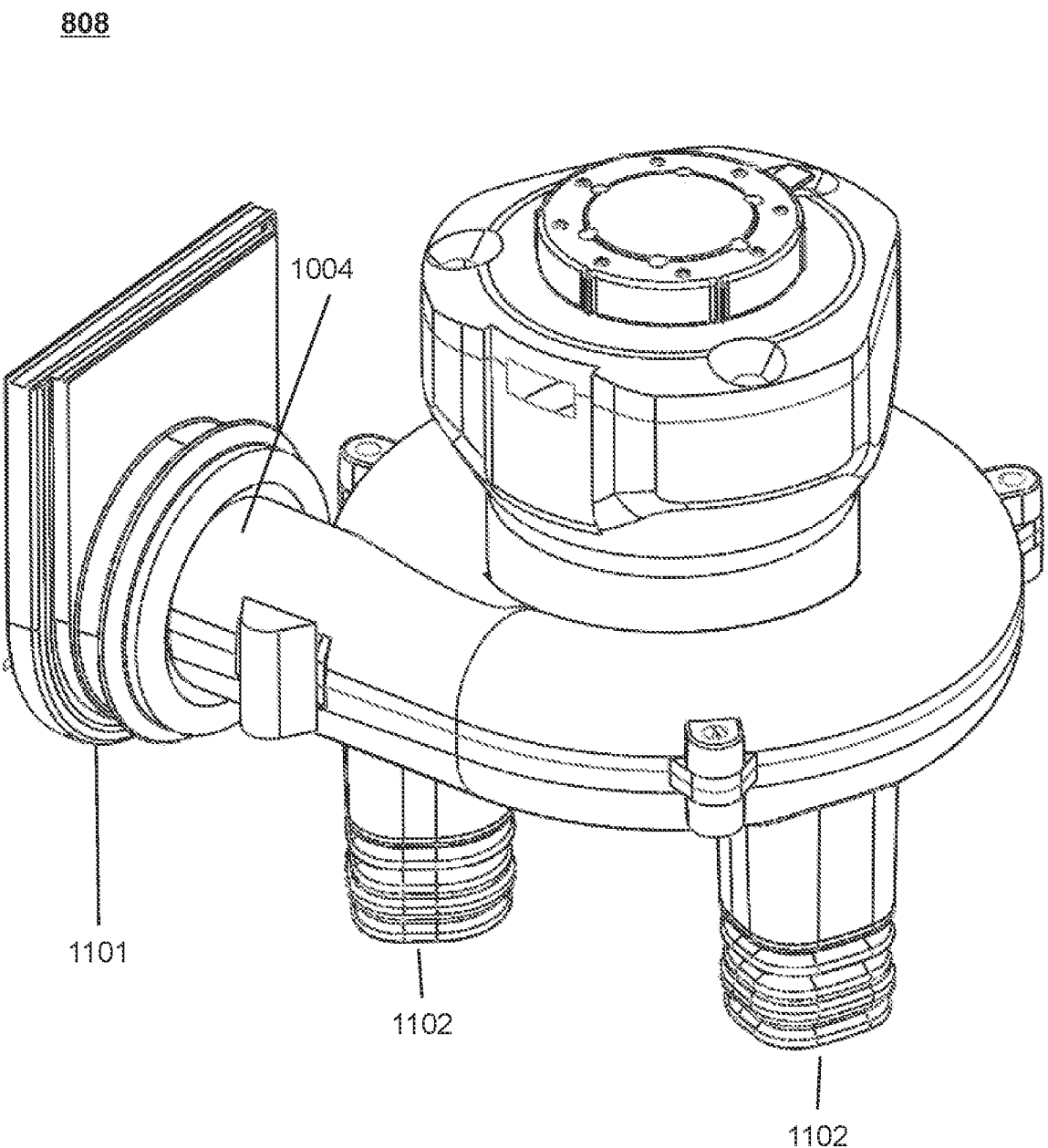
FIGS. 12A-12C illustrate an exemplary gas pressurization unit according to some embodiments of the present disclosure.
Figure 12B:
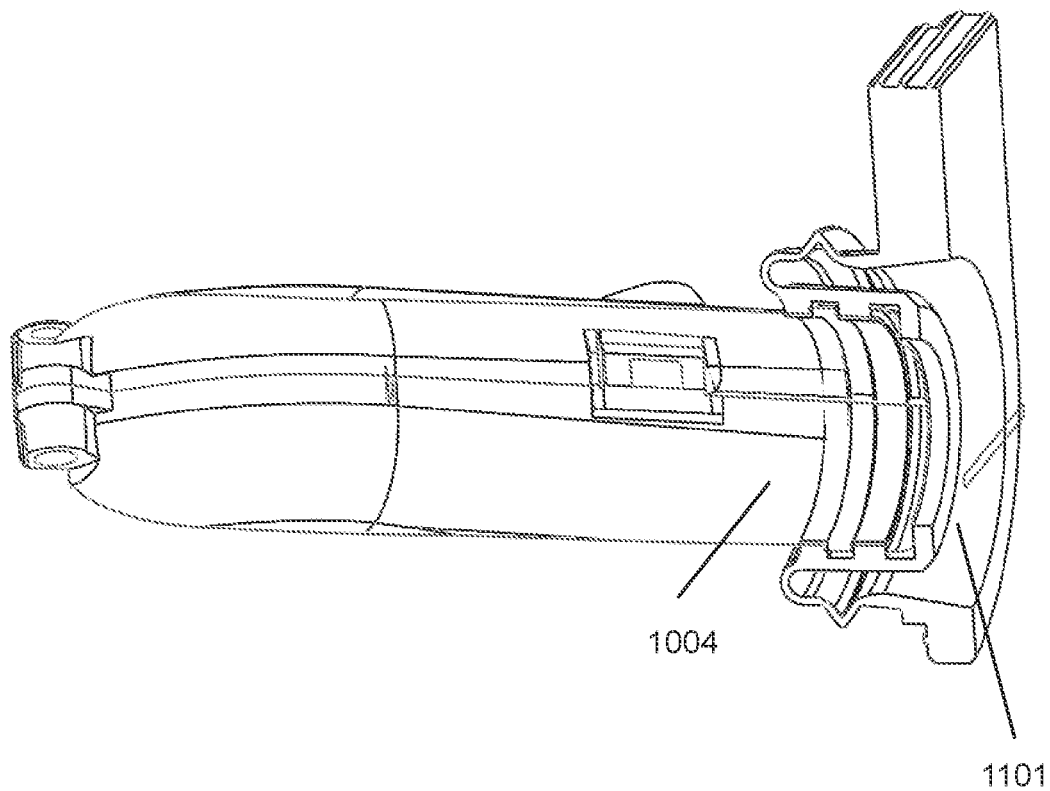
Figure 12C:
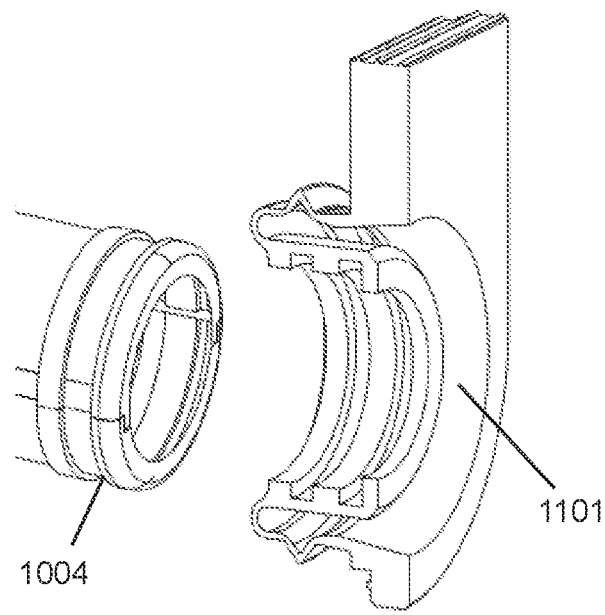

FIGS. 12A-12C illustrate an exemplary gas pressurization unit according to some embodiments of the present disclosure. As shown in FIG. 12A, the gas pressurization unit 808 may include a connecting piece 1101 and one or more supports 1102. The connecting piece 1101 may be configured to fix the gas pressurization unit 808 to an internal space of the main body of the respiratory ventilation apparatus 110. In some embodiments, the connecting piece 1101 may be configured to damp the vibration and/or impede the transmission of vibration of the gas pressurization unit 808 (e.g., to the noise reduction box 801) in one or more directions. The vibration of the gas pressurization unit 808 may be generated in transportation, operation, etc. In some embodiments, the connecting piece 1101 may be detachably connected with the gas outlet port 1004 of the gas pressurization unit 808.

FIG. 12B shows a side cross-sectional view of the connecting piece 1101 coupled to the blower according to some embodiments of the present disclosure. In some embodiments, the gas outlet port 1004 of the gas pressurization unit 808 may be connected to the connecting piece 1101 by one or more screw threads. In some embodiments, the gas outlet port 1004 of the gas pressurization unit 808 may be connected to the connecting piece 1101 by one or more protruding bumps and one or more corresponding grooves. In some embodiments, an inner surface of the gas outlet port 1004 may be connected to an outer surface of the connecting piece 1101. In some embodiments, as shown in FIG. 12B, an inner surface of the connecting piece 1101 may be connected to an outer surface of the gas outlet port 1004. Merely by way of example, as shown in FIG. 12C, two annular grooves in the inner surface of the connecting piece 1101 may be coupled to two annular protrusions on the outer surface of the gas outlet port 1004 of the gas pressurization unit 808. In some embodiments, the connecting piece 1101 may be manufactured by or include a flexible material (e.g. silicone) with elasticity. In some embodiments, the gas outlet port 1004 of the gas pressurization unit 808 may be directly inserted into the connecting piece 1101 or may be pivoted relative to the gas pressurization unit 808, such that the gas outlet port 1004 can be connected to the connecting piece 1101.

Figure 13A:
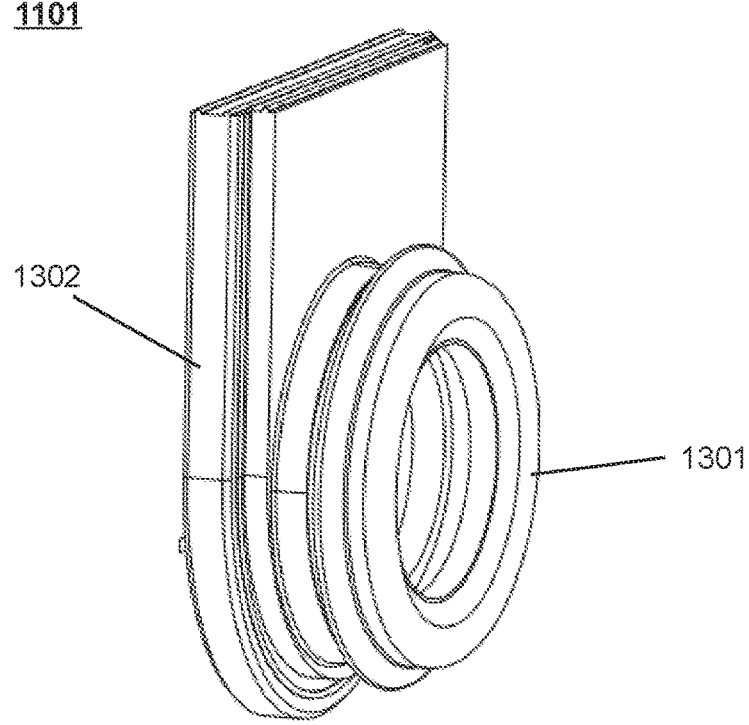
FIGS. 13A and 13B illustrate an exemplary connecting piece according to some embodiments of the present disclosure.
Figure 13B:
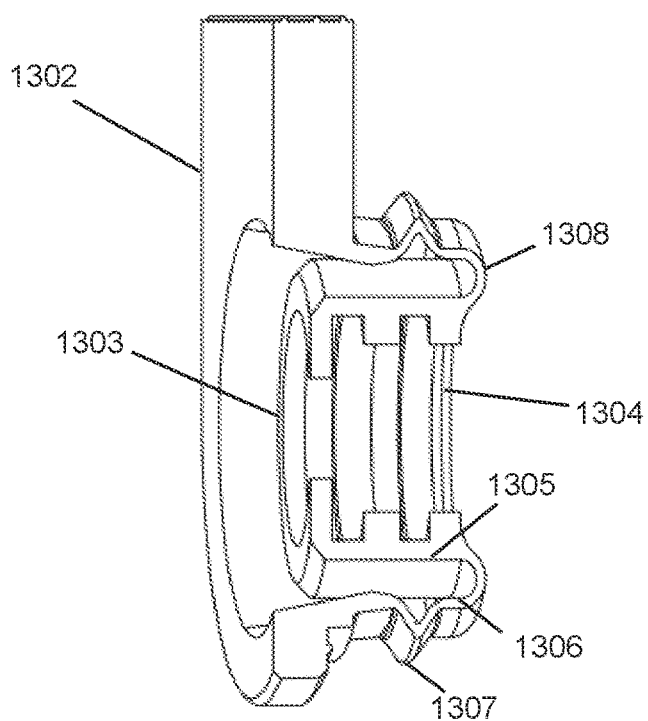

FIGS. 13A and 13B illustrate an exemplary connecting piece according to some embodiments of the present disclosure. FIG. 13A shows an axonometric drawing of the connecting piece 1101. FIG. 13B shows a side cross-sectional view of the connecting piece 1101. As shown in FIGS. 13A and 13B, the connecting piece 1101 may include a connecting part 1301 and a fixing part 1302. The connecting part 1301 and the fixing part 1302 may be made of the same or different materials. In some embodiments, the connecting part 1301 may be configured to connect with the gas outlet port 1004 (see FIG. 12B) of the gas pressurization unit 808 and/or form a sealed connection between the connecting piece 1101 and the gas pressurization unit 808. In some embodiments, to prevent the gas outlet port 1004 of the gas pressurization unit 808 from separating from the connecting part 1301, the connecting part 1301 may be made of one or more flexible materials (e.g., silicone), so that the connecting piece 1101 may tolerate or damp vibration of the gas pressurization unit 808 induced by rough handling of the respiratory ventilation apparatus 110.

Figure 11A:
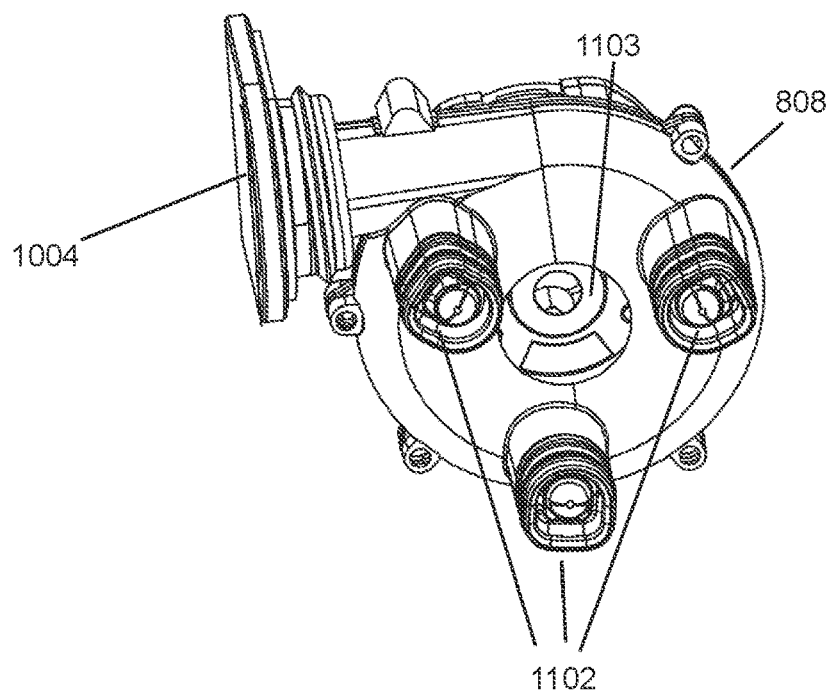
FIGS. 11A-11F illustrate an exemplary connection between a gas pressurization unit and a noise reduction box according to some embodiments of the present disclosure.
Figure 11B:
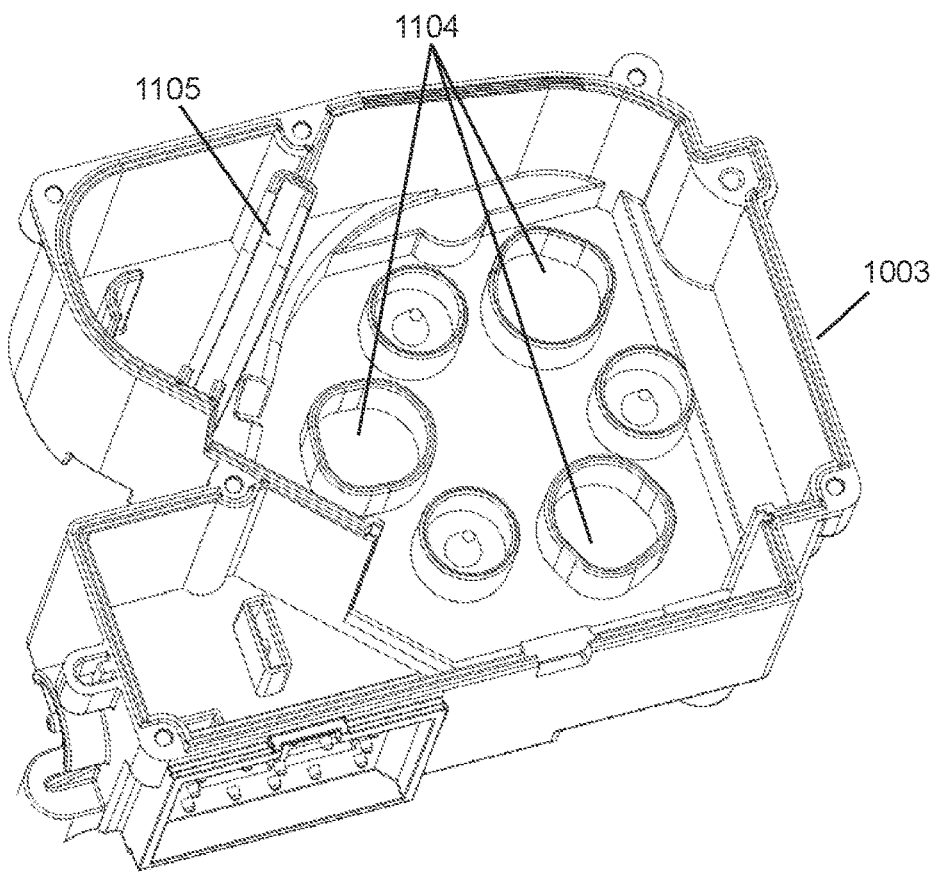
Figure 11C:
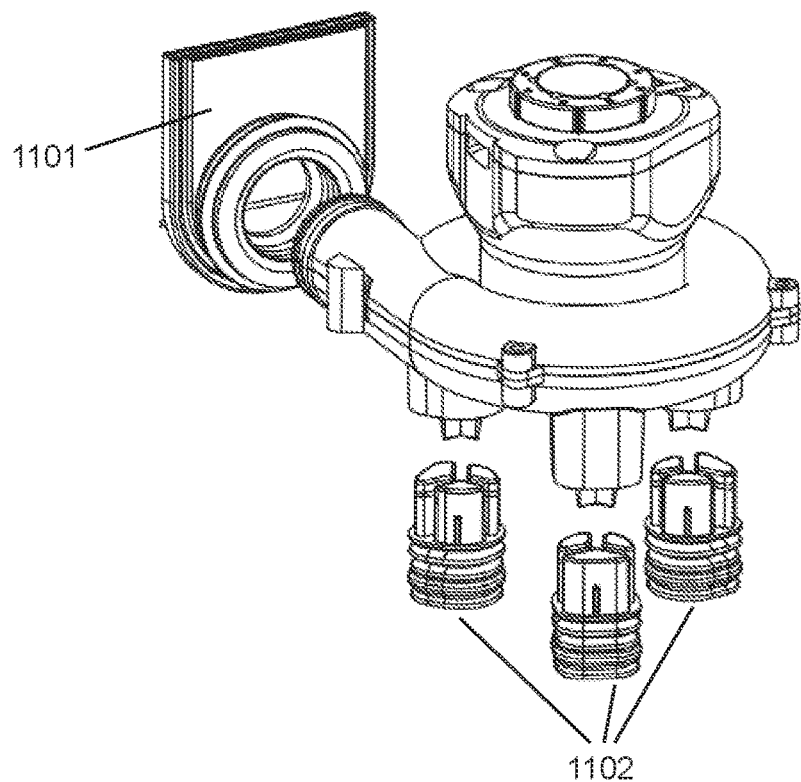
Figure 11D:
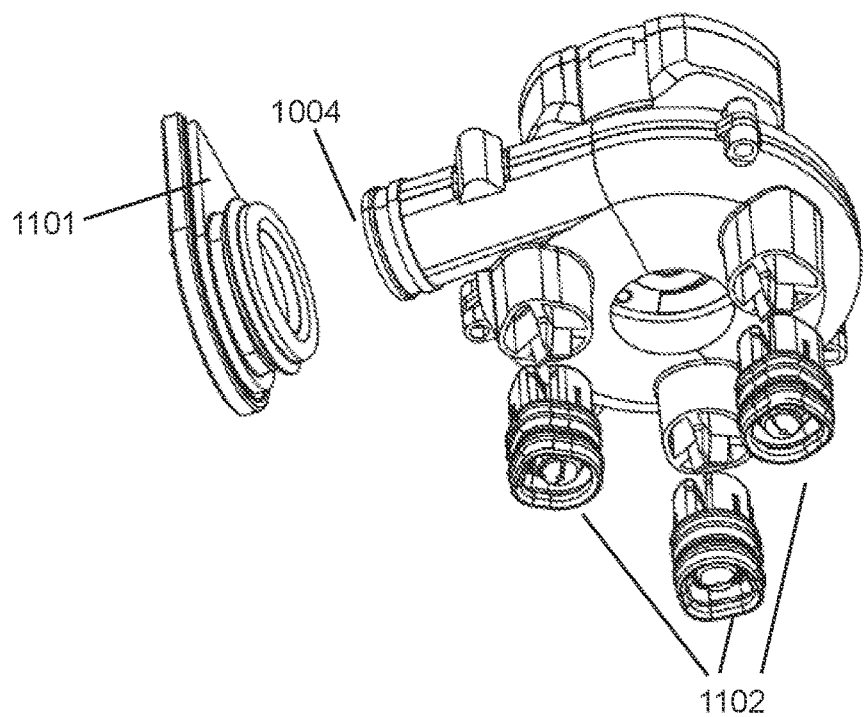
Figure 11E:
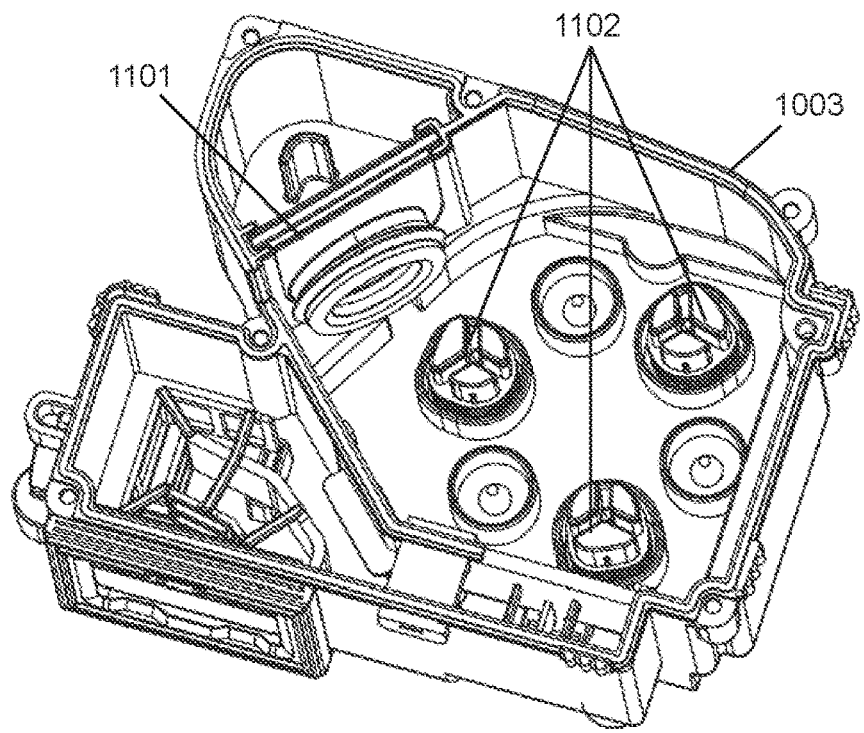
Figure 11F:
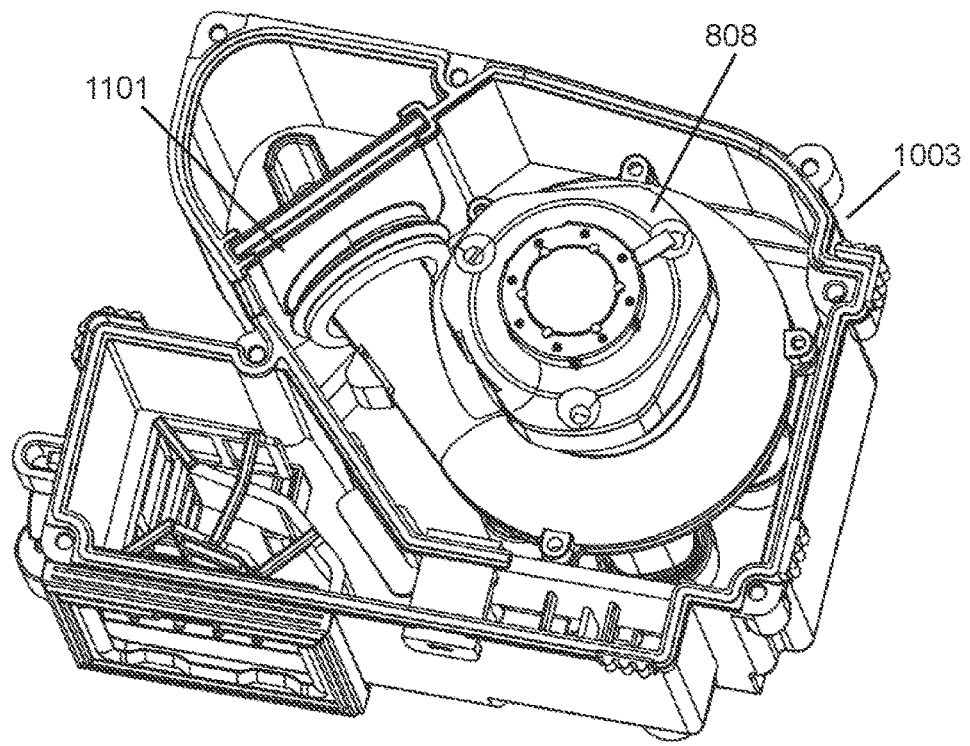

In some embodiments, the fixing part 1302 may be configured to fix the connecting piece 1101 to the internal space of the main body of the respiratory ventilation apparatus 110 and/or form a fastening connection between the connecting piece 1101 and the main body of the respiratory ventilation apparatus 110. In some embodiments, the fixing part 1302 may be configured to fix the connecting piece 1101 to a noise reduction box (e.g., the noise reduction box 801 shown in FIG. 8B) and/or form a fastening connection between the connecting piece 1101 and the noise reduction box. As shown in FIG. 11B, the noise reduction box 801 may include one or more limitation grooves 1105 (e.g., fixing slot(s)) coupled to the fixing part 1302 of the connecting piece 1101. In some embodiments, by sticking two opposite sides of the fixing part 1302 into the fixing slot(s), the gas pressurization unit 808 may be fixed in a fixed position inside the noise reduction box 801.

In some embodiments, the fixing part 1302 may be made of one or more hard materials, such as Teflon, a thermoplastic polymer with relatively high strength and/or toughness. In some embodiments, as shown in FIG. 13A, the fixing part 1302 may have a sheet structure. In some embodiments, the fixing part 1302 may include an aperture configured to allow the (pressurized) respiratory gas to pass. In some embodiments, the connecting part 1301 may have a tubular structure. The tubular structure may include a first end 1303 and a second end 1304. In some embodiments, the first end 1303 of the connecting part 1301 may be fixed to the fixing part 1302. In some embodiments, the second end 1304 of the connecting part 1301 may be connected to the outlet port of the gas pressurization unit 808. The connecting part 1301 may be capable of allowing the (pressurized) respiratory gas to pass through the tubular structure to the aperture of the fixing part 1302. In some embodiments, the (pressurized) respiratory gas may be discharged from the gas pressurization unit 808 and successively flow through the gas outlet port 1004, the connecting part 1301, the aperture of the fixing part 1302, the gas outlet port 810 of the noise reduction box 801, and into an inner gas passage of the respiratory ventilation apparatus 110.

In some embodiments, the connecting part 1301 may include one or more annular structures. The one or more annular structures may be connected end to end. In some embodiments, there may be a certain distance between each two adjacent annular structures of the one or more annular structures. In some embodiments, each of the one or more annular structures may include an outer annular structure and inner annular structure. The outer annular structure(s) may be connected with the fixing part 1302. The inner annular structures may be connected with the noise reduction box, fix the connecting piece 1101 to the noise reduction box, and/or form a fastening connection between the connecting piece 1101 and the noise reduction box.

In some embodiments, as shown in FIG. 13B, the connecting part 1301 and the fixing part 1302 may be configured as an integral piece. In some embodiments, the second end 1304 of the connecting part 1301 may have an annular double-layer structure including an inner layer 1305 and an outer layer 1306. In some embodiments, the second end 1304 of the connecting part 1301 may have an annular multi-layer structure including an inner layer 1305, an outer layer 1306, and one or more intermediate layers (not shown in FIG. 13B).

In some embodiments, as shown in FIG. 13B, the outer layer 1306 may connect with the fixing part 1302 of the connecting piece 1101 in one end and may connect with the inner layer 1305 in the other end. In some embodiments, the inner layer 1305 may not connect with the fixing part 1302. In some embodiments, the inner layer 1305 may be connected to an outer surface of the gas outlet port 1004 of the gas pressurization unit 808. In some embodiments, the outer surface of the gas outlet port 1004 of the gas pressurization unit 808 may include one or more protruding bumps, and the inner surface of the inner layer 1305 may include one or more corresponding grooves to match with the one or more protruding bumps, so that the gas outlet port 1004 of the gas pressurization unit 808 can be fixed to the connecting piece 1101. In some embodiments, the outer surface of the gas outlet port 1004 of the gas pressurization unit 808 may include one or more grooves, and the inner surface of the inner layer 1305 may include one or more corresponding protruding bumps to match with the one or more grooves, so that the gas outlet port 1004 of the gas pressurization unit 808 can be fixed to the connecting piece 1101. The protruding bumps and/or the grooves may have various shapes (e.g., cuboid, cube, cylinder, cone, truncated cone, prism, pyramid, truncated pyramid, or the like, or any combine thereof). Merely by way of example, as shown in FIG. 13B, the protruding bumps and the corresponding grooves may be annular. In some embodiments, the protruding bumps and/or the corresponding grooves may be uniformly arranged. Alternatively or additionally, the protruding bumps and/or the corresponding grooves may be disorderly arranged. In some embodiments, the outer layer 1306 may include a first annular flexible structure 1307 configured to tolerate or damp vibration of the gas pressurization unit 808 along an axial direction of the connecting part 1301. In some embodiments, the first annular flexible structure 1307 may have a U shape, a V shape, a Z shape, an M shape, an S shape, a C shape, an O shape, or the like, or a combination thereof. In some embodiments, the first annular flexible structure 1307 may have one or more folds.

In some embodiments, the inner layer 1305 may connect with the fixing part 1302 of the connecting piece 1101 in one end and may connect with the outer layer 1306 in the other end. In some embodiments, the outer layer 1306 may not connect with the fixing part 1302. In some embodiments, the outer layer 1306 may be connected to an inner surface of the gas outlet port 1004 of the gas pressurization unit 808. In some embodiments, the inner surface of the gas outlet port 1004 of the gas pressurization unit 808 may include one or more grooves, and the outer surface of the outer layer 1306 may include one or more corresponding protruding bumps to match with the one or more grooves, so that the gas outlet port 1004 of the gas pressurization unit 808 can be fixed to the connecting piece 1101. In some embodiments, the inner surface of the gas outlet port 1004 of the gas pressurization unit 808 may include one or more protruding bumps, and the outer surface of the outer layer 1306 may include one or more corresponding grooves to match with the one or more protruding bumps, so that the gas outlet port 1004 of the gas pressurization unit 808 can be fixed to the connecting piece 1101. The protruding bumps and/or the grooves may have various shapes (e.g., cuboid, cube, cylinder, cone, truncated cone, prism, pyramid, truncated pyramid, or the like, or any combine thereof). Merely by way of example, as shown in FIG. 13B, the protruding bumps and the corresponding grooves may be annular. In some embodiments, the protruding bumps and/or the corresponding grooves may be uniformly arranged. Alternatively or additionally, the protruding bumps and/or the corresponding grooves may be disorderly arranged. In some embodiments, the inner layer 1305 may include a first annular flexible structure configured to tolerate or damp vibration of the gas pressurization unit 808 along an axial direction of the connecting part 1301. In some embodiments, the first annular flexible structure may have a U shape, a V shape, a Z shape, an M shape, an S shape, a C shape, an O shape, or the like, or a combination thereof. In some embodiments, the first annular flexible structure may have one or more folds.

In some embodiments, a joint of the inner layer 1305 and the outer layer 1306 may include a second annular flexible structure 1308 configured to tolerate or damp vibration of the gas pressurization unit 808 along a radial direction of the connecting part 1301. In some embodiments, the second annular flexible structure 1308 may have a U shape, a V shape, a Z shape, an M shape, an S shape, a C shape, an O shape, or the like, or any combine of thereof. In some embodiments, the second annular flexible structure 1308 may have one or more folds.

In some embodiments, if the second end 1304 of the connecting part 1301 has an annular multi-layer structure including an inner layer 1305, an outer layer 1306, and one or more intermediate layers, the one or more intermediate layers may include a first annular flexible structure configured to tolerate or damp vibration of the gas pressurization unit 808 along an axial direction of the connecting part 1301. In some embodiments, the first annular flexible structure may have a U shape, a V shape, a Z shape, an M shape, an S shape, a C shape, an O shape, or the like, or any combine of thereof. In some embodiments, the first annular flexible structure may have one or more folds. In some embodiments, a joint of the inner layer 1305 and an intermediate layer, a joint of the outer layer 1306 and an intermediate layers, and/or a joint of two intermediate layers may include one or more second annular flexible structures configured to tolerate or damp vibration of the gas pressurization unit 808 along a radial direction of the connecting part 1301. In some embodiments, each second annular flexible structure may have a U shape, a V shape, a Z shape, an M shape, an S shape, a C shape, an O shape, or the like, or any combine of thereof. In some embodiments, each second annular flexible structure may have one or more folds.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the number of the first annular flexible structure may be larger than one. In some embodiments, the number of the second annular flexible structure may be larger than one. In some embodiments, the first annular flexible structure, the second annular flexible structure, the inner layer 1305, and/or the outer layer 1306 may be made of the same or different materials. For example, the first annular flexible structure and/or the second annular flexible structure may be made of material(s) with relatively high elasticity (e.g., flexible material(s)), while the inner layer 1305 and/or the outer layer 1306 may be made of material(s) with relatively low elasticity (e.g., hard material(s)). In some embodiments, the first annular flexible structure, the second annular flexible structure, the inner layer 1305, and/or the outer layer 1306 may have the same or different thicknesses. For example, the first annular flexible structure and/or the second annular flexible structure may have relatively small thickness, while the inner layer 1305 and/or the outer layer 1306 may have relatively large thickness. In some embodiments, the first annular flexible structure, the second annular flexible structure, the inner layer 1305, and/or the outer layer 1306 may be partially strengthened by one or more fibers. In some embodiments, the connecting piece 1101 may be manufactured base on 3D printing. In some embodiments, the structure of the connecting part 1301 may be applied in various connecting pieces of the respiratory ventilation apparatus 110, including for example, the connecting piece between the gas outlet port 111 and the respiration tube 160, the connecting piece between the main body of the respiratory ventilation apparatus 110 and a liquid chamber, the connecting piece between the respiration tube 160 and the subject interface 170, etc.

Figure 14A:
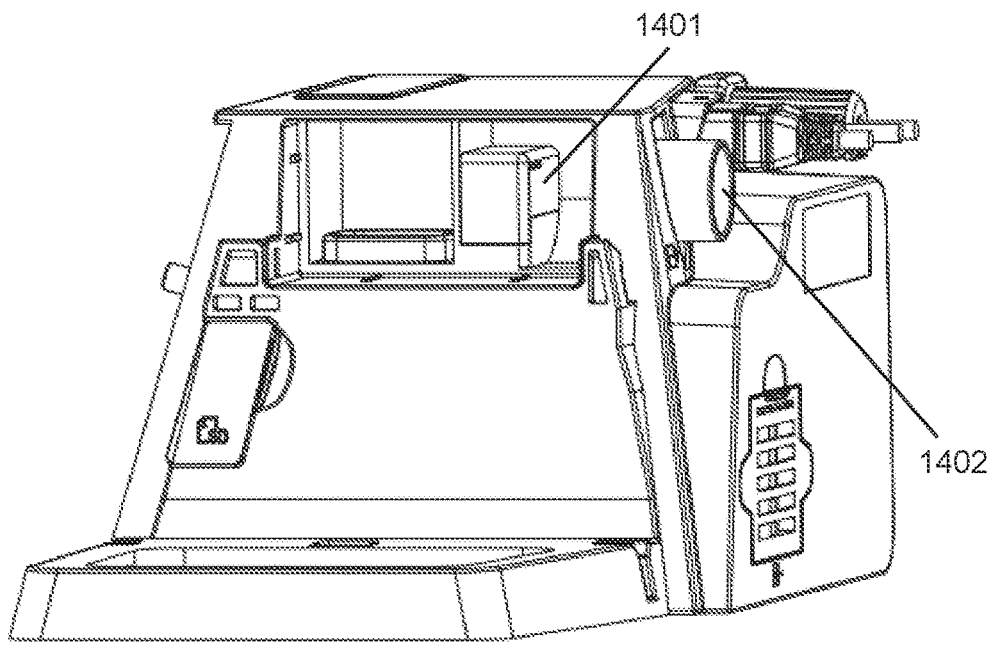
FIGS. 14A and 14B illustrate an exemplary respiratory ventilation apparatus including a gas parameter detection assembly according to some embodiments of the present disclosure.
Figure 14B:
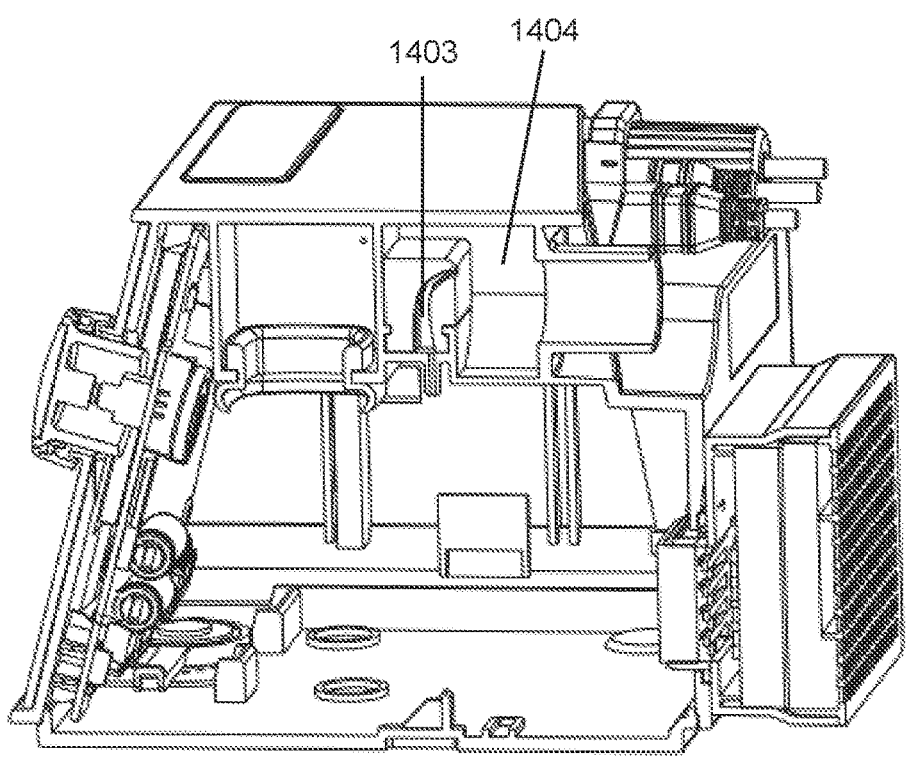

FIGS. 14A and 14B illustrate an exemplary respiratory ventilation apparatus including a gas parameter detection assembly according to some embodiments of the present disclosure. The gas parameter detection assembly may be configured to detect one or more gas parameters of (pressurized and/or humidified) respiratory gas e.g., from the down stream of the humidification assembly 220. In some embodiments, the parameter(s) detected by the gas parameter detection may include a snore of a user (e.g., the subject 180) of the respiratory ventilation apparatus 110. FIG. 14A shows an axonometric drawing of the main body 1400 of the respiratory ventilation apparatus 110 including the gas parameter detection assembly. FIG. 14B shows a cross-section view of the respiratory ventilation apparatus 110 including the gas parameter detection assembly. In some embodiments, as shown in FIGS. 14A and 14B, the gas parameter detection assembly may include an acquisition part 1401. The acquisition part 1401 may be configured to acquire a gas flow. In some embodiments, the acquisition part 1401 may be placed in a downstream of the humidified and pressurized respiratory gas relative to the humidification assembly 220. In some embodiments, the gas flow may be disturbed by a snore of a user (e.g., the subject 180) of the respiratory ventilation apparatus 110. In some embodiments, a main body of the respiratory ventilation apparatus 110 may include a gas return chamber 1404. The gas return chamber 1404 may be connected with the gas outlet port 1402 of the respiratory ventilation apparatus 110. In the present disclosure, the gas outlet port 1402 of the respiratory ventilation apparatus 110 may also be referred to as the main gas outlet port of the respiratory ventilation apparatus 110. The gas return chamber 1404 may be configured to guide the (pressurized and humidified) respiratory gas to flow to the gas outlet port 1402. In some embodiments, the acquisition part 1401 may be set in the gas return chamber 1404. In some embodiments, the acquisition part 1401 may be set facing the gas outlet port 1402 of the respiratory ventilation apparatus 110. In some embodiments, the acquisition part 1401 may be in a detachable connection with the respiratory ventilation apparatus 110. In some embodiments, the acquisition part 1401 may be fixed to the respiratory ventilation apparatus 110 via one or more slots (e.g., two slots) set on one or more sides of the acquisition part 1401 (see FIG. 16B).

In some embodiments, as shown in FIGS. 14A, 14B, and 16A-16D, the acquisition part 1401 may include an input port 1601, an output port 1602, and/or at least one channel 1403 (also referred as a gas passage). In some embodiments, the channel 1403 may be a curved channel. In some embodiments, the channel 1403 may be set inside the acquisition part 1401. In some embodiments, a first end of the channel 1403 may be the input port 1601. In some embodiments, the input port 1601 may be opening on a first surface (e.g. a front surface) of the acquisition part 1401. In some embodiments, the first surface may face the gas outlet port 1402 of the respiratory ventilation apparatus 110. In some embodiments, a second end of the channel 1403 may be the output port 1602. In some embodiments, the output port 1602 may be opening on a second surface (e.g. a bottom surface) of the acquisition part 1401. In some embodiments, the second surface may be different from the first surface. In some embodiments, the second surface of the acquisition part 1401 may be in a sealed connection with an inner surface of the main body of the respiratory ventilation apparatus 110 (e.g., a bottom surface of the gas return chamber 1404). In some embodiments, the input port 1601 may be set above the bottom surface of the gas return chamber 1404. In some embodiments, the input port 1601 may be set above the second surface of the acquisition part 1401. In some embodiments, the acquisition part 1401 may be protruding from the inner surface of the main body of the respiratory ventilation apparatus 110 (e.g., a bottom surface of the gas return chamber 1404), to prevent water from flowing in the acquisition part 1401. In some embodiments, the cross-sectional area of the channel 1403 may be gradually increasing from the input port 1601 to the output port 1602. In some embodiments, one or more ports (e.g., a first port 1501, a second port 1502) may be set in the inner space of the apparatus beneath the output port 1602 of the acquisition part 1401. In some embodiments, the gas flow may be introduced into the inner space of the respiratory ventilation apparatus 110 via the acquisition part 1401 and the one or more ports. In some embodiments, the acquisition part 1401 may be made of a flexible material (e.g., silicone) or a hard material. In some embodiments, the acquisition part 1401 may be made of a hydrophobic material.

Figure 15A:
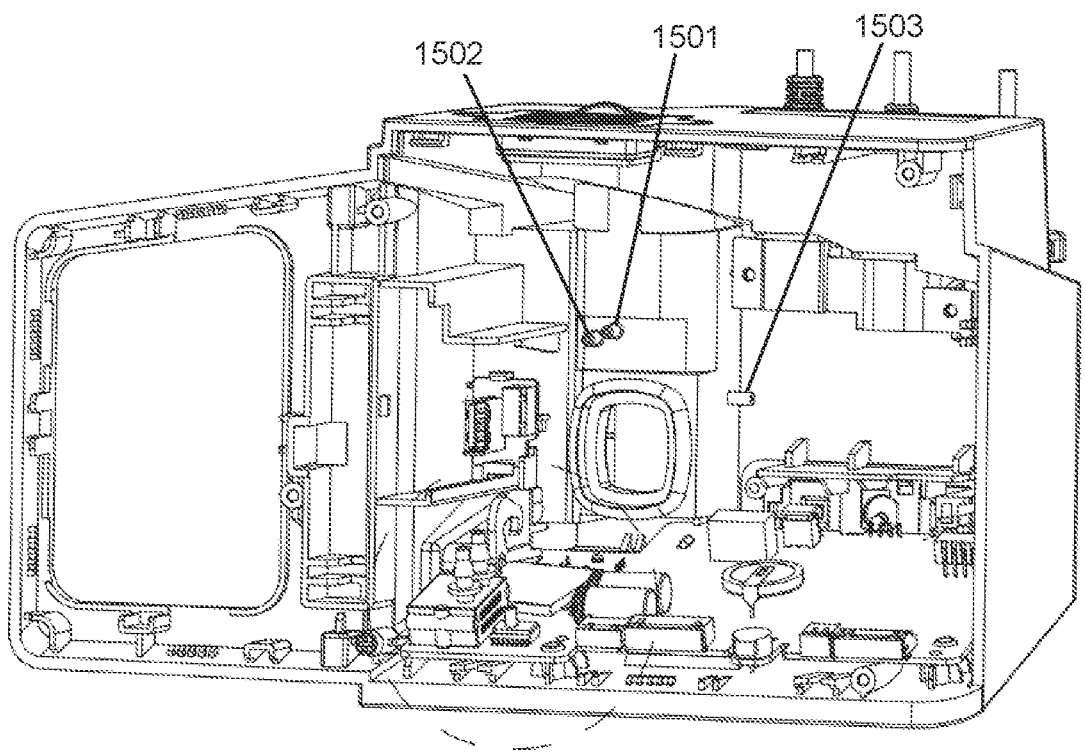
FIGS. 15A and 15B illustrate an inner space of an exemplary respiratory ventilation apparatus including a gas parameter detection assembly according to some embodiments of the present disclosure.
Figure 15B:
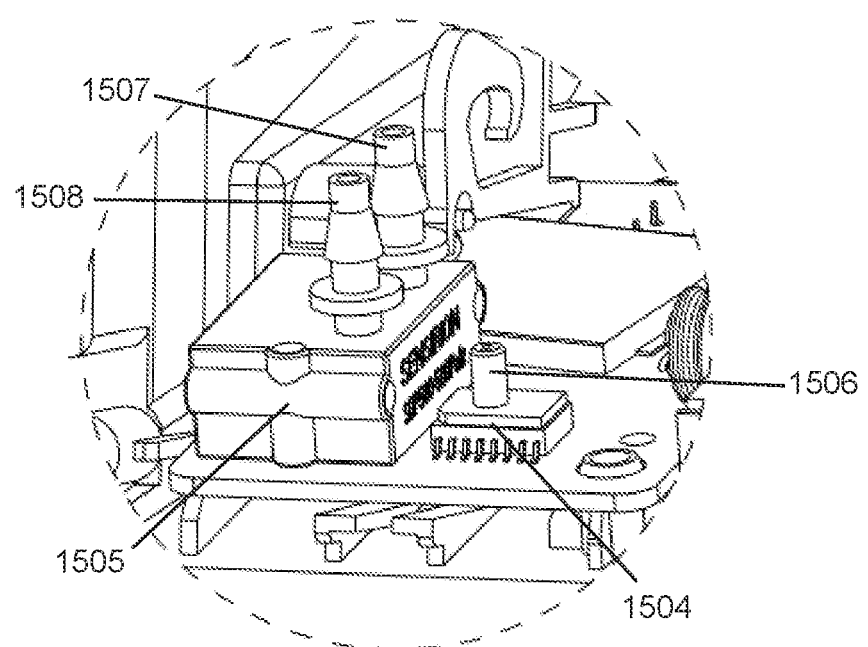

FIGS. 15A and 15B illustrate an inner space of an exemplary respiratory ventilation apparatus including a gas parameter detection assembly according to some embodiments of the present disclosure. In some embodiments, a printed circuit board (PCB) may be mounted in the inner space of the respiratory ventilation apparatus 110. In some embodiments, one or more sensors (e.g., a first sensor 1504, a second sensor 1505) may be integrated into the PCB. FIG. 15A shows a bottom view of the inner space of the respiratory ventilation apparatus 110. FIG. 15B shows a magnified view of the one or more sensors integrated into the printed circuit board (PCB) mounted in the inner space of the respiratory ventilation apparatus 110. As shown in FIGS. 15A and 15B, the gas parameter detection assembly may include a first sensor 1504. In some embodiments, the first sensor 1504 may be configured to measure a gas parameter associated with the snore based on the gas flow. In some embodiments, the first sensor 1504 may be configured to measure a pressure of the gas flow. In some embodiments, the first sensor 1504 may include a third port 1506 on its surface. In some embodiments, the third port 1506 may be integrally formed on the surface of the first sensor 1504. In some embodiments, the first sensor 1504 may be a pressure sensor. In some embodiments, the gas parameter detection assembly may include a first tube (not shown). The first tube may connect the first port 1501 with the third port 1506. The first tube may be configured to introduce the gas flow from the acquisition part 1401 to the surface of the first sensor 1504.

In some embodiments, the first sensor 1504 (e.g., pressure sensor) may be further configured to detect the pressure of the respiratory gas in one or more gas passages of the respiratory ventilation apparatus 110. In some embodiments, the pressure of the respiratory gas in the gas passage(s) of the respiratory ventilation apparatus 110 may be detected based on a low-frequency part of the signal detected by the first sensor 1504, while a snoring signal may be detected based on a high-frequency part of the signal detected by the first sensor 1504. In some embodiments, the control module 260 may control and/or adjust the rotation speed of the gas pressurization unit 210 to achieve a desired pressure of the respiratory gas based on the detected pressure of the respiratory gas.

In some embodiments, the respiratory ventilation apparatus 110 may include a flow detection assembly. The flow detection assembly may be configured to detect a flux of one or more gases in one or more passages of the respiratory ventilation apparatus 110. In some embodiments, the first sensor and the second sensor may share a same acquisition part 1401. In some embodiments, the flow detection assembly may include the second sensor 1505. The second sensor 1505 may be configured to detect a flux signal associated with the one or more gases in the one or more passages of the respiratory ventilation apparatus 110. In some embodiments, the second sensor 1505 may be a flow sensor. In some embodiments, the second sensor 1505 may include a fourth port 1507 and/or a fifth port 1508 on its surface. In some embodiments, the fourth port 1507 and/or the fifth port 1508 may be integrally formed on the surface of the second sensor 1505. In some embodiments, the flow detection assembly may include a sixth port 1503 (also referred to as an auxiliary acquisition port). The sixth port 1503 may be set in the main body of the respiratory ventilation apparatus 110. In some embodiments, the sixth port 1503 may be set at upstream of the one or more gases that flow to the acquisition part 1401. In some embodiments, the sixth port 1503 may be configured to acquire a gas flow from the gas outlet port of the gas pressurization unit 210. In some embodiments, the flow detection assembly may include a second tube (not shown) and/or a third tube (not shown). The second tube may be configured to introduce a gas flow from the acquisition part 1401 to a surface of the second sensor 1505. In some embodiments, the second tube may connect the second port 1502 with the fourth port 1507 to introduce the gas flow from the acquisition part 1401 to the surface of the second sensor 1505. The third tube may be configured to introduce a gas flow from the auxiliary acquisition port to a surface of the second sensor 1505. In some embodiments, the third tube may connect the fifth port 1508 with the sixth port 1503 to introduce the gas flow from the auxiliary acquisition port to the surface of the second sensor 1505.

Figure 16A:
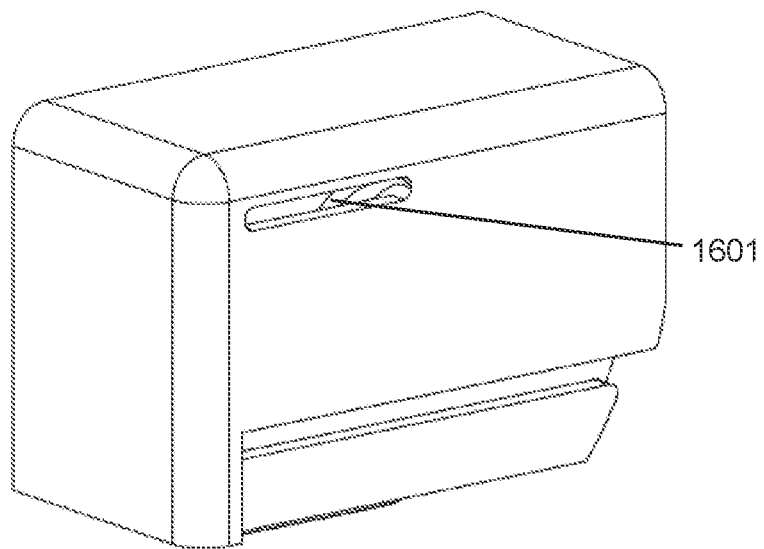
FIGS. 16A-16D illustrate an exemplary acquisition part of a gas parameter detection assembly and/or a flow detection assembly according to some embodiments of the present disclosure.

FIGS. 16A-16D illustrate an exemplary acquisition part of a gas parameter detection assembly and/or a flow detection assembly according to some embodiments of the present disclosure. The acquisition part 1401 may be set in the main body of the respiratory ventilation apparatus 110 facing the gas outlet port 1402 of the respiratory ventilation apparatus 110. In some embodiments, the acquisition part 1401 may acquire the pressurized and humidified respiratory gas from the down stream of the humidification assembly 220. Therefore, the gas flow acquired by the acquisition part 1401 may be more stable, and the parameter(s) (such as, snore, pressure, flow rate, or the like) detected may be more accurate. FIG. 16A shows a perspective view of the acquisition part 1401 according to some embodiments of the present disclosure. In some embodiments, as shown in FIG. 16A, the acquisition part 1401 may have an approximate rounded cuboid structure with six surfaces (e.g. a front surface, a back surface, a top surface, a bottom surface, a left surface, and a right surface). The front surface of the acquisition part 1401 may face the gas outlet port 1402 of the respiratory ventilation apparatus 110. In some embodiments, the acquisition part 1401 may have another structure including a cuboid, a cube, a cylinder, a prism, or the like, or any combine thereof.

In some embodiments, the acquisition part 1401 may include an input port 1601. In some embodiments, the input port 1601 may be set at the front surface of the acquisition part 1401 facing the gas outlet port 1402 of the respiratory ventilation apparatus 110. In some embodiments, the input port 1601 may be set below an upper edge of the gas outlet port 1402 of the respiratory ventilation apparatus 110 but above a lower edge of the gas outlet port 1402. In some embodiments, the input port 1601 may be set at the upper left corner of the front surface. In some embodiments, the input port 1601 may be set on another position of the front surface. For example, the input port 1601 may be set on the upper right corner or the center of the front surface. In some embodiments, the input port 1601 may set on another surface of the acquisition part 1401, such as the top surface of the acquisition part 1401. In some embodiments, the input port 1601 may have a shape of a long and thin rounded rectangle (or a strip). In some embodiments, the input port 1601 may have another shape including a square, a circle, a polygon, or the like, or any combine of thereof. In some embodiments, the input port 1601 may have one or more openings.

Figure 16B:
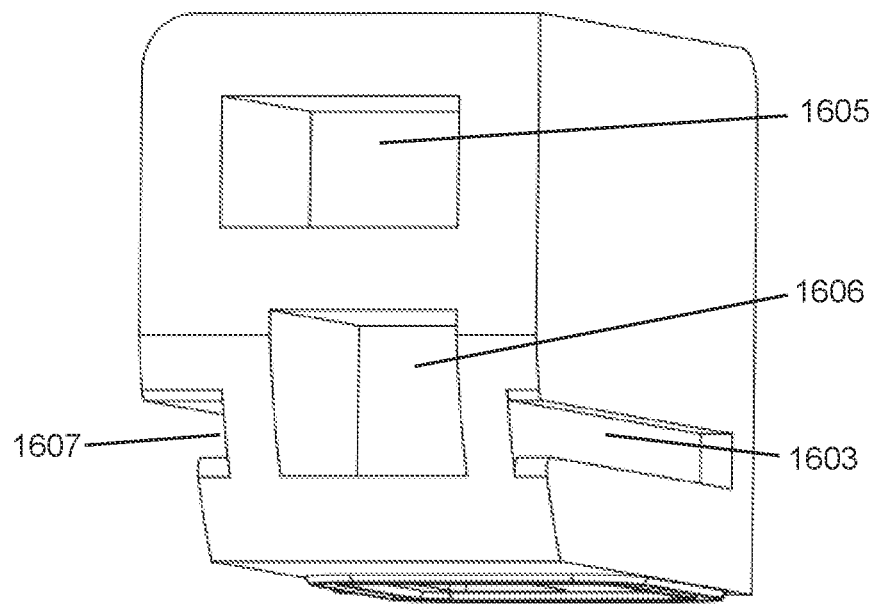

FIG. 16B shows a side perspective view of the acquisition part 1401 according to some embodiments of the present disclosure. In some embodiments, as shown in FIG. 16B, the acquisition part 1401 may include one or more slots. The one or more slots may be configured to establish a detachable connection between the acquisition part 1401 and the main body of the respiratory ventilation apparatus 110. In some embodiments, the one or more slots may include a first fixing slot 1607 and a second fixing slot 1603. The first fixing slot 1607 and the second fixing slot 1603 may be set on the same or different surfaces of the acquisition part 1401. For example, the first fixing slot 1607 may be set on the front surface of the acquisition part 1401, while the second fixing slot 1603 may be set on the back surface of the acquisition part 1401. In some embodiments, the first fixing slot 1607 and the second fixing slot 1603 may be set parallel to fix the acquisition part 1401 in the horizontal direction. In some embodiments, the first fixing slot 1607 and the second fixing slot 1603 may be set on the right surface and left surface, respectively. In some embodiments, the first fixing slot 1607 and the second fixing slot 1603 may be set closer to the bottom surface of the acquisition part 1401. In some embodiments, the acquisition part 1401 may include a first groove 1605 and a second groove 1606 set on any surface of the acquisition part 1401 (e.g., the right surface).

In some embodiments, one or more claws may be set on the bottom surface of the acquisition part 1401. Correspondingly, one or more slots coupled to the one or more claws may be set in the main body of the respiratory ventilation apparatus 110 to fix the acquisition part 1401. In some embodiments, one or more slots may be set on the bottom surface of the acquisition part 1401, and one or more claws coupled to the one or more slots may be set in the main body of the respiratory ventilation apparatus 110 to fix the acquisition part 1401.

Figure 16C:
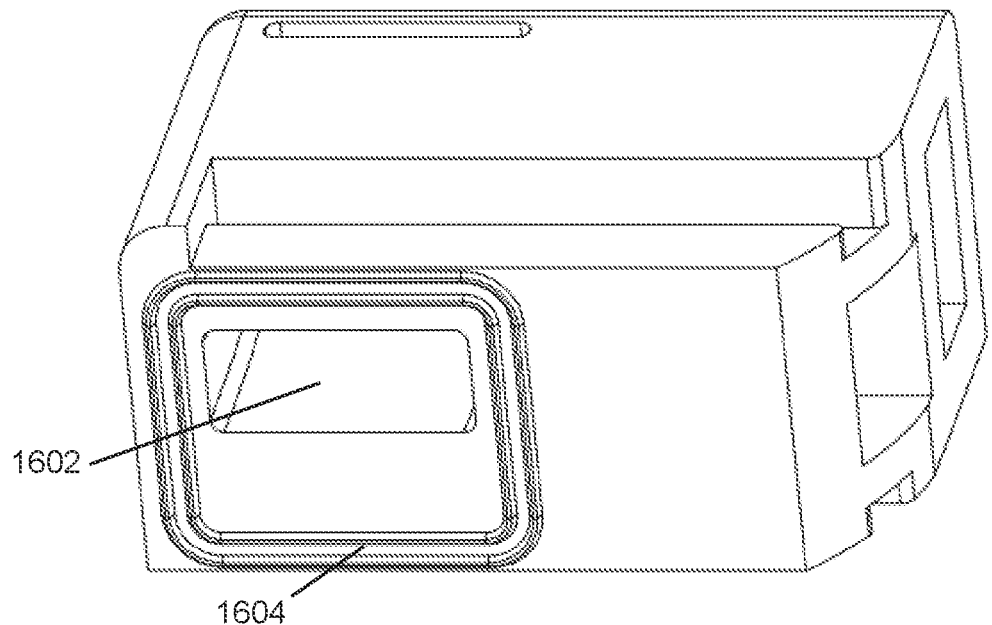

FIG. 16C shows a bottom perspective view of the acquisition part 1401 according to some embodiments of the present disclosure. As shown in FIG. 16C, the acquisition part 1401 may include an output port 1602. In some embodiments, as shown in FIG. 16C, the output port 1602 may be set on the bottom surface of the acquisition part 1401. In some embodiments, the output port 1602 may be set on another surface of the acquisition part 1401, for example, the back surface of the acquisition part 1401. The output port 1602 may be set below the input port 1601. In some embodiments, the output port 1602 may have a shape of a rounded rectangle. In some embodiments, the output port 1602 may have a shape of a square, a circle, a polygon, or the like, or any combine of thereof. In some embodiments, a silicone gasket 1604 may be set on the acquisition part 1401 to ensure a sealed connection between the acquisition part 1401 and the main body of the respiratory ventilation apparatus 110. In some embodiments, the silicone gasket 1604 may be set around the output port 1602. In some embodiments, the output port 1602 may be set closer to the upper edge of the silicone gasket 1604.

Figure 16D:
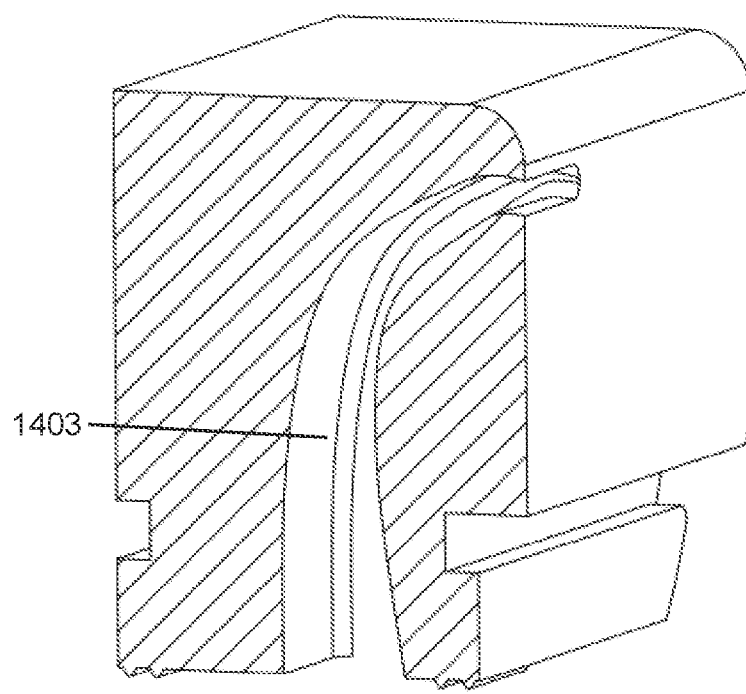

FIG. 16D shows a side cross-sectional view of the acquisition part 1401 according to some embodiments of the present disclosure. As shown in FIG. 16D, the acquisition part 1401 may include a channel 1403. The channel 1403 may be set inside the acquisition part 1401. The channel 1403 may be configured to connect the input port 1601 and the output port 1602. In some embodiments, the channel 1403 may have a relatively small area of cross section near the input port 1601 and a relatively large area of cross section near the output port 1602. In some embodiments, from the input port 1601 to the output port 1602, the cross-sectional area of the channel 1403 may increase gradually. In some embodiments, the pressurized respiratory gas may include a certain amount of moisture. In some embodiments, one or more water droplets may be generated near the input port 1601 because of the condensation of the water vapor in the pressurized respiratory gas. In some embodiments, to prevent the condensate water droplets from flowing from the input port 1601 and the channel 1403 onto the surface of the first sensor 1504, the channel 1403 may include a droop near the input port 1601, so that the input port 1601 may be below the top of the channel 1403. Therefore, the condensate water droplets may be prevented from flowing back through the channel 1403 to the surface of the first sensor under the force of gravity.

In some embodiments, the respiratory ventilation apparatus 110 may include a pressure sensor (e.g., the first sensor 1504) and a flow sensor (e.g., the second sensor 1505) for snore detection, and a humidified gas inlet port (e.g., the input port 1601) configured to introduce pressurized and humidified respiratory gas from the humidification assembly 220. In some embodiments, the pressure sensor and the flow sensor may be connected via a (curved) channel (e.g., the channel 1403) to a section between a main gas outlet port of the respiratory ventilation apparatus 110 (e.g., the gas outlet port 1402) and the humidified gas inlet port.

Figure 17:
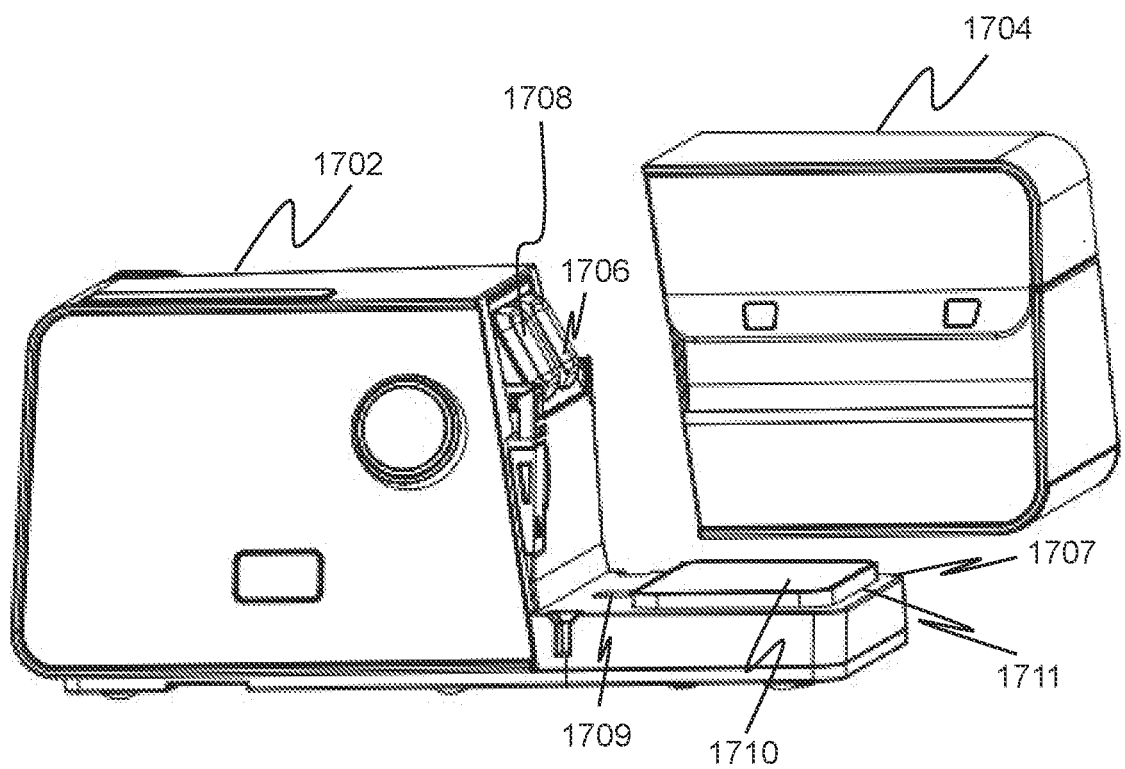
FIG. 17 illustrates an exemplary respiratory ventilation apparatus according to some embodiments of the present disclosure.

FIG. 17 illustrates an exemplary respiratory ventilation apparatus according to some embodiments of the present disclosure. The respiratory ventilation apparatus 1700 may include a main body 1702, and/or a humidification assembly. In some embodiments, the humidification assembly may be configured to humidify the pressurized respiratory gas to generate pressurized and humidified respiratory gas. In some embodiments, the humidification assembly may include a liquid chamber 1704, a heater plate 1710, and a heat-conducting plate 1810 (see FIGS. 18A and 18B). The liquid chamber 1704 may be configured to accommodate one or more liquids (e.g., water and/or drug). The heat-conducting plate may be configured to conduct heat from the heater plate 1710 to heat the one or more liquids and generate vapor to humidify the pressurized respiratory gas. In some embodiments, the heat-conducting plate may be set on the bottom of the liquid chamber 1704. In some embodiments, the heat-conducting plate may include a metallic heat conducting material.

In some embodiments, the main body 1702 may include a gas pressurization unit (not shown in FIG. 17) located in the main body 1702, a gas inlet port 1706, a gas outlet port 1708, and/or a support plate 1707. In some embodiments, the gas inlet port 1706 and/or the gas outlet port 1708 may be set on a first interface of the main body 1702 and the liquid chamber 1704. In some embodiments, the support plate 1707 may be set on a second interface of the main body 1702 and the liquid chamber 1704. In some embodiments, the support plate 1707 may be fixed to a base plate of the main body 1702. In some embodiments, the first interface (see FIGS. 23A-23D) of the main body 1702 and the liquid chamber 1704 may refer to a side surface of the main body 1702 and a corresponding side surface of the liquid chamber 1704. In some embodiments, the second interface (see FIGS. 17-21D) of the main body 1702 and the liquid chamber 1704 may refer to a bottom surface of the liquid chamber 1704 and a corresponding surface of the support plate 1707 of the main body 1702. In some embodiments, the gas outlet port 1708 may be configured to discharge the pressurized respiratory gas from the main body 1702 to the liquid chamber 1704. In some embodiments, the gas inlet port 1706 may be configured to introduce the pressurized and humidified respiratory gas from the liquid chamber 1704 back into the main body 1702. In some embodiments, the support plate 1707 may include a first hole 1709 and/or a second hole 1711. In some embodiments, the first hole 1709 and/or the second hole 1711 may be set on the second interface. In some embodiments, at least a portion of the heater plate 1710 may be set in the second hole 1711.

The heater plate 1710 may be configured to heat one or more liquids in the liquid chamber 1704 and/or generate vapor to humidify the pressurized respiratory gas. In some embodiments, the heater plate 1710 may be mounted on the base of the main body 1702 through one or more springs 2202 (see FIG. 22C). The heater plate 1710 may be capable of moving up and down through the second hole 1711 upon being driven by a pressure or upon releasing the pressure.

In some embodiments, the liquid chamber 1704 may be in detachable connection with the main body 1702, such that the humidification assembly may be removably coupled to the main body 1702. For example, the liquid chamber 1704 may be in detachable connection with the main body 1702 through a push-push mechanism (see FIGS. 19-21D) via a hole (e.g., the first hole 1709) of the support plate 1707. If the liquid chamber 1704 is mounted on the main body 1702 of the respiratory ventilation apparatus 1700, the bottom of the liquid chamber 1704 (e.g., a heat-conducting plate of the liquid chamber 1704) may be in close contact with the heater plate 1710. More descriptions of the humidification assembly may be found elsewhere in the present disclosure (e.g., FIGS. 18A and 18B and the descriptions thereof).

Figure 18A:
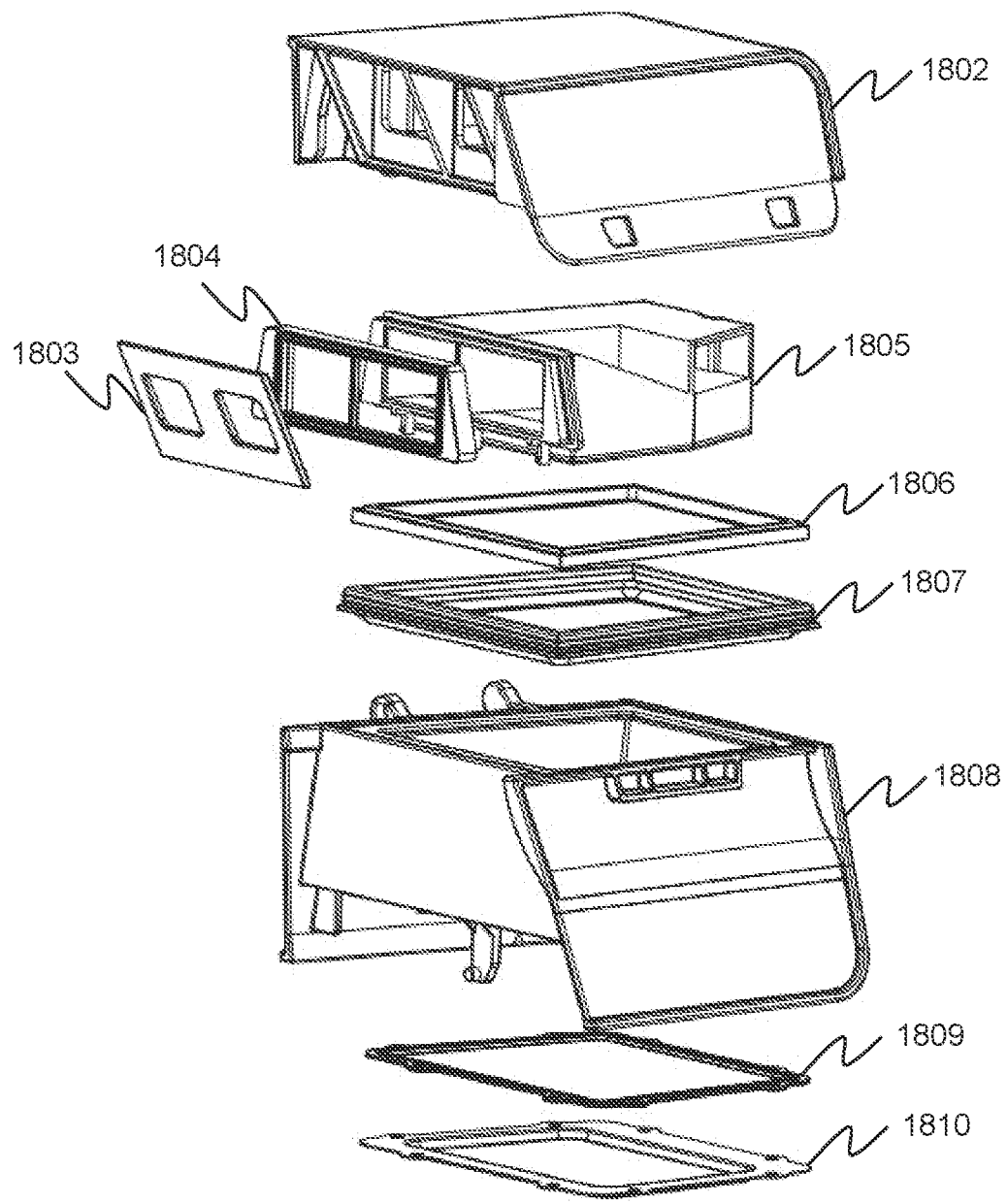
FIGS. 18A and 18B illustrate exploded views of an exemplary liquid chamber according to some embodiments of the present disclosure.
Figure 18B:
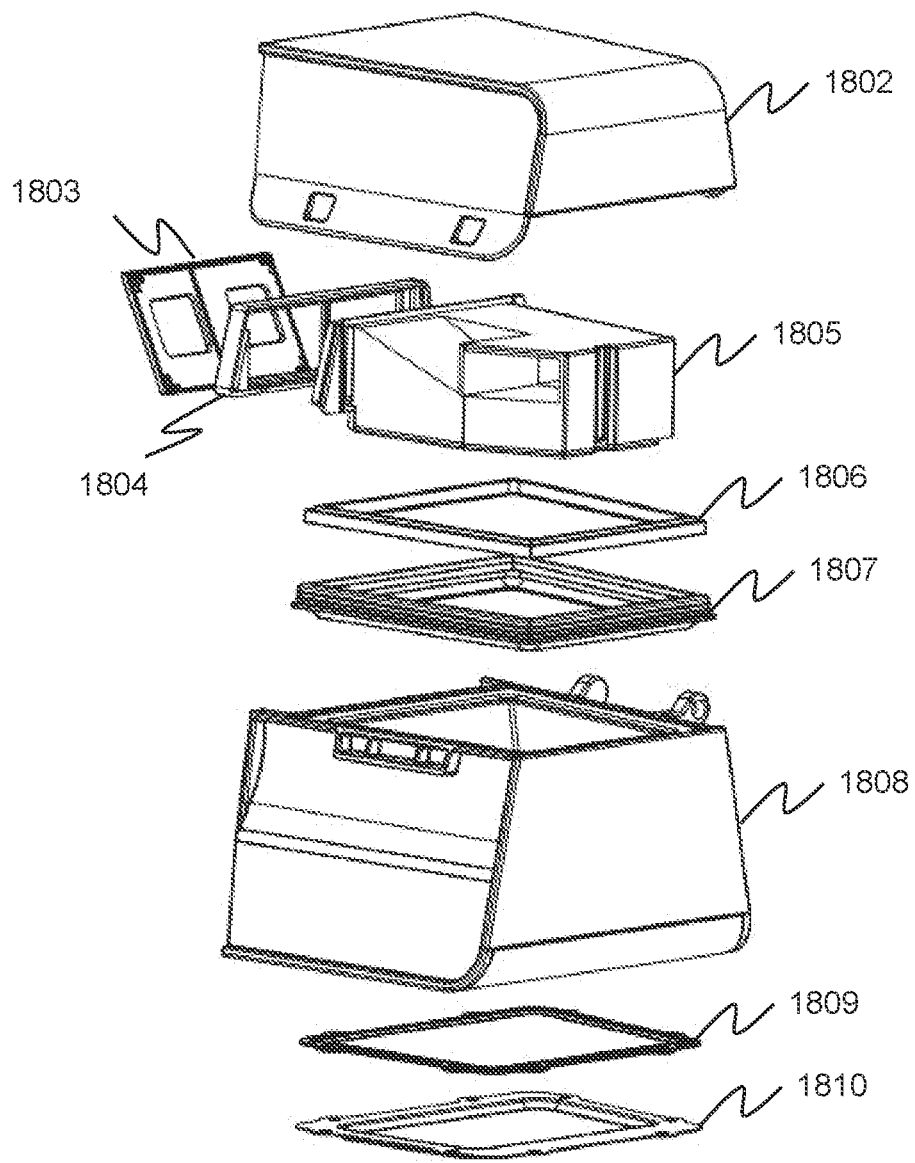

FIGS. 18A and 18B illustrate exploded views of an exemplary liquid chamber according to some embodiments of the present disclosure. In some embodiments, as shown in FIGS. 18A and 18B, the liquid chamber 1704 may include a tank cover and a tank. In some embodiments, the tank cover may include a cover shell 1802 and one or more gas passages 1805. In some embodiments, the tank may include a tank shell 1808, a heat-conducting plate sealing gasket 1809, and a heat-conducting plate 1810. It should be noted that in some embodiments, the gas passage(s) 1805 may be set in the tank. In some embodiments, the liquid chamber 1704 may include a fixing gasket 1806 and/or a tank cover sealing gasket 1807 between the tank and the tank cover. The fixing gasket 1806 and/or the tank cover sealing gasket 1807 may be configured to enable a sealed connection between the tank and the tank cover. In some embodiments, the liquid chamber 1704 may include a connecting plate 1803 and/or a gas passage sealing gasket 1804 to cooperate with the main body 1702.

In some embodiments, the components of the liquid chamber 1704 may be in detachable connection. For example, the connecting plate 1803 may be set on and/or fixed to the cover shell 1802 by cementing, riveting, joggling, clamping, meshing, or the like, or any combination thereof. As another example, the gas passage sealing gasket 1804 may be connected and/or fixed to the gas passage(s) 1805. As another example, the fixing gasket 1806 and/or the tank cover sealing gasket 1807 may be set on and/or fixed to the tank shell 1808 to improve air tightness between the cover shell 1802 and the tank shell 1808. In some embodiments, the fixing gasket 1806 may be set inside the tank cover sealing gasket 1807. As a further example, the heat-conducting plate sealing gasket 1809 may be set between the heat-conducting plate 1810 and a bottom frame of the tank shell 1808. As still a further example, the heat-conducting plate 1810 may be connected with the heat-conducting plate sealing gasket 1809 by cementing, riveting, joggling, clamping, meshing, or the like, or any combination thereof. As still a further example, the heat-conducting plate sealing gasket 1809 may be fixed to the bottom frame of the tank shell 1808 by cementing, riveting, joggling, clamping, meshing, or the like, or any combination thereof.

Figure 19:
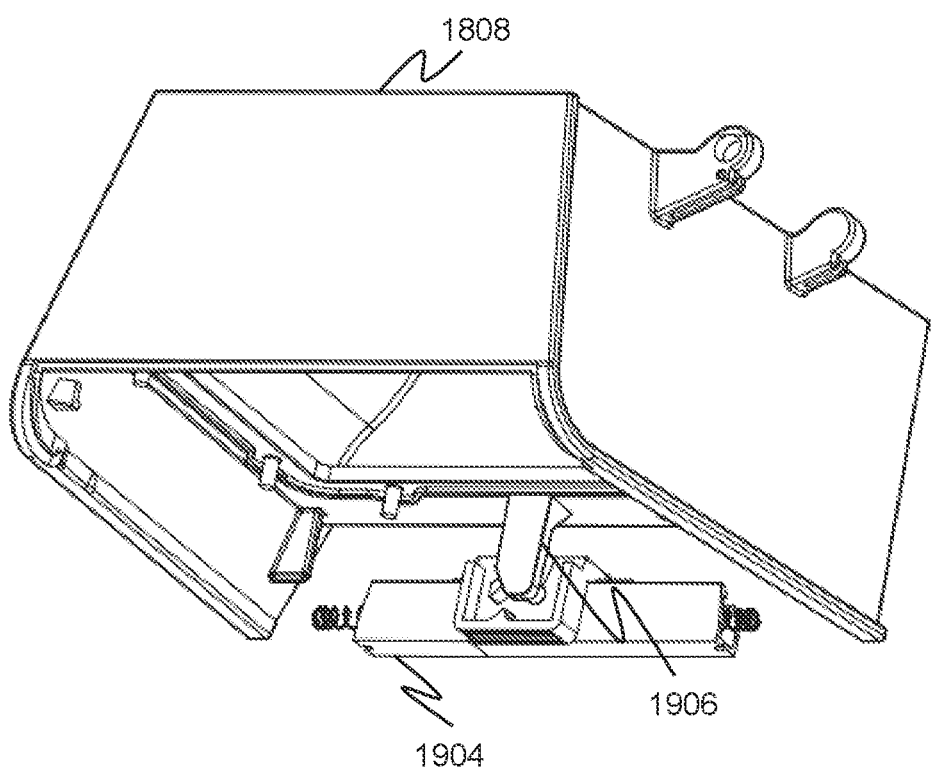
FIG. 19 illustrates an exemplary push-push mechanism in connection with a liquid chamber of a respiratory ventilation apparatus according to some embodiments of the present disclosure.

FIG. 19 illustrates an exemplary push-push mechanism in connection with a liquid chamber of a respiratory ventilation apparatus according to some embodiments of the present disclosure. In some embodiments, the push-push mechanism 1904 may be set underneath the support plate 1707. In some embodiments, the tank shell 1808 of the liquid chamber 1704 may be in a detachable connection with the push-push mechanism 1904 by a pushrod 1906. In some embodiments, the pushrod 1906 may be set below a bottom surface of the liquid chamber 1704.

In some embodiments, the liquid chamber 1704 may be driven by a first pushing force. When the first pushing force is released, the pushrod 1906 may be locked with the push-push mechanism 1904, such that the liquid chamber 1704 can be mounted on the main body 1702 of the respiratory ventilation apparatus 1700. If the liquid chamber 1704 is driven by a second pushing force and when the second pushing force is released, the pushrod 1906 may be removed from the push-push mechanism 1904, such that the liquid chamber 1704 can be released from the main body 1702 of the respiratory ventilation apparatus 1700. In some embodiments, the direction of the first pushing force may be the same as the direction of the second pushing force. For example, the direction of the first pushing force and the direction of the second pushing force may be vertically downward. In some embodiments, the push-push mechanism 1904 may be set on a side of the first interface between the main body 1702 and the liquid chamber 1704, and then, the first pushing force and the second pushing force may be in the horizontal direction.

Figure 20A:
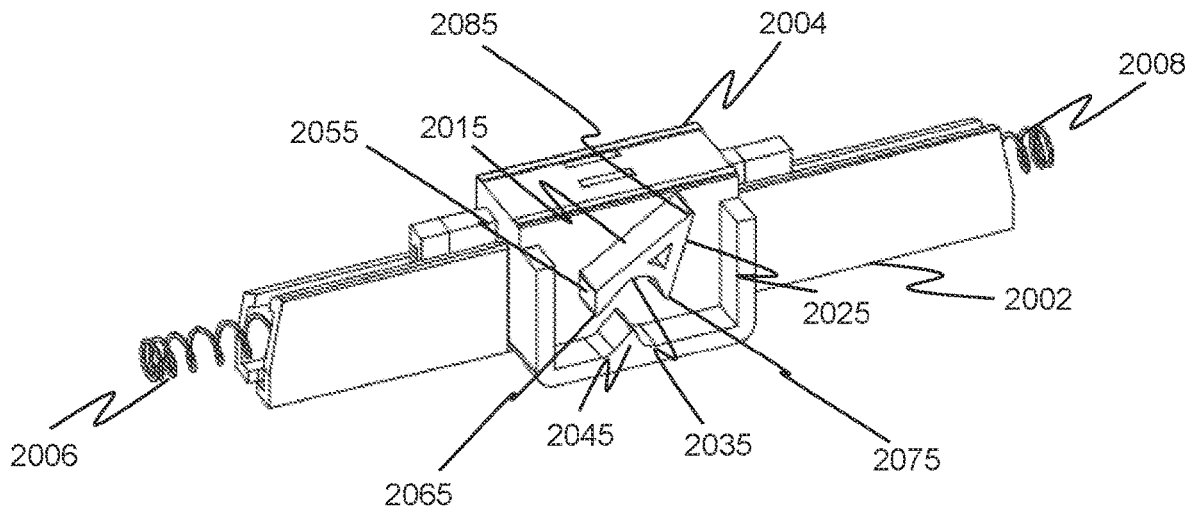
FIGS. 20A and 20B illustrate an exemplary push-push mechanism according to some embodiments of the present disclosure.
Figure 20B:
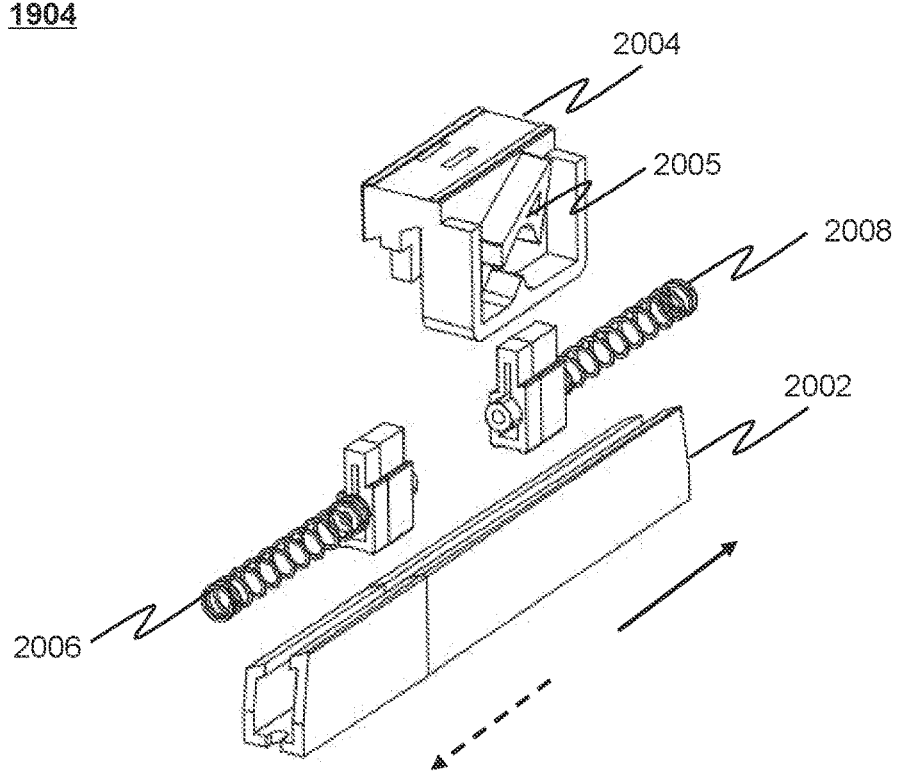

FIGS. 20A and 20B illustrate an exemplary push-push mechanism according to some embodiments of the present disclosure. FIG. 20A shows an axonometric drawing of the push-push mechanism 1904. FIG. 20B shows an exploded view of the push-push mechanism 1904. In some embodiments, as shown in FIGS. 20A and 20B, the push-push mechanism 1904 may include a guide slot 2002, a slide block 2004, a first spring 2006, a second spring 2008, a pushrod 1906 (see FIG. 19), etc.

The guide slot 2002 may be configured to accommodate the first spring 2006 and the second spring 2008, and guide the moving of the slide block 2004. In some embodiments, the guide slot 2002 may be set on the main body (e.g., the main body 1702) of a respiratory ventilation apparatus 1700. For example, the guide slot 2002 may be set beneath the support plate 1707 of the main body (e.g., the main body 1702) of the respiratory ventilation apparatus 1700. In some embodiments, the guide slot 2002 may be fixed to the main body (e.g., the main body 1702) by cementing, riveting, joggling, clamping, meshing, or the like, or any combination thereof. In some embodiments, the guide slot 2002 may be made of a material such as cast iron, stainless steel, nonferrous metal, plastic, or the like, or any combination thereof.

The slide block 2004 may be mounted on the guide slot 2002. In some embodiments, the slide block 2004 may move along the guide slot 2002 in a first direction back and forth. In some embodiments, the first direction may be parallel to the guide slot C0402. In some embodiments, the slide block 2004 may include a guide block 2005. The guide block 2005 may be configured to guide or limit a moving position of the pushrod 1906. In some embodiments, as shown in FIGS. 20A and 20B, the guide block 2005 may has a frame similar to character A. In some embodiments, the guide block 2005 may include a frame different from the character A (e.g., a frame of character N or M, etc.). In some embodiments, the guide block 2005 may include a first slope 2015, a groove 2035, a second slope 2025, and a third slope 2055. In some embodiments, the third slope 2055 may be substantially vertical. In some embodiments, the inclined direction of the first slope 2015 may be different from the inclined direction of the second slope 2025. In some embodiments, a first angle between the first slope 2015 and a vertical direction may be greater than a second angle between the second slope 2025 and the vertical direction. The first slope 2015, the second slope 2025, and/or the third slope 2055 may be configured to guide the moving position of the pushrod 1906. The groove 2035 may be configured to limit the moving position of the pushrod 1906. In some embodiments, the guide block 2005 may include a first protrusion 2065, a second protrusion 2075, and/or a third protrusion 2085. The first protrusion 2065 and/or the second protrusion 2075 may be configured to prevent the pushrod 1906 from moving out of the groove 2035 when the liquid chamber 1704 is mounted on the main body 1702, such that the liquid chamber 1704 can be fixed to the main body 1702. In some embodiments, the first protrusion 2065 and/or the second protrusion 2075 may be sharp. In some embodiments, the bottom end of the first protrusion 2065 may be lower than that of the second protrusion 2075. In some embodiments, the first protrusion 2065 and the second protrusion 2075 may be set on the same side of the third protrusion 2085 in the horizontal direction.

In some embodiments, the slide block 2004 may further include a bulge 2045 (or bump) below the groove 2035 of the guide block 2005. The bulge 2045 may include a first slope and a second slope. The first slope of the bulge 2045 may be close to the first slope of the guide block 2005. The second slope of the bulge 2045 may be close to the second slope of the guide block 2005. In some embodiments, the groove 2035 may limit the moving position of the pushrod 1906 through cooperating with the bulge 2045. In some embodiments, the slide block 2004 may be made of a material such as cast iron, stainless steel, nonferrous metal, plastic, or the like, or any combination thereof. In some embodiments, the material of the slide block 2004 may be the same as or different from the material of the guide slot 2002.

The first spring 2006 and the second spring 2008 may be set in the guide slot 2002. The first spring 2006 may include a first end and a second end. The first end of the first spring 2006 may be connected to a first end of the guide block 2005. The second end of the first spring 2006 may be fixed to the main body (e.g., the main body 1702) of the respiratory ventilation apparatus 1700. The second spring 2008 may include a first end and a second end. The first end of the second spring 2008 may be connected to a second end of the guide block 2005. The second end of the second spring 2008 may be fixed to the main body (e.g., the main body 1702) of the Respiratory ventilation apparatus. In some embodiments, the first spring 2006 may be the same as or different from the second spring 2008, for example, in materials (e.g., carbon steels, or alloy steels), types (e.g., coil springs, wave springs, shaped springs, or conical springs), sizes, or the like, or any combination thereof.

In some embodiments, the first spring 2006 and the second spring 2008 may be configured to guide a moving direction of the guide block 2005 (or slide block 2004). In some embodiments, if the guide block 2005 (or slide block 2004) is driven to move along the first direction (e.g., the direction indicated by the solid arrow in FIG. 20B), the second spring 2008 may be compressed. The compressed second spring 2008 may be capable of driving the guide block 2005 (or slide block 2004) to move along an opposite direction of the first direction (e.g., the direction indicated by the dotted arrow in FIG. 20B). Additionally or alternatively, if the guide block 2005 (or slide block 2004) is driven to move along the opposite direction of the first direction, the first spring 2006 may be compressed. The compressed first spring 2006 may be capable of driving the guide block 2005

(or slide block 2004) to move along the first direction. In some embodiments, the first spring 2006 may be omitted.

In some embodiments, the pushrod 1906 may include a first end and a second end. The first end of the pushrod 1906 may be mounted on the liquid chamber 1704 (e.g., the tank shell 1808). The second end of the pushrod 1906 may cooperate with the guide block 2005. In some embodiments, the pushrod 1906 may be movable along a second direction back and forth. In some embodiments, the second direction may be perpendicular to the first direction of the movement of the guide block 2005 (or slide block 2004). In some embodiments, the second end of the pushrod 1906 may include a fixed structure such as a bulge (e.g., a cylinder). In some embodiments, the second end of the pushrod 1906 may include a rotatable structure such as a bearing assembly. In some embodiments, the second end of the pushrod 1906 including a fixed structure may be capable of sliding along the first slope 2015, the third slope 2055, the groove 2035, and the second slope 2025 of the guide block 2005. In some embodiments, the second end of the pushrod 1906 including a rotatable structure may be capable of rolling along the first slope 2015, the third slope 2055, the groove 2035, and the second slope 2025 of the guide block 2005.

Figure 21A:
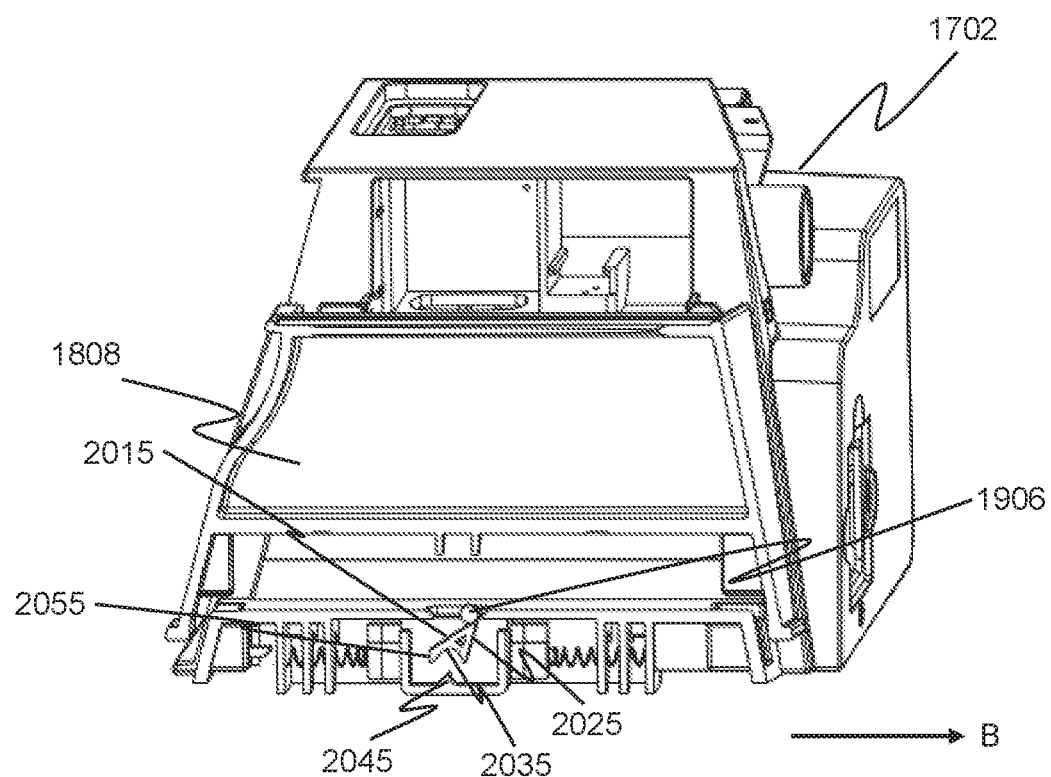
FIGS. 21A and 21B illustrate an exemplary process for mounting a liquid chamber on a main body of a respiratory ventilation apparatus by a push-push mechanism according to some embodiments of the present disclosure.
Figure 21B:
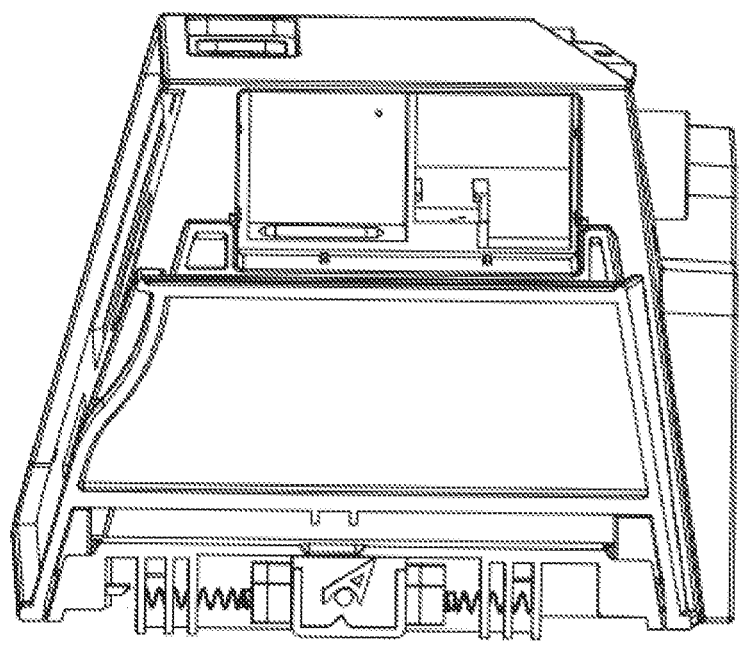

FIGS. 21A and 21B illustrate an exemplary process for mounting a liquid chamber on a main body of a respiratory ventilation apparatus by a push-push mechanism according to some embodiments of the present disclosure. As shown in FIG. 21A, the liquid chamber 1704 may be driven by a first pushing force and then be mounted on the main body 1702. In some embodiments, the first pushing force may be generated by a user (e.g., the subject 180). The direction of the first pushing force may be indicated by the arrow A (e.g., a vertical direction, also referred to as the second direction). In some embodiments, the pushrod 1906 may be capable of passing through the first hole 1709 and interact with the guide block 2005. In some embodiments, the center position of the pushrod 1906 may be on the right side of the bottom of the second protrusion 2075 along the first direction in its natural state. Upon being driven by the first pushing force, the pushrod 1906 may move with the liquid chamber 1704 along the second direction (indicated by the arrow A) and slide down along the first slope 2015 of the guide block 2005, and accordingly, the pushrod 1906 may push the guide block 2005 to move along the first direction (indicated by the arrow B) while the pushrod 1906 is moving downward, and the second spring 2008 may be compressed. At the same time, the compressed second spring 2008 may generate a reactive force tending to make the pushrod 1906 being pressed with the guide block 2005. In some embodiments, the first direction may be substantially perpendicular to the second direction. In some embodiments, if the first pushing force is larger than the reactive force, the pushrod 1906 may slide down along the third slope 2055 and move to or be close to the bottom edge of the third slope 2055. Then the pushrod 1906 may be separated from the first slope and/or the third slope 2055 and may reach below the bottom of the first protrusion 2065.

In some embodiments, if the first pushing force is released, the pushrod 1906 may move along an opposite direction of the second direction, and the pushrod 1906 may slide in a left part of a region formed by the bulge 2045 of the guide block 2005 and the groove 2035. At the same time, the guide block 2005 may move along an opposite direction of the first direction. The pushrod 1906 and the guide block 2005 may stop moving when the pushrod 1906 moves to a top position of the groove 2035, and accordingly, the pushrod 1906 may be stuck into the groove 2035 of the guide block 2005 (see FIG. 21B). Therefore, the liquid chamber 1704 may be mounted on the main body 1702 of the respiratory ventilation apparatus. In some embodiments, during the first pushing force is imposed on the liquid chamber 1704, and/or when the liquid chamber 1704 is mounted on the main body 1702, the heater plate 1710 may be pressed by the bottom surface of the liquid chamber 1704, and may move down in the second hole 1711. In some embodiments, one or more springs 2202 beneath the heater plate 1710 may be pressed, and then the heater plate 1710 and the heat-conducting plate 1810 at the bottom of the liquid chamber 1704 may form a close contact (or an intimate contact).

Figure 21C:
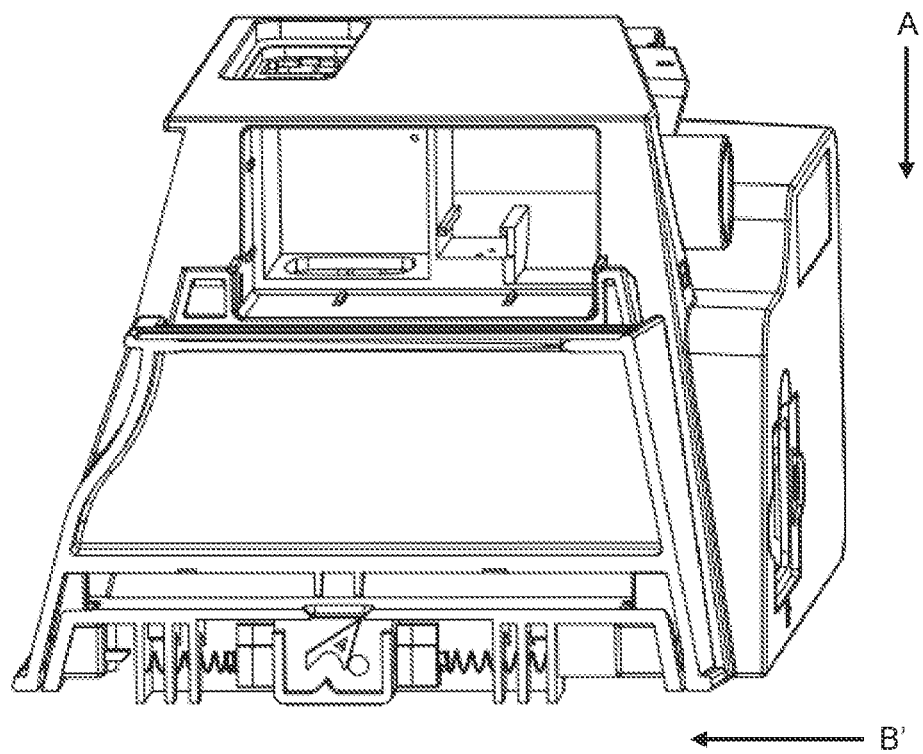
FIGS. 21C and 21D illustrate an exemplary process for removing a liquid chamber from a main body of a respiratory ventilation apparatus by a push-push mechanism according to some embodiments of the present disclosure.
Figure 21D:
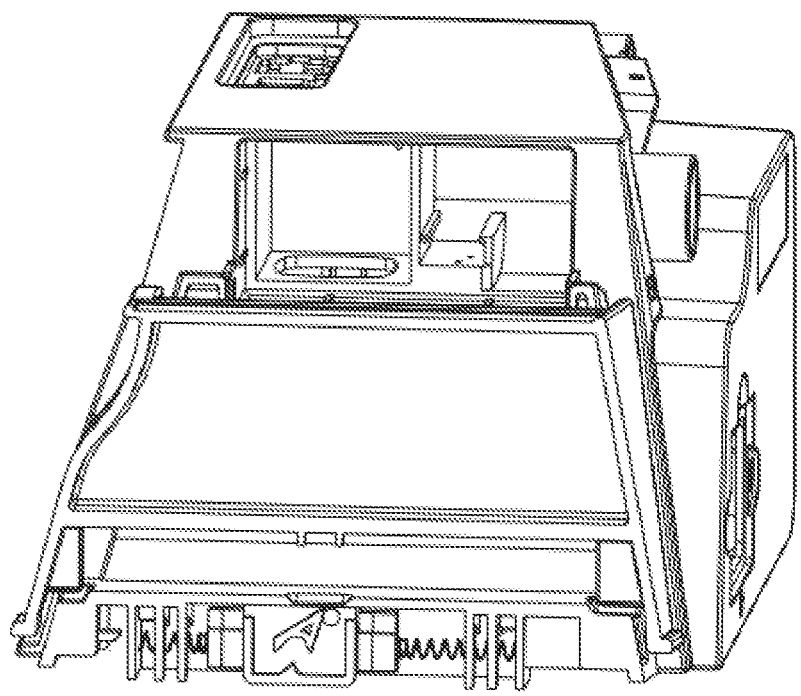
Figure 22A:
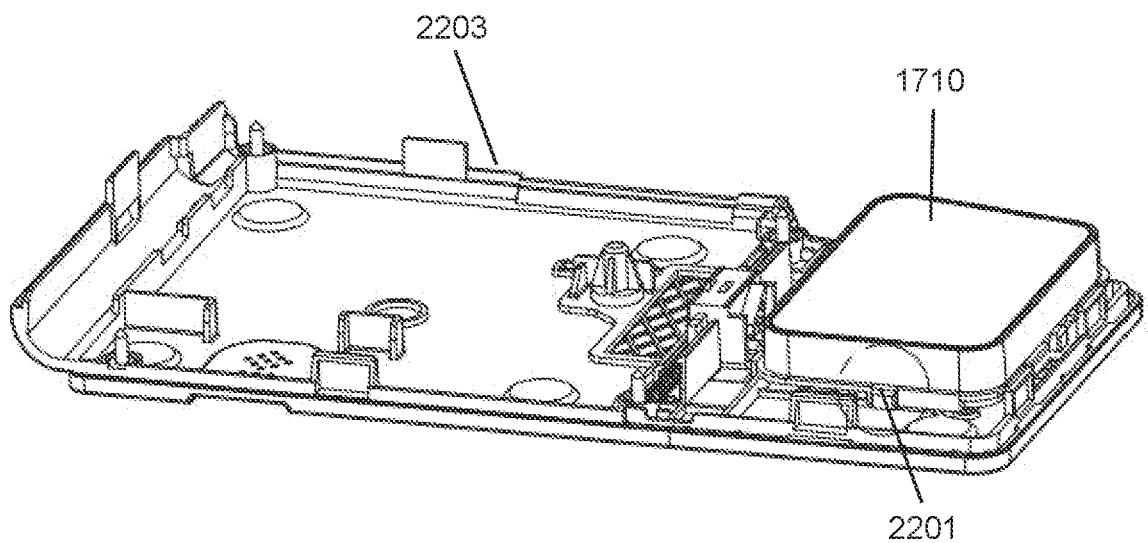
FIGS. 22A-22D illustrate an exemplary heater plate according to some embodiments of the present disclosure.
Figure 22B:
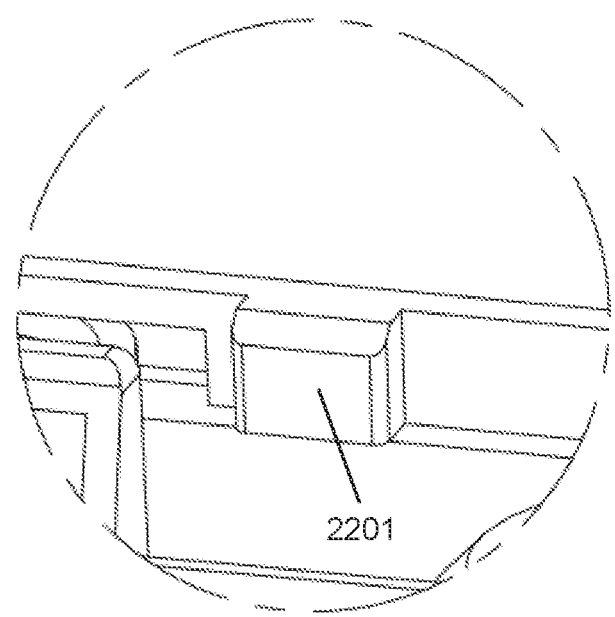
Figure 22C:
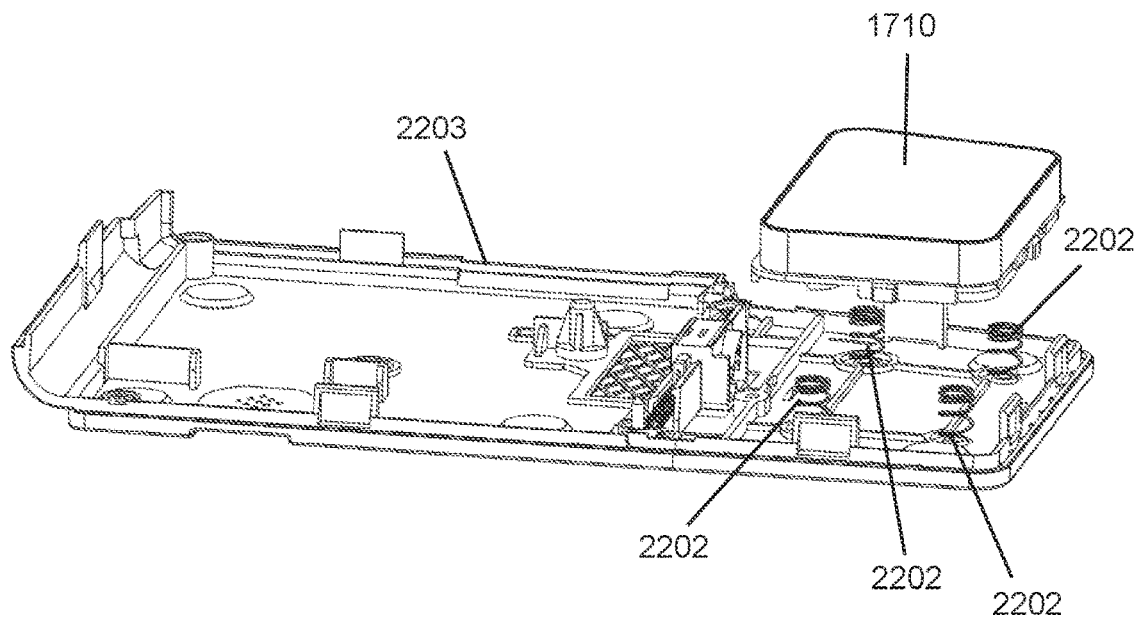
Figure 22D:
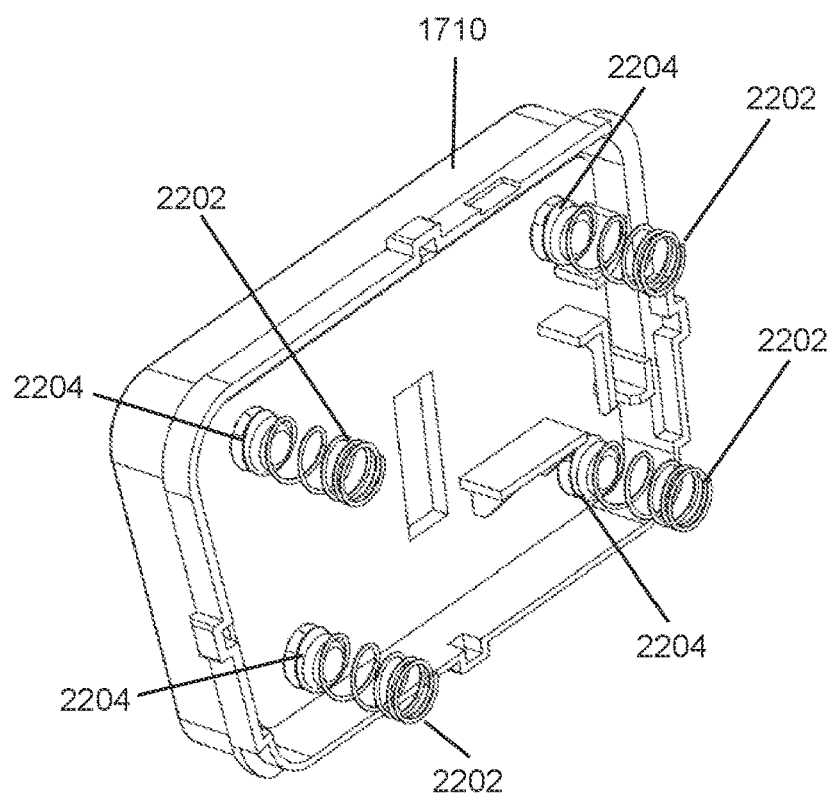

FIGS. 21C and 21D illustrate an exemplary process for removing a liquid chamber from a main body of a respiratory ventilation apparatus by a push-push mechanism according to some embodiments of the present disclosure. As shown in FIG. 21C, the liquid chamber 1704 may be driven by a second pushing force and then be released from the main body 1702. In some embodiments, the second pushing force may be generated by a user (e.g., the subject 180). The direction of the second pushing force may be indicated by the arrow A (e.g., a vertical direction, also referred to as the second direction). Upon being driven by the second pushing force, the pushrod 1906 may move with the liquid chamber 1704 along the second direction (indicated by the arrow A) and move down in a right part of a region formed by the bulge 2045 of the guide block 2005 and the groove 2035. At the same time, the guide block 2005 may move along the opposite direction of the first direction (indicated by the arrow B'). In some embodiments, the movement of the guide block 2005 along the opposite direction of the first direction may be driven by the reactive force of the second spring 2008. Then the pushrod 1906 may be released from the groove 2035 and may reach below the bottom of the second protrusion 2075.

In some embodiments, if the second pushing force is released, the one or more pressed springs CH 0902 beneath the heater plate 1710 may drive the heater plate 1710 to move along the opposite direction of the second direction. The movement of the heater plate 1710 may drive the liquid chamber 1704 to move along the opposite direction of the second direction, and the movement of the liquid chamber 1704 may lead the pushrod 1906 to move along the opposite direction of the second direction. Then the pushrod 1906 may move along the second slope of the guide block 2005, and the guide block 2005 may move along an opposite direction of the first direction (indicated by the arrow B'). Therefore, the liquid chamber 1704 may be released from the main body 1702 of the respiratory ventilation apparatus 1700 (see FIG. 21D), and the liquid chamber 1704 may be removed from the main body 1702.

It should be noted that the above description of the push-push mechanism 1904 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the push-push mechanism 1904 may be mounted on the main body 1702 of the respiratory ventilation apparatus in different directions, thus different pushing forces may be needed to mount and/or remove the liquid chamber 1704 from the main body 1702. In some embodiments, the guide block 2005 may be set as mirror symmetrical to that shown in FIGS. 20A-21D. In some embodiments, the push-push mechanism 1904 may include more than one pushrod. In some embodiments, the push-push mechanism 1904 may be configured for unlocking the liquid chamber 1704 from the main body of the respiratory ventilation apparatus 110 by pushing the liquid chamber 1704 in a push direction. The push direction may be substantially perpendicular to a liquid level in the liquid chamber 1704. In some embodiments, the push-push mechanism 1904 may be configured to form an energy storage means for storing the energy of the pushing action and for releasing the stored energy after the liquid chamber 1704 is unlocked by applying a force on the liquid chamber substantially in the opposite direction of the push direction. It should be noted that in some embodiments, the tank cover of the liquid chamber 1704 may be configured to be closable by pushing in the push direction. In some embodiments, the tank cover of the liquid chamber 1704 may be configured to be openable by pulling substantially in a direction opposite to the push direction. In some embodiments, in the operation of the respiratory ventilation apparatus 110, a user may couple the humidification assembly (e.g., the liquid chamber 1704) with the main body of the respiratory ventilation apparatus 110 by pushing the liquid chamber 1704 in the push direction, and/or unlock the humidification assembly with the main body by pushing the liquid chamber 1704 substantially in the push direction. In some embodiments, the user may place the humidification assembly on a surface of the respiratory ventilation apparatus 110 before the operation of coupling. In some embodiments, the operation of coupling the humidification assembly may include locking the tank cover with the tank by pushing the tank cover substantially in the push direction.

FIGS. 22A-22D illustrate an exemplary heater plate according to some embodiments of the present disclosure. In some embodiments, the heater plate 1710 may include one or more fixing columns 2204 (e.g., four fixing columns illustrated in FIG. 22D) configured to fix a first end of one or more springs 2202 (e.g., four springs illustrated in FIGS. 22C and 22D). Correspondingly, the base plate 2203 of the main body 1702 may include one or more fixing columns or bolts configured to fix a second end the springs 2202. Therefore, the heater plate 1710 may be mounted on or fixed to the base plate 2203 of the main body 1702 via the one or more springs 2202. As illustrated in FIG. 17, the heater plate 1710 may be capable of moving up and down through the second hole 1711 upon being driven by a pressure or upon releasing the pressure. To facilitate the movement of the heater plate 1710 in the second hole 1711, the heater plate 1710 may include one or more guide bumps 2201. For example, the heater plate 1710 may include one guide bump 2201 in each side of the heater plate 1710. Correspondingly, the side wall(s) of the second hole 1711 may include one or more guide grooves (not shown). The guide bumps and the guide grooves may be configured to guide the movement of the heater plate 1710 and/or limit the position of the heater plate 1710. For example, the second hole 1711 may include one guide groove in each side wall thereof. It should be noted that in some embodiments, the heater plate 1710 may include one or more guide grooves while the second hole 1711 may include one or more guide bumps corresponding to the guide grooves.

Figure 23A:
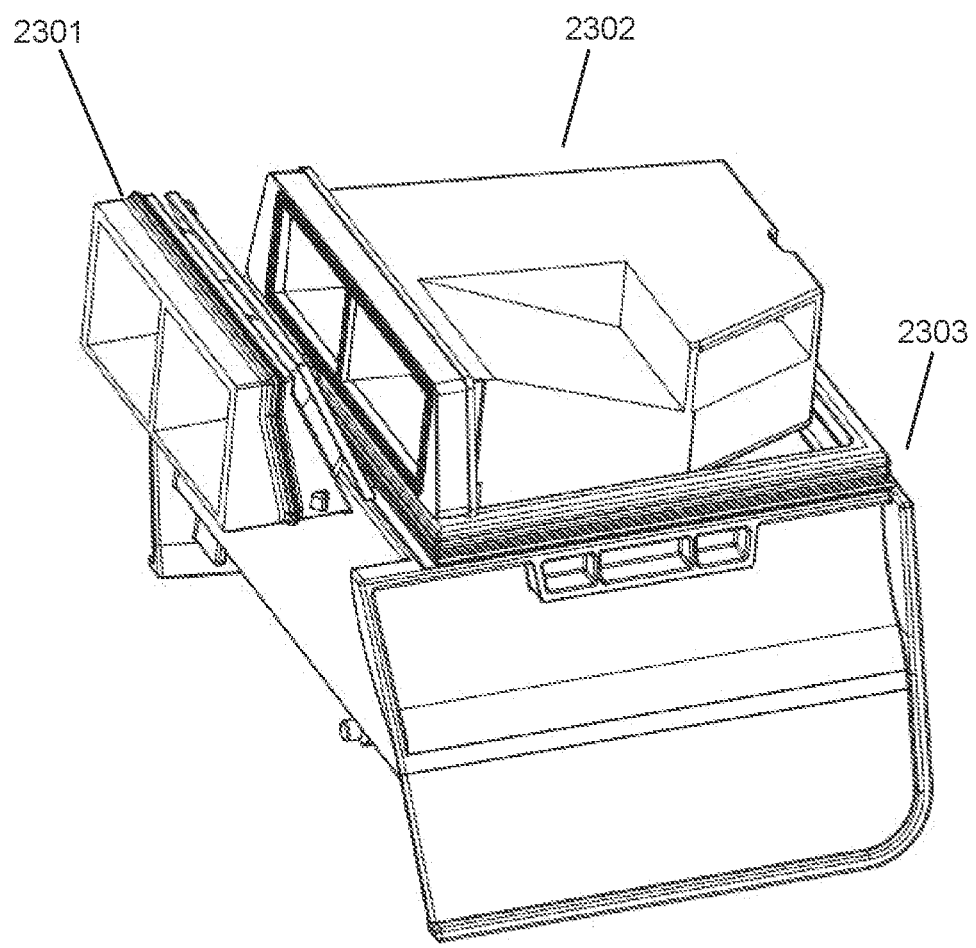
FIG. 23A-23D illustrate an exemplary connection between a liquid chamber and a main body of a respiratory ventilation apparatus according to some embodiments of the present disclosure.
Figure 23B:
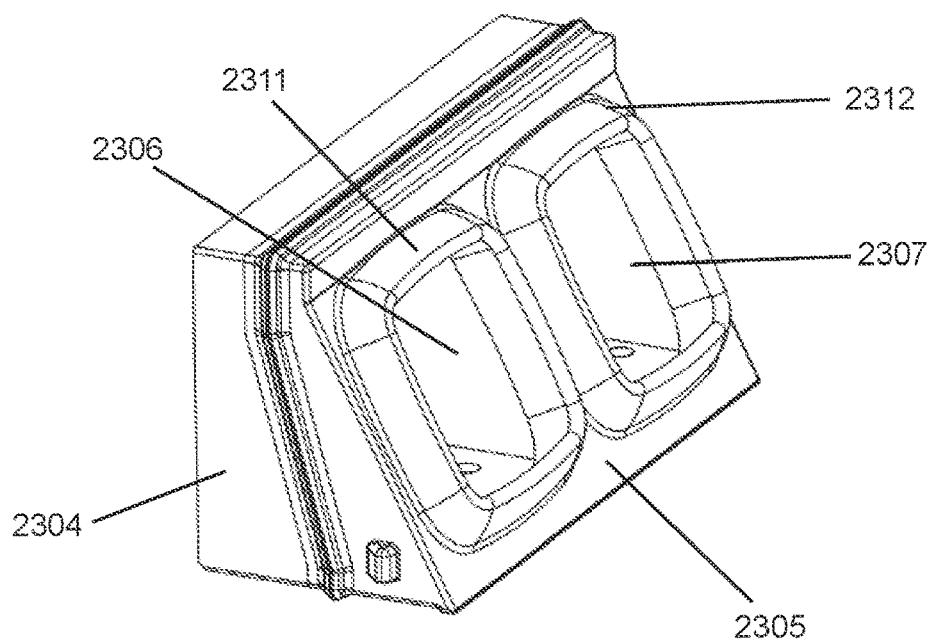
Figure 23C:
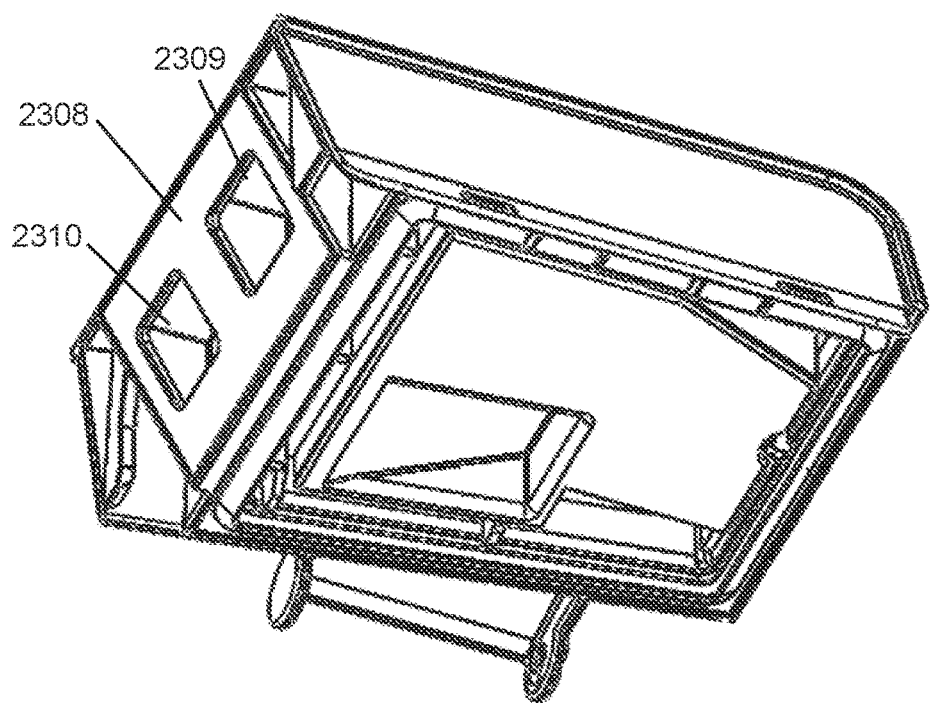
Figure 23D:
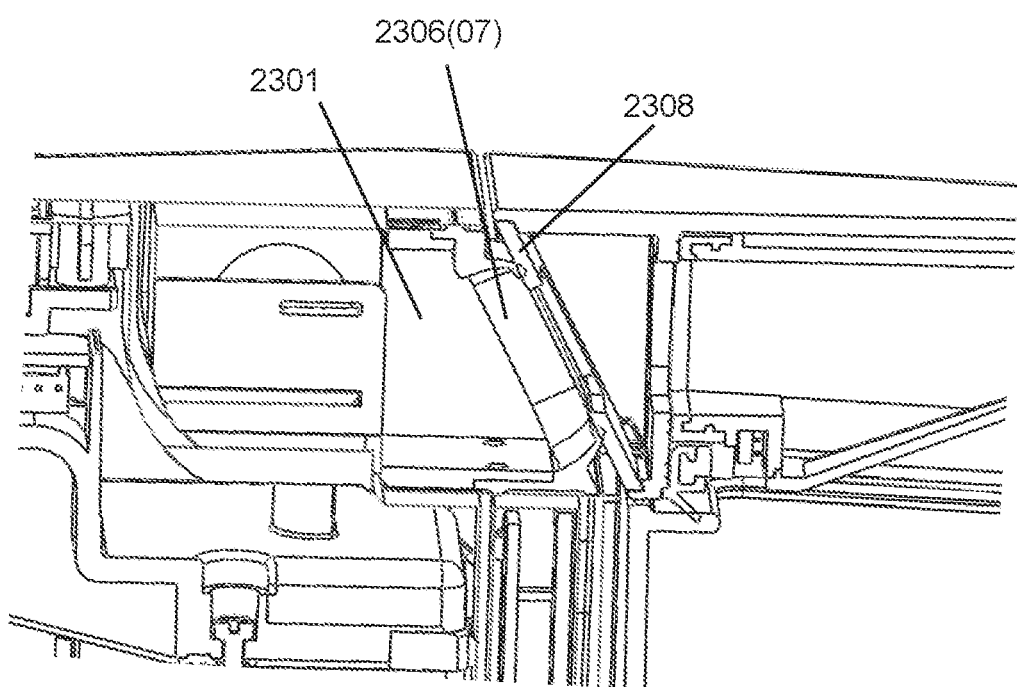

FIG. 23A-23D illustrate an exemplary connection between a liquid chamber and a main body of a respiratory ventilation apparatus according to some embodiments of the present disclosure. FIG. 23A shows an axonometric drawing of a connecting piece 2301 coupled with a tank cover 2302 of a liquid chamber 2303. It should be noted that the cover shell of the tank cover 2302 is not shown in FIG. 23A for illustration purposes. FIG. 23B shows an axonometric drawing of the connecting piece 2301. FIG. 23C shows an axonometric drawing of the tank cover 2302. FIG. 23D shows a section view of a sealed connection between the gasket 2305 of the connecting piece 2301 and the tank cover 2302.

The connecting piece 2301 may be configured to provide a sealed connection between the tank cover 2302 and the main body of the respiratory ventilation apparatus 110, so as to ensure the air tightness of the pressurized respiratory gas flowing between the liquid chamber 2303 and the main body of the respiratory ventilation apparatus 110. In some embodiments, the connecting piece 2301 may be fixed to the main body of the respiratory ventilation apparatus 110. In some embodiments, the connecting piece 2301 may be in detachable connection with the main body of the respiratory ventilation apparatus 110. In some embodiments, the housing of the main body of the respiratory ventilation apparatus 110 may include a space (e.g., the chamber 2502) for accommodating the connecting piece 2301. In some embodiments, the connecting piece 2301 and the main body may be an integral piece. In some embodiments, if the liquid chamber 2303 is fixed to a support plate (e.g., the support plate 1707 shown in FIG. 17) of the main body of the respiratory ventilation apparatus 110, and the tank cover 2302 is closed with the tank of the liquid chamber 2303, the connecting piece 2301 may provide a sealed connection between the tank cover 2302 and the main body of the respiratory ventilation apparatus 110. In some embodiments, the connecting piece 2301 may be fixed to or mounted on the tank cover 2302. In some embodiments, the connecting piece 2301 may be in detachable connection with the tank cover 2302. In some embodiments, the tank cover 2302 may include a space for mounting the connecting piece 2301. In some embodiments, the connecting piece 2301 and the tank cover 2302 may be an integral piece.

As shown in FIG. 23B, the connecting piece 2301 may include a support frame 2304 and/or a gasket 2305. The support frame 2304 may be configured to support the gasket 2305 and/or facilitate the fixation of the gasket 2305 with the main body of the respiratory ventilation apparatus 110. In some embodiments, the gasket 2305 may include a declining surface. In some embodiment, there may be a tilt angle between the declining surface of the connecting piece 2301 (or the gasket 2305) and a horizontal plane. In some embodiments, the tilt angle may be substantially within 0 degree to 90 degrees (e.g., within 30 to 60 degrees). The gasket 2305 may be configured to form a sealed connection between the tank cover 2302 and the main body of the respiratory ventilation apparatus 110. In some embodiments, the gasket 2305 may include a first aperture 2306 and/or a second aperture 2307 set on the declining surface. In some embodiments, support frame 2304 may include at least one gas flow passage in connection with the first aperture 2306 and/or the second aperture 2307. Each of the at least one gas flow passage may be in connection with one or more gas passages in the main body of the respiratory ventilation apparatus 110. In some embodiments, the edge of the first aperture 2306 may form a first protruding structure 2311. In some embodiments, the edge of the second aperture 2307 may include a second protruding structure 2312. The first protruding structure 2311 and/or the second protruding structure 2312 may protrude to the tank cover 2302. The first protruding structure 2311 and/or the second protruding structure 2312 may facilitate the sealing connection between the connecting piece 2301 and the tank cover 2302. In some embodiments, the cross section of the first protruding structure 2311 and/or the second protruding structure 2312 may have a C shape, an S shape, an O shape, a V shape, an M shape, an N shape, a Z shape, a U shape, or one or more folds, or the like, or a combination thereof. In some embodiments, the first protruding structure 2311 and/or the second protruding structure 2312 may be made of a soft material (e.g., silicone, soft glue, or the like, or any combination thereof). In some embodiments, the first protruding structure 2311 and/or the second protruding structure 2312 may be made of the same material(s) as that of the gasket 2305. In some embodiments, the first protruding structure 2311 and/or the second protruding structure 2312 may be made of different material(s) from that of the gasket 2305. In some embodiments, the thickness of the first protruding structure 2311 and/or the second protruding structure 2312 may be less than that of the gasket 2305.

In some embodiments, the gasket 2305 may be fixed on the main body (e.g., the support frame 2304 of the connecting piece 2301) of the respiratory ventilation apparatus 110. In some embodiments, the gasket 2305 may be detachably connected to the main body (e.g., the support frame 2304 of the connecting piece 2301) of the respiratory ventilation apparatus 110 through a, for example, glue joint, bonding, bolted connection, or the like, or a combination thereof. In some embodiments, the support frame 2304 may be made of a rigid plastic material. Exemplary rigid plastic materials may include acrylonitrile butadiene styrene (ABS) resins materials, polyformaldenyde (POM) plastics materials, polystyrene (PS) plastics materials, polymethyl methacrylate (PMMA) plastic materials, polycarbonate (PC) plastic materials, poly(ethylene terephthalate) (PET) plastic materials, poly(butylene terephthalate) (PBT) plastic materials, or poly(phenylene oxide) (PPO) plastic materials, or the like, or any combination thereof. In some embodiments, the gasket 2305 may be made of an elastic material including, for example, elastomer, rubber (e.g., silicone), or the like, or a combination thereof. In some embodiments, the gasket 2305 may include a protruding edge at the interface of the support frame 2304 and the gasket 2305. The protruding edge of the gasket 2305 may facilitate a sealing connection between the connecting piece 2301 and the main body of the respiratory ventilation apparatus 110.

As shown in the FIGS. 23A-23D, the declining surface of the gasket 2305 may face a corresponding declining surface of the connecting plate 2308 of the tank cover 2302. The tank cover 2302 may include a gas inlet port 2309 and a gas outlet port 2310. The first aperture 2306 on the declining surface of the gasket 2305 may correspond to the gas inlet port 2309 of the tank cover 2302, the second aperture 2307 on the declining surface of the gasket 2305 may correspond to the gas outlet port 2310 of the tank cover 2302. In some embodiments, if the liquid chamber 2303 is fixed to a support plate (e.g., the support plate 1707 shown in FIG. 17) of the main body of the respiratory ventilation apparatus 110, and the tank cover 2302 is closed with the tank of the liquid chamber 2303, the tank cover 2302 may be in a sealed connection with the main body of the respiratory ventilation apparatus 110 through the gasket 2305. The first aperture 2306 of the gasket 2305 and the gas inlet port 2309 of the tank cover 2302 may be capable of introducing the pressurized respiratory gas from the main body of the respiratory ventilation apparatus 110 into the liquid chamber 2303. The second aperture 2307 of the gasket 2305 and the gas outlet port 2310 of the tank cover 2302 may be capable of introducing the humidified and pressurized respiratory gas from the liquid chamber 2303 back into the main body of the respiratory ventilation apparatus 110.

As shown in FIG. 23D, if the tank cover 2302 is closed, the first protruding structure 2311 may be extruded and deform, and then may form a closed line contact with the connecting plate 2308 (e.g., around the edge of the gas inlet port 2309 and/or the gas outlet port 2310) of the tank cover 2302. Therefore, the air tightness of the respiratory gas flowing between the main body of the respiratory ventilation apparatus 110 and the liquid chamber 2303 may be ensured.

Figure 24:
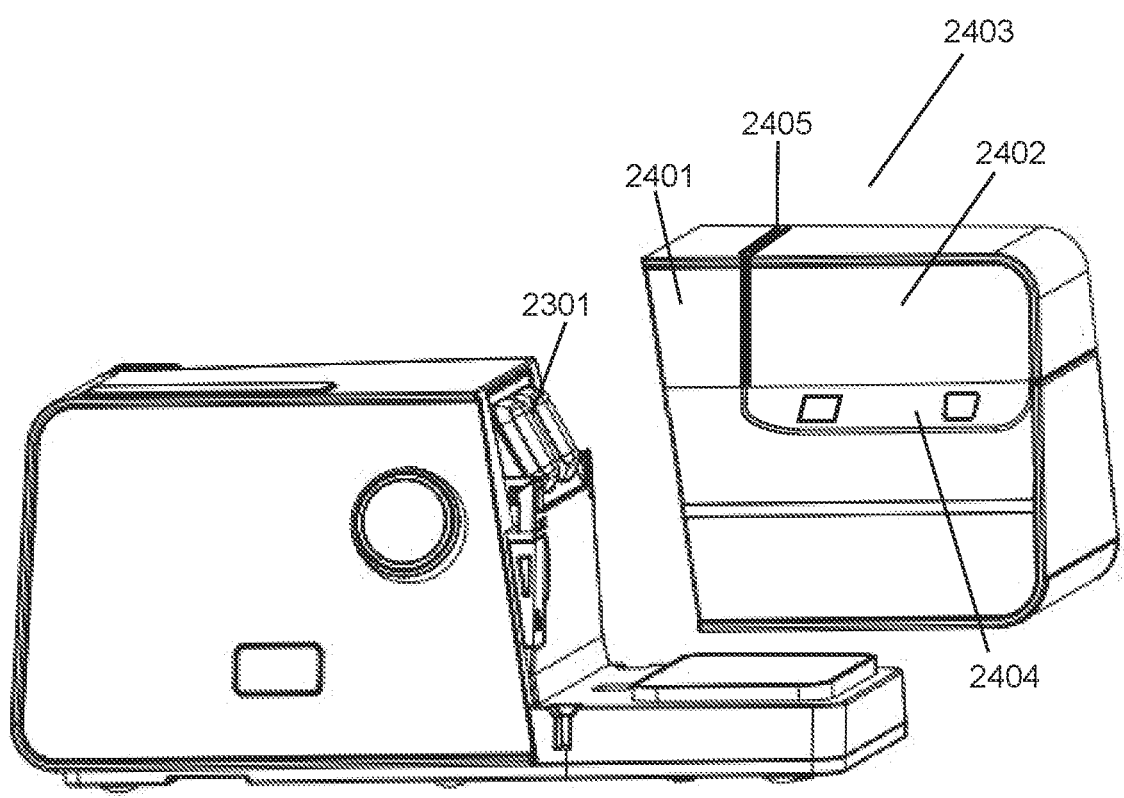
FIG. 24 illustrates another exemplary connection between a liquid chamber and a main body of a respiratory ventilation apparatus according to some embodiments of the present disclosure.

FIG. 24 illustrate another exemplary connection between a liquid chamber and a main body of a respiratory ventilation apparatus according to some embodiments of the present disclosure. As shown in FIG. 24, the liquid chamber 2403 may include a tank 2401 and a tank cover 2402. The connection piece 2301 may be configured to provide a sealed connection between a portion of the tank 2401 and the main body of the respiratory ventilation apparatus 110. In some embodiments, the connection piece 2301 may not directly contact with the tank cover 2402. Therefore, the state of the tank cover 2402 (open or close) may not affect the connection between the connection piece 2301 and the tank 2401. In some embodiments, the tank cover 2402 may be opened up by a handle 2404. The handle 2404 may have one or more notches which may make the handle 2404 easier to operate. In some embodiments, the tank cover 2402 may be a slide cover. In some embodiments, the tank cover 2402 may slide along the horizontal direction or slide along a direction with a tilt angle (such as, 10 degrees, 20 degrees, 30 degrees, or the like) relative to the horizontal direction. In some embodiments, to ensure a sealed connection between the tank 2401 and the tank cover 2402, an interface 2405 of the tank 2401 and the tank cover 2402 may be equipped with a sealing material (or an elastic material) including for example, a silicone, or the like.

Figure 25:
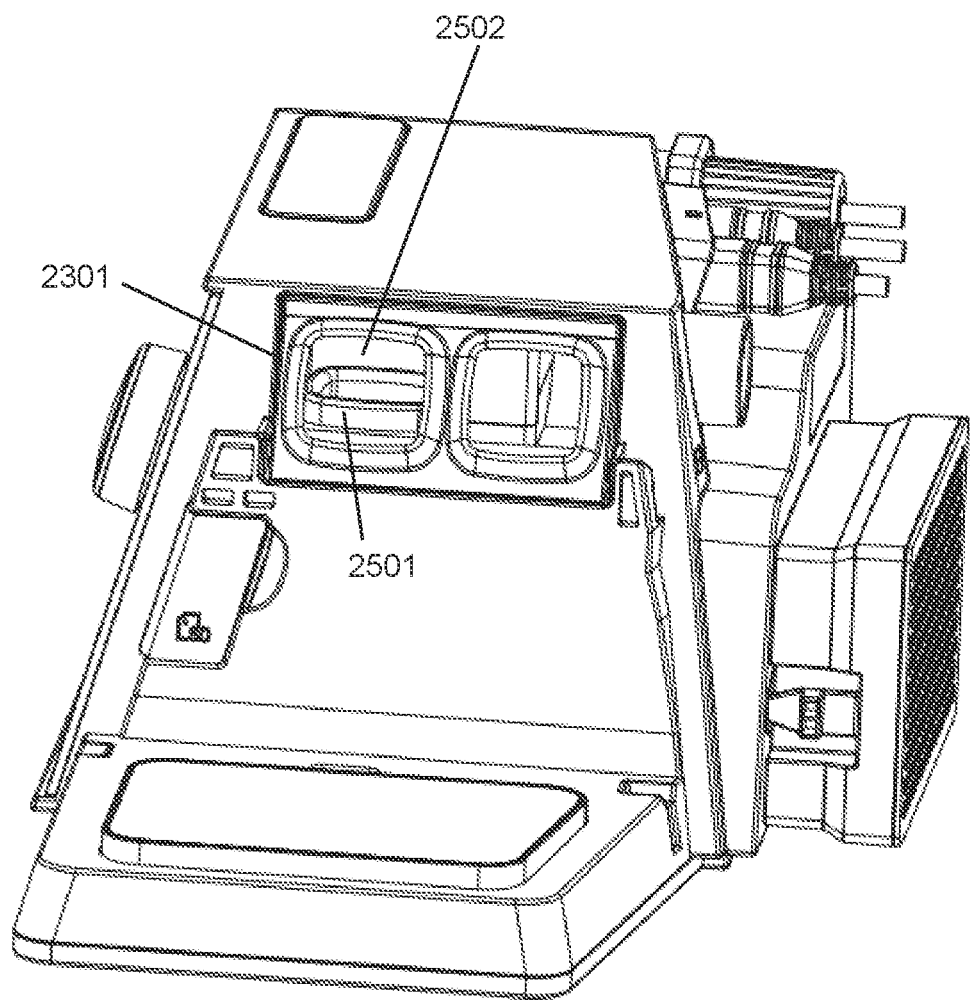
FIG. 25 illustrates an exemplary connection piece fixed to a main body of a respiratory ventilation apparatus according to some embodiments of the present disclosure.

FIG. 25 illustrate an exemplary connection piece fixed to a main body of a respiratory ventilation apparatus according to some embodiments of the present disclosure. In some embodiments, as shown in FIG. 25, a protruding platform 2501 may be set at the gas outlet port of a noise reduction box (e.g., the noise reduction box 801) or in a gas passage between the gas outlet port of the noise reduction box and the connecting piece 2301. In some embodiments, the protruding platform 2501 may include a gas passage corresponding to a gas outlet. In some embodiments, the gas passage between the gas outlet port of the noise reduction box and the connecting piece 2301 may form a chamber 2502. The chamber 2502 may include a bottom surface. In some embodiments, if the gas outlet of the protruding platform 2501 is in the vertical direction, the upper edge of the protruding platform 2501 may be set higher than the bottom surface of the chamber 2502. In some embodiments, if the gas outlet of the protruding platform 2501 is in the horizontal direction, the lower edge of the gas passage in the protruding platform 2501 may be set higher than the bottom surface of the chamber 2502. In some situations, if the respiratory ventilation apparatus 110 is placed obliquely (i.e., the liquid chamber is placed obliquely), a certain amount of liquid in the liquid chamber (e.g., the liquid chamber 1704, the liquid chamber 2403) may accidentally flow from the liquid chamber, via the gas inlet port (e.g., the gas inlet port 2309) and/or the gas outlet port (e.g., the gas outlet port 2310) of the liquid chamber, and/or the connecting piece 2301, and into the chamber 2502 of the main body of the respiratory ventilation apparatus 110. In some embodiments, the protruding platform 2501 may prevent the liquid from entering or reaching an interior space of the main body of the respiratory ventilation apparatus, the detection module 250, the noise reduction assembly 240, and/or the gas pressurization unit 210.

In some embodiments, the protruding platform 2501 may be fixed to the gas outlet port of the noise reduction assembly 240, the gas pressurization unit 210, or may be fixed in the chamber 2502. In some embodiments, the protruding platform 2501 may be detachably connected with the gas outlet port of the noise reduction assembly 240, the gas pressurization unit 210, or the chamber 2502 through a detachable connection structure, for example, a thread structure, a slot structure, or a snap joint structure, or the like, or any combination thereof.

Figure 26A:
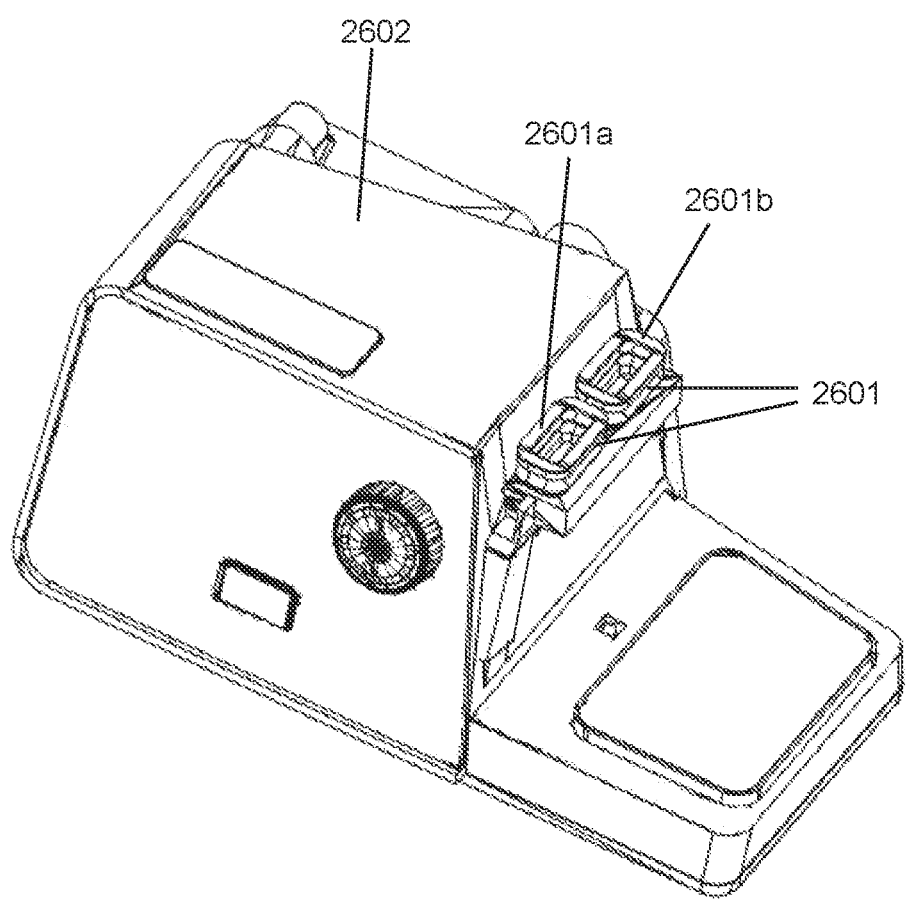
FIGS. 26A-26C illustrate an exemplary connection between a liquid chamber and a main body of a respiratory ventilation apparatus according to some embodiments of the present disclosure.
Figure 26B:
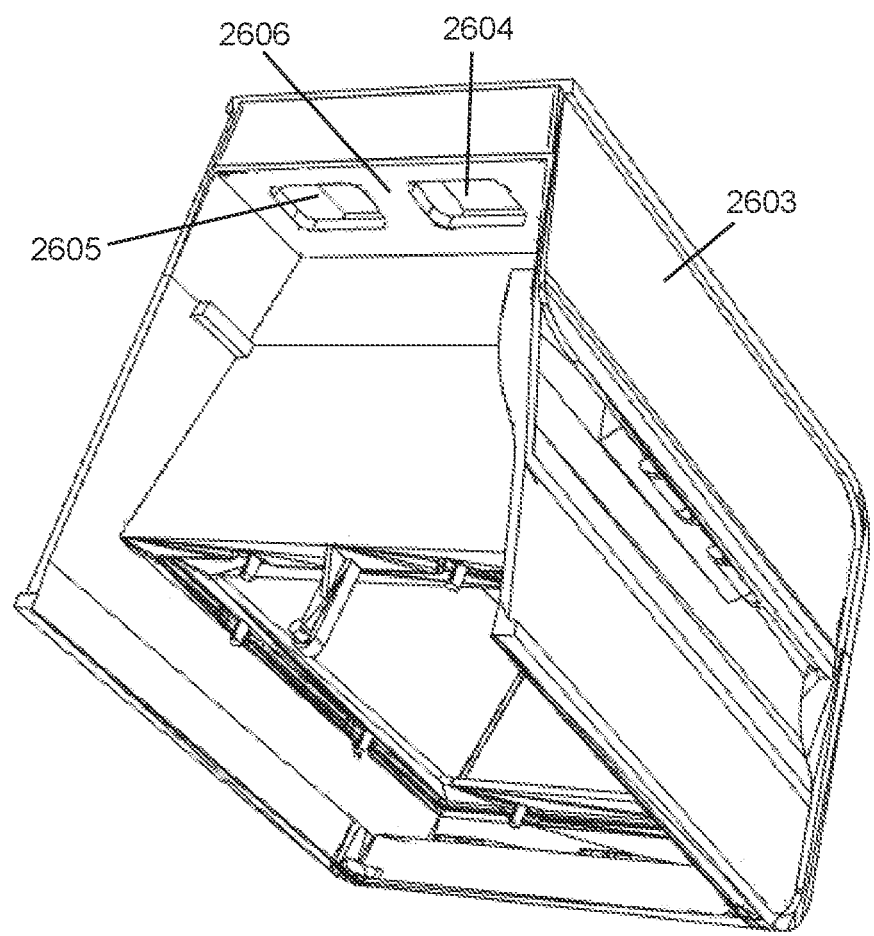
Figure 26C:
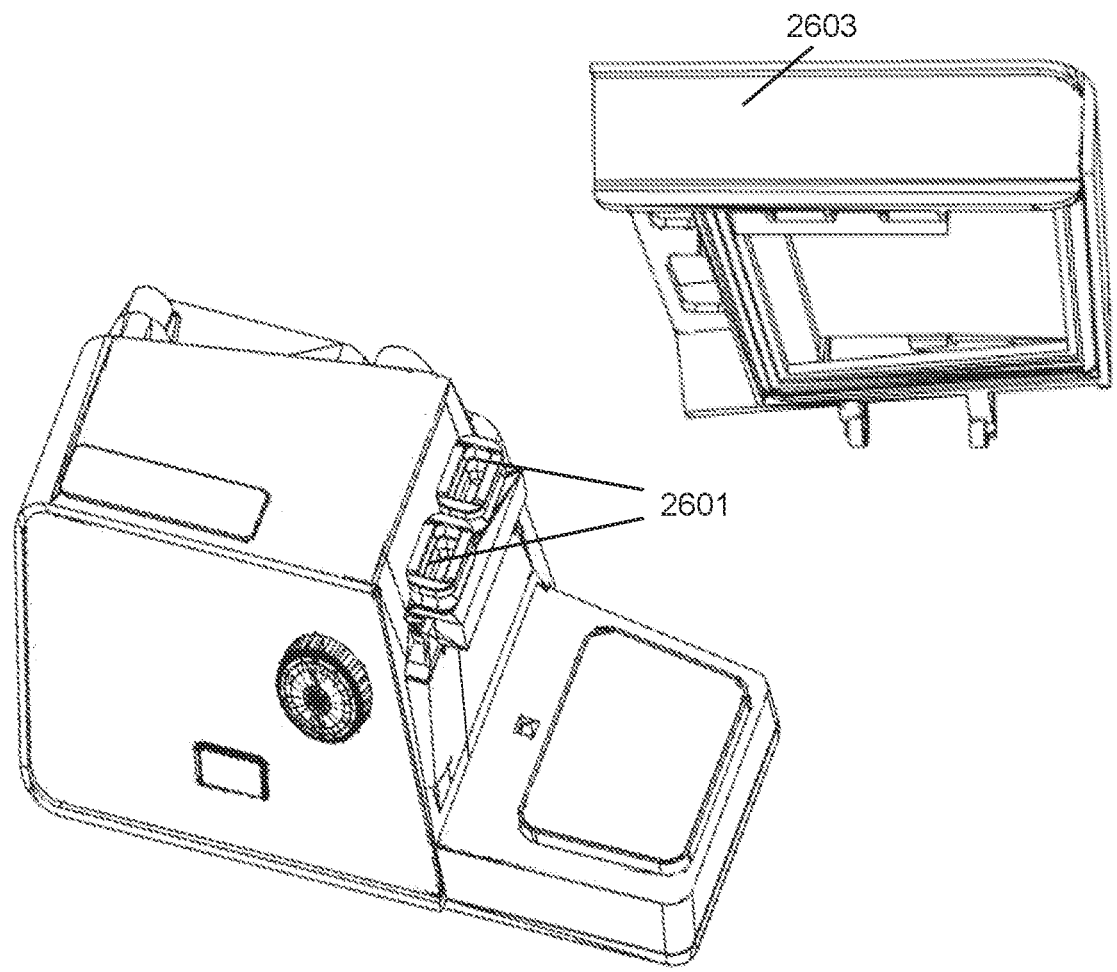

FIGS. 26A-26C illustrate an exemplary connection between a liquid chamber and a main body of a respiratory ventilation apparatus according to some embodiments of the present disclosure. The connecting piece 2601 may be configured to provide a sealed connection between the tank cover 2603 and the main body 2602 of the respiratory ventilation apparatus 110. In some embodiments, the connecting piece 2601 may include a first thread hose 2601a and/or a second thread hose 2601b. The hollow hole of the first thread hose 2601a may form a gas outlet port of the main body 2602. The hollow hole of the second thread hose 2601b may form a gas inlet port of the main body 2602. In some embodiments, the first thread hose 2601a and/or the second thread hose 2601b may be made of an elastic material including, for example, elastomer, rubber (e.g., silicone), or the like, or a combination thereof.

In some embodiments, the tank cover 2603 of the liquid chamber may include a connecting plate 2606 equipped with a gas inlet port 2604 and/or a gas outlet port 2605 of the tank cover 2603. The gas outlet port of the main body 2602 may correspond to the gas inlet port 2604 of the tank cover 2603. The gas inlet port of the main body 2602 may correspond to the gas outlet port 2605 of the tank cover 2603. In some embodiments, as shown in FIG. 26A, the hollow holes of the first thread hose 2601a and the second thread hose 2601b of the connecting piece 2601 may be set substantially vertical at the first interface between the main body 2602 of the respiratory ventilation apparatus 110 and the liquid chamber. Correspondingly, the connecting plate 2606 may be set substantially horizontal on the tank cover 2603. Therefore, if the tank cover 2603 is closed, a sealed connection may be formed between the main body 2602 of the respiratory ventilation apparatus 110 and the liquid chamber through the connecting piece 2601.

Figure 27:
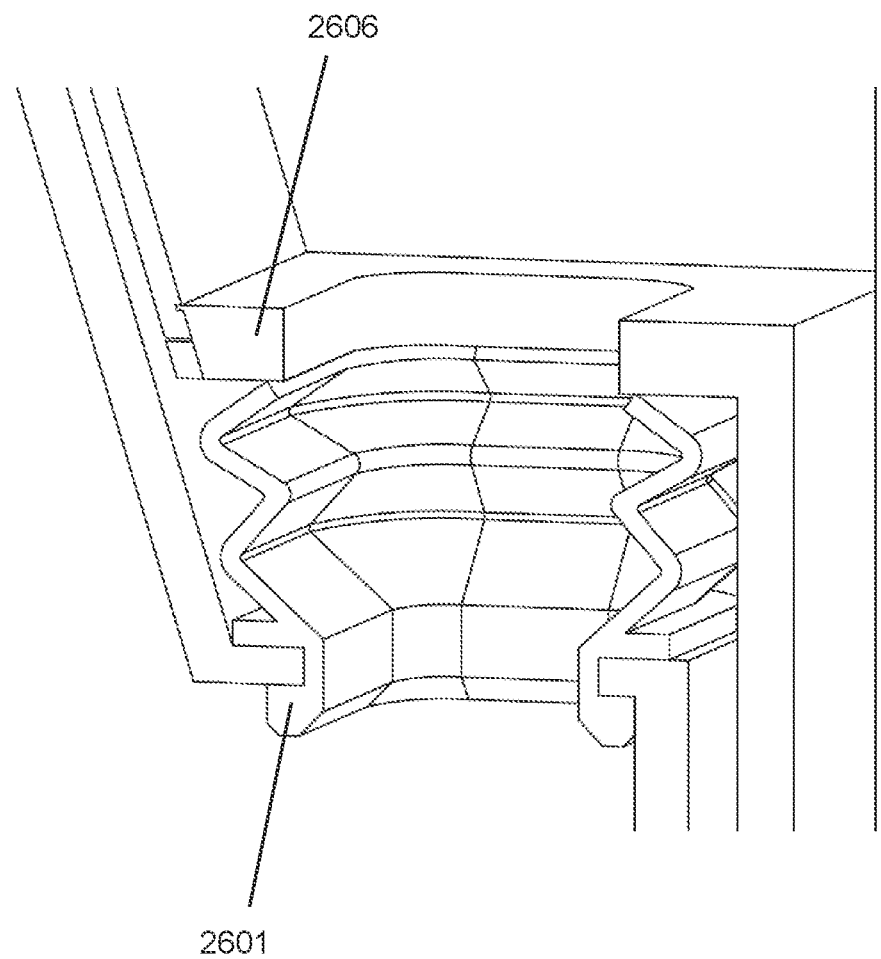
FIG. 27 illustrates an exemplary connection between a connecting piece and a connecting plate of a tank cover when the tank cover is closed according to some embodiments of the present disclosure.

FIG. 27 illustrates an exemplary connection between a connecting piece 2601 and a connecting plate 2606 of a tank cover 2603 when the tank cover 2603 is closed according to some embodiments of the present disclosure. As shown in FIG. 27, if the tank cover 2603 is closed, the connecting piece 2601 may be connected with the connecting plate 2606 of the tank cover 2603, and may form a closed line contact with the connecting plate 2606, which may ensure the air tightness of the pressurized respiratory gas flowing between the liquid chamber and the main body of the respiratory ventilation apparatus 110.

FIGS. 28A-28E illustrate exemplary thread hoses of a connecting piece according to some embodiments of the present disclosure. In some embodiments, a thread hose of the connecting piece may include one or more pleated structures on its side wall(s). The one or more pleated structures may be any shape such as, a quarter-circle shape, a semicircle shape, an arc shape, a slot shape, a U shape, a V shape, a Z shape, an M shape, an S shape, a C shape, an O shape, or the like, or any combine of thereof. The one or more pleated structures may provide a certain elasticity for the connecting piece to form a closed line contact with the tank cover 2603 when the tank cover 2603 is closed.

In some embodiments, at the top edge of the thread hose of the connecting piece, there may be one or more flexural structures having, for example, a circle shape, an annulus shape, an arc shape, a crescent shape, a tilt linear shape, a slot shape, a U shape, a V shape, a Z shape, an M shape, an S shape, a C shape, an O shape, or the like, or any combine of thereof. The one or more flexural structures may cause the connecting piece to form one or more closed line contacts with the tank cover 2603 to ensure the air tightness of the pressurized respiratory gas flowing between the liquid chamber and the main body of the respiratory ventilation apparatus 110.

Figure 28A:
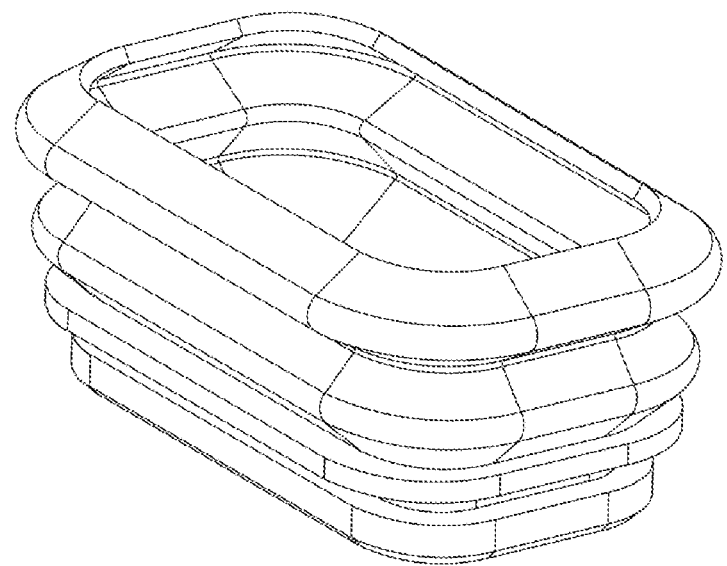
FIGS. 28A-28E illustrate exemplary thread hoses of a connecting piece according to some embodiments of the present disclosure.
Figure 28B:
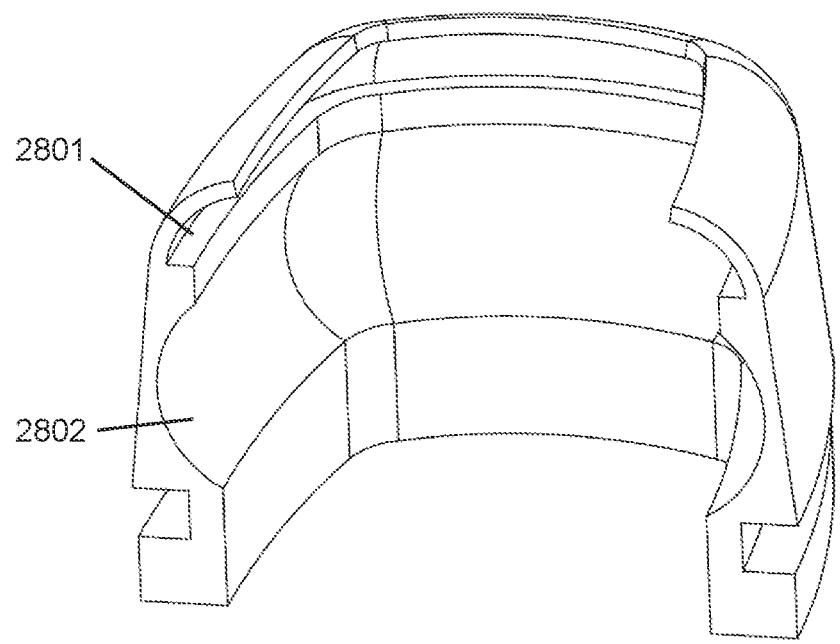
Figure 28C:
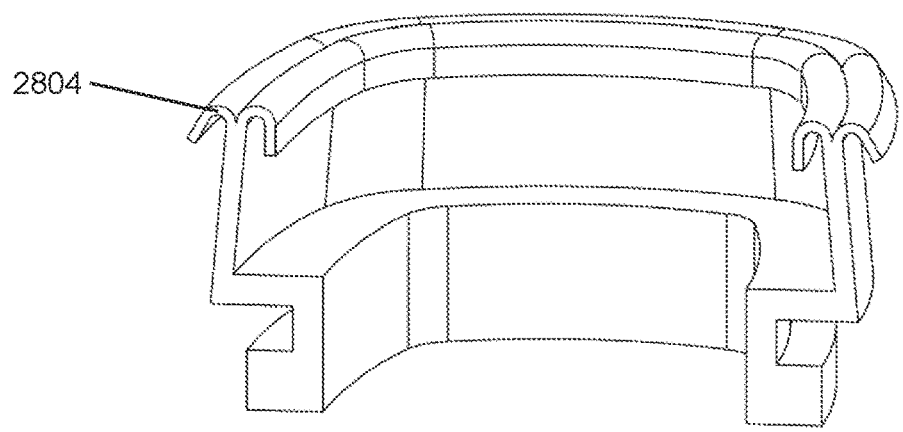
Figure 28D:
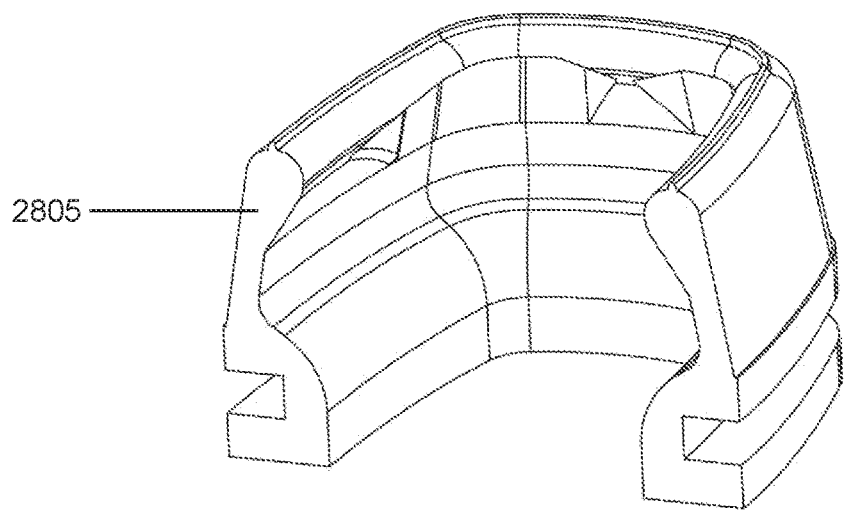
Figure 28E:
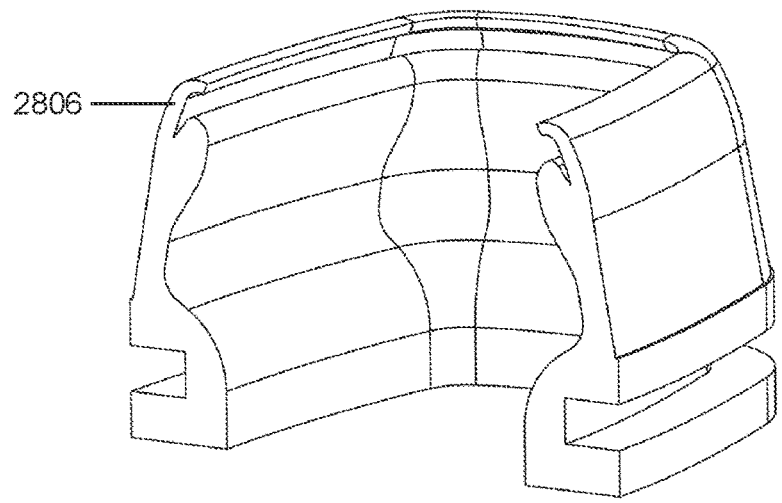

For example, in FIG. 28A, the thread hose of the connecting piece may have a two layer pleated structure on the side wall(s) thereof. In FIG. 28B, the thread hose of the connecting piece may include a quarter-circle shaped pleated structure 2801 close to the top edge of the thread hose and an arc shaped pleated structure 2802 close to the bottom of the thread hose. In some embodiments, the quarter-circle shaped pleated structure 2801 and/or the arc shaped pleated structure 2802 may be set on the inner surface of the thread hose. In some embodiments, the thread hose may include an S shaped flexural structure (not shown) on its top edge. In FIG. 28C, the thread hose may include a double C shaped flexural structure 2804 on its top edge. The double C shaped flexural structure 2804 may form two closed line contacts between the connecting piece and the tank cover when the tank cover is closed. In FIG. 28D, the thread hose may include an approximate round structure 2805 on its top edge. In FIG. 28E, the thread hose may include a half-crescent shaped flexural structure 2806. The approximate round structure 2805 and the half-crescent shaped flexural structure 2806 may provide a sealed closed line contact between the connecting piece and the tank cover when the tank cover is closed. In some embodiments, the thread hose may include a tilt linear shaped flexural structure (not shown) on its top edge and a trapezoid shaped slot (not shown) on its inner surface. All the thread hoses described above may be configured to ensure the air tightness of the pressurized respiratory gas flowing between the liquid chamber and the main body of the respiratory ventilation apparatus 110.

Figure 29A:
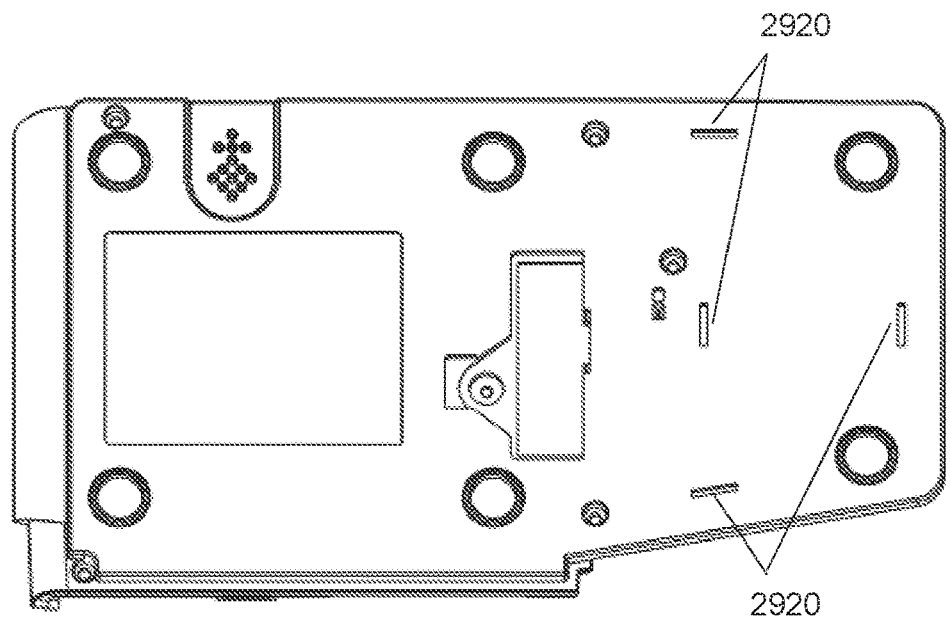
FIG. 29A-29D illustrate an exemplary baseplate of a respiratory ventilation apparatus according to some embodiments of the present disclosure.
Figure 29B:
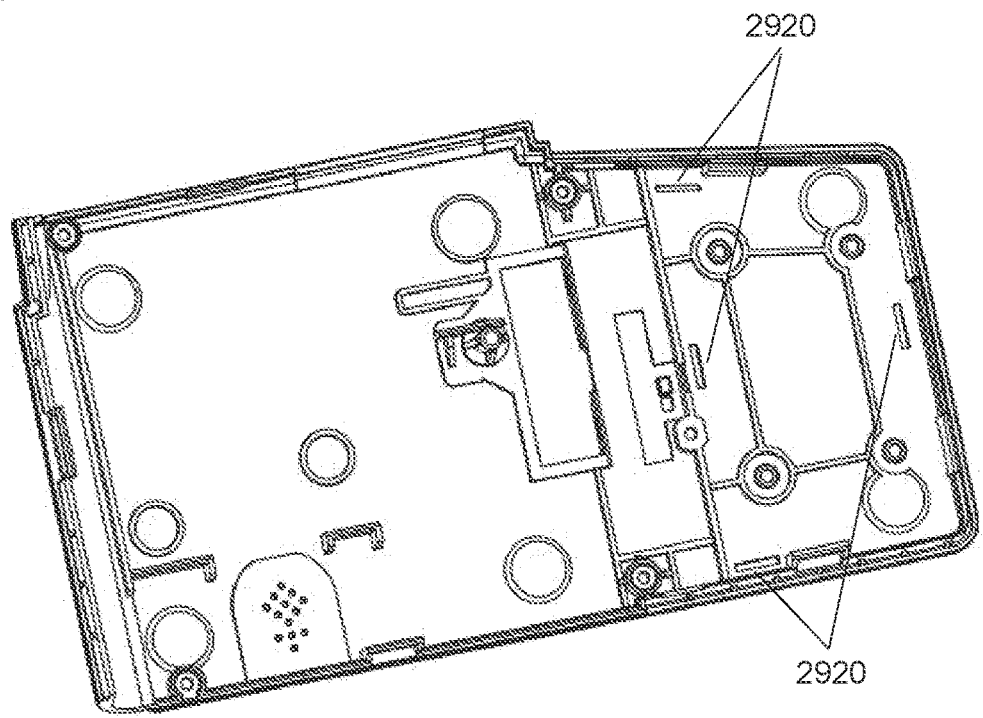
Figure 29C:
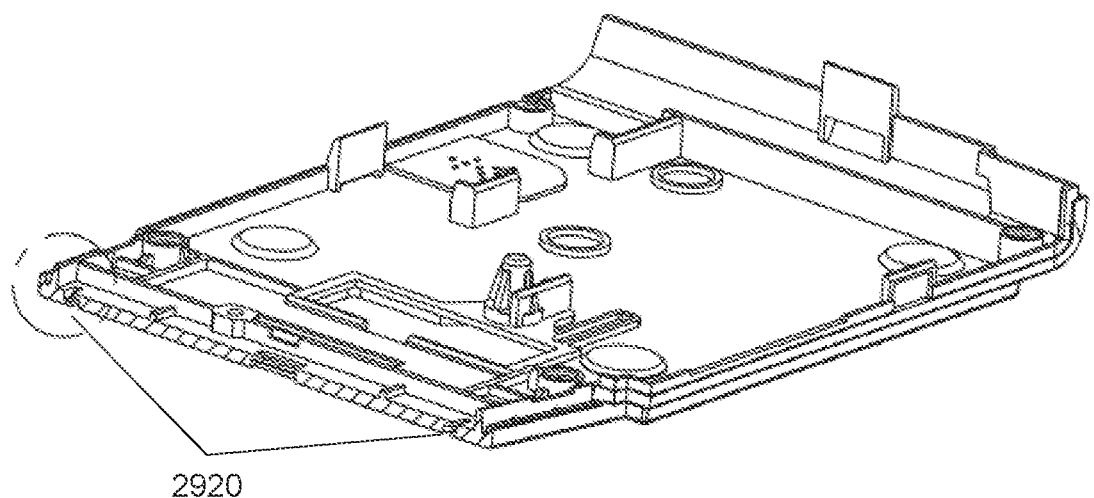
Figure 29D:
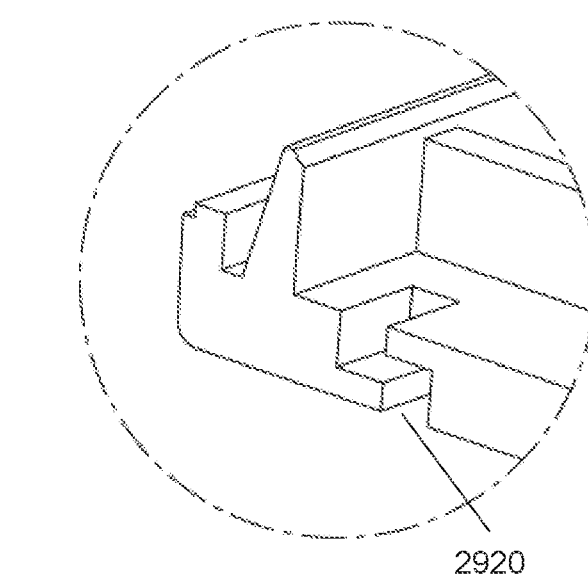

FIG. 29A-29D illustrate an exemplary baseplate of a respiratory ventilation apparatus 110 according to some embodiments of the present disclosure. FIG. 29A shows an outer surface of the baseplate 2900. FIG. 29B shows an inner surface of the baseplate 2900. FIG. 29C shows a side cross-sectional view of the baseplate 2900. FIG. 29D shows an enlarged view of one or more holes 2920 set on the baseplate 2900. The one or more holes 2900 may be configured to drain a certain amount of liquids leaking from a liquid chamber (e.g., the liquid chamber 1704 shown in FIG. 17). In some embodiments, during adding liquids into the liquid chamber or in other situations (e.g., if the respiratory ventilation apparatus 110 is placed obliquely (i.e., the liquid chamber is placed obliquely), or the liquid chamber is untightly sealed), a certain amount of liquids may leak from the liquid chamber and onto the baseplate 2900 below the liquid chamber. The leaked liquids may flow out of the respiratory ventilation apparatus 110 through the holes 2920. Therefore, the leaked liquids may not accumulate on the baseplate 2900. As shown in FIG. 29C and FIG. 29D, the cross section of each of the one or more holes 2920 may have a step shape. In some embodiments, the holes 2920 may facilitate the draining of the leaked liquids. In some embodiments, the holes 2920 may prevent a foreign matter (e.g., a finger of the subject 180) from entering the respiratory ventilation apparatus 110. In some embodiments, the one or more holes 2920 may conform to international standards to make the overall appearance of the respiratory ventilation apparatus 110 more elegant and/or to prevent the subject 180 from directly looking into the internal space of the respiratory ventilation apparatus 110 from the outside.

Figure 30A:
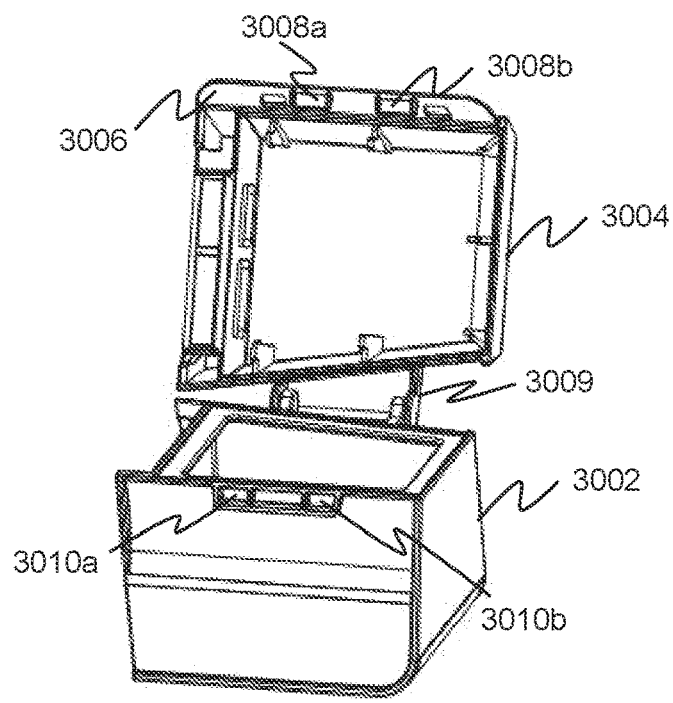
FIGS. 30A and 30B illustrate an exemplary liquid chamber of a respiratory ventilation apparatus according to some embodiments of the present disclosure.
Figure 30B:
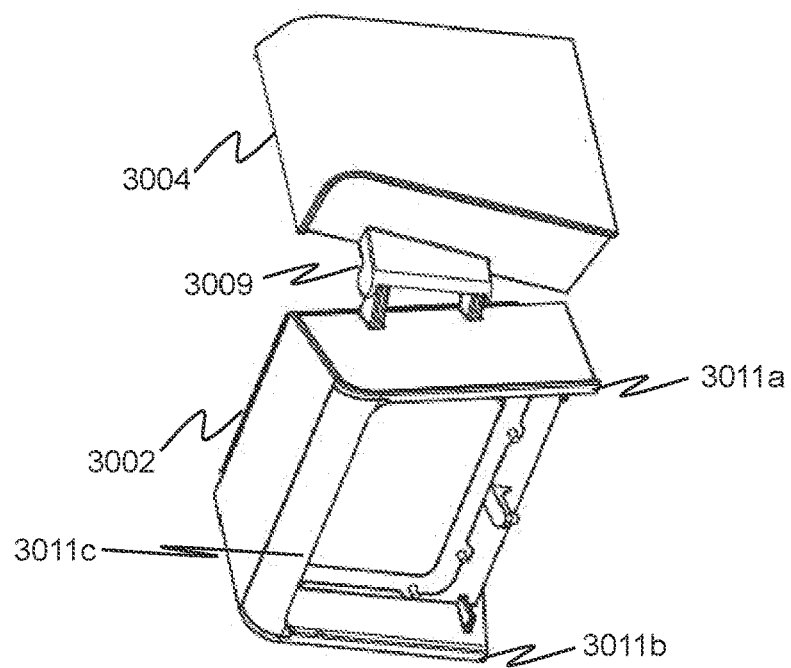

FIGS. 30A and 30B illustrate an exemplary liquid chamber of a respiratory ventilation apparatus according to some embodiments of the present disclosure. FIGS. 30A and 30B shows schematic diagrams of the liquid chamber 3000 in an open mode from different views. As shown in FIGS. 30A and 30B, the liquid chamber 3000 may include a tank 3002 and a tank cover 3004. In some embodiments, the tank cover 3004 may be pivotally connected to the tank 3002 through a connection mechanism. In some embodiments, the liquid chamber 3000 may be openable from a front surface of the respiratory ventilation apparatus 110.

The tank 3002 may be configured to accommodate one or more liquids (e.g., water and/or drug). In some embodiments, the tank 3002 may include an opening for filling at least one of the one or more liquids. In some embodiments, the opening may be openable by opening the tank cover 3004 and/or closable by closing the tank cover 3004. In some embodiments, the humidification assembly 220 and the main body of the respiratory ventilation apparatus 110 may be fluidically connectable by closing the tank cover 3004 and/or fluidically disconnectable by opening the tank cover 3004. In some embodiments, the tank 3002 and the main body may be attachable with each other by moving the tank 3002 in an attaching direction relative to the main body with an angle between the rotational axis and the attaching direction between 20°-160°. In some embodiments, the tank 3002 and the main body may be unlockable from each other by moving the tank 3002 in an unlocking direction relative to the main body with an angle between the rotational axis and the unlocking direction between 20°-160°. In some embodiments, the angle between the attaching direction and the unlocking direction may be between −45° and 45°.

In some embodiments, the humidification assembly 220 and the main body of the respiratory ventilation apparatus 110 may be fluidically connectable through at least a connecting port for forming at least one flow channel between the main body of the respiratory ventilation apparatus 110 and the liquid chamber 3000. In some embodiments, the at least one connecting port (e.g., the connecting piece 2301) may include a gas inlet port (e.g., the second aperture 2307) and a gas outlet port (e.g., the first aperture 2306). In some embodiments, the connecting port (e.g., the connecting piece 2301) may include an axial sealing member (e.g., the first protruding structure 2311 and/or the second protruding structure 2312) for fluidically sealingly connecting the gas inlet port 3102 and the gas outlet port 3104. In some embodiments, an inner surface of the axial sealing member may form at least partially the flow channel. In some embodiments, the axial sealing member may define a sealing plane. In some embodiments, the angle between the sealing plane and the liquid level in the liquid chamber 3000 may be between −75°-75° (e.g., −30°-30°). In some embodiments, the angle between the sealing plane and the attaching direction may be between 15°-65°. In some embodiments, the angle between the liquid level and the attaching direction and/or the unlocking direction may be between 45°-135°.

In some embodiments, the liquid chamber 3000 may be in detachable connection with the main body of the respiratory ventilation apparatus 110 through a push-push mechanism (e.g., the push-push mechanism 1904).

In some embodiments, a push direction of the push-push mechanism may be substantially perpendicular to the rotational axis of the connection mechanism. In some embodiments, the humidification assembly 220 and the main body of the respiratory ventilation apparatus 110 may be fluidically connectable by closing the tank cover 3004 in the push direction of the push-push mechanism while the tank 3002 is attached to the main body, and/or by attaching the liquid chamber 3000 to the main body in the push direction while the tank cover 3004 is closed.

The shape of the tank 3002 may include a cube, a cuboid or an irregular shape that may fit with a main body of the respiratory ventilation apparatus 110. The tank 3002 may be transparent, opaque, or semi-transparent. In some embodiments, the tank 3002 may include one or more marks for indicating the liquid level (e.g., water level) of the one or more liquids in the tank 3002. For example, the tank 3002 may include a first stick mark on a side surface of the tank 3002 indicating an allowable minimum liquid level, and/or a second stick mark on a side surface of the tank 3002 indicating an allowable maximum liquid level. As another example, the tank 3002 may include a flotage (e.g., a colored floating ball) inside the tank 3002 floating on the one or more liquids. In some embodiments, the tank 3002 may be equipped with a sensor for detecting the liquid level of the one or more liquids. More descriptions of the tank 3002 may be found elsewhere in the present disclosure (e.g., FIGS. 18A, 18B, and 32A-32C and the descriptions thereof).

In some embodiments, the shape of the tank cover 3004 may be similar to or different from the shape of the tank 3002. The shape of the tank cover 3004 may include a cube, a cuboid or an irregular shape that may fit with the main body of the respiratory ventilation apparatus 110. The material of the tank cover 3004 may be similar to or different from the material of the tank 3002. The tank cover 3004 may be transparent, opaque, or semi-transparent. More descriptions of the tank cover 3004 may be found elsewhere in the present disclosure (e.g., FIGS. 31, and 37A-42B, and the descriptions thereof).

In some embodiments, the tank cover 3004 may include a handle 3006, one or more buckles (e.g., a first buckle 3008a, or a second buckle 3008b) on the rear side of the handle 3006. The handle 3006 may be configured to facilitate the opening and/or closing of the tank cover 3004. The tank 3002 may include one or more notches (e.g., a first notch 3010a, and/or a second notch 3010b) in positions relative to the handle 3006, specifically corresponding to the one or more buckles of the handle 3006. If the tank cover 3004 is closed, the tank cover 3004 may be fastened with the tank 3002 through the cooperation of the one or more buckles and the one or more notches. In some embodiments, the lower edge of the first notch 3010a and/or the second notch 3010b may be equipped with a transverse bar. In some embodiments, the first buckle 3008a and/or the second buckle 3008b may be fastened by the transverse bar, so that the tank cover 3004 can be fastened with the tank 3002.

In some embodiments, the tank cover 3004 may be pivotally connected to the tank 3002 through a connection mechanism 3009. In some embodiments, the tank cover 3004 may be pivotally connected to the tank 3002 through the connection mechanism 3009 with a rotational axis. In some embodiments, the tank cover 3004 may be opened by rotating relative to the tank 3002 to a certain angle (e.g., 90 degrees, 100 degrees, etc.). The certain angle may be associated with a maximum rotary movement of the tank cover 3004. In some embodiments, the liquid chamber 3000 may be capable of being opened from a front surface of the respiratory ventilation apparatus 110. In some embodiments, as shown in FIGS. 30A and 30B, the connection mechanism 3009 may be set on a rear side (or back surface) of the respiratory ventilation apparatus 110, the handle 3006 may be set on a front surface of the respiratory ventilation apparatus 110, so that when the tank cover 3004 is opened, an undersurface of the tank cover 3004 may be substantially upright and facing the front surface of the respiratory ventilation apparatus 110. In some embodiments, the connection mechanism 3009 may be set on a side surface of the respiratory ventilation apparatus 110 away from the main body of the respiratory ventilation apparatus 110, the handle 3006 may be set on a top surface of the respiratory ventilation apparatus 110, and the tank cover 3004 may be opened such that an undersurface of the tank cover 3004 may be substantially upright and facing the main body of the respiratory ventilation apparatus 110 (not shown). In some embodiments, the connection mechanism 3009 may be configured as a guide slot (not shown), and the tank cover 3004 may be opened by moving horizontally relative to the tank 3002. More descriptions of the connection mechanism 3009 may be found elsewhere in the present disclosure (e.g., FIGS. 33A-36B and the descriptions thereof).

In some embodiments, the liquid chamber 3000 may include a connecting piece (e.g., the fixing gasket 1806, and/or the tank cover sealing gasket 1807 shown in FIGS. 18A and 18B) configured to provide a sealed connection between the tank 3002 and the tank cover 3004, so that when the tank cover 3004 is closed with the tank 3002, the liquid chamber 3000 may be sealed. The connecting piece may be made a material with a property of sealing, flexibility, elasticity, or the like, or any combination thereof. For example, the connecting piece may include flexible rubber (e.g., silicone) or a mixture of flexible rubber and hard rubber. In some embodiments, the connecting piece may be fixed on the bottom surface of the tank cover 3004 and/or the upper surface of the tank 3002.

It should be noted that the above description of the liquid chamber 3000 is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure. For example, the tank 3002 of the liquid chamber 3000 may be equipped with a sensor for detecting the liquid level of the one or more liquids. The respiratory ventilation apparatus 110 may generate a reminder based on the signal of the sensor when the liquid level is less than a predetermined level. As another example, the tank cover 3004 may slide inclinedly relative to the tank 3002. As a further example, the tank cover 3004 may slide in a certain degree of arc relative to the tank 3002.

Figure 31:
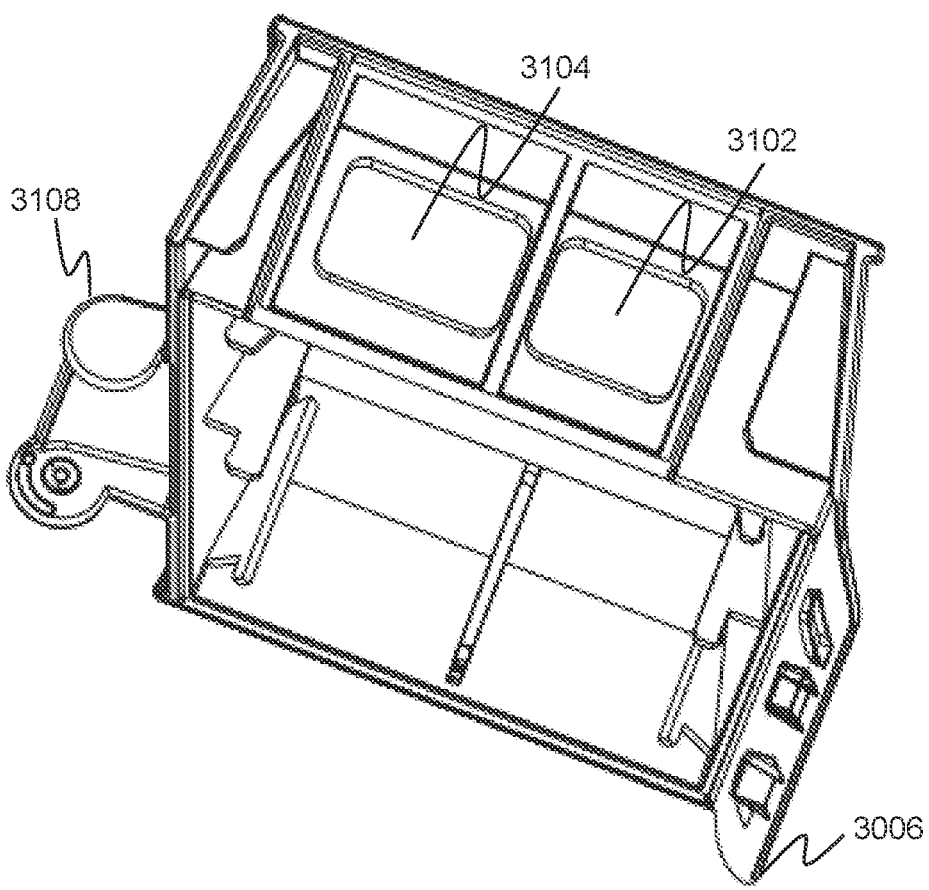
FIG. 31 illustrates an exemplary tank cover of a liquid chamber of a respiratory ventilation apparatus according to some embodiments of the present disclosure.

FIG. 31 illustrates an exemplary tank cover of a liquid chamber of a respiratory ventilation apparatus according to some embodiments of the present disclosure. The tank cover 3004 may include a cover shell. The cover shell may include a front surface corresponding to the front surface of the respiratory ventilation apparatus 110, a back surface corresponding to the back surface the respiratory ventilation apparatus 110, a top surface away from a corresponding tank (e.g., the tank 3002), a bottom surface that may contact with the tank 3002, a side surface close to the main body of the respiratory ventilation apparatus 110, a side surface away from the main body of the respiratory ventilation apparatus 110, etc. The tank cover 3004 may include a gas inlet port 3102, a gas outlet port 3104, a handle 3006, a connecting piece 3108 of the connection mechanism 3009, etc. The gas inlet port 3102 may be configured to introduce the pressurized respiratory gas from the main body of the respiratory ventilation apparatus 110 into the liquid chamber (e.g., the liquid chamber 3000). The gas outlet port 3104 may be configured to introduce the humidified and pressurized respiratory gas from the liquid chamber back into the main body of the respiratory ventilation apparatus 110.

As shown in FIG. 31, the handle 3006 may be set on the front surface of the tank cover 3004. The connecting piece 3108 of the connection mechanism 3009 may be set on a back surface of the tank cover 3004. The gas inlet port 3102 and the gas outlet port 3104 may be set on the side surface (e.g., a declining surface) of the tank cover 3004 close to the main body of the respiratory ventilation apparatus 110. In some embodiments, the gas inlet port 3102 and the gas outlet port 3104 may be set on a portion of the bottom surface of the tank cover 3004 (see FIG. 26B). The gas inlet port 3102 and the gas outlet port 3104 may be set close to the main body of the respiratory ventilation apparatus and may not contact with the tank 3002.

Figure 32A:
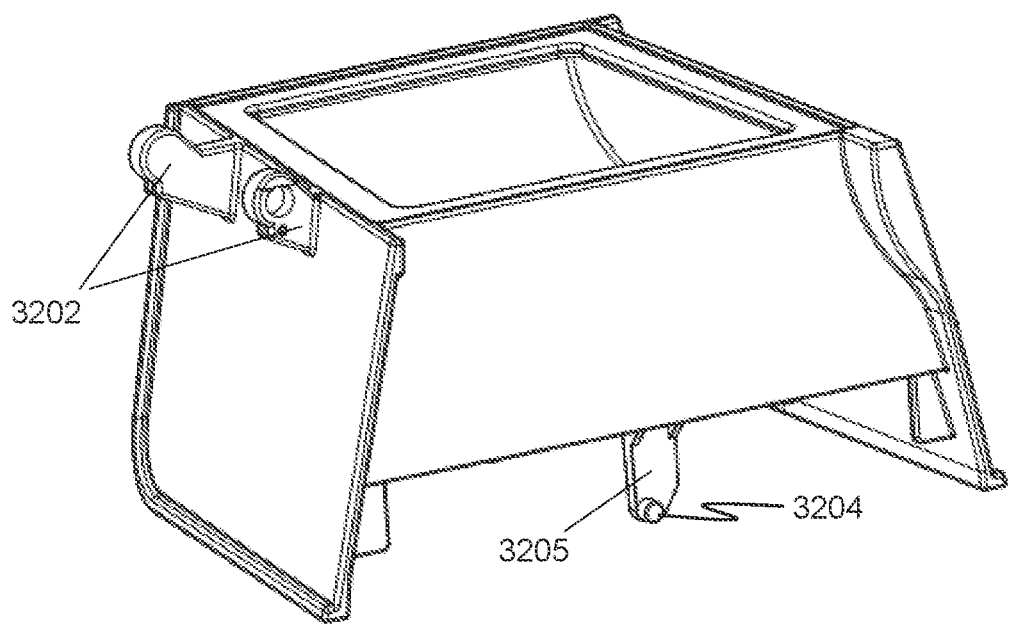
FIGS. 32A-32C illustrate an exemplary tank of a liquid chamber of a respiratory ventilation apparatus according to some embodiments of the present disclosure.
Figure 32B:
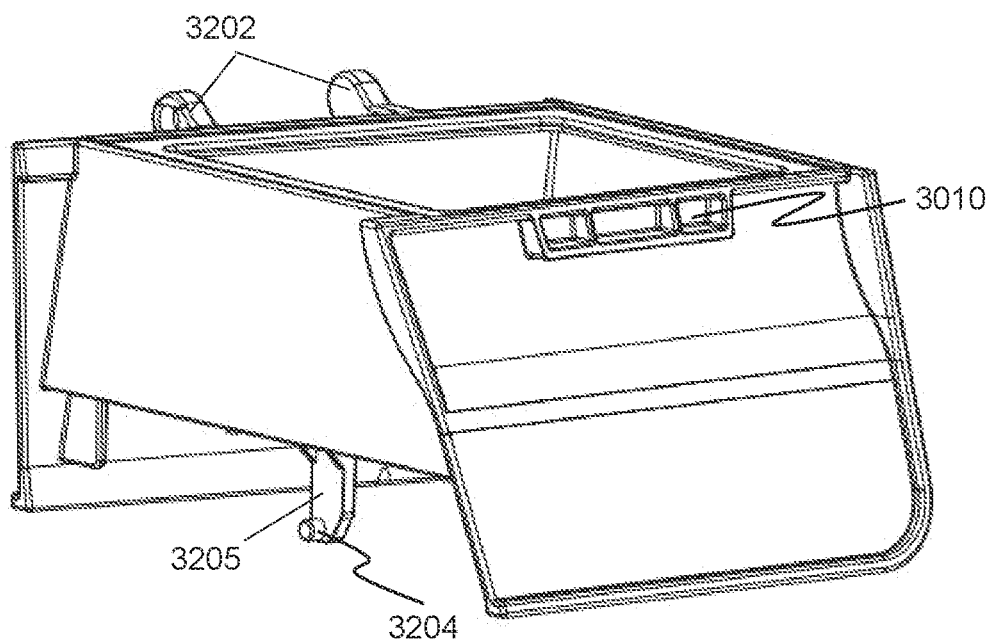
Figure 32C:
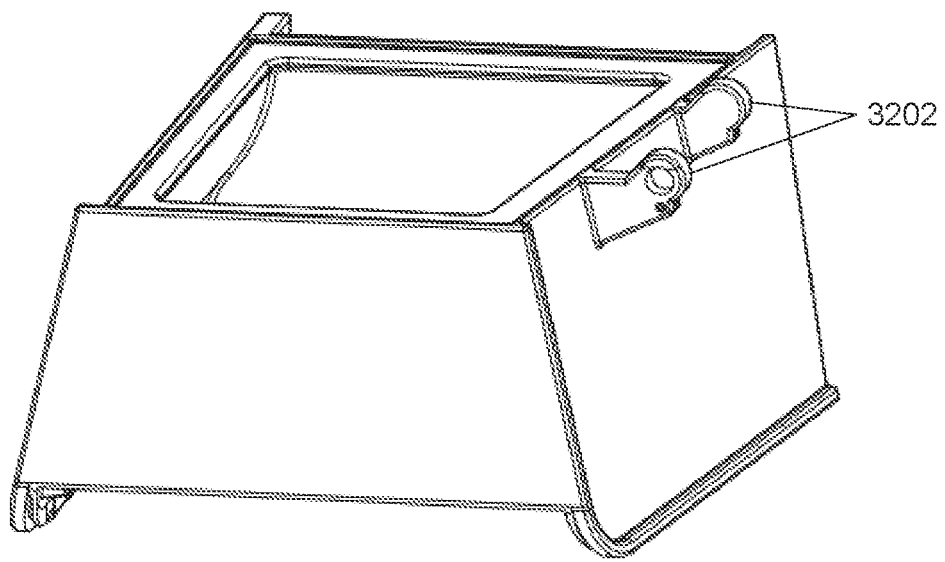

FIGS. 32A-32C illustrate an exemplary tank of a liquid chamber of a respiratory ventilation apparatus according to some embodiments of the present disclosure. FIGS. 32A-32C shows the tank 3002 in different views. The tank 3002 may include a front surface facing a user of the respiratory ventilation apparatus 110, a back surface away from the user of the respiratory ventilation apparatus 110, a top surface that may contact with the tank cover 3004, a bottom surface away from the tank cover 3004, a side surface close to the main body of the respiratory ventilation apparatus 110, a side surface away from the main body of the respiratory ventilation apparatus 110, etc. The tank 3002 may include a connecting piece 3202 of the connection mechanism 3009, a bolt 3204, one or more notches 3010, etc.

As shown in FIGS. 32A-32C, the connecting piece 3202 of the connection mechanism 3009 may be set on the back surface of the tank 3002. The connecting piece 3202 of the connection mechanism 3009 and the connecting piece 3108 of the connection mechanism 3009 may form an integral connection mechanism 3009. The bolt 3204 may be set below the bottom surface of the tank 3002. The bolt 3204 may be fixed to the bottom surface of the tank 3002 via a connecting piece 3205. In some embodiments, the bolt 3204 may be involved in a push-push mechanism (e.g., the push-push mechanism 1904 shown in FIGS. 19-21D). The one or more notches 3010 may be set on a front surface of the tank 3002 to be in accordance with the handle 3006 of the tank cover 3004.

In some embodiments, the side surface of the liquid chamber 3000 close to the main body of the respiratory ventilation apparatus 110 may have an angle relative to the horizontal plane. In some embodiments, the angle between the side surface of the tank 3002 close to the main body of the respiratory ventilation apparatus 110 and the horizontal plane may be greater than the angle between the declining surface of the tank cover 3004 and the horizontal plane, which may facilitate a sealed connection between the tank cover 3004 and the main body of the respiratory ventilation apparatus 110. In some embodiments, the front surface of the tank 3002, the back surface of the tank 3002, and/or the side surface of the tank 3002 away from the main body of the respiratory ventilation apparatus 110 may extend downwards to form one or more baffles (e.g., the baffles 3011a, 3011b, and/or 3011c) below the bottom surface. If the liquid camber is mounted on the respiratory ventilation apparatus 110, the baffles 3011a, 3011b, and/or 3011c may form a space to accommodate a part of base of the main body of the respiratory ventilation apparatus 110 (e.g., a portion of the baseplate 4410, and/or the heating device 4414, etc.). If the liquid chamber is placed separately, the baffles 3011a, 3011b, and/or 3011c may support the tank 3002 (or the liquid chamber) and/or protect the bolt 3204 and the connecting piece 3205. In some embodiments, the bolt 3204 and the connecting piece 3205 may also be referred to as a pushrod (e.g., the pushrod 1906 illustrated in FIG. 19).

Figure 33A:
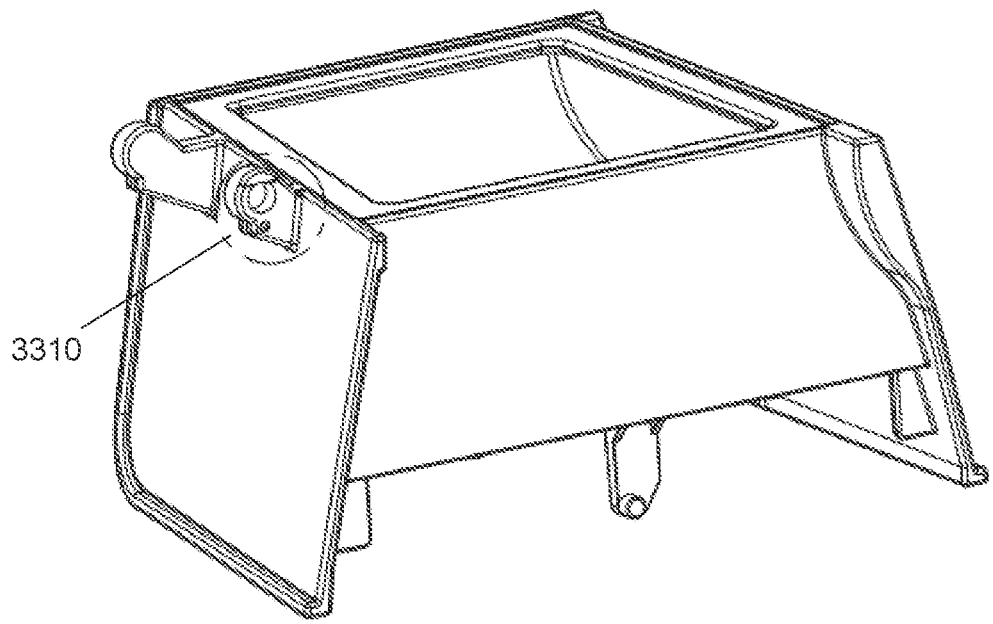
FIGS. 33A and 33B illustrate an exemplary tank according to some embodiments of the present disclosure.
Figure 33B:
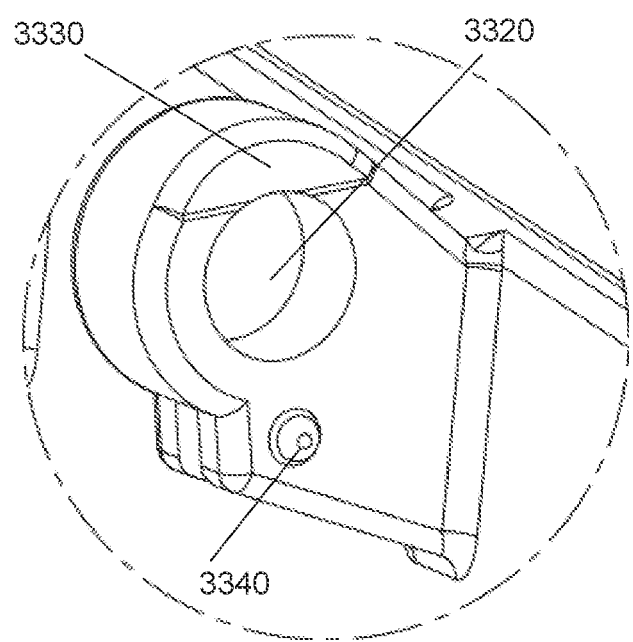

FIGS. 33A and 33B illustrate an exemplary tank according to some embodiments of the present disclosure. As shown in FIGS. 33A and 33B, the tank 3300 may include one or more first connecting pieces 3310. In some embodiments, each of the one or more first connecting pieces 3310 may include a pin hole 3320, a protruding column 3340, and/or a first inclined guide surface 3330.

Figure 34A:
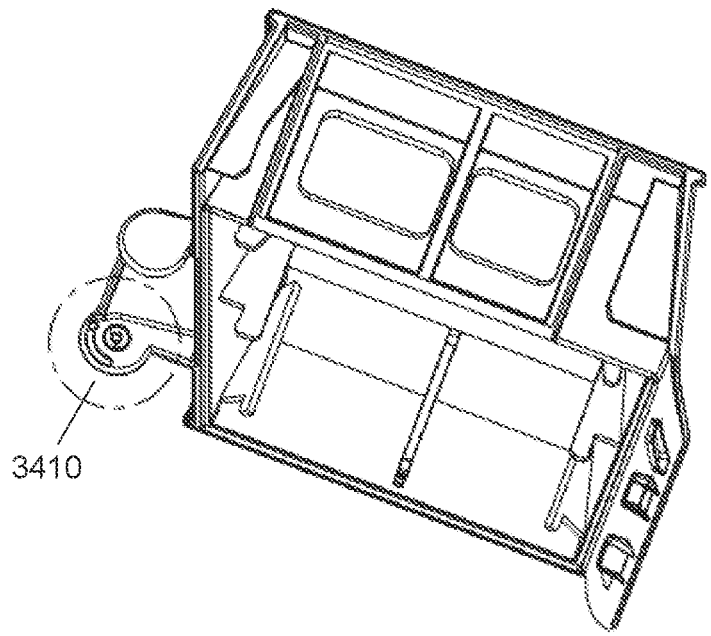
FIGS. 34A and 34B illustrate an exemplary tank cover according to some embodiments of the present disclosure.
Figure 34B:
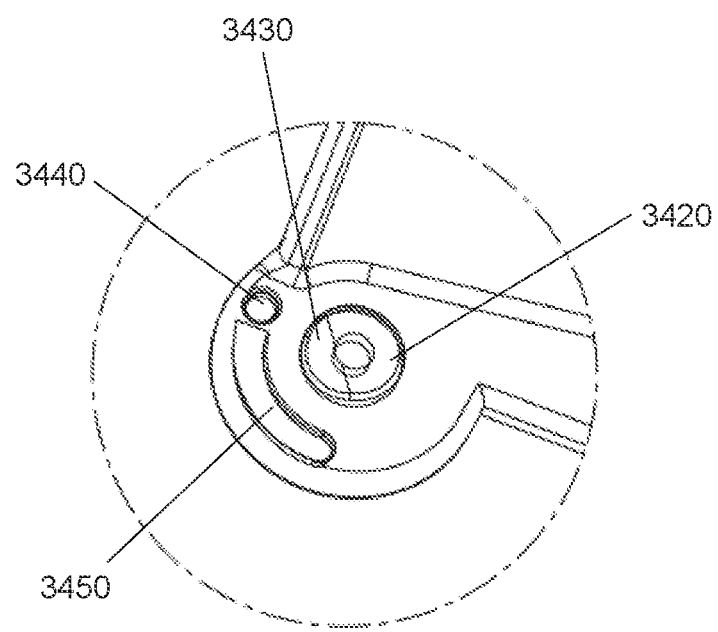

FIGS. 34A and 34B illustrate an exemplary tank cover according to some embodiments of the present disclosure. As shown in FIGS. 34A and 34B, the tank cover 3400 may include one or more second connecting pieces 3410. In some embodiments, each of the one or more second connecting pieces 3410 may include a pin 3420, a second inclined guide surface 3430, a groove 3440, and/or a guide slot 3450. In some embodiments, the pin 3420 may be placed into the pin hole 3320, so that the tank cover 3400 may be fixed to the tank 3300. In the process of opening and/or closing of the tank cover 3400, the pin 3420 may rotate in the pin hole 3320. In some embodiments, the first inclined guide surface 3330 of the first connecting piece(s) 3310 and the second inclined guide surface 3430 of the second connecting piece(s) 3410 may configured to facilitate the installation of the tank cover 3400 on the tank 3300. In some embodiments, the guide slot 3450 may include a first end adjacent to the groove 3440 and a second end away from the groove 3440. In some embodiments, the depth of the guide slot 3450 may be gradually changed from a relatively small value at the first end to a relatively large value at the second end. In some embodiments, the guide slot 3450 may be curved to fit with the rotation movement of the tank cover 3400 relative to the tank 3300.

Figure 35A:
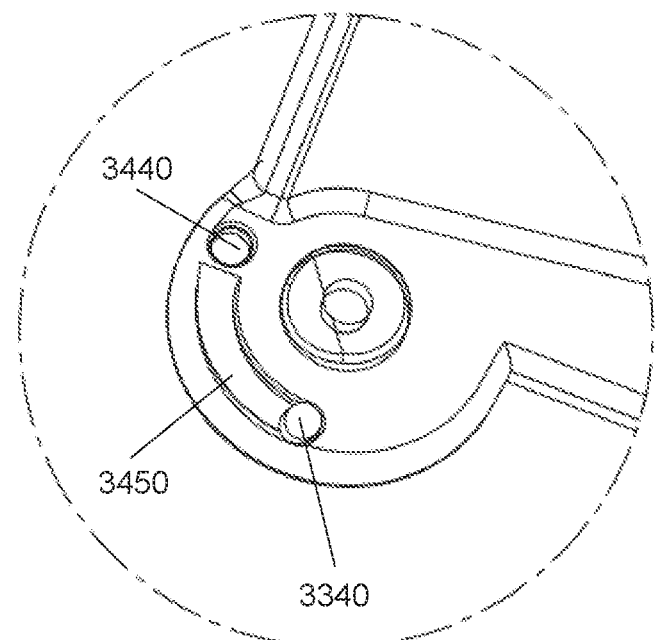
FIGS. 35A and 35B illustrate a corporation of a protruding column of a first connecting piece of a tank and a groove of a second connecting piece of a tank cover according to some embodiments of the present disclosure.
Figure 35B:
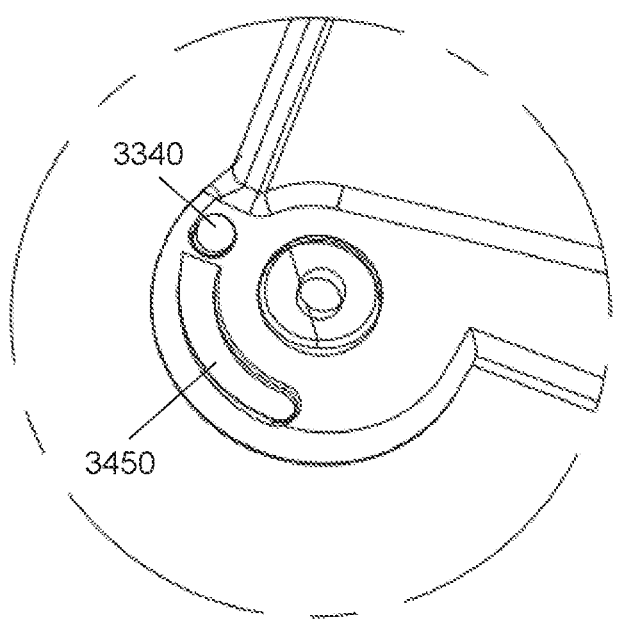

FIGS. 35A and 35B illustrate a corporation of a protruding column of a first connecting piece of a tank and a groove of a second connecting piece of a tank cover according to some embodiments of the present disclosure. In some embodiments, as shown in FIG. 35A, if the tank cover 3400 is closed, the protruding column 3340 may be located at or close to the second end of the guide slot 3450. In the process of opening the tank cover 3400, the protruding column 3340 may gradually slide along the guide slot 3450 from the second end to the first end of the guide slot 3450. The design of the relatively small depth of the first end of the guide slot 3450 relative to the second end of the guide slot 3450 may make it easy for the protruding column 3340 to fall into the groove 3440. The design of the relatively large depth of the second end of the guide slot 3450 relative to the first end of the guide slot 3450 may facilitate the second end of the guide slot 3450 to accommodate the protruding column 3340 when the tank cover 3400 is closed. In some embodiments, if the tank cover 3400 is opened to a certain angle, the protruding column 3340 may fall into the groove 3440 and limit the tank cover 3400 to move back rotarily. Because the groove 3440 and the guide slot 3450 are disconnected and/or the depth of the first end of the guide slot 3450 is smaller than the depth of the groove 3440, the protruding column 3340 may not be easily detached from the groove 3440.

When the protruding column 3340 falls into the groove 3440, the design of the disconnection between the groove 3440 and the guide slot 3450, and/or the design of the relatively small depth of the first end of the guide slot 3450 may prevent the tank cover 3400 from rotating back under no external force (e.g., a force from the user). If a force is imposed (e.g., by a user (e.g., the subject 180)) on the tank cover 3400 to close the tank cover 3400, the protruding column 3340 may be detached from the groove 3440 and may gradually slide along the guide slot 3450 from the first end to the second end of the guide slot 3450 until the tank cover 3400 is closed. In some embodiments, the protruding column 3340 may have a hemispherical shape, semi-ellipsoidal shape, or a shape of other convex structure having a curved surface to reduce the friction between the protruding column 3340 and the guide slot 3450.

Figure 36A:
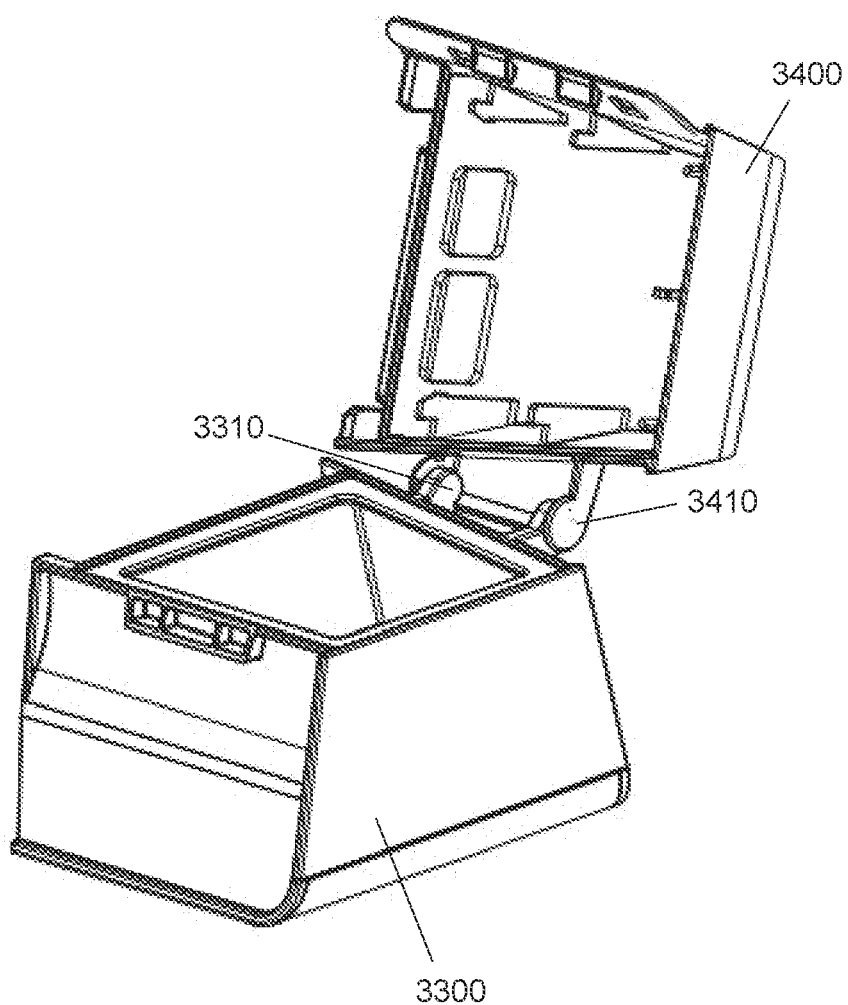
FIGS. 36A and 36B illustrate an exemplary connection between a tank and a tank cover of a liquid chamber according to some embodiments of the present disclosure.
Figure 36B:
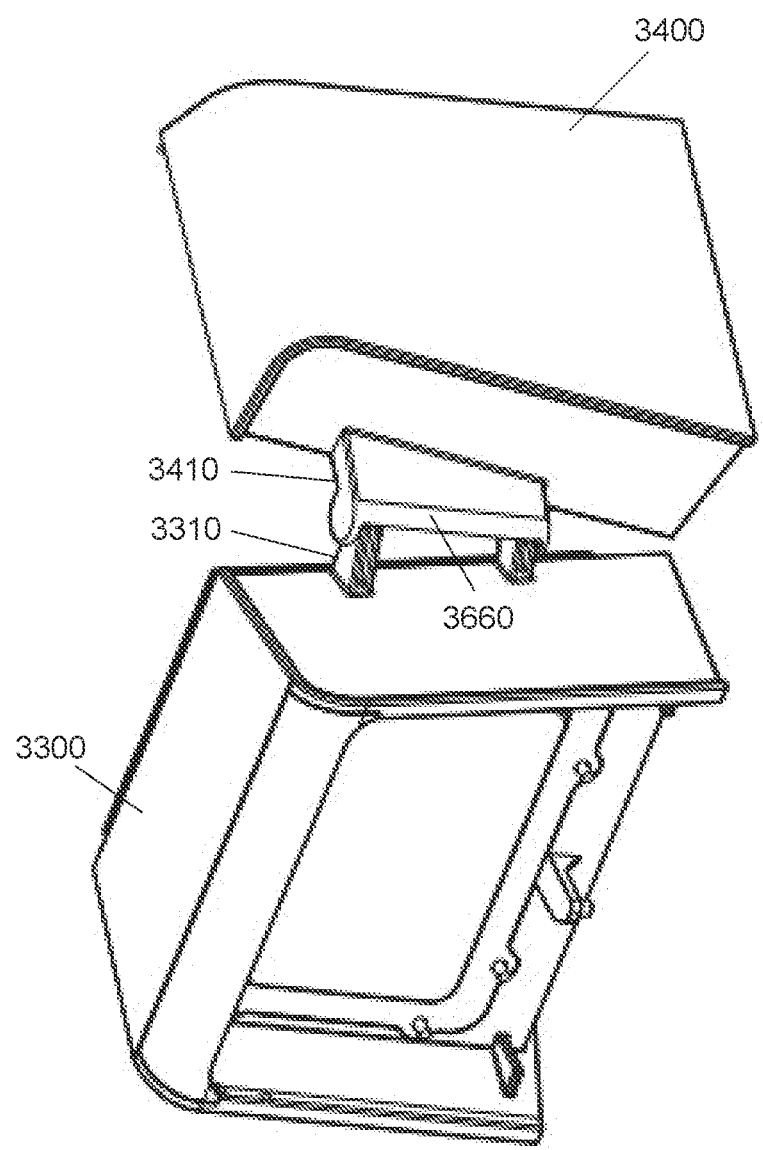

FIGS. 36A and 36B illustrate an exemplary connection between a tank and a tank cover of a liquid chamber 3600 according to some embodiments of the present disclosure. In some embodiments, the tank cover 3400 may be in pivoted connection with the tank 3300 through a connection mechanism (e.g., the connection mechanism 3009) including the first connecting piece(s) 3310 and the second connecting piece(s) 3410. In some embodiments, the first connecting piece(s) 3310 may be in pivot connection with the second connecting piece(s) 3410.

In some embodiments, as shown in FIGS. 36A and 36B, a pair of first connecting piece 3310 may be located between a pair of second connecting pieces 3410. In some embodiments, the pair of second connecting pieces 3410 may be located between the pair of first connecting pieces 3310. In some embodiments, as shown in FIGS. 36A and 36B, the first connecting piece(s) 3310 may be set on a back surface of the tank 3300. In some embodiments, the first connecting piece(s) 3310 may be set on another surface of the tank 3300. For example, the first connecting piece(s) 3310 may be respectively set on the two side surfaces of the tank 3300 and close to the back surface of the tank 3300, and correspondingly, the second connecting piece(s) 3410 may be set on the side surfaces of the tank cover 3400 and close to the back surface of the tank cover 3400. An another example, the first connecting piece(s) 3310 and the second connecting piece(s) 3410 may be concealed in the tank 3300 or the tank cover 3400, occupying a portion of the space of the tank 3300 or the tank cover 3400. As a further example, the first connecting piece(s) 3310 and the second connecting piece(s) 3410 may be set on a side surface of the liquid chamber 3600 and opposite to the gas inlet port and/or the gas outlet port of the gas passages above the tank 3300 (i.e., if the user faces the front surface of the respiratory ventilation apparatus 110, the first connecting piece(s) 3310 and the second connecting piece(s) 3410 may be set on the right side surface of the liquid chamber 3600).

In some embodiments, the tank 3300 and/or the tank cover 3400 may have an irregular shape. Accordingly, the shapes or sizes of the first connecting piece(s) 3310 and/or the second connecting piece(s) 3410 may be irregular. For example, as shown in FIGS. 36A and 36B, in order to match with the irregular shape of the tank 3300 or the tank cover 3400, the lengths of the pair of first connecting pieces 3310 may be different, so that when the tank cover 3400 is opened, an undersurface of the tank cover 3400 may be substantially upright and facing the front surface of the respiratory ventilation apparatus 110. In some embodiments, if the shape of the tank 3300 and/or the tank cover 3400 are regular, the first connecting pieces 3310 and/or the second connecting pieces 3410 may be regularly symmetrical.

As shown in FIG. 36B, the second connecting piece(s) 3410 may include or be connected by a baffle 3660. In some embodiments, if the tank cover 3400 is opened to a certain angle, the baffle 3660 may be blocked by a portion of the first connecting piece(s) 3310, thereby preventing over rotation of the tank cover 3400, and limiting a maximum rotary movement of the tank cover 3400. In some embodiments, the liquid chamber 3600 may include one or more mounting shafts between the tank cover 3400 and the tank 3300. An exemplary mounting shaft may refer to a pin 3420 (see FIG. 34B). In some embodiments, the mounting shaft(s) may include a first mounting shaft and a second mounting shaft. In some embodiments, the height of the first mounting shaft may be larger than the height of the second mounting shaft. In some embodiments, the first mounting shaft may be set higher than the second mounting shaft.

It should be noted that the above description of the connection between the tank 3300 and the tank cover 3400 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the connection between the tank 3300 and the tank cover 3400 may be realized in other ways, such as in hinged connection. For example, the tank 3300 and the tank cover 3400 may include a column-shaped hole on the same horizontal line, respectively, and the tank 3300 and the tank cover 3400 may be connected by a hinge pin passing through the hole(s). As another example, one end of the tank 3300 may include a hollow column with a shape of "C", and correspondingly, one end of the tank cover 3400 may include a column matching with the hollow column, so that if the tank cover 3400 is installed on the tank 3300, the column may be clamped in the C-shaped hollow column to realize the pivoted connection between the tank 3300 and the tank cover 3400.

Figure 37A:
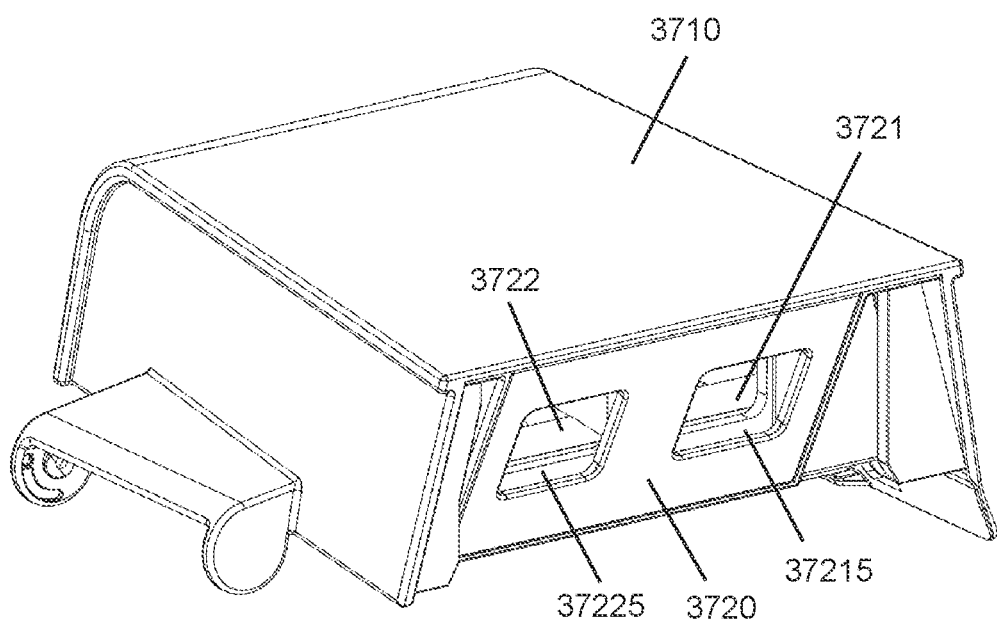
FIGS. 37A and 37B illustrate an exemplary tank cover according to some embodiments of the present disclosure.
Figure 37B:
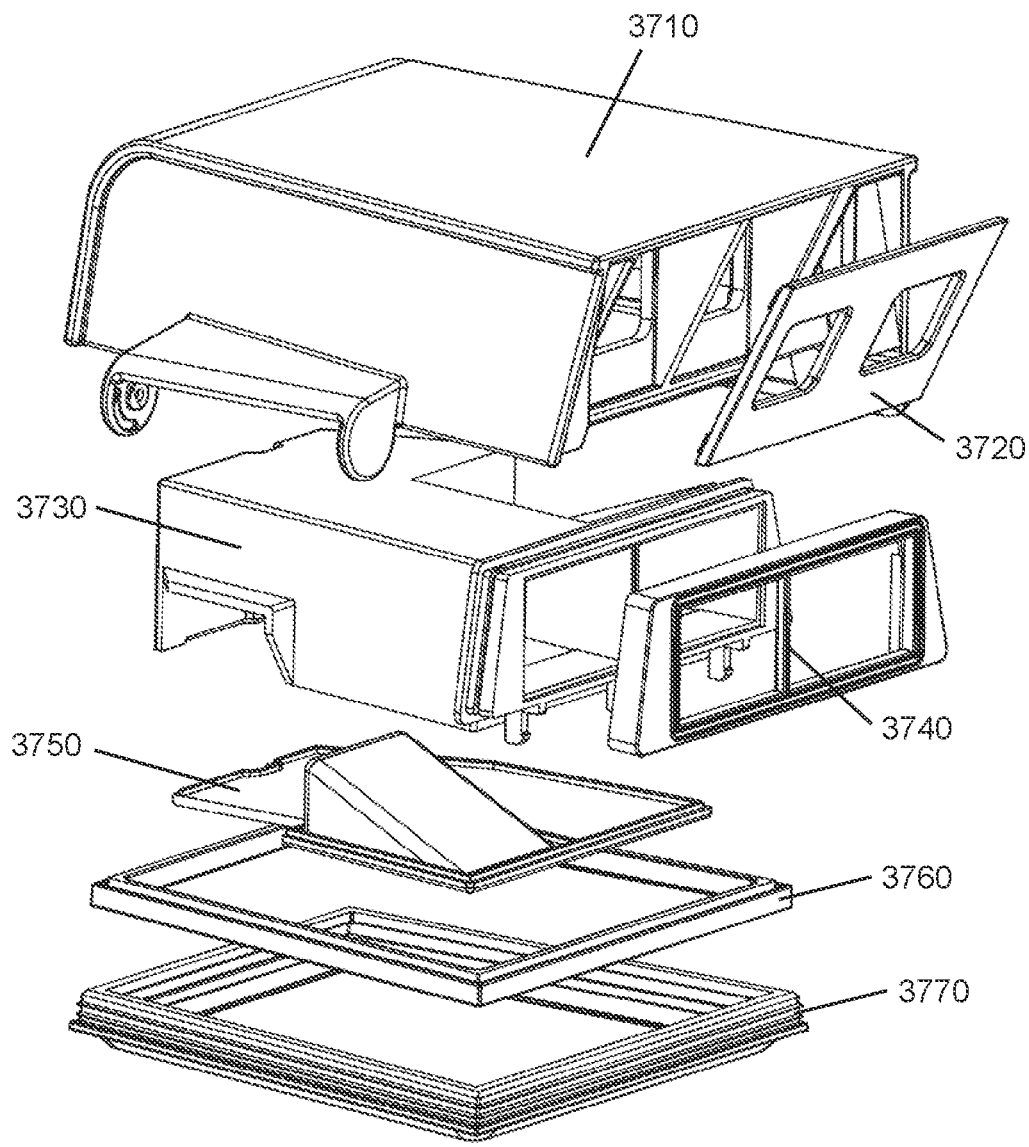

FIGS. 37A and 37B illustrate an exemplary tank cover according to some embodiments of the present disclosure. In some embodiments, as shown in FIGS. 37A and 37B, the tank cover 3700 may include a cover shell 3710, a connecting plate 3720, an inner shell 3730, a gas passage sealing frame 3740, a bottom plate 3750, a fixing frame 3760 and a tank cover sealing frame 3770. In some embodiments, the connecting plate 3720 may include a first aperture 3721 and a second aperture 3722. In some embodiments, the first aperture 3721 may be a gas inlet port of the tank cover 3700 (also referred to as a humidification assembly gas inlet port). In some embodiments, the second aperture 3722 may be a gas outlet port of the tank cover 3700 (also referred to as a humidification assembly gas outlet port). In some embodiments, the connecting plate 3720 may be set as inclined outside the cover shell 3710.

Figure 38:
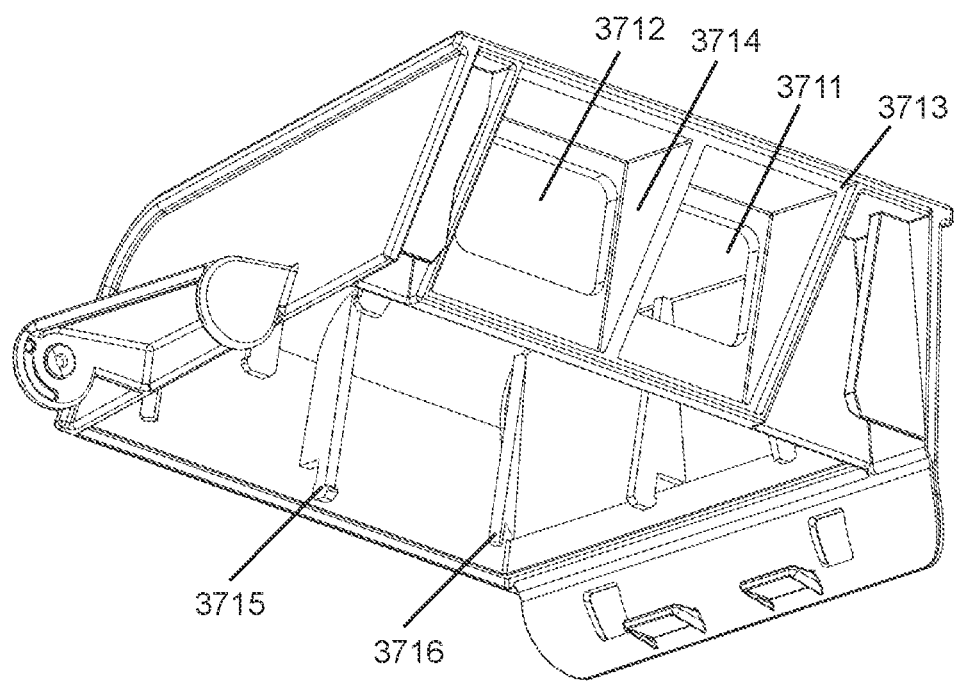
FIG. 38 illustrates an exemplary cover shell according to some embodiments of the present disclosure.

FIG. 38 illustrates an exemplary cover shell according to some embodiments of the present disclosure. In some embodiments, as shown in FIG. 38, the cover shell 3710 may include a first aperture 3711, a second aperture 3712, a connecting frame 3713, a barrier 3714, one or more first clasps 3715, and one or more second clasps 3716. The first aperture 3711 and the first aperture 3721 of the connecting plate 3720 may function as the gas inlet port of the tank cover 3700. The second aperture 3712 and the second aperture 3722 of the connecting plate 3720 may function as the gas outlet port of the tank cover 3700. The connecting plate 3720 may be connected (e.g., fixed) to the connecting frame 3713. In some embodiments, the connecting plate 3720 may be connected to the connecting frame 3713 by cementing, riveting, joggling, clamping, meshing, or the like, or any combination thereof. The barrier 3714 may be configured to separate the gas inlet port and the gas outlet port of the tank cover 3700 between the cover shell 3710 and the connecting plate 3720, so that the respiratory gas flowing into the tank cover 3700 may be isolated from the respiratory gas flowing out of the tank cover 3700.

In some embodiments, a sealing strip (not shown) may be used to improve the air tightness of the connection between the connecting frame 3713 and the connecting plate 3720. For example, all joints between the connecting frame 3713 and the connecting plate 3720 may be equipped with the sealing strip. In some embodiments, a sealing strip (not shown) may be set at the joint between the barrier 3714 and the connecting plate 3720. In some embodiments, as shown in FIG. 37A, a first groove 37215 and/or a second groove 37225 may be set between the cover shell 3710 and the connecting plate 3720. The first groove 37215 and/or the second groove 37225 may be configured to accommodate a portion of the liquid(s) leaking from a tank (e.g., the tank 3300 shown in FIGS. 36A and 36B) and prevent the liquid(s) from entering the main body of the respiratory ventilation apparatus 110. For example, if the liquid chamber (e.g., the liquid chamber 3600 shown in FIGS. 36A and 36B) is tilted or placed obliquely, a portion of the liquids loaded in the tank 3300 may flow into the tank cover 3700, and the first groove 37215 and/or the second groove 37225 may accommodate the portion of the liquids and prevent the portion of the liquids from entering the main body of the respiratory ventilation apparatus 110.

In some embodiments, the bottom plate 3750 may be fixed to the inner shell 3730 by cementing, riveting, joggling, clamping, meshing, or the like, or any combination thereof. In some embodiments, the bottom plate 3750 and the inner shell 3730 may be configured as an integral piece. In some embodiments, the first clasp(s) 3715 may be configured to fix the inner shell 3730 and the bottom plate 3750 to the cover shell 3710. For example, through the first clasp 3715, the inner shell 3730 and the bottom plate 3750 may be clamped to the cover shell 3710. In some embodiments, the first clasp 3715 may be set at the middle of an inner side wall of the cover shell 3710 opposite to the connecting frame 3713. In some embodiments, the second clasp 3716 may be configured to fix the fixing frame 3760 to the cover shell 3710. In some embodiments, several (e.g., 4, 6, 8, etc.) second clasps 3716 may be set at the inner side wall(s) of the cover shell 3710 to fix the fixing frame 3760 to the cover shell 3710. For example, as shown in FIG. 38, each of the two side walls of the cover shell 3710 adjacent to the connecting frame 3713 may include three second clasps 3716. In some embodiments, the tank cover sealing frame 3770 may be fixed to the fixing frame 3760. In some embodiments, the fixing frame 3760 and the tank cover sealing frame 3770 may be connected by cementing, clamping, meshing, or the like, or any combination thereof. The tank cover sealing frame 3770 may be configured to improve the air tightness of the connection between the tank (e.g. the tank 3300 shown in FIGS. 36A and 36B) and the tank cover 3700. In some embodiments, the tank cover sealing frame 3770 may be made of a sealing material including for example, silicone, rubber, nylon, or the like, or any combination thereof. In some embodiments, some or all of the components of the cover shell 3710 (e.g., the first aperture 3711, the second aperture 3712, the connecting frame 3713, the barrier 3714, the first clasp 3715 and/or the second clasp 3716) may be configured as an integral piece.

In some embodiments, the cover shell 3710 may be connected and/or connectable to the tank and/or the tank cover 3700. In some embodiments, the cover shell 3710 may be arranged pivotally relative to the tank. In some embodiments, a liquid contacting side wall of the liquid chamber may be at least partially formed by an outer side wall of the tank forming the outer surface of the humidification assembly 220. In some embodiments, the tank may be formed with only one opening for filling liquid(s) and/or for exchange of pressurized respiratory gas. In some embodiments, the tank cover 3700 may be pivotally connected to the tank through a connection mechanism. In some embodiments, at least a portion of the side of the first gas passage near the connection mechanism may be covered in the flow direction by a side edge of the humidification assembly gas inlet port of the liquid chamber. In some embodiments, at least a portion of the side of the second gas passage near the connection mechanism may be covered in the flow direction by a side edge of the humidification assembly gas outlet port of the liquid chamber. In some embodiments, the distance between the connection mechanism and the humidification assembly gas outlet port may be less than the distance between the connection mechanism and the humidification assembly gas inlet port.

Figure 39A:
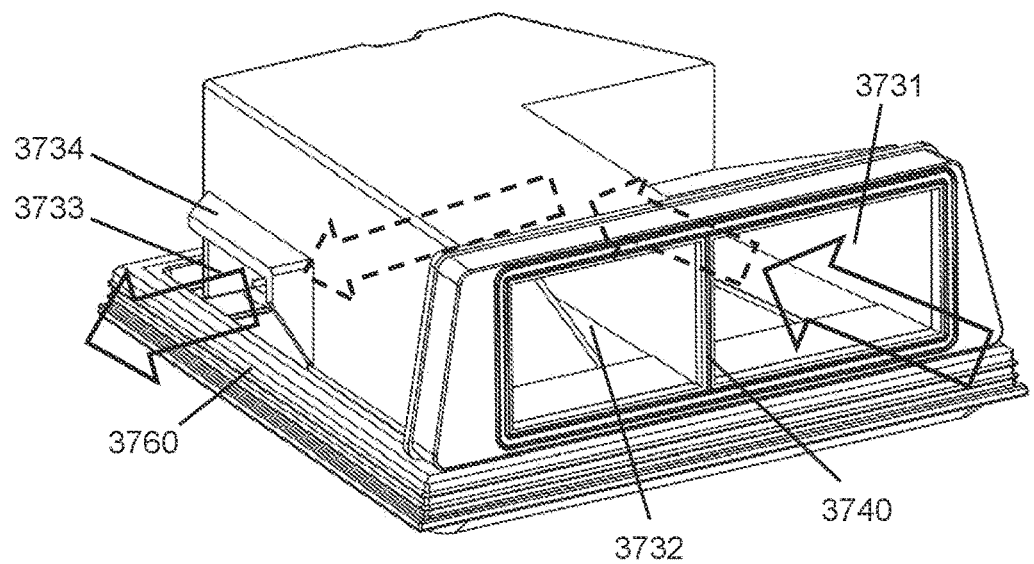
FIGS. 39A and 39B illustrate an exemplary inner shell of a tank cover according to some embodiments of the present disclosure.
Figure 39B:
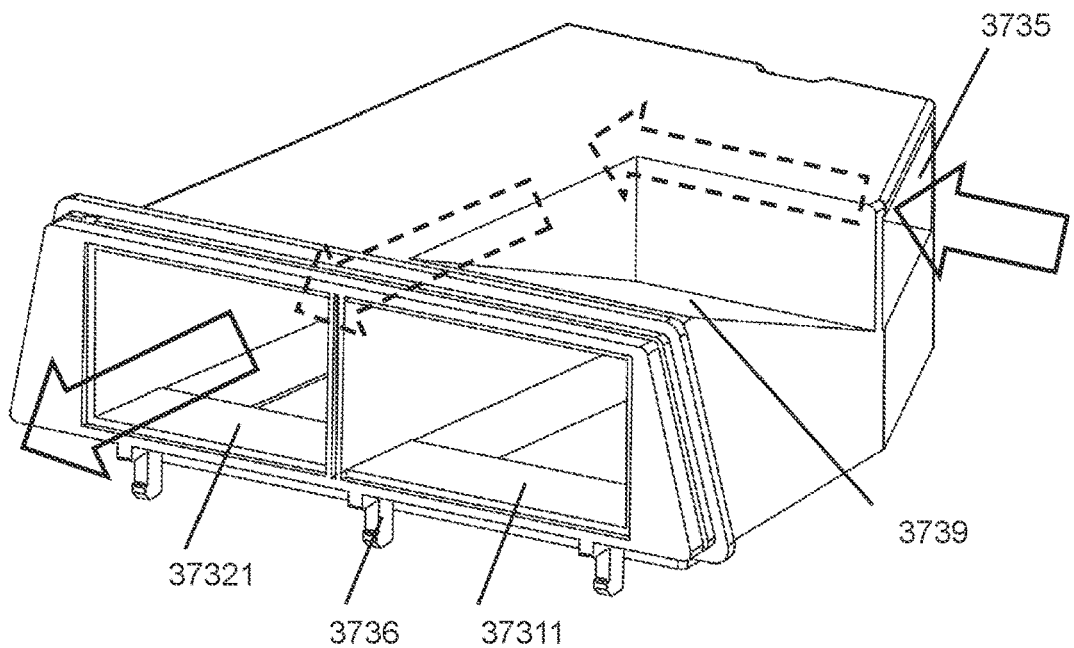

FIGS. 39A and 39B illustrate an exemplary inner shell of a tank cover according to some embodiments of the present disclosure. In some embodiments, as shown in FIGS. 39A and 39B, the inner shell 3730 may include a gas inlet port 3731 and/or a gas outlet port 3732. In some embodiments, the gas inlet port 3731 may be configured to introduce a gas (e.g., the pressurized respiratory gas), via a first gas passage (e.g., a gas passage as indicated by the arrows shown in FIG. 39A), into the liquid chamber. As shown in FIG. 39A, the first gas passage (also referred to as the gas inlet passage) may include an output port 3733. In some embodiments, the output port 3733 of the first gas passage may be configured for connecting the first gas passage with the tank. The gas may come out of the first gas passage through the output port 3733 and enter into the liquid chamber. In some embodiments, the inner shell 3730 may include a guide plate 3734. In some embodiments, the guide plate 3734 may be set on an edge of the output port 3733 of the first gas passage. In some embodiments, the guide plate 3734 may be set on an upper edge and/or a side edge (e.g., the side edge closer to the gas inlet port 3731 and/or the gas outlet port 3732 of the inner shell 3730) of the output port 3733 of the first gas passage. In some embodiments, the guide plate 3734 may be configured to guide the gas to flow downward to the tank below the tank cover 3700. Therefore, the guide plate 3734 may reduce the amount of gas flowing into other spaces (e.g., the space between the cover shell 3710 and the inner shell 3730). In some embodiments, the gas passage sealing frame 3740 may be connected to the inner shell 3730, ensuring air tightness between the inner shell 3730 and the cover shell 3710. In some embodiments, the gas passage sealing frame 3740 may be fixed to the inner shell 3730 by cementing, riveting, joggling, clamping, meshing, or the like, or any combination thereof.

In some embodiments, the gas inlet port 3731 (also referred to as the humidification assembly gas inlet port) and the output port 3733 of the first gas passage may be set on different side surfaces of the inner shell 3730. For example, as shown in FIG. 39A, the gas inlet port 3731 may be set on a right portion of a first side surface of the inner shell 3730, and the output port 3733 of the first gas passage may be set on a left portion of a second side surface of the inner shell 3730, wherein the second side surface of the inner shell 3730 may be adjacent to the first side surface of the inner shell 3730 in a clockwise direction. The gas inlet port 3731 and the output port 3733 of the first gas passage may be set as shown in FIG. 39A, such that the liquid(s) (e.g., water) in the tank may be difficult to enter the main body of the respiratory ventilation apparatus 110, regardless of how the respiratory ventilation apparatus 110 is placed or moved. In some embodiments, the distance between the output port 3733 of the first gas passage and the humidification assembly gas inlet port may be larger than the distance between the output port 3733 of the first gas passage and the humidification assembly gas outlet port. In some embodiments, the first side surface of the cover shell 3710 of the liquid chamber may face the first side wall of the housing of the main body of the respiratory ventilation apparatus 110.

In some embodiments, the gas outlet port 3732 (also referred to as the humidification assembly gas outlet port) may be configured to introduce a gas (e.g., the humidified and pressurized respiratory gas), via a second gas passage (e.g., a gas passage as indicated by the arrows shown in FIG. 39B) back into the main body of the respiratory ventilation apparatus 110. As shown in FIG. 39B, the second gas passage (also referred to as the gas outlet passage) may include an input port 3735. In some embodiments, the input port 3735 of the second gas passage may be configured for connecting the second gas passage with the tank. The gas may flow into the second gas passage through the input port 3735 from the liquid chamber. In some embodiments, the first gas passage and/or the second gas passage may have a substantially rectangular cross-section. In some embodiments, the first gas passage and the second gas passage may cross each other.

In some embodiments, the gas outlet port 3732 (also referred to as the humidification assembly gas outlet port) and the input port 3735 of the second gas passage may be set on different side surfaces of the inner shell 3730. For example, as shown in FIG. 39B, the gas outlet port 3732 may be set on a left portion of the first side surface of the inner shell 3730, and the input port 3735 of the second gas passage may be set on a right portion of a third side surface of the inner shell 3730, wherein the third side surface of the inner shell 3730 may be adjacent to the first side surface of the inner shell 3730 in an anti-clockwise direction. The gas outlet port 3732 and the input port 3735 of the second gas passage may be set as shown in FIG. 39B, such that the liquid(s) (e.g., water) in the tank may be difficult to enter the main body of the respiratory ventilation apparatus 110, regardless of how the respiratory ventilation apparatus 110 is placed or moved. In some embodiments, the first gas passage and the second gas passage may be set as non-parallel (such as crossed) in the liquid chamber, thereby making the output port 3733 of the first gas passage and the input port 3735 of the second gas passage opening in different directions. In some embodiments, the distance between the input port 3735 of the second gas passage and the humidification assembly gas outlet port may be larger than the distance between the input port 3735 of the second gas passage and the humidification assembly gas inlet port.

In some embodiments, the gas inlet port and/or the gas outlet port of the tank cover 3700 (i.e., the humidification assembly gas inlet port of the liquid chamber and/or the humidification assembly gas outlet port of the liquid chamber) may be set on a first side surface of the cover shell 3710 (corresponding to the first side surface of the inner shell 3730) of the liquid chamber. In some embodiments, the output port 3733 of the first gas passage and the input port 3735 of the second gas passage may be set on opposite side surfaces of the inner shell 3730. For example, the output port 3733 of the first gas passage may be set on the second side surface of the inner shell 3730, while the input port 3735 of the second gas passage may be set on the third side surface of the inner shell 3730. That is, the output port 3733 of the first gas passage may face a second side surface of the cover shell 3710 corresponding to the second side surface of the inner shell 3730, while the input port 3735 of the second gas passage may face a third side surface of the cover shell 3710 corresponding to the third side surface of the inner shell 3730.

In some embodiments, as shown in FIG. 39B, a portion or all portions of the bottom plate 3750 may be set below a lower edge of the gas inlet port 37311 and/or a lower edge of the gas outlet port 37321 of the tank cover 3700. Therefore, the bottom plate 3750 may be capable of accommodating a portion of the liquid(s) in the tank, and the height difference between the bottom plate 3750 and the lower edge of the gas inlet port 37311 and/or the lower edge of the gas outlet port 37321 may prevent the liquid(s) in the tank from entering the main body of the respiratory ventilation apparatus 110. In some embodiments, the inner shell 3730 may include one or more third clasps 3736. The third clasps 3736 may be configured to connect the gas passage sealing frame 3740 with the inner shell 3730. As shown in FIG. 39B, the inner shell 3730 may include three clasps 3736 that may be equally spaced on the bottom edge of the first side surface of the inner shell 3730.

Figure 40:
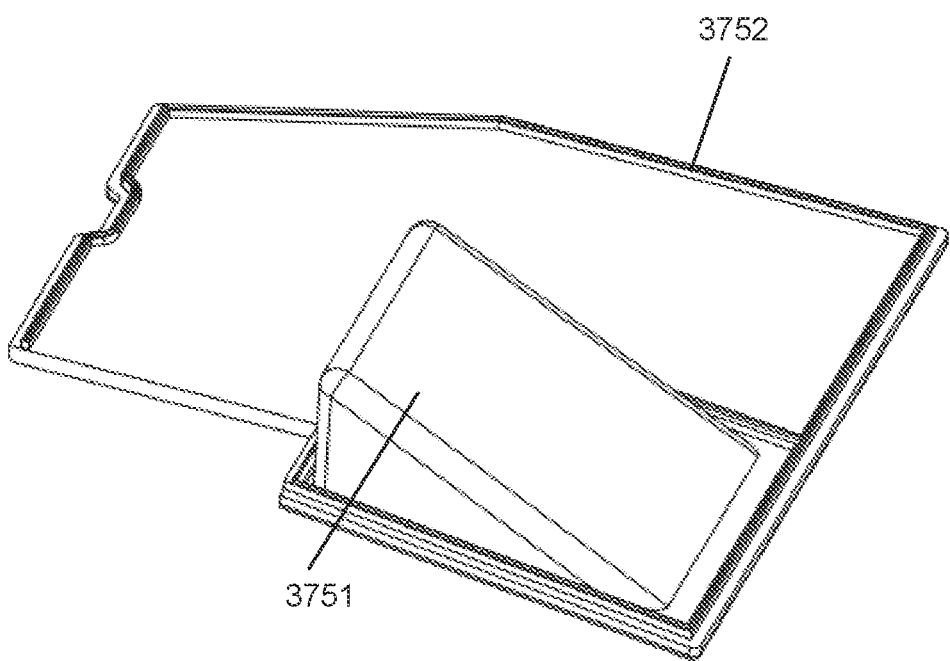
FIG. 40 illustrates an exemplary bottom plate of an inner shell of a tank cover according to some embodiments of the present disclosure.

FIG. 40 illustrate an exemplary bottom plate of an inner shell of a tank cover according to some embodiments of the present disclosure. As shown in FIG. 40, the bottom plate 3750 may include one or more sealing strips 3752 set along the edge(s) of the bottom plate 3750. The sealing strip(s) 3752 may be configured to improve the air tightness of the connection between the bottom plate 3750 and the inner shell 3730. In some embodiments, the bottom plate 3750 may include a bottom of the second gas passage (e.g., the second inclined plate 3751) and a bottom of the first gas passage (e.g., the rest of the bottom plate 3750 except for the second inclined plate 3751).

Figure 41A:
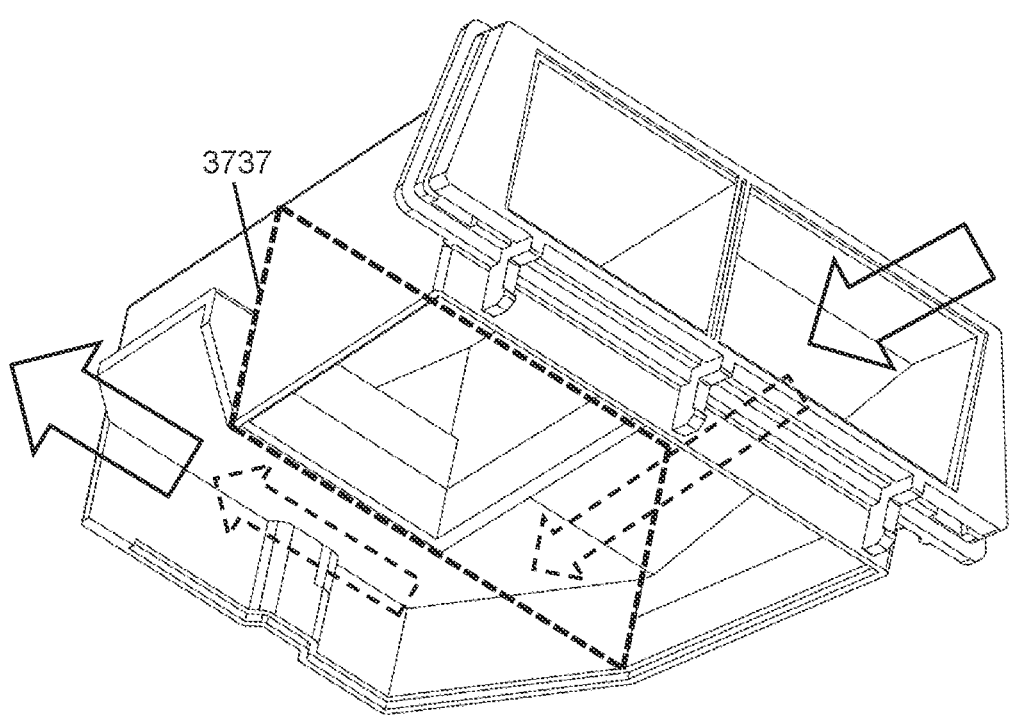
FIGS. 41A and 41B illustrate an exemplary inner structure of an inner shell of a tank cover according to some embodiments of the present disclosure.
Figure 41B:
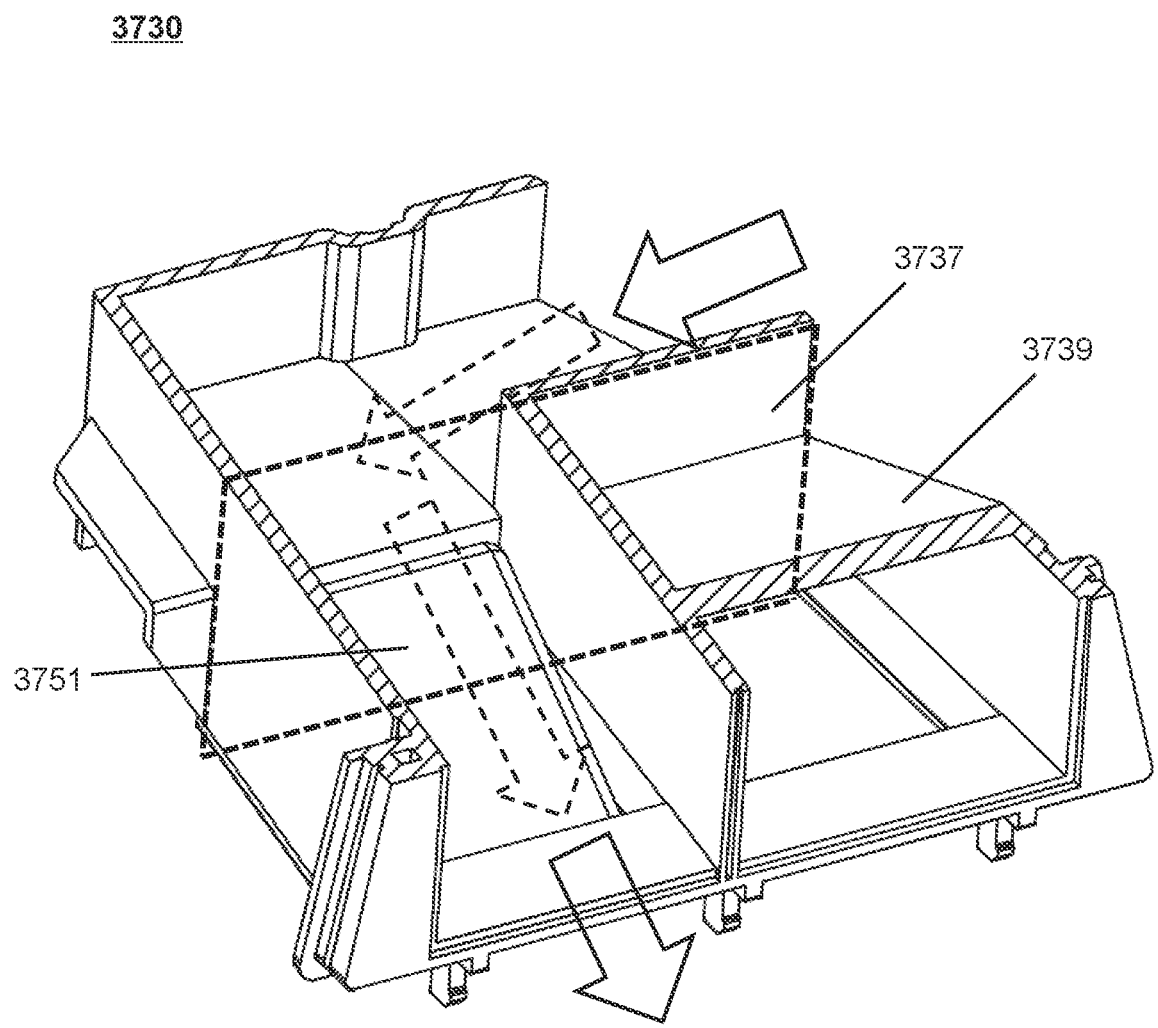

FIGS. 41A and 41B illustrate an exemplary inner structure of an inner shell of a tank cover according to some embodiments of the present disclosure. FIG. 41A shows the gas inlet passage of the tank cover 3700. FIG. 41A shows an upward view of the tank cover 3710 without the bottom plate 3750. FIG. 41B shows the gas outlet passage of the tank cover 3700. FIG. 41B shows a sectional view of the tank cover 3700. In some embodiments, the gas inlet passage (i.e., the first gas passage as indicated by the arrows shown in FIG. 41A) may include a first portion and a second portion. The first portion of the first gas passage may extend from the gas inlet port (e.g., the first aperture 3721) of the tank cover 3700 to a common plane (e.g., the common plane 3737 indicated by the parallelogram with dotted lines in FIGS. 41A and 41B). The second portion of the first gas passage may extend from the common plane 3737 to the output port 3733 of the first gas passage. In some embodiments, the second gas passage may include a first portion and a second portion. The first portion of the second gas passage may extend from the input port of the second gas passage 3735 to the common plane 3737. The second portion of the second gas passage may extend from the common plane 3737 to the gas outlet port (e.g., the second aperture 3722) of the tank cover 3700.

In some embodiments, the first portion of the first gas passage may be substantially parallel to the second portion of the second gas passage along a direction having an angle with (e.g., substantially perpendicular to) the first side surface (e.g., the side surface including the connecting frame 3713 as shown in FIG. 38) of the cover shell 3710 of the tank cover 3700. In some embodiments, the second portion of the first gas passage and the first portion of the second gas passage may be set in different layers. In some embodiments, a first projection of the second portion of the first gas passage on a horizontal plane and a second projection of the first portion of the second gas passage on the horizontal plane may be intersecting or at least partially overlapping. In some embodiments, as shown in FIGS. 41A and 41B, the second portion of the first gas passage may be set below the first portion of the second gas passage. In some embodiments, the first portion of the second gas passage may be set below the second portion of the first gas passage. In some embodiments, an area of a first cross section of the first gas passage on the common plane may be equal to or less than a portion (e.g., a half) of an area of the gas inlet port (e.g., the first aperture 3721) of the tank cover 3700. In some embodiments, an area of a second cross section of the second gas passage on the common plane may be equal to or less than a portion (e.g., a half) of an area of the gas outlet port (e.g., the second aperture 3722) of the tank cover 3700.

In some embodiments, a first inclined plate 3739 (see FIGS. 39B and 41B) may be set between the first cross section and the gas inlet port (e.g., the first aperture 3721) of the tank cover 3700. The first inclined plate 3739 may be configured to smooth the flowing of the pressurized respiratory gas in the first gas passage. In some embodiments, the first inclined plate 3739 (see FIGS. 39B and 41B) may be set as a part of the inner shell 3730. In some embodiments, a second inclined plate 3751 may be set between the second cross section and the gas outlet port (e.g., the second aperture 3722) of the tank cover 3700. The second inclined plate 3751 may be configured to smooth the flowing of the humidified and pressurized respiratory gas in the second gas passage. In some embodiments, the second inclined plate 3751 (see FIGS. 40 and 41B) may be set on the bottom of the tank cover 3700. For example, the second inclined plate 3751 may be a part of the bottom plate 3750.

Figure 42A:
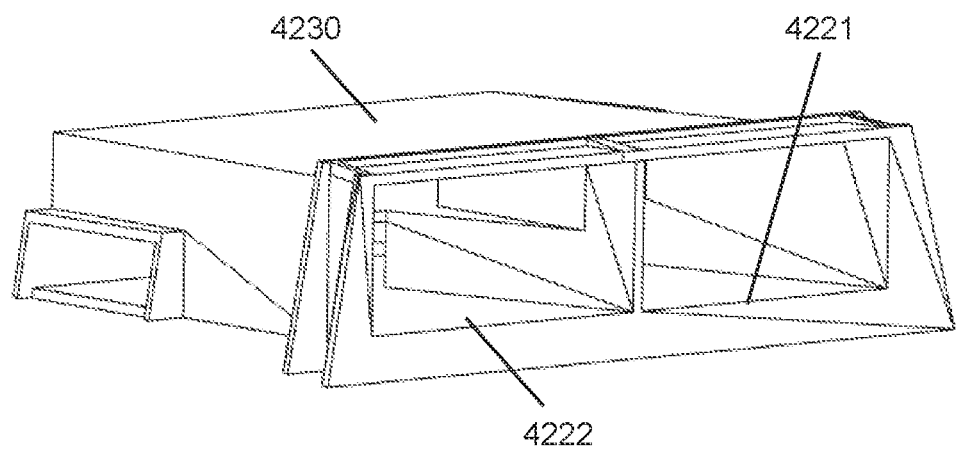
FIGS. 42A and 42B illustrate another exemplary tank cover according to some embodiments of the present disclosure.
Figure 42B:
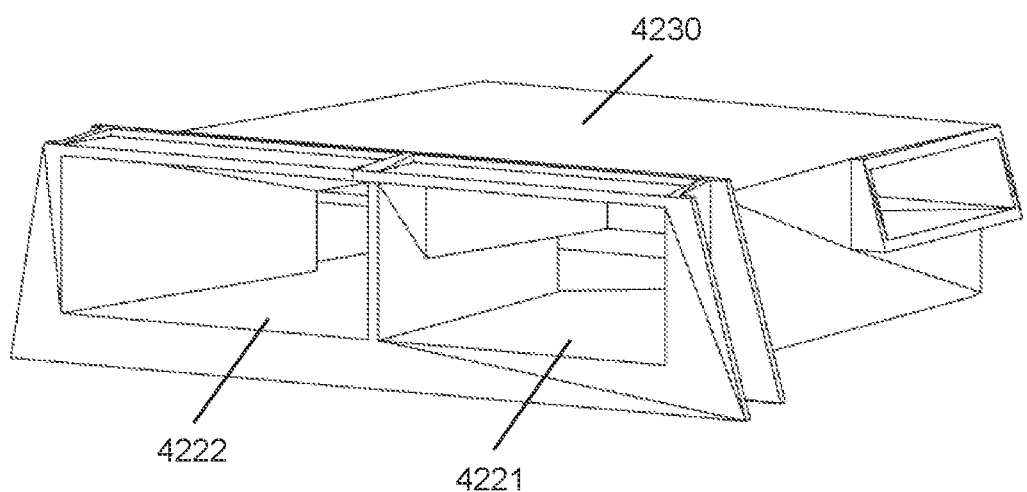

It should be noted that the above description of the tank cover 3700 is merely provided for the purposes of illustration and not intended to limit the scope of the present disclosure. For persons having ordinary skill in the art, multiple variations and modifications may be made under the teachings of the present disclosure. However, those variations and modifications do not depart from the scope of the present disclosure. For example, as shown in FIGS. 42A and 42B, the inner shell 4230 of the tank cover 4200 may not include the first inclined plate. As another example, the tank cover 4200 may not include the second inclined plate. As a further example, the bottom of the tank cover 4200 may align to a lower edge of the gas inlet port 4221 and/or a lower edge of the gas outlet port 4222 in the horizontal plane. FIGS. 42A and 42B illustrate another exemplary tank cover according to some embodiments of the present disclosure.

Figure 43A:
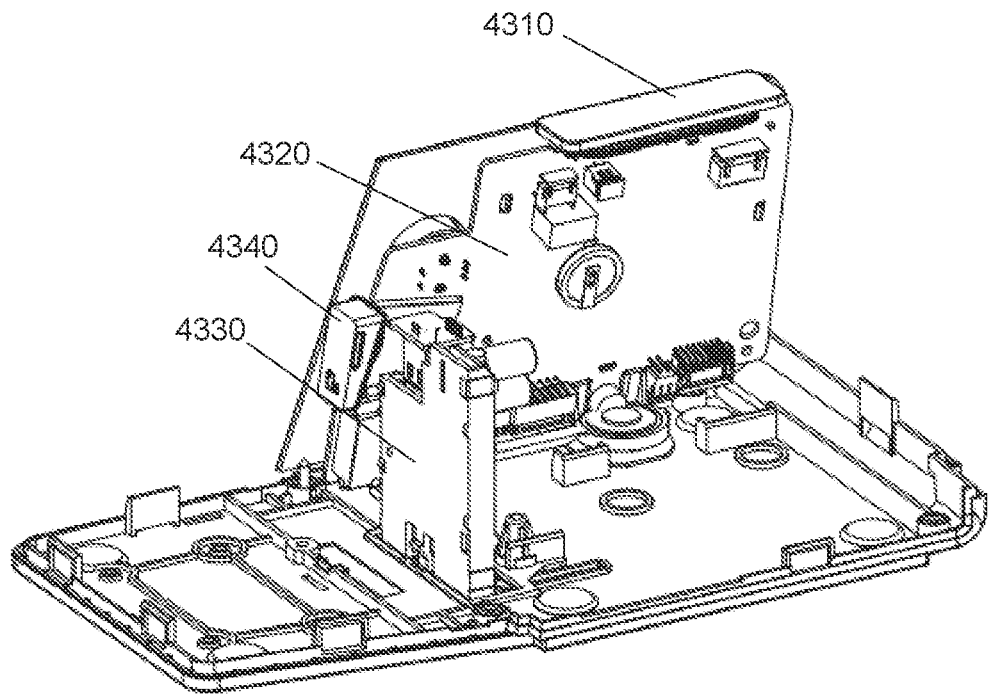
FIGS. 43A-43C illustrate exemplary electronic components in a main body of a respiratory ventilation apparatus according to some embodiments of the present disclosure.
Figure 43B:
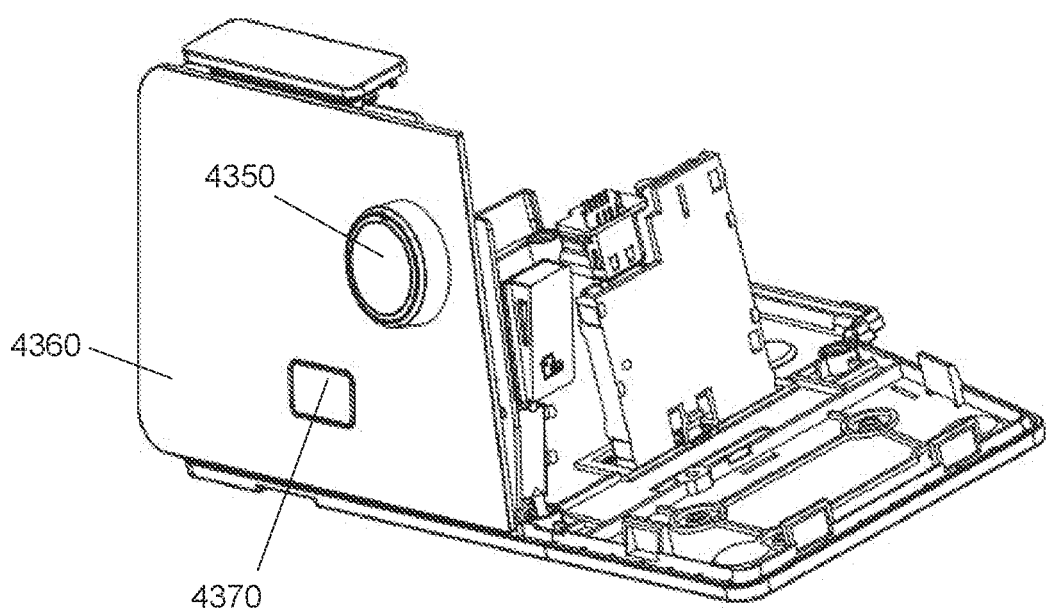
Figure 43C:
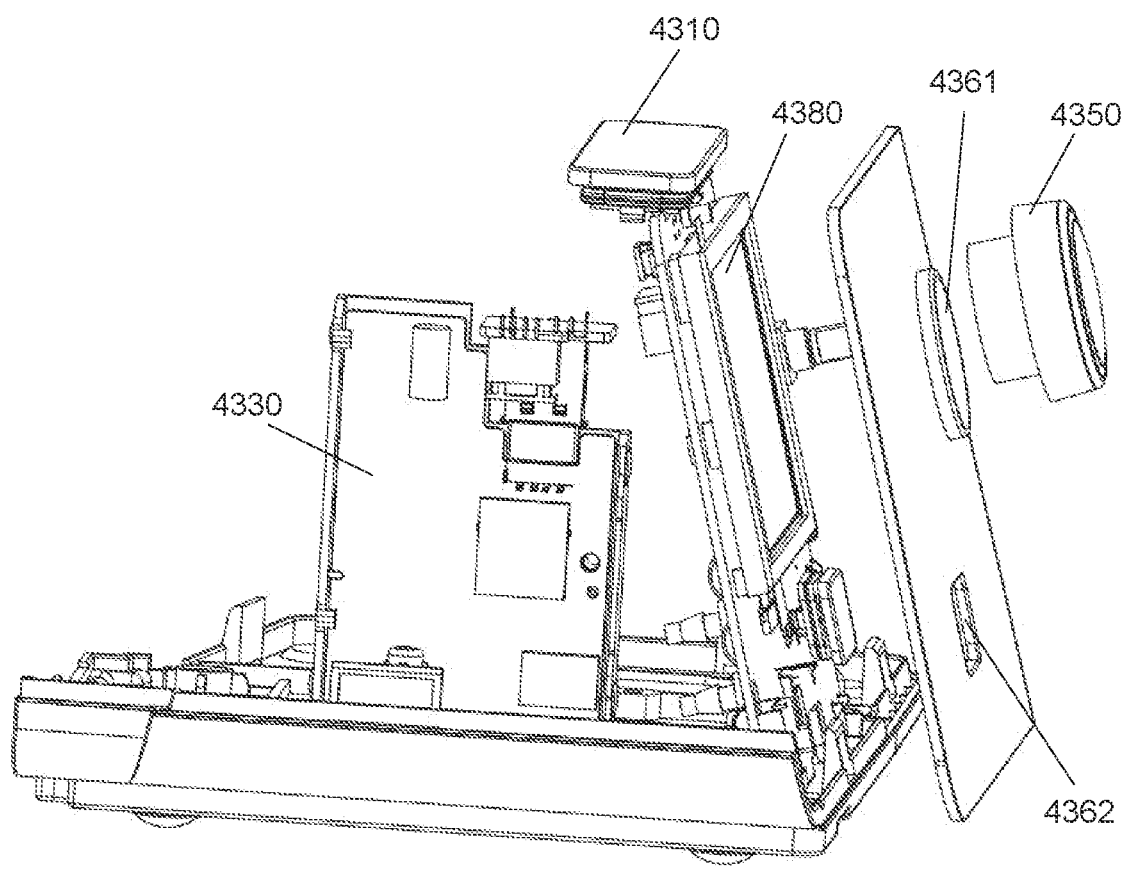

FIGS. 43A-43C illustrate exemplary electronic components in a main body of a respiratory ventilation apparatus according to some embodiments of the present disclosure. In some embodiments, as shown in FIG. 43A, the electronic components 4300 in the main body may include one or more printed circuit board (PCB) 4320, an on-off button 4310, a wireless module assembly 4330, a rotary knob 4350, a secure digital (SD) card read-write storage module 4340, a panel 4360, a home button 4370, and a displayer 4380. In some embodiments, the printed circuit board (PCB) 4320 may include one or more processors (e.g., ARM, PLD, MCU, DSP, FPGA, SoC), one or more controllers, one or more resistors, one or more capacitors, one or more inductors, one or more crystal oscillators, one or more ceramic filters, one or more mechanical switches, one or more connectors, one or more diodes, one or more transistors, one or more thyristors, one or more integrated circuits, one or more sensors (e.g., a flow sensor, a pressure sensor, a humidity sensor, a temperature sensor, etc.). In some embodiments, the one or more processors (and/or the one or more controllers) may be coupled with one or more electronic components 4300 of the printed circuit board (PCB) 4320, the on-off button 4310, the wireless module assembly 4330, the rotary knob 4350, the home button 4370, and the displayer 4380 to control the operation of the respiratory ventilation apparatus 110. For example, if a user (e.g., the subject 180) presses the on-off button 4310, the processor(s) may be triggered to control the start or stop of the respiratory ventilation apparatus 110. In some embodiments, the gas pressurization unit 210 may be coupled with (or electrically connected with) the electronic components 4300. In some embodiments, the electronic components 4300 may include the gas pressurization unit 210.

In some embodiments, a first hole 4361 may be set on the panel 4360, and the rotary knob 4350 may be connected to (or coupled with) the printed circuit board (PCB) 4320 through the first hole 4361. In some embodiments, if the rotary knob 4350 is turned, the controller(s) may control the operation of one or more of the electronic components 4300. In some embodiments, the rotary knob 4350 may be configured to adjust the brightness of the displayer 4380. For example, if the rotary knob 4350 is turned gradually toward a certain direction (clockwise or anti-clockwise), the brightness of the displayer 4380 may become larger, and accordingly, if the rotary knob 4350 is turned in the opposite direction, the brightness of the displayer 4380 may become smaller. In some other embodiments, the rotary knob 4350 may be configured to adjust the gas flow. For example, if the rotary knob 4350 is turned gradually toward a certain direction (clockwise or anti-clockwise), the gas flow may become larger, and accordingly, if the rotary knob 4350 is turned in the opposite direction, the gas flow may become smaller. In some embodiments, the rotary knob 4350 may be used as an on-off button. In some embodiments, the rotary knob 4350 may be configured to adjust the pressure of the respiratory gas flowing in the gas passage(s) of the respiratory ventilation apparatus 110. For example, if the rotary knob 4350 is turned gradually toward a certain direction (clockwise or anti-clockwise), the pressure of the respiratory gas may become larger, and accordingly, if the rotary knob 4350 is turned in the opposite direction, the pressure of the respiratory gas may become smaller.

In some embodiments, the panel 4360 may be configured to protect the displayer 4380 from damage and/or make the overall appearance of the respiratory ventilation apparatus 110 more elegant. In some embodiments, the panel 4360 may be transparent. In some embodiments, the information displayed on the displayer 4380 may be observed through the panel 4360. The information displayed on the displayer 4380 may include a user interface, one or more working parameters generated or detected during the operation of the respiratory ventilation apparatus 110, vital sign information of the user (e.g., the subject 180), etc. In some embodiments, the working parameters may include the pressure of the respiratory gas, the temperature of the respiratory gas, the humidity of the respiratory gas, a working mode of the respiratory ventilation apparatus 110, a status of the peripheral device, a working time, etc. In some embodiments, the vital sign information may include a respiratory frequency of the user, a snoring of the user, a sleeping status of the user, a tidal volume of the user, etc. In some other embodiments, a light sensor that is configured to detect an intensity of ambient light may be set outside of the respiratory ventilation apparatus 110 and coupled with the electronic components 4300, so that the processor(s) (and/or controller(s)) may control the brightness of the displayer 4380 automatically based on the intensity of the ambient light. In some embodiments, the displayer 4380 may include a liquid crystal display (LCD) screen, a light-emitting diode (LED) screen, or the like.

In some embodiments, the home button 4370 may be configured to reset the working parameter(s) to original or initial value(s). In some embodiments, the home button 4370 may be configured to control the interface to return to a home page or a previous page. In some embodiments, a second hole 4362 may be set on the panel 4360, and the home button 4370 may be connected to (or coupled with) the printed circuit board (PCB) 4320 through the second hole 4362.

In some embodiments, the wireless module assembly 4330 may be configured to control the respiratory ventilation apparatus 110. In some embodiments, the wireless module assembly 4330 may include a Bluetooth module, a ZigBee module, a mobile communication module, a radio frequency (RF) communication module, a WiFi module, or the like, or a combination thereof. In some embodiments, the respiratory ventilation apparatus 110 may connect to the internet through the WiFi module. In some embodiments, the working parameter(s) of the respiratory ventilation apparatus 110 may be adjusted (or controlled, or changed) by a remote computer (e.g., a mobile terminal). In some embodiments, the radio frequency (RF) communication module may be coupled with a remote controller, and a user (e.g., the subject 180) may start, stop, adjust, and/or control the operation of the respiratory ventilation apparatus 110 via the remote controller remotely. In some embodiments, the wireless module assembly 4330 may be coupled with one or more sensors equipped in the respiratory ventilation apparatus 110 to obtain information detected by the sensor(s). For example, the wireless module assembly 4330 may be coupled with a flow sensor located in the gas passage(s) of the respiratory ventilation apparatus 110 to obtain the flux of the respiratory gas.

In some embodiments, the secure digital (SD) card read-write storage module 4340 may be configured to accommodate a secure digital (SD) card, read information from the SD card, and/or write information to the SD card. It should be noted that the secure digital (SD) card may be dispensable. In some embodiments, the secure digital (SD) card may be configured to store the user's vital sign information, the working parameters generated or detected during the operation of the respiratory ventilation apparatus 110, and/or one or more preset working parameters. In some embodiments, the memory size of the secure digital (SD) card may be selected by the user.

Figure 44A:
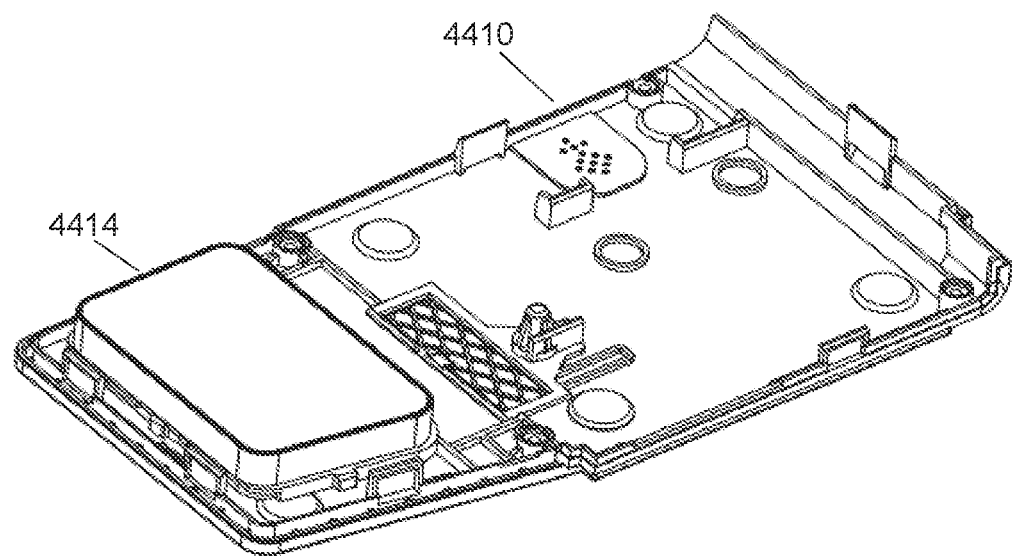
FIGS. 44A and 44B illustrate an exemplary heating device according to some embodiments of the present disclosure.
Figure 44B:
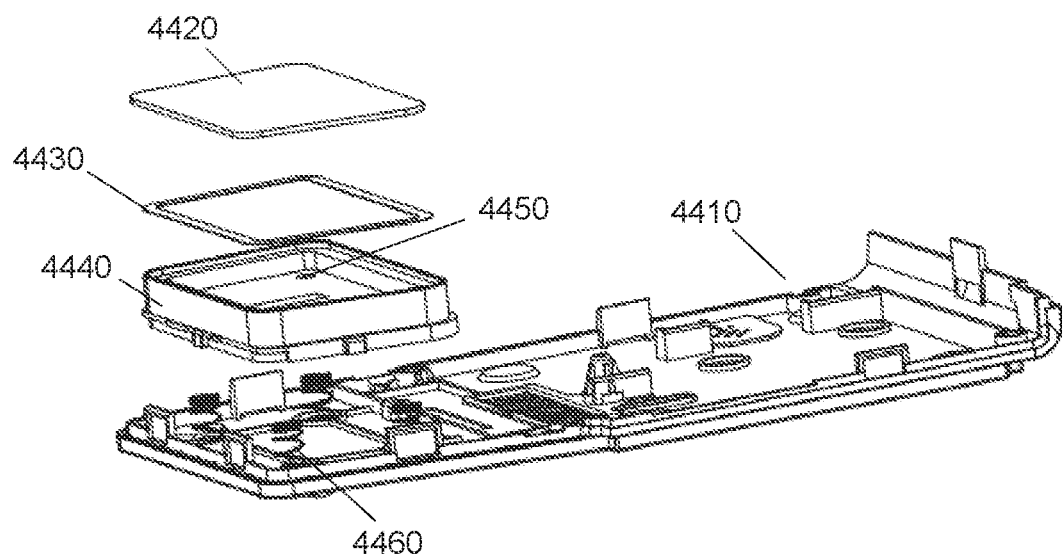

FIGS. 44A and 44B illustrate an exemplary heating device according to some embodiments of the present disclosure. As shown in FIG. 44A, a heating device 4414 may be set on the baseplate 4410 of a main body of a respiratory ventilation apparatus 110. In some embodiments, at least a portion of the baseplate 4410 may be set underneath a liquid chamber (e.g., the liquid chamber 320). The heating device 4414 may be configured to heat the liquid(s) in the liquid chamber and/or accelerate the evaporation of the liquid(s) in the liquid chamber. In some embodiments, as shown in FIG. 44B, the heating device 4414 may include a bracket 4440, a heater plate 4420 and a fixing frame 4430. The fixing frame 4430 may be configured to fix the heater plate 4420 to the bracket 4440. In some embodiments, the heater plate 4420 may be fixed to the bracket 4440 by one or more screws (or snaps) or any other fixing mechanism. The heater plate 4420 may include for example, a stainless steel electric heater plate (mica electric heater plate), a ceramic electric heater plate, a cast aluminum electric heater plate, a cast copper electric heater plate, or the like, or a combination thereof. In some embodiments, one or more springs 4460 may be set underneath the bracket 4440, so that the heating device 4414 may be capable of moving up and down if a pressure is imposed on or removed from the heater plate 4420. More descriptions of the connection between the heating device 4414 and the baseplate 4410 may be found elsewhere in the present disclosure (e.g., FIGS. 22A-22D and the descriptions thereof).

Figure 45:
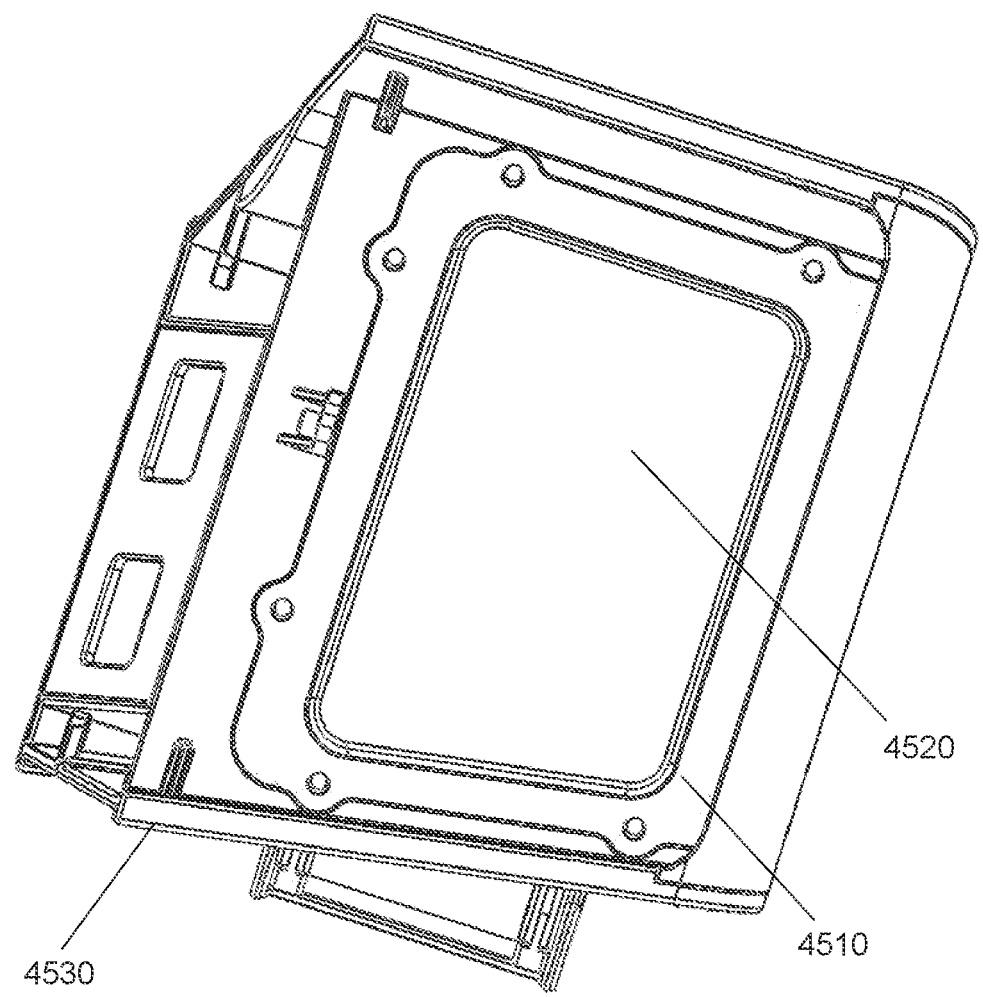
FIG. 45 illustrates an exemplary liquid chamber according to some embodiments of the present disclosure.

FIG. 45 illustrate an exemplary liquid chamber according to some embodiments of the present disclosure. In some embodiments, the liquid chamber 4500 may include a tank 4530. The tank 4530 may be configured to accommodate one or more liquids. In some embodiments, the tank 4530 may include a heat conducting plate 4510. The heat conducting plate 4510 may be configured to conduct the heat generated by the heater plate 4420 to the liquid(s) in the tank 4530, so that the liquid(s) may evaporate to generate vapor to humidify the respiratory gas. In some embodiments, the heat conducting plate 4510 may be made of a heat conducting material including for example, one or more metals with capability of heat conductivity (e.g., copper, aluminum), heat conducting silica gel, or the like, or a combination thereof. In some embodiments, one or more heat conducting coatings, such as heat conducting silica gel, may be disposed on the surface of the heat conducting plate 4510 to promote thermal contact between the heater plate 4420 and the heat conducting plate 4510.

In some embodiments, the heat conducting plate 4510 may be fixed to the bottom of the tank 4530 by screw(s) or glue. In some embodiments, the bottom of the tank 4530 may include a groove 4520. In some embodiments, the shape of the groove 4520 may fit with the shape the heater plate 4420, so that if the tank 4530 is mounted on the baseplate 4410, the heating device 4414 may be totally or partly trapped in the groove 4520. Therefore, the heater plate 4420 and the heat conducting plate 4510 can be closely connected.

In order to reduce heat loss, it may be necessary to ensure that the heater plate 4420 and the heat conducting plate 4510 are in close contact with each other. As illustrated in FIG. 44B, one or more springs 4460 may be set below the heater plate 4420. If the tank 4530 is mounted above the heating device 4414, the spring(s) 4460 may be compressed, and the compressed spring(s) 4460 may push the heater plate 4420 to the heat conducting plate 4510, increasing the contact pressure between the heater plate 4420 and the heat conducting plate 4510 and ensuring the close contact therebetween. In some embodiments, a plurality of elastic columns may be used instead of the spring(s) 4460.

In some other embodiments, one or more heating rods, one or more electrodes or one or more ultrasonic atomizers may be directly installed in the tank 4530 to heat the liquid(s) in the tank 4530. In some embodiments, the heating device 4414 may be coupled to (or electrically connected with) the electronic components 4300. The controller(s) may control the start, stop, suspend, resume of the heating of the heating device 4414, the heating rate of the heating device 4414, the heating power of the heating device 4414, etc., so as to control the humidity of the respiratory gas.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A humidification assembly configured to humidify pressurized respiratory gas from a respiratory ventilation apparatus,
    the humidification assembly including a liquid chamber configured to accommodate liquid,
    the liquid chamber including:
        a tank,
        a tank cover, and
        the tank cover including:
            a first gas passage,
            a second gas passage,
            a humidification assembly gas inlet port configured to introduce the pressurized respiratory gas, via the first gas passage, into the tank, wherein the first gas passage includes an output port, a humidification assembly gas outlet port configured to introduce the humidified and pressurized respiratory gas, via the second gas passage, out of the tank, wherein the second gas passage includes an input port and the humidification assembly gas outlet port is an output port of the second gas passage,
        the first gas passage and the second gas passage cross each other, wherein at least a portion of the first gas passage and a portion of the second gas passage extend substantially along a same plane,
        the output port and the input port are set inside the liquid chamber, and the output port and the input port opening in different directions,
    wherein a bottom of at least a portion of the second gas passage is below the lower edge of the output port of the second gas passage and the lower edge of the input port of the second gas passage, and
    the lower edge of the input port of the second gas passage is above the lower edge of the output port of the second gas passage.

2. The humidification assembly of claim 1, wherein at least one of the first gas passage and the second gas passage includes a plurality of extension directions along its length.

3. The humidification assembly of claim 1, wherein
    the first gas passage includes a plurality of portions extending in a plurality of extension directions, and/or
    the second gas passage includes a plurality of portions extending in a plurality of extension directions.

4. The humidification assembly of claim 1, wherein
    a portion of the first gas passage and a portion of the second gas passage are set in different layers, and
    a first projection of the portion of the first gas passage on a horizontal plane and a second projection of the portion of the second gas passage on the horizontal plane are intersecting or at least partially overlapping.

5. The humidification assembly of claim 1, wherein
    at least a portion of a bottom of the first gas passage is below a lower edge of the humidification assembly gas inlet port of the liquid chamber, or
    at least a portion of a bottom of the second gas passage is below a lower edge of the humidification assembly gas outlet port of the liquid chamber.

6. The humidification assembly of claim 1, including at least one of:
    that the distance between the output port of the first gas passage and the humidification assembly gas inlet port is larger than the distance between the output port of the first gas passage and the humidification assembly gas outlet port, or
    that the distance between the input port of the second gas passage and the humidification assembly gas outlet port is larger than the distance between the input port of the second gas passage and the humidification assembly gas inlet port.

7. The humidification assembly of claim 1, wherein the first and second gas passages have a substantially rectangular cross-section.

8. The humidification assembly of claim 1, including:
    the shape of the tank is an irregular shape that can fit with a main body of the respiratory ventilation apparatus, and
    the shape of the tank cover is an irregular shape that can fit with the main body of the respiratory ventilation apparatus.

9. The humidification assembly of claim 1, including:
    the tank cover is pivotally connected to the tank through a connection mechanism, and
    the distance between the connection mechanism and the humidification assembly gas outlet port is different from the distance between the connection mechanism and the humidification assembly gas inlet port.

10. The humidification assembly of claim 1, wherein
    at least one of the humidification assembly gas inlet port of the liquid chamber and the humidification assembly gas outlet port of the liquid chamber is set on a first side surface of the tank cover.

11. The humidification assembly of claim 1, including:
    introduce the humidified and pressurized respiratory gas, via the second gas passage back into a main body of the respiratory ventilation apparatus; or
    introduce the humidified and pressurized respiratory gas, via the second gas passage, into a respiration tube.

12. A respiratory ventilation apparatus configured to deliver a respiratory gas to a patient interface, comprising the humidification assembly according to claim 1 and further comprising:

a gas pressurization unit configured to generate the pressurized respiratory gas by pressurizing the respiratory gas, the gas pressurization unit being located in a main body of the respiratory ventilation apparatus, the main body of the respiratory ventilation apparatus including a housing with a first side wall configured to discharge the pressurized respiratory gas;

a main gas inlet port configured to introduce the respiratory gas into the respiratory ventilation apparatus, the main gas inlet port being set on a second side wall of the housing of the main body of the respiratory ventilation apparatus; and a main gas outlet port configured to discharge the humidified and pressurized respiratory gas to a respiration tube.

13. The respiratory ventilation apparatus of claim 12, wherein the main gas outlet port is set on the main body of a respiratory ventilation apparatus.

14. The humidification assembly of claim 1, including:
the humidification assembly gas inlet port comprises a sealing member, the humidification assembly gas inlet port is spaced apart by the sealing member in the axial direction of the sealing member thereof in a sealed or attached state of the humidification assembly,
when the humidification assembly and the main body of the respiratory ventilation apparatus are fluidically connected through the humidification assembly gas inlet port for forming a flow channel between the main body of the respiratory ventilation apparatus and the liquid chamber, and an inner surface of the sealing member at least partially forms the flow channel.

15. The humidification assembly of claim 14, including:
the humidification assembly gas inlet port comprises an inlet aperture, and
the sealing member is formed around the inlet aperture.

16. The humidification assembly of claim 15, wherein the inlet aperture is spaced apart at least 1 mm by the sealing member in the axial direction thereof in a sealed and attached state of the humidification assembly.

17. The humidification assembly of claim 15, including:
the inlet aperture is formed by one or more materials having a higher hardness than an elastic material forming the sealing member.

18. The respiratory ventilation apparatus of claim 17, including
a first side surface of the tank cover of the liquid chamber faces the first side wall of the housing of the main body of the respiratory ventilation apparatus.

19. The humidification assembly of claim 14, including:
the sealing member is compressed along the axial direction by 10%-50% or by 0.5-6 mm in a sealed state comparing to a state, wherein a main body of the respiratory ventilation apparatus and the humidification assembly are unlocked.

* * * * *